US012248826B2

(12) United States Patent
Gnanasambandam et al.

(10) Patent No.: US 12,248,826 B2
(45) Date of Patent: Mar. 11, 2025

(54) CLOUD-BASED HEALTHCARE PLATFORM

(71) Applicant: HEALTHPOINTE SOLUTIONS, INC., Austin, TX (US)

(72) Inventors: Nathan Gnanasambandam, Irvine, CA (US); Mark Henry Anderson, Newport Coast, CA (US)

(73) Assignee: HEALTHPOINTE SOLUTIONS, INC., Austin, TX (US)

( * ) Notice: Subject to any disclaimer, the term of this patent is extended or adjusted under 35 U.S.C. 154(b) by 0 days.

(21) Appl. No.: 17/773,224

(22) PCT Filed: Oct. 30, 2020

(86) PCT No.: PCT/US2020/058378
§ 371 (c)(1),
(2) Date: Apr. 29, 2022

(87) PCT Pub. No.: WO2021/087370
PCT Pub. Date: May 6, 2021

(65) Prior Publication Data
US 2022/0391270 A1    Dec. 8, 2022

Related U.S. Application Data

(60) Provisional application No. 62/928,738, filed on Oct. 31, 2019.

(51) Int. Cl.
*G06F 9/54* (2006.01)
(52) U.S. Cl.
CPC .............. *G06F 9/543* (2013.01); *G06F 9/547* (2013.01)

(58) Field of Classification Search
CPC ......... G06F 9/543; G06F 9/547; G16H 10/20; G16H 20/30; G16H 20/60; G16H 20/70; G16H 70/20; G16H 70/60; G16H 50/20
See application file for complete search history.

(56) References Cited

U.S. PATENT DOCUMENTS 9,077,773 B2 *   7/2015   Marietti .................... G06F 8/30
10,534,851 B1 *   1/2020   Chan .................. G06Q 30/0255
(Continued)

OTHER PUBLICATIONS

RapidAPI, "RapidAPI Hub" (Sep. 11, 2019), pp. 1-11 [retrieved from https://rapidapi.com/hub]. (Year: 2019).*
(Continued)

*Primary Examiner* — Brian W Wathen
(74) *Attorney, Agent, or Firm* — Dickinson Wright PLLC

(57) ABSTRACT

A system and a method directed to various techniques for creating an autonomous multipurpose application using a platform of application programming interfaces (APIs). In one embodiment, a method comprising operations performed by a cognitive intelligence platform is disclosed. The method includes: publishing, for implementation in the autonomous multipurpose application, at least one API that uses artificial intelligence to perform analytics based on a knowledge graph pertaining to ontological data of a medical condition, wherein the at least one API is included in a set of APIs; providing the at least one API in a user interface of a computing device; receiving, from the computing device, a request to subscribe to the at least one API; implementing computer instructions of the at least one API in the autonomous multipurpose application; and providing the autonomous multipurpose application to the computing device for execution on the computing device.

20 Claims, 107 Drawing Sheets

(56) References Cited

U.S. PATENT DOCUMENTS

| | | | | |
|---|---|---|---|---|
| 2013/0132584 A1* | 5/2013 | Palladino | ............... | G06F 8/30 |
| | | | | 709/226 |
| 2016/0048648 A1* | 2/2016 | Sanchez | ............... | G16H 50/20 |
| | | | | 706/12 |
| 2016/0063191 A1 | 3/2016 | Vesto et al. | | |
| 2016/0335546 A1 | 11/2016 | Ptitsyn | | |
| 2019/0171958 A1* | 6/2019 | Sudharsan | ............... | G06N 7/01 |
| 2020/0159597 A1* | 5/2020 | Gino | ............... | G06F 9/5038 |
| 2022/0283805 A1* | 9/2022 | Dasa | ............... | H04L 67/1097 |
| 2022/0291974 A1* | 9/2022 | Gino | ............... | G06F 9/547 |

OTHER PUBLICATIONS

Wirefree Thought, "GeoDB Cities API Getting Started Take It Out For a Spin" (Aug. 18, 2018), pp. 1-4 [retrieved from https://web.archive.org/web/20180618032726/http://geodb-cities-api.wirefreethought.com/docs/guides/getting-started/test-drive]. (Year: 2018).*

International Search Report of PCT/US2020/058378 dated Feb. 2, 2021.

* cited by examiner

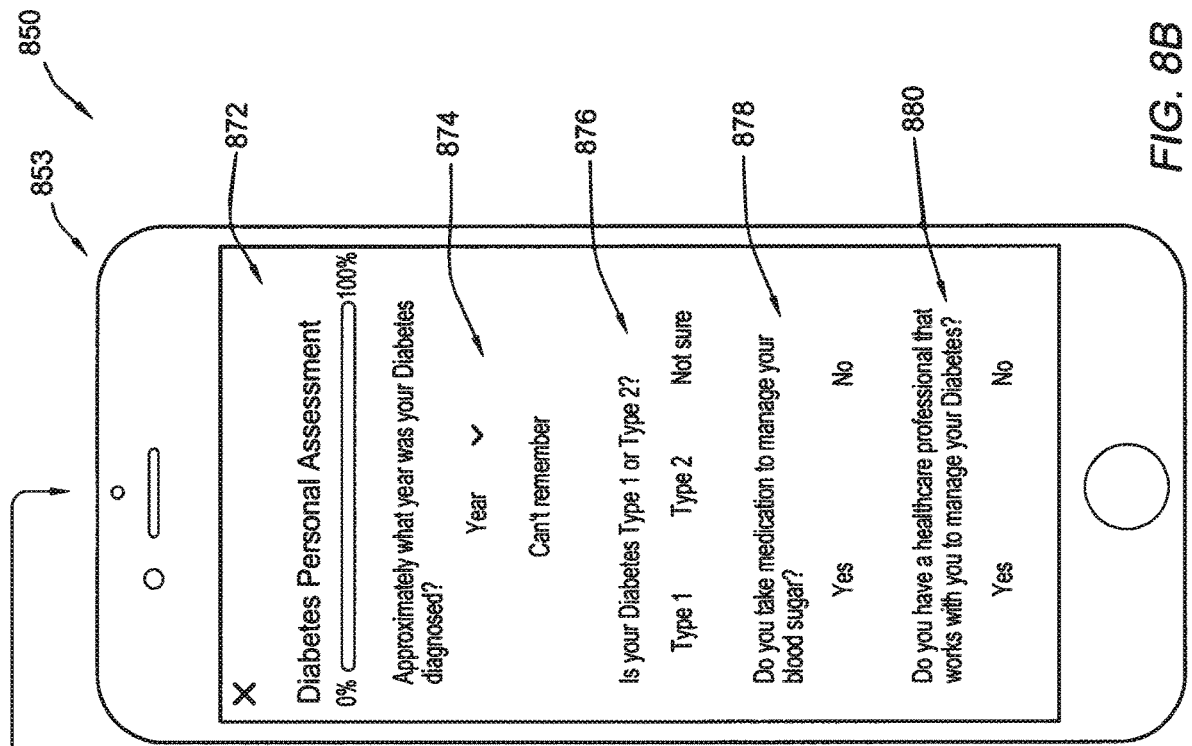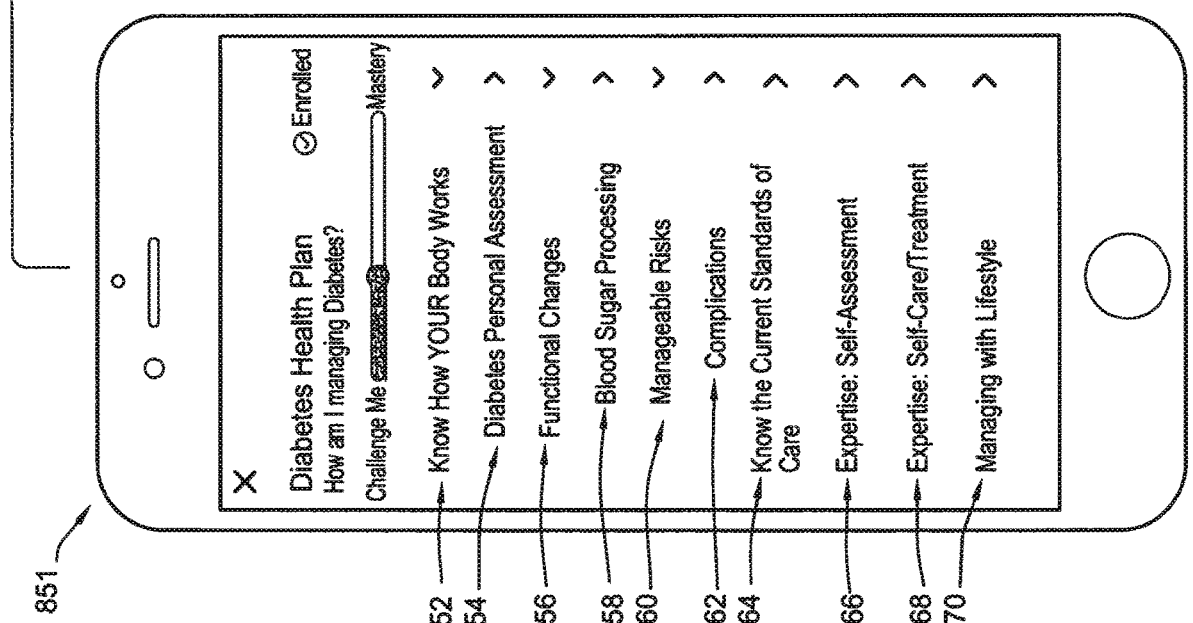
FIG. 8B

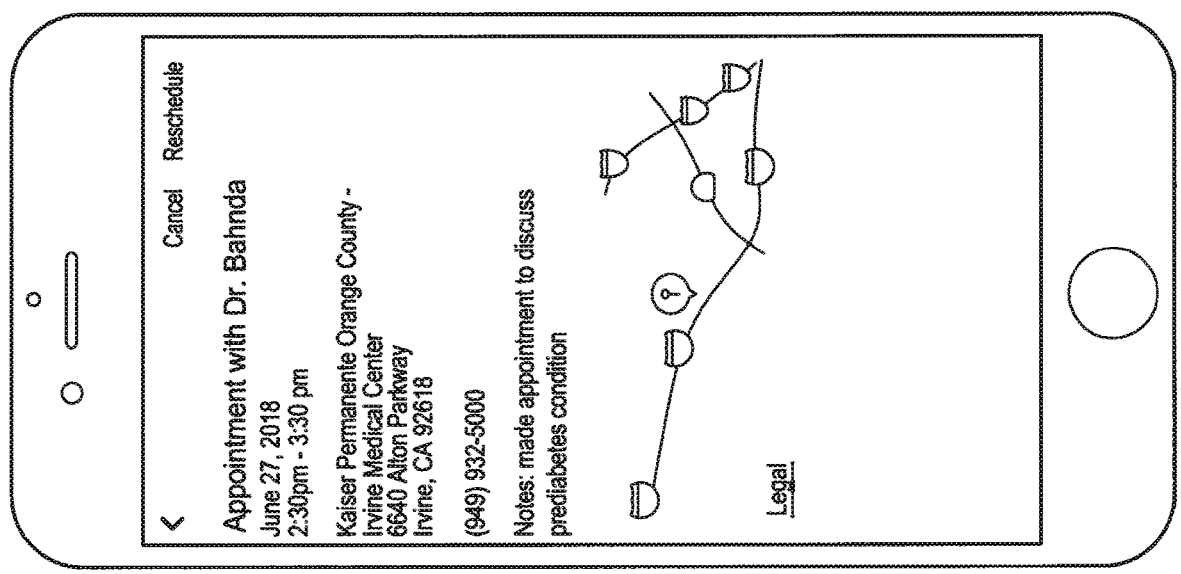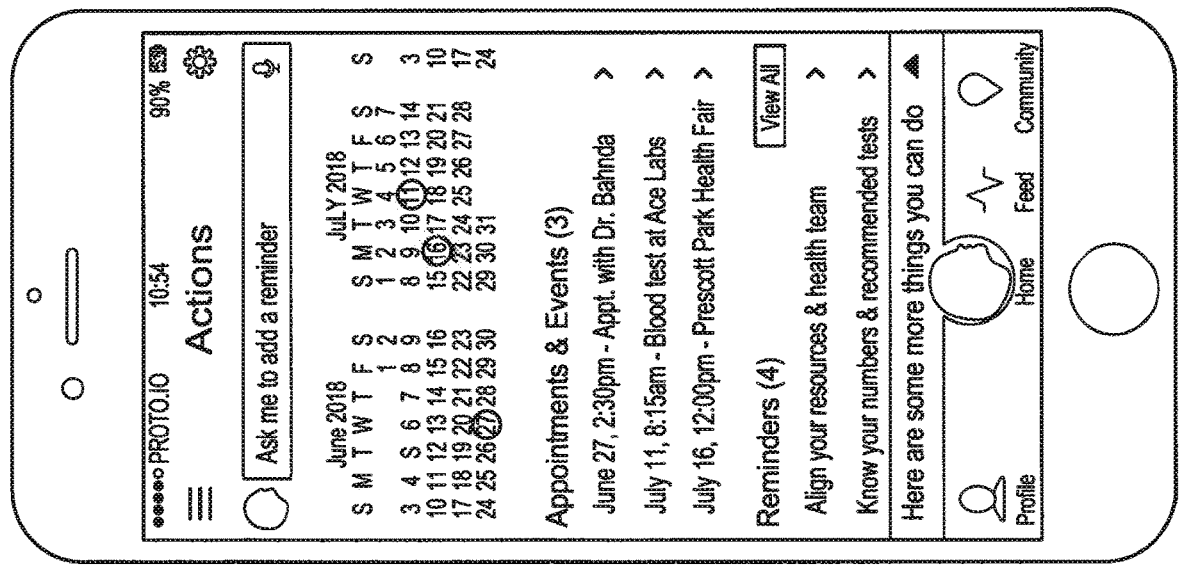
FIG. 11

FIG. 12

✗ Provider Information

James Johnson, MD
Family Practice

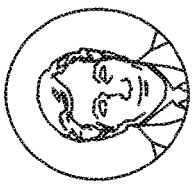

Dr. Johnson is committed to educating his patients about their medical conditions and empowering them to improve their quality of life. Outside the office, he enjoys spending time outdoors with his wife and children, as well as international travel, hiking, biking, swimming, and crossfit.

Education

James Johnson, MD, earned his medical degree from Jefferson Medical College in Philadelphia, Pennsylvania. He completed internships in radiology and internal medicine at Milton S. Hershey Medical Center in Hershey, Pennsylvania. He is board-certified in internal medicine.

Services

Provides primary and preventive care for adults
Manages chronic and complex health conditions
Evaluates and treats acute illness Languages English
Spanish

COGNITIVE INTELLIGENCE PLATFORM 102

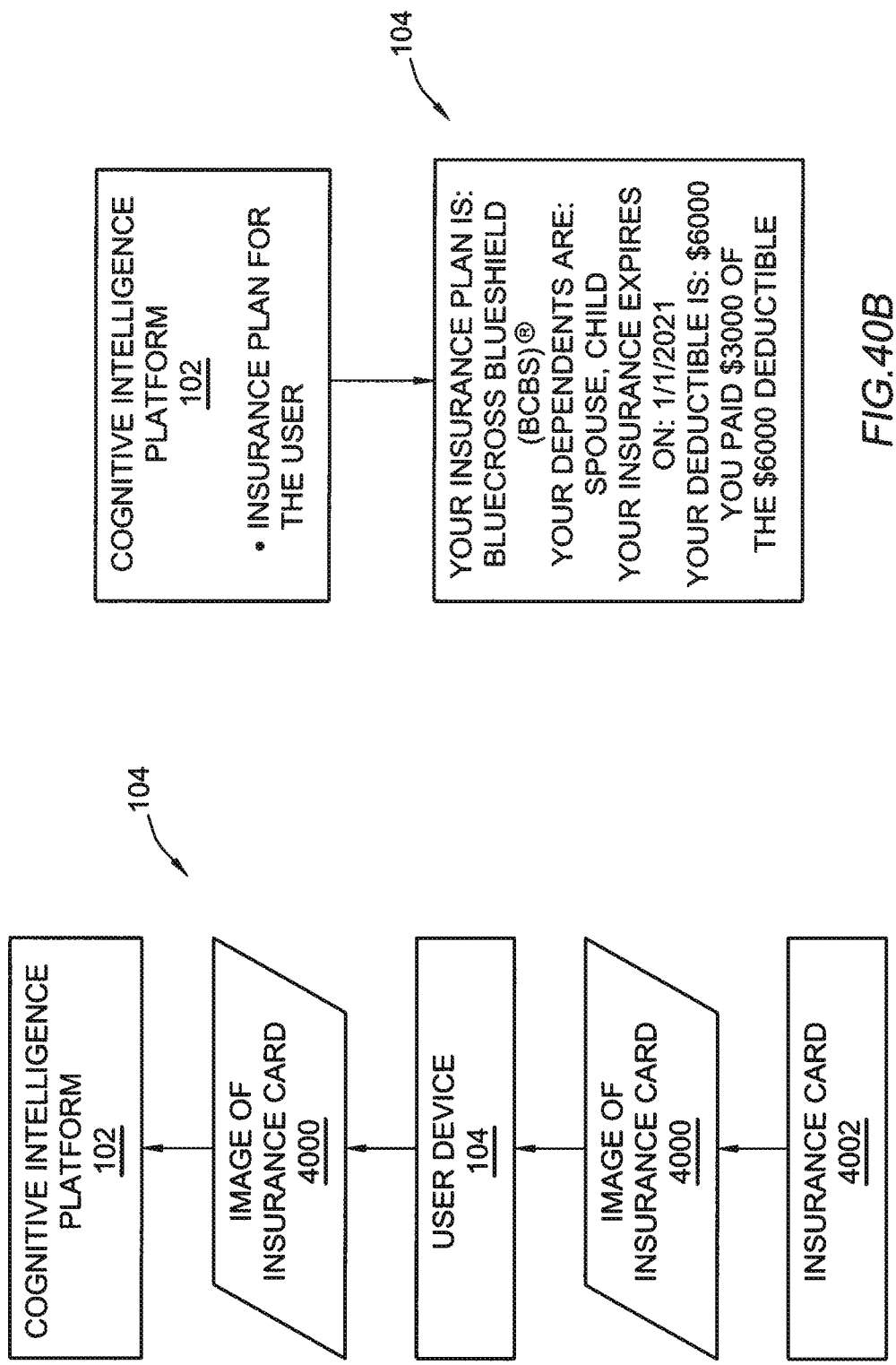

Success!
Upload another file

| Field | Result |
|---|---|
| First Name | Regina b |
| Last Name | ranoa |
| Sex | Female |
| Eye Color | - |
| Height | - |
| Weight | - |
| Date of Birth | 06/21/1961 |
| Address | 655 12 S 224, OAKLAND CA 94607 OAKLAND CA-94607 |
| Issue Date | 09/30/2011 |
| Expiration Date | 10/31/2016 |
| ID number | 62364178 |
| Document Discriminator | - |
| Country Identification | - |
| Inventory Control Number | - |
| Jurisdiction Specific Restriction Codes | - |

FIG.40C

```
20 minutes until Adrian's appointment
```

Zahra S. ▼ — 4810

< Your Appointments      ( Need Help? Call a Neighbor )   A A
                                                          Text Size

Today's Appointments                    Future Appointments

| Estimated wait time for first appointment 20 minutes | Estimated total for today $90.00 |

4812

( Add Another Appointment )    ( Check In For Today )   — 4814

Today
May 30
10:30 am

Medical appointment for Adrian Smith

Grace Bahnda, MD
This Clinic

Self-pay estimate $45.00

Cancel or Reschedule        ( Change Payment Method )

Today
May 30

Medical appointment for Zahra Smith

Grace Bahnda, MD

*FIG.48B*

Please find information and/or action instructions pertaining to the 3 areas you selected relating to Type 2 Diabetes Mellitus below:

- Medications

The types of medication available to treat Type 2 Diabetes Mellitus include: medication A, medication B, and medication C.

You are currently prescribed medication A. If it is not working as desired, discuss medication change with your physician.

We see that you are also prescribed medication D for condition Y. Medication B and medication D are not compatible and may cause issues. Be sure to discuss this with your physician.

- Symptoms

Type 2 Diabetes Mellitus has the following symptoms: High Blood Sugar

If you have high blood sugar, contact your physician.

- Tests

The types of tests for Type 2 Diabetes Mellitus include: A1c Test and Blood Glucose Test.

You have already had a Blood Glucose Test. You can take a A1c Test to get additional results, or you can retake the Blood Glucose Test.

COGNITIVE INTELLIGENCE PLATFORM 102

*FIG. 57D*

Please find updated information and/or action instructions relating to Type 2 Diabetes Mellitus below:

- Medications
The types of medication available to treat Type 2 Diabetes Mellitus include: medication A, medication B, and medication C.

You are currently prescribed medication A. if it is not working as desired, discuss medication change with your physician.

We see that you are also prescribed medication D for condition Y. Medication B and medication D are not compatible and may cause issues. Be sure to discuss this with your physician.

- Tests
The types of tests for Type 2 Diabetes Mellitus include: A1c Test and Blood Glucose Test.

You have already had an A1c Test. You can take a Blood Glucose Test to get additional results, or you can retake the A1c Test.

- Complications
Type 2 Diabetes Mellitus has complications of stroke, coronary artery disease, diabetes foot problems, diabetic neuropathy, diabetic retinopathy.

Here is recommended medical content relating to those complications. Please read them.

Speak to your physician about the complications.

COGNITIVE INTELLIGENCE PLATFORM 102

FIG. 60D

Please find updated information and/or action instructions pertaining to Type 2 Diabetes Mellitus below:

- Medications

The types of medication available to treat Type 2 Diabetes Mellitus include: medication A, medication B, and medication C.

You are currently prescribed medication A. if it is not working as desired, discuss medication change with your physician.

We see that you are also prescribed medication D for condition Y. Medication B and medication D are not compatible and may cause issues. Be sure to discuss this with your physician.

- Symptoms

Type 2 Diabetes Mellitus has the following symptoms: High Blood Sugar

If you have high blood sugar, contact your physician.

- Tests

The types of tests for Type 2 Diabetes Mellitus include: A1c Test and Blood Glucose Test.

You have already had an A1c Test. You can take a Blood Glucose Test to get additional results, or you can retake the A1c Test.

- Self-care

Try self-care treatments for Type 2 Diabetes Mellitus including: weight management, diabetic diet, healthy eating, diabetes foot care, being active.

COGNITIVE INTELLIGENCE PLATFORM 102

FIG. 60E

DISPLAY 1410

Recommended Reading: → 8000

Glucose Management by Registered Nurses for Adult Patients Hospitalized in Medical Wards: Structured Guidelines (Protocol) and Working Process
Inbal Savion, RN, MMedSc*, Khalil Khoury, RN, MSc Pharm*, Gila Alkoken, RN, Itamar Raz, MD, PhD, Gil Leibovitz, MD, PhD, Roy Eldor, MD and Orly Toren, RN, PhD Diabetes Spectrum 2010 Oct; 23(4): 268-271.
https://doi.org/10.2337/diaspect.23.4.268

COGNITIVE INTELLIGENCE PLATFORM 102

AI ENGINE 109

*FIG. 81*

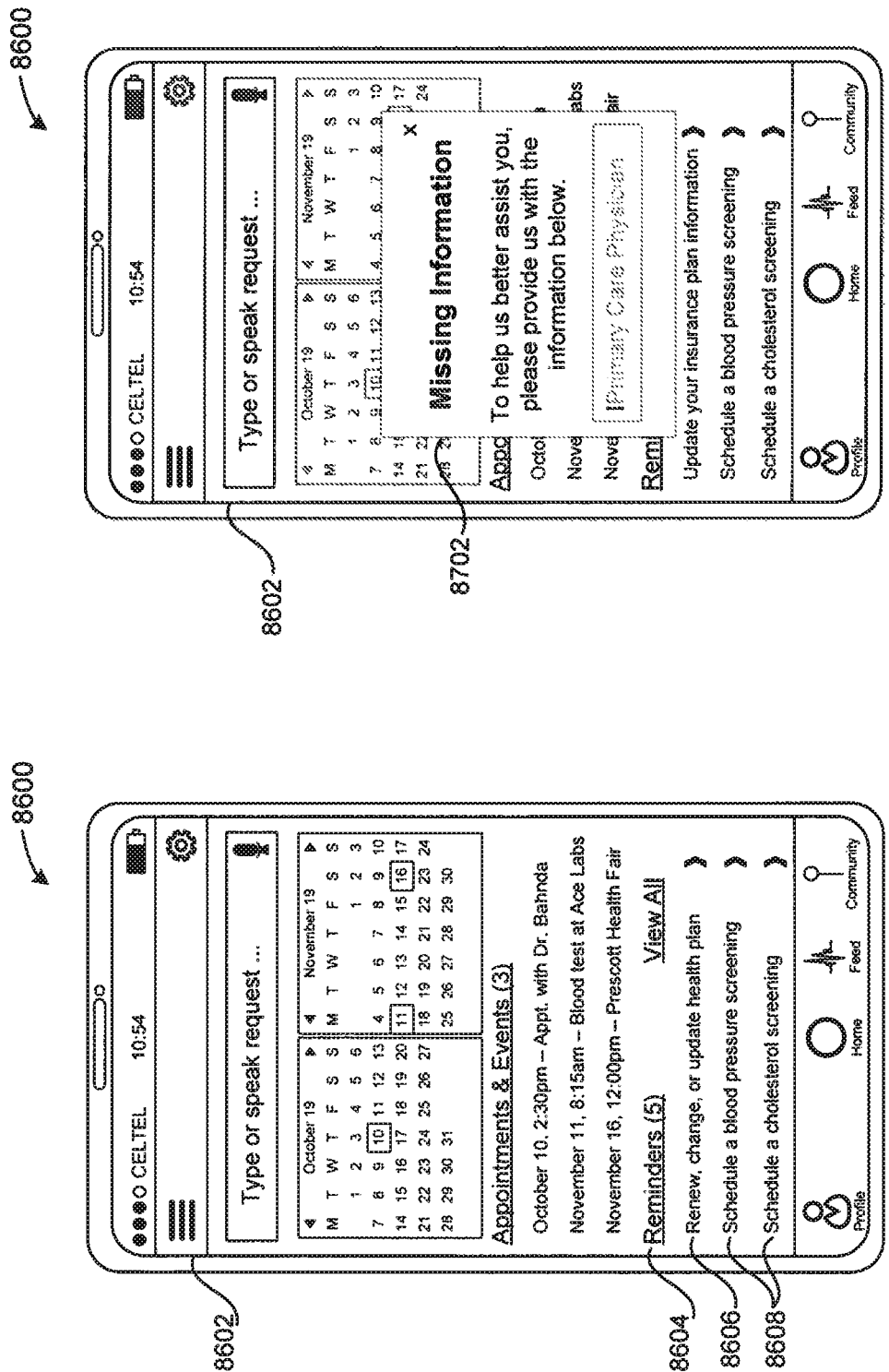

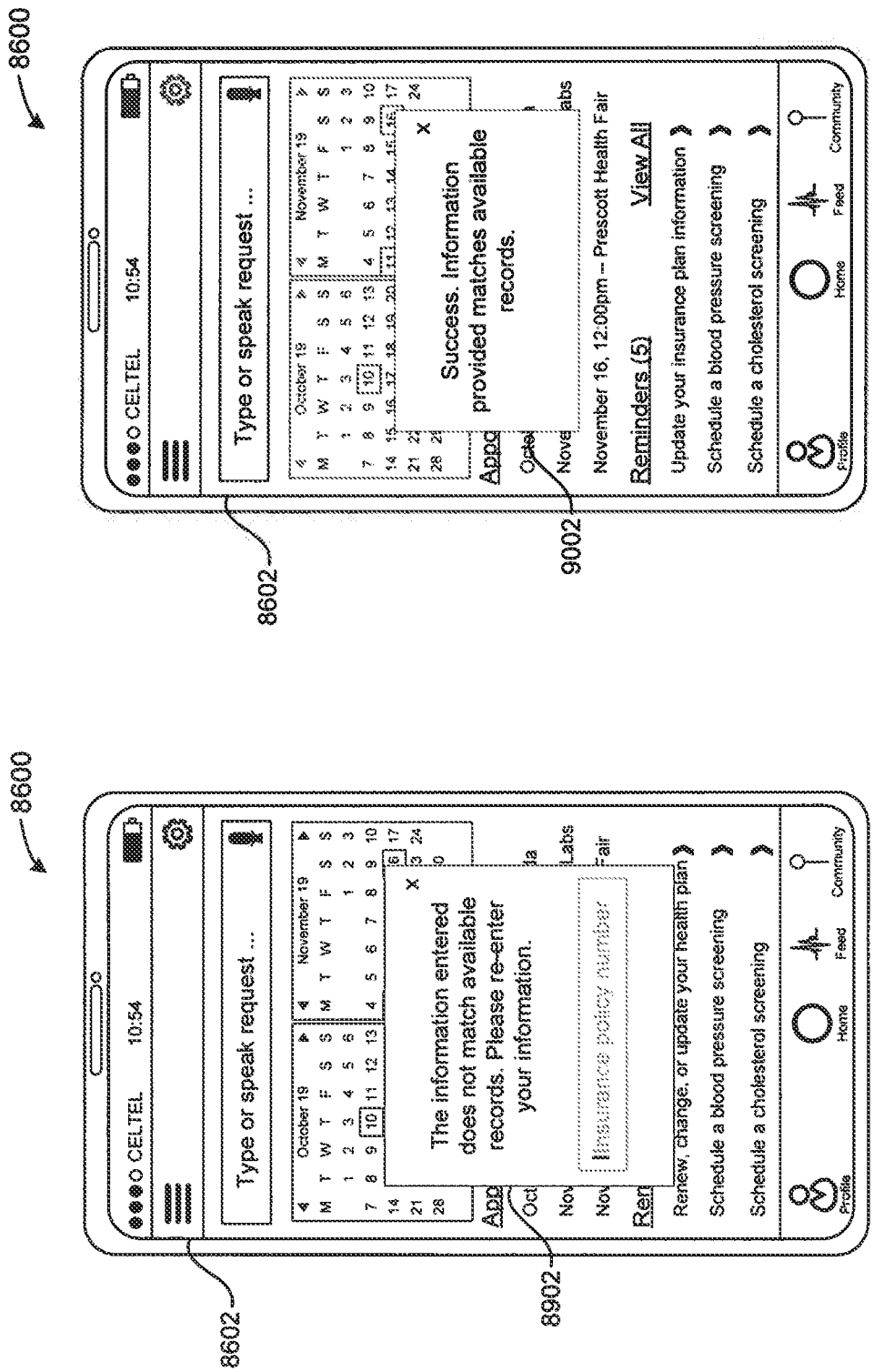

CLOUD-BASED HEALTHCARE PLATFORM

CROSS-REFERENCE TO RELATED APPLICATIONS

This application is a U.S. National Phase Entry of PCT Application Serial No. PCT/US2020/058378 filed Oct. 30, 2020 and titled "Cloud-Based Healthcare Platform". The PCT application claims the benefit of U.S. Provisional Application Ser. No. 62/928,738 filed Oct. 31, 2019 titled "Cloud-Based Healthcare Platform." All of the above listed applications are incorporated by reference herein as if reproduced in full below.

BACKGROUND

Population health management entails aggregating patient data across multiple health information technology resources, analyzing the data with reference to a single patient, and generating actionable items through which care providers can improve both clinical and financial outcomes. A population health management service seeks to improve the health outcomes of a group by improving clinical outcomes while lowering costs.

SUMMARY

Representative embodiments set forth herein disclose various techniques for creating an autonomous multipurpose application using a platform of application programming interfaces (APIs).

In one embodiment, a method comprising operations performed by a cognitive intelligence platform is disclosed. The method includes: publishing, for implementation in the autonomous multipurpose application, at least one API that uses artificial intelligence to perform analytics based on a knowledge graph pertaining to ontological data of a medical condition, wherein the at least one API is included in a set of APIs; providing the at least one API in a user interface of a computing device; receiving, from the computing device, a request to subscribe to the at least one API; implementing computer instructions of the at least one API in the autonomous multipurpose application; and providing the autonomous multipurpose application to the computing device for execution on the computing device.

In another embodiment, a tangible, non-transitory computer-readable medium storing instructions that, when executed, cause a processing device to execute the following steps disclosed. The steps include publishing, for implementation in the autonomous multipurpose application, at least one API that uses artificial intelligence to perform analytics based on a knowledge graph pertaining to ontological data of a medical condition, wherein the at least one API is included in a set of APIs; providing the at least one API in a user interface of a computing device; receiving, from the computing device, a request to subscribe to the at least one API; implementing computer instructions of the at least one API in the autonomous multipurpose application; and providing the autonomous multipurpose application to the computing device for execution on the computing device.

In still yet another embodiment, a system comprising a memory device storing instructions and a processing device, communicatively coupled to the memory device, executing the instructions is disclosed. The instructions include: publishing, for implementation in the autonomous multipurpose application, at least one API that uses artificial intelligence to perform analytics based on a knowledge graph pertaining to ontological data of a medical condition, wherein the at least one API is included in a set of APIs; providing the at least one API in a user interface of a computing device; receiving, from the computing device, a request to subscribe to the at least one API; implementing computer instructions of the at least one API in the autonomous multipurpose application; and providing the autonomous multipurpose application to the computing device for execution on the computing device.

BRIEF DESCRIPTION OF THE DRAWINGS

For a detailed description of example embodiments, reference will now be made to the accompanying drawings in which:

FIGS. 8A, 8B, 8C, and 8D show aspects of a user interface, in accordance with various embodiments.

FIG. 11 shows aspects of an action calendar, in accordance with various embodiments.

FIG. 12 shows aspects of a feed, in accordance with various embodiments.

FIG. 37 shows an example of providing a user interface for presenting a profile of a person, in accordance with various embodiments.

FIG. 40A shows an example of a cognitive intelligence platform receiving an image of an insurance card, in accordance with various embodiments.

FIG. 40B shows an example of the cognitive intelligence platform extracting insurance plan information and causing it to be presented on a user device, in accordance with various embodiments.

FIG. 40C shows an example of the cognitive intelligence platform extracting driver's license information and causing it to be presented on a user device, in accordance with various embodiments.

FIG. 48B shows an example of providing a user interface that shows an estimated wait time for a scheduled appointment, in accordance with various embodiments.

FIGS. 57A-57D show examples for generating a care plan using a knowledge graph and a patient graph, in accordance with various embodiments.

FIG. 60A-E show examples of modifying a care plan based on a detected emotion of the patient, a detected tone of the patient, a different medical outcome entered by a physician, or some combination thereof, in accordance with various embodiments.

FIG. 81 shows a display presenting recommended curated content pertaining to a condition of a patient as an example of a step of the method of FIG. 63.

FIG. 86 provides an example embodiment of a mobile user interface that enables a user to interact with cognitive intelligence platform.

FIG. 87 provides another example embodiment of a mobile user interface that enables a user to interact with cognitive intelligence platform.

FIG. 89 provides an example embodiment of a mobile user interface that enables a user to interact with cognitive intelligence platform.

FIG. 90 provides another example embodiment of a mobile user interface that enables a user to interact with cognitive intelligence platform.

NOTATION AND NOMENCLATURE

Figure 1:
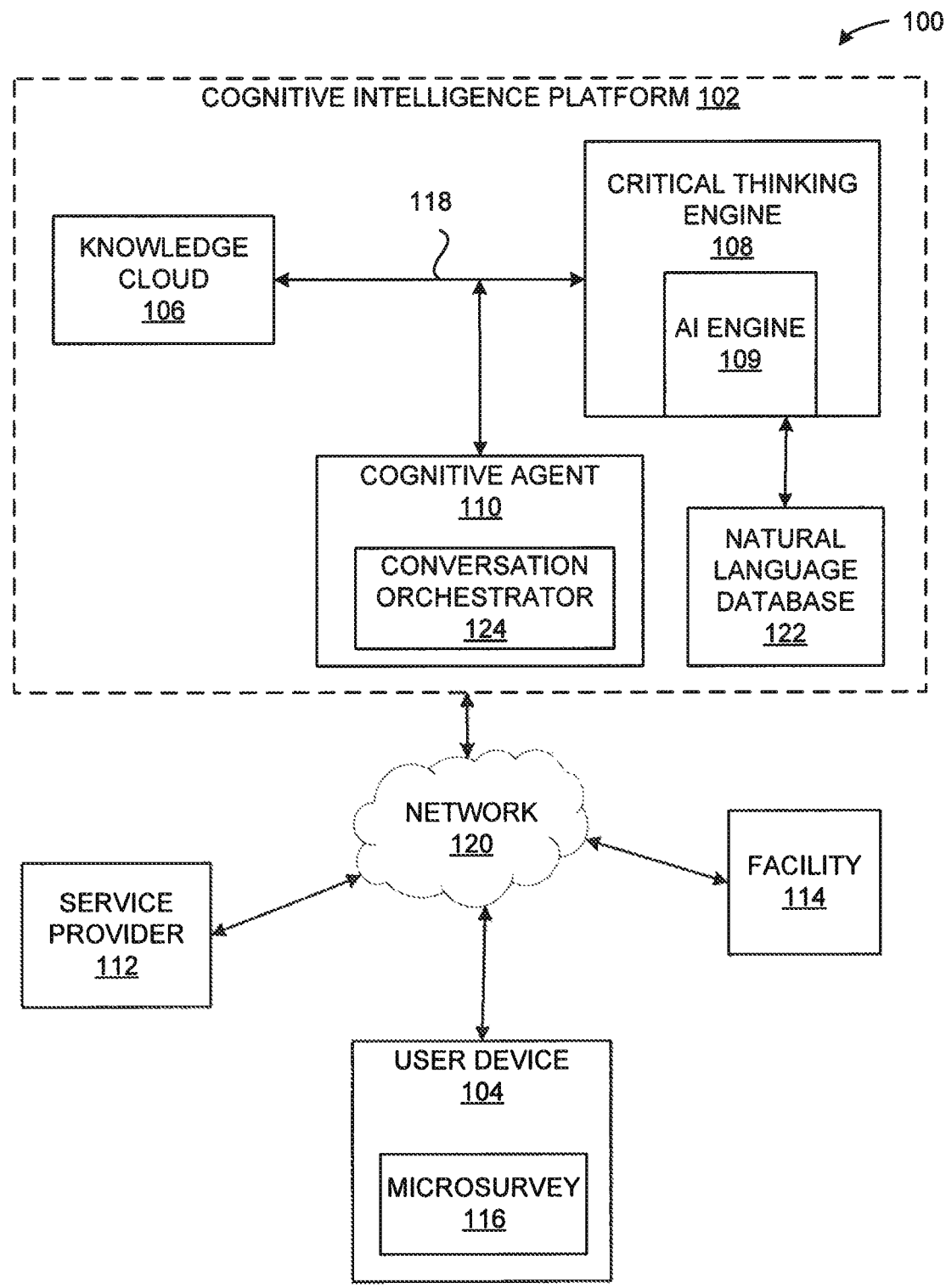
FIG. 1 illustrates, in block diagram form, a system architecture 100 that can be configured to provide a population health management service, in accordance with various embodiments.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

According to some embodiments, a cognitive intelligence platform integrates and consolidates data from various sources and entities and provides a population health management service. The cognitive intelligence platform has the ability to extract concepts, relationships, and draw conclusions from a given text posed in natural language (e.g., a passage, a sentence, a phrase, and a question) by performing conversational analysis which includes analyzing conversational context. For example, the cognitive intelligence platform has the ability to identify the relevance of a posed question to another question.

The benefits provided by the cognitive intelligence platform, in the context of healthcare, include freeing up physicians from focusing on day to day population health management. Thus a physician can focus on her core competency—which includes disease/risk diagnosis and prognosis and patient care. The cognitive intelligence platform provides the functionality of a health coach and includes a physician's directions in accordance with the medical community's recommended care protocols and also builds a systemic knowledge base for health management.

Accordingly, the cognitive intelligence platform implements an intuitive conversational cognitive agent that engages in a question and answering system that is human-like in tone and response. The described cognitive intelligence platform endeavors to compassionately solve goals, questions and challenges.

In addition, physicians often generate patient notes before, during, and/or after consultation with a patient. The patient notes may be included in an electronic medical record (EMR). When a patient returns for a subsequent visit, the physician may review numerous EMRs for the patient. Such a review process may be time consuming and inefficient. Insights may be hidden in the various EMRs and may result in the physician making an incorrect diagnosis. Further, it may involve the physician accessing numerous screens and performing multiple queries on a database to obtain the various EMRs. As a result, the computing device of the physician may waste computing resources by loading various screens and sending requests for EMR data to a server. The server that receives the requests may also waste computing resources by processing the numerous requests and transmitting numerous responses. In addition, network resources may be wasted by transmitting the requests and responses between the server and the client.

Accordingly, some embodiments of the present disclosure address the issues of reviewing the EMRs, by cognifying unstructured data. Unstructured data may include patient notes entered into one or more EMRs by a physician. The patient notes may explain symptoms described by the patient or detected by the physician, vital signs, recommended treatment, risks, prior health conditions, familial health history, and the like. The patient notes may include numerous strings of characters arranged into sentences. The sentences may be organized in one or more paragraphs. The sentences may be parsed and indicia may be identified. The indicia may include predicates, objectives, nouns, verbs, cardinals, ranges, keywords, phrases, numbers, concepts, or some combination thereof.

The indicia may be compared to one or more knowledge graphs that each represents health related information (e.g., a disease) and various characteristics of the health related information. The knowledge graph may also include how the various diseases are related to one another (e.g., bronchitis can lead to pneumonia). The knowledge graph may represent a model that includes individual elements (nodes) and predicates that describe properties and/or relationships between those individual elements. A logical structure (e.g., Nth order logic) may underlie the knowledge graph that uses the predicates to connect various individual elements. The knowledge graph and the logical structure may combine to form a language that recites facts, concepts, correlations, conclusions, propositions, and the like. The knowledge graph and the logical structure may be generated and updated continuously or on a periodic basis by an artificial intelligence engine with evidence-based guidelines, physician research, patient notes in EMRs, physician feedback, and so forth. The predicates and individual elements may be generated based on data that is input to the artificial intelligence engine. The data may include evidence-based guidelines that is obtained from a trusted source, such as a physician. The artificial intelligence engine may continuously learn based on input data (e.g., evidence-based guidelines, clinical trials, physician research, electronic medical records, etc.) and modify the individual elements and predicates.

For example, a physician may indicate that if a person has a blood sugar level of a certain amount and various other symptoms (e.g., unexplained weight loss, sweating, etc.), then that person has type 2 diabetes mellitus. Such a conclusion may be modeled in the knowledge graph and the logical structure as "Type 2 diabetes mellitus has symptoms of a blood sugar level of the certain amount and various other symptoms," where "Type 2 diabetes mellitus," "a blood sugar level of the certain amount," and "various other symptoms" are individual elements in the knowledge graph, and "has symptoms of" is a predicate of the logical structure that relates the individual element "Type 2 diabetes mellitus" to the individual elements of "a blood sugar level of the certain amount" and "various other symptoms".

The indicia extracted from the unstructured data may be correlated with one or more closely matching knowledge graphs by comparing similarities between the indicia and the individual elements. Tags related to possible health related information may be generated and associated with the indicia in the unstructured data. For example, the tags may specify "A leads to B" (where A is a health related information and B is another health related information), "B causes C" (where C is yet another health related information), "C has complications of D" (where D is yet another health related information), and so forth. These tags associated with the indicia may be correlated with the logical structure (e.g., predicates of the logical structure) based on structural similarity to generate cognified data. For example, if a person exhibits certain symptoms and has certain laboratory tests performed, then that person may have a certain medical condition (e.g., type 2 diabetes mellitus) that is identified in the knowledge graphs using the logical structures.

A pattern may be detected by identifying structural similarities between the tags and the logical structure in order to generate the cognified data. Cognification may refer to instilling intelligence into something. In the present disclosure, unstructured data may be cognified into cognified data by instilling intelligence into the unstructured data using the knowledge graph and the logical structure. The cognified data may include a summary of a health related condition of a patient, where the summary includes insights, conclusions, recommendations, identified gaps (e.g., in treatment, risk, quality of care, guidelines, etc.), and so forth.

The cognified data may be presented on a computing device of a physician. Instead of reading pages and pages of digital medical charts (EMRs) for a patient, the physician may read the cognified data that presents pointed summarized information that can be utilized to more efficiently and effectively treat the patient. As a result, computing resources may be saved by preventing numerous searches for EMRs and preventing accessing numerous screens displaying the EMRs. In some embodiments, the physician may submit feedback pertaining to whether or not the cognified data is accurate for the patient. The feedback may be used to update the artificial intelligence engine that uses the knowledge graph and logical structure to generate the cognified data.

In some embodiments, the cognified data may be used to diagnose a medical condition of the patient. For example, the medical condition may be diagnosed if a threshold criteria is satisfied. The threshold criteria may include matching a certain number of predicates and tags for a particular medical condition represented by a particular knowledge graph. The computing device of the physician and/or the patient may present the diagnosis and a degree of certainty based on the threshold criteria. In some embodiments, the physician may submit feedback pertaining to whether or not the diagnosis is accurate for the patient. The feedback may be used to update the artificial intelligence engine that uses the knowledge graph and logical structure to generate the diagnosis using the cognified data.

Further, patients may be inundated with information about a particular medical condition with which they are diagnosed and/or inquiring about. The information may not be relevant to a particular stage of the medical condition. The amount of information may waste memory resources of the computing device of the patient. Also, the user may have a bad experience using the computing device due to the overwhelming amount of information.

In some embodiments, user experience of using a computing device may be enhanced by running an application that performs various techniques described herein. The user may be interacting with the cognitive agent and the cognitive agent may be steering the conversation as described herein. In some embodiments, the cognitive agent may provide recommendations based on the text entered by the user, and/or patient notes in EMRs, which may be transformed into cognified data. The application may present health related information, such as the cognified data, pertaining to the medical condition to the computing device of the patient and/or the physician.

Instead of overwhelming the patient with massive amounts of information about the medical condition, the distribution of information may be regulated to the computing device of the patient and/or the physician. For example, if the patient is diagnosed as having type 2 diabetes mellitus, a controlled traversing of the knowledge graph associated with type 2 diabetes mellitus may be performed to provide information to the patient. The traversal may begin at a root node of the knowledge graph and first health related information may be provided to the computing device of the patient at a first time. The first health related information may pertain to a name of the medical condition, a definition of the possible medical condition, or some combination thereof. At a second time, health related information associated with a second node of the knowledge graph may be provided to the computing device of the patient. The second health related information may pertain to how the medical condition affects people, signs and symptoms of the medical condition, a way to treat the medical condition, complications of the medical condition, a progression of the medical condition, or some combination thereof. The health related information associated with the remaining nodes in the knowledge graph may be distributed to the computing device of the patient at different respective times. In some embodiments, the health related information to be provided and/or the times at which the health related information is provided may be selected based on relevancy to a stage of the medical condition of the patient.

In other scenarios, users (also referred to as patients herein) may use various computing devices (e.g., smartphone, tablet, laptop, etc.) to schedule an appointment with a person (also referred to as care providers herein) having a particular specialty to perform a service. For example, a patient may schedule appointments with care providers to provide one or more services to the patient. A patient may call an office where the care provider having a specialty works and speak to a person who finds an available appointment to book for the care provider and the patient. To book an appointment with another care provider having a different specialty, the patient may call the office of the other care provider having the different specialty to book an available appointment. Further, to book an appointment with a care provider for a dependent (e.g., child), the parent/guardian may contact yet another office where a care provider having yet another specialty (e.g., pediatrician) works to book an appointment. In some instances, the patient may access multiple different websites associated with the care providers to attempt to schedule an appointment. This is inconvenient for the patient and wastes resources by making multiple phone calls or accessing multiple different websites. Switching between websites to find contact information for people having different specialties may cause undesirable network, computing, and/or memory usage to occur. Additionally, typical software applications do not include functionality for scheduling appointments for an entire family (e.g., primary, spouse, dependents (children, senior citizens)) covered by an insurance plan, and/or functionality for scheduling multiple appointments for the same patient and/or different patients.

When the patient arrives for the scheduled appointments, the patient typically has to fill out paper check-in documents at each office. Even when the information requested by the check-in documents is redundant, such as medical history information, medication information, etc., various offices still request the same information. Part of the issue is a lack of interoperability of electronic medical records systems. Also, when a computing device is used to complete the check-in documents, the check-in documents are not shared with other systems associated with other specialties, and the user may have to reenter their information using a computing device of another system associated with the other specialties. As such, computing resources of the computing devices may be wasted by running an application to enable entry of information into the check-in documents, instead of just sharing the already completed check-in documents with requesting systems.

Once check-in is complete, the patient may be presented with paper reading materials in a waiting room. The reading materials may include information (e.g., symptoms, causes, treatments, etc.) pertaining to various different medical conditions. It can oftentimes be overwhelming to a patient to be presented with too much information, especially when the information does not pertain to the condition or conditions for which the patient is seeking treatment. Further, even if the patient knows what he or she is looking for, searching for the paper reading material is inefficient. To that end, even if the user finds reading material that discusses a desired topic, there typically is not a guarantee the reading material was authored/reviewed by a person having proper credentials (e.g., a medical doctor). Educating the patient with pertinent curated content that is tailored for the patient is desired.

Accordingly, some embodiments of the present disclosure address the above-identified issues, among other things. For example, an autonomous multipurpose application may execute in a cognitive intelligence platform. In some embodiments, the autonomous multipurpose application may be implemented as one or more application programming interfaces (API) executing via one or more computing devices (e.g., servers), as described in more detail below. The term "autonomous" used in conjunction with the "multipurpose application" may refer to the multipurpose application executing a set of operations on behalf of a person or another application with some degree of independence or autonomy in an intelligent manner using knowledge or representation of a user's goals or desires. The terms "autonomous multipurpose application" and "cognitive agent" may be used interchangeably herein.

In some embodiments, the autonomous multipurpose application may present different user interfaces based on a role associated with a person that logs into the autonomous multipurpose application. The various roles may include a medical personnel (e.g., medical doctor, physician, nurse, dentist, optometrist, psychiatrist, behavioral specialist, physician assistant, and the like), an administrator, a patient/user, and so forth. The user interface presented on a computing device when a person having the medical personnel role is logged in may be referred to as "clinic viewer" herein. The user interface presented on a computing device when a person having the administrator role is logged in may be referred to as "administrator viewer" herein. The user interface presented on a computing device when a person having the patient/user role may be referred to as "patient viewer" herein.

The autonomous multipurpose application may perform numerous operations pertaining to scheduling appointments for patients, checking-in patients for scheduled appointments, educating the patients about medical conditions, and/or searching for content based on search queries, among other things. For scheduling purposes, the autonomous multipurpose application may be communicatively coupled with computing devices of care providers (e.g., medical personnel) and/or electronic medical record (EMR) systems used by the care providers (e.g., medical personnel). These computing devices and/or electronic medical record systems may execute patient management systems or scheduling management systems that maintain schedules of appointments for the care providers. For example, a schedule for a care provider may show which appointments are scheduled or booked and which appointments are available by date and time.

The autonomous multipurpose application may obtain the schedules for people having a desired specialty within a certain geographic location (e.g., within a radius of a geo-location of a computing device of the user, within a radius of an entered address, etc.). A user may elect to enable electronic scheduling. If an available appointment is found within the certain geographic region, and the user is available at the same date and time as the available appointment, the autonomous multipurpose application may electronically schedule the available appointment as a booked appointment. If the user has not enabled electronic scheduling, the autonomous multipurpose application may recommend one or more available appointments to the computing device of the user for presentation.

The autonomous multipurpose application may enable a user to schedule numerous appointments for himself or herself with people having different specialties via a single user interface. For example, the specialties may include a medical doctor (physician), a dentist, an optometrist, a physician's assistant, a chiropractor, a behavioral specialist, a lab technician, a masseuse, a barber, an orthodontist, a dermatologist, and the like. Also, the autonomous multipurpose application may enable the user to schedule appointments for dependents (e.g., children, spouse, senior citizen, etc.) of an insurance plan.

In some embodiments, the autonomous multipurpose application may provide service cost transparency. For example, the autonomous multipurpose application may use the insurance plan information extracted from an insurance card and/or provided by a user to determine what a service may cost. The autonomous multipurpose application may determine a co-pay cost based on the deductible of the insurance plan. The autonomous multipurpose application may determine a self-pay cost without considering the insurance plan. The co-pay cost and the self-pay cost may be presented on the computing device of the user, administrator, or person having a specialty. In some embodiments, if electronic scheduling is enabled, the autonomous multipurpose application may electronically select the cost that is the lowest.

Further, the autonomous multipurpose application may function as a centralized manager and repository for documents pertaining to the user and the dependents of the user. For example, when a user checks-in using a computing device (e.g., kiosk) executing the autonomous multipurpose application at a clinic, check-in documents pertaining to the user stored in a database may be checked to determine whether the check-in documents are complete. The check-in documents may refer to consent forms, medical history documents, health information release authorization forms, new patient sheets, massage client intake forms, mental health intake forms, consent treatment for minor child forms, doctor referral forms, adult health history forms, school physical forms, insurance verification sheets, medical reports, therapy intake forms, initial exam reports, pain assessment sheets, and the like. In some embodiments, the autonomous multipurpose application may communicate with external systems, such as EMR systems, to request the documents for the user from those systems. For example, if the user checked-in for another appointment with a different physician, the user may have already completed the various check-in documents and the autonomous multipurpose application may retrieve those completed check-in documents and store them for future reference. The autonomous multipurpose application may transmit the completed check-in documents to the EMR system associated with the person with which the user has an appointment.

If the check-in documents are partially complete, the autonomous multipurpose application may cause the portions of information that are missing to be presented for completion. If the check-in documents are incomplete, the autonomous multipurpose application may cause the check-in documents to be presented on a computing device for completion by the user, an administrator, a person having a specialty, or the like.

The autonomous multipurpose application may also manage and store other information for the users. For example, the user may capture an image of their driver's license, insurance card, and the like, and transmit the image to the autonomous multipurpose application. The autonomous multipurpose application may analyze the image (e.g., using machine learning and/or optical character recognition) to extract information from the image. For example, the autonomous multipurpose application may extract a picture of the user from a driver's license, a name of the user, a birthdate of the user, an address of the user, an identification number, an insurance plan number, a type of insurance, an expiration date of the user's driver's license, an expiration date of the user's insurance plan, and the like. The autonomous multipurpose application may electronically fill information in corresponding documents based on the extracted information. Further, the autonomous multipurpose application may perform logic based on the extracted information. For example, if the user's insurance is about to expire, the autonomous multipurpose application may transmit a message (e.g., email, text message, phone call, onscreen notification, etc.) to the user to renew their insurance. Similar types of information may be managed and stored for each person in a family. The information may be disbursed to a requesting client, such as an EMR system used by an entity at which the users make appointments.

The autonomous multipurpose application may communicate with a knowledge cloud that includes knowledge graphs that each pertain to a respective medical condition. For example, each knowledge graph may include individual elements (e.g., health artifacts) and predicates that describe relationships between the individual elements in a logical structure. Each knowledge graph may include nodes representing the individual elements and branches representing the predicates that connect the nodes. Each knowledge graph may begin at a root node that includes a type or name of the medical condition, for example. One knowledge graph may include a root node representing "Diabetes". A predicate may represent "is caused by" branch that connects to another node "high blood sugar". The logical structure may be formulated as "Diabetes is caused by high blood sugar".

When a user successfully checks-in for a scheduled appointment, the autonomous multipurpose application may access the knowledge cloud to obtain curated content pertaining to one or more conditions of the user. For example, the user may specify the condition for which the user is seeking treatment, and educational curated content about that condition may be recommended and/or provided to the computing device of the user. The autonomous multipurpose application may also recommend other curated content to the user for the medical conditions of the user that are known by the autonomous multipurpose application. Each time a user has an appointment, the autonomous multipurpose application may update information pertaining to the user to keep knowledge about the user up to date.

In addition, when the user is checked-in, a wait time estimator model may be used by the autonomous multipurpose application to provide an estimated wait time. For example, the wait time estimator may be a machine learning model that is trained using data representing an average amount of time it takes a person having a specialty to perform a service. The training data may be specific for each different person and the amount of time it takes that person to perform the service. The wait time estimator may use training data pertaining to each patient. For example, if John Smith is at an appointment in the doctor's office immediately before Jane Doe, the average time that John Smith stays in the office may be used to estimate the wait time for Jane Doe. The wait times from different offices and/or clinics may be aggregated for each specialty in that office and/or for each person having the specialties to perform the service associated with the specialties.

Various timestamps associated with interactions between the user and the person having the specialty may be obtained from a system (e.g., EMR) used by the person having the specialty. For example, a timestamp of when the user checked-in for a scheduled appointment may be obtained, a timestamp of how long it took for the user to be called back to the doctor's office may be obtained, a timestamp of how long the user waited in the doctor's office prior to the doctor entering, a timestamp of any patient notes made by the doctor, a timestamp of any patient notes made by a nurse, a timestamp of when the doctor leaves after performing a service, a timestamp of when the user pays, or some combination thereof. The timestamps may be used to estimate wait times for users that have appointments scheduled with that doctor.

The autonomous multipurpose application may provide natural language searching for content. For example, the user may search "information about Diabetes" and the autonomous multipurpose application may return curated content pertaining to Diabetes to the computing device of the user.

The disclosed autonomous multipurpose application may provide an enhanced experience for users by improving scheduling, check-in, wait time estimation, cost transparency, and/or content distribution, among other things. The autonomous multipurpose application may use artificial intelligence to make decisions and perform actions.

In addition, the cognitive intelligence platform may use a knowledge graph pertaining to a condition of a user and a data structure (e.g., a patient graph) corresponding to the condition and the user to electronically generate a care plan for the condition of the user. The patient graph may include elements (e.g., health artifacts) and branches representing relationships between the elements. The elements may be represented as nodes in the patient graph. The elements may represent interactions and/or actions the user has had and/or performed pertaining to the condition. For example, if the condition is diabetes and the user has already performed a blood glucose test, then the user may have a patient graph corresponding to diabetes that includes an element for the blood glucose test. The element may include one or more associated information, such as a timestamp of when the blood glucose test was taken, if it was performed at-home or at a care provider, a result of the blood glucose test, and so forth.

The autonomous multipurpose application may cause the patient viewer to be presented on the computing device of the user, and the patient viewer may present the various conditions of the user. Further, the patient viewer may ask the user to specify a number of areas of the condition the user would like to manage, and to select which areas of the condition the user would like to manage.

The patient graph for the condition of the user may be compared (e.g., projected on) to the knowledge graph for the condition of the user to generate a care plan. The cognitive intelligence platform may generate the care plan based on the areas of the condition the user specified to manage, based on areas of the condition on which the user has not taken action and/or interacted with in view of the knowledge graph and patient graph, based on a detected emotion of the user, based on a detected tone of the user, based on a medical outcome selected by a medical personnel, or some combination thereof. For example, the cognitive intelligence platform may determine that the user currently is prescribed medication A for diabetes based on the user's patient graph for diabetes, but medication A is ineffective for the user. The cognitive intelligence platform may compare the patient graph to the knowledge graph pertaining to diabetes to determine that medication B can be prescribed to treat diabetes for the user. The care plan may include an action instruction that instructs the medical personnel to prescribe medication B and/or discuss information pertaining to medication A and/or medication B. The care plan may be transmitted to the user device for presentation in the patient viewer, the clinic viewer, and/or the administrator viewer.

The patient graph for each condition may also include an engagement profile that may be used to determine a compliance of the user with the care plan. The engagement profile may store information at a meta data level that corresponds to the actions and/or interactions the user performs pertaining to the care plan for the condition. In some embodiments, activity of the user on the computing device may be tracked; medical records may be obtained from EMR systems, claims systems, clinical systems, and the like; and so forth. For example, if the care plan recommends the user read a certain article pertaining to diabetes, and the user selects the article, the engagement profile may store information related to the user selecting the article, how long the user read the article, if the user finished the article, and so forth. Further, if the medical records indicate the user had a blood glucose test performed, the engagement profile may store information pertaining to the blood glucose test being performed.

The patient graph for the diabetes of the user may be updated based on the information stored in the engagement profile. For example, if information in the engagement profile indicates the user completes performance of a blood glucose test, an element pertaining to the blood glucose test may be added to a section of the patient graph of the user corresponding to diabetes. In some embodiments, certain conditions may specify the same elements as each other. For example, two conditions may include knowledge graphs that both include elements for testing for the condition using a blood glucose test. If the patient performs the blood glucose test for one of the conditions, the patient graphs for both conditions may be updated to include the information for the blood glucose test at the appropriate elements. As a result, if a knowledge graph for one condition includes an element for a test, and the user has already performed the test for another condition, as represented in the patient graph for the other condition, the cognitive intelligence platform may not include an action instruction to perform the test in the care plan for the user for the one condition. In this way, the care plans may be not include redundant data and/or action instructions.

In some embodiments, the patient graph may represent a checklist of items (e.g., elements, actions, interactions, content, etc.) pertaining to the condition that the user performed. The knowledge graph may represent a superset of items pertaining to the condition, and if the user complies with the superset of items (e.g., completes a care plan for a condition), the user may be managing the condition in a desired manner (e.g., the user is taking medications on a specified basis, the values of certain tests for the user are within a desired range, the user has been informed by the recommended content, etc.). The compliance with the care plan may be determined based on the engagement profile and/or the patient graph.

In some embodiments, the patient graph for a condition may be compared (e.g., projected on) to the knowledge graph for the condition, and if the patient graph includes each element of the knowledge graph, then a determination may be made that the user is managing the condition in a desired manner. In some embodiments, a notification may be presented on the patient viewer, the clinic viewer, and/or the administrator viewer indicating the same. If some of the elements of the knowledge graph are missing in the patient graph, the cognitive intelligence platform may provide a care plan including action instructions pertaining to those missing elements. Based on the engagement profile, if certain elements are partially completed, performed, and/or interacted with, the cognitive intelligence platform may provide a care plan including action instructions pertaining to those partially completed, performed, and/or interact with elements.

In some embodiments, an emotion of the user, a tone of the user, and/or a medical outcome desired by a medical personnel may be used to modify the care plan presented to the user. For example, data (e.g., video, image, text, etc.) may be received by the cognitive intelligence platform from a computing device of the user while the user is interacting with the patient viewer and/or interacting with the computing device of the user. The cognitive intelligence platform may perform certain emotion detecting and/or tone detecting techniques using the data. For example, facial recognition techniques may be performed to determine an emotion the user is experiencing. Such a determination may be made in response to the care plan presented to the user, content presented to the user, responses provided by the cognitive intelligence platform, or the like. Further, a tone and/or emotion of the user may be determined using text input by the user while interacting with the patient viewer and/or interacting with the computing device of the user. In addition, the cognitive intelligence platform may receive a desired medical outcome input by a medical personnel using the clinic viewer.

The cognitive intelligence platform may modify the care plan based on the detected emotion, detected tone, and/or the desired medical outcome. The modified care plan may be presented in the patient viewer, the clinic viewer, and/or the administrator viewer.

In some embodiments, a clinic viewer may be generated and/or presented by the cognitive intelligence platform on a computing device of a care provider (e.g., medical personnel). The clinic viewer may display a reason that a patient scheduled an appointment. The clinic viewer may display a condition with which a patient has been diagnosed. The clinic viewer may display a care plan for the patient. The clinic viewer may display a recommendation to prescribe a certain dosage of a certain medication to the patient based on the patient's condition and vital statistics. The clinic viewer may display a recommended action for medical personnel to take when the patient visits. The clinic viewer may display information about current medication that the patient is taking. The clinic viewer may display a notification that medication that a patient is currently taking is incompatible with another medication that relates to the condition of the patient. The clinic viewer may display a recommendation that the medical personnel perform a service for the patient. The clinic viewer may display a quality of care recommendation and an evidence trail that explains why the quality of care recommendation was made. The clinic viewer may display curated content, such as medical journal articles, related to the patient's condition. The clinic viewer may display a user interface in which the medical personnel can update information about the clinic. The clinic viewer may display current and prior information about the patient. The clinic viewer may display a knowledge graph about the patient's condition and a patient graph specific for the patient having the condition. The clinic viewer may allow medical personnel to input medical information about the patient. The clinic viewer may be configured to allow medical personnel to schedule a future appointment with the patient. The clinic viewer may be configured to allow medical personnel to send a prescription for the patient to a pharmacy. The clinic viewer may be configured to allow medical personnel to schedule an appointment for the patient at another medical provider.

The described methods and systems are described as occurring in the healthcare space, though other areas are also contemplated, such as finance, career, etc.

FIG. 1 shows a system architecture 100 that can be configured to provide a population health management service, in accordance with various embodiments. Specifically, FIG. 1 illustrates a high-level overview of an overall architecture that includes a cognitive intelligence platform 102 communicably coupled to a user device 104. The cognitive intelligence platform 102 includes several computing devices, where each computing device, respectively, includes at least one processor, at least one memory, and at least one storage (e.g., a hard drive, a solid-state storage device, a mass storage device, and a remote storage device). The individual computing devices can represent any form of a computing device such as a desktop computing device, a rack-mounted computing device, and a server device. The foregoing example computing devices are not meant to be limiting. On the contrary, individual computing devices implementing the cognitive intelligence platform 102 can represent any form of computing device without departing from the scope of this disclosure.

The several computing devices work in conjunction to implement components of the cognitive intelligence platform 102 including: a knowledge cloud 106; a critical thinking engine 108; a natural language database 122; and a cognitive agent 110. The cognitive intelligence platform 102 is not limited to implementing only these components, or in the manner described in FIG. 1. That is, other system architectures can be implemented, with different or additional components, without departing from the scope of this disclosure. The example system architecture 100 illustrates one way to implement the methods and techniques described herein.

The knowledge cloud 106 represents a set of instructions executing within the cognitive intelligence platform 102 that implement a database configured to receive inputs from several sources and entities. For example, some of the sources and entities include a service provider 112, a facility 114, and a microsurvey 116—each described further below.

The critical thinking engine 108 represents a set of instructions executing within the cognitive intelligence platform 102 that execute tasks using artificial intelligence, such as recognizing and interpreting natural language (e.g., performing conversational analysis), and making decisions in a linear manner (e.g., in a manner similar to how the human left brain processes information). Specifically, an ability of the cognitive intelligence platform 102 to understand natural language is powered by the critical thinking engine 108. In various embodiments, the critical thinking engine 108 includes a natural language database 122. The natural language database 122 includes data curated over at least thirty years by linguists and computer data scientists, including data related to speech patterns, speech equivalents, and algorithms directed to parsing sentence structure.

Furthermore, the critical thinking engine 108 is configured to deduce causal relationships given a particular set of data, where the critical thinking engine 108 is capable of taking the individual data in the particular set, arranging the individual data in a logical order, deducing a causal relationship between each of the data, and drawing a conclusion. The ability to deduce a causal relationship and draw a conclusion (referred to herein as a "causal" analysis) is in direct contrast to other implementations of artificial intelligence that mimic the human left brain processes. For example, the other implementations can take the individual data and analyze the data to deduce properties of the data or statistics associated with the data (referred to herein as an "analytical" analysis). However, these other implementations are unable to perform a causal analysis—that is, deduce a causal relationship and draw a conclusion from the particular set of data. As described further below—the critical thinking engine 108 is capable of performing both types of analysis: causal and analytical.

In some embodiments, the critical thinking engine 108 includes an artificial intelligence engine 109 ("AI Engine" in FIG. 1) that uses one or more machine learning models. The one or more machine learning models may be generated by a training engine and may be implemented in computer instructions that are executable by one or more processing device of the training engine, the artificial intelligence engine 109, another server, and/or the user device 104. To generate the one or more machine learning models, the training engine may train, test, and validate the one or more machine learning models. The training engine may be a rackmount server, a router computer, a personal computer, a portable digital assistant, a smartphone, a laptop computer, a tablet computer, a camera, a video camera, a netbook, a desktop computer, a media center, or any combination of the above. The one or more machine learning models may refer to model artifacts that are created by the training engine using training data that includes training inputs and corresponding target outputs. The training engine may find patterns in the training data that map the training input to the target output, and generate the machine learning models that capture these patterns.

The one or more machine learning models may be trained to generate one or more knowledge graphs each pertaining to a particular medical condition. The knowledge graphs may include individual elements (nodes) that are linked via predicates of a logical structure. The logical structure may use any suitable order of logic (e.g., higher order logic and/or Nth order logic). Higher order logic may be used to admit quantification over sets that are nested arbitrarily deep. Higher order logic may refer to a union of first-, second-, third-, . . . , Nth order logic. Clinical-based evidence, clinical trials, physician research, and the like that includes various information (e.g., knowledge) pertaining to different medical conditions may be input as training data to the one or more machine learning models. The information may pertain to facts, properties, attributes, concepts, conclusions, risks, correlations, complications, etc. of the medical conditions. Keywords, phrases, sentences, cardinals, numbers, values, objectives, nouns, verbs, concepts, and so forth may be specified (e.g., labeled) in the information such that the machine learning models learn which ones are associated with the medical conditions. The information may specify predicates that correlates the information in a logical structure such that the machine learning models learn the logical structure associated with the medical conditions.

In some embodiments, the one or more machine learning models may be trained to transform input unstructured data (e.g., patient notes) into cognified data using the knowledge graph and the logical structure. The machine learning models may identify indicia in the unstructured data and compare the indicia to the knowledge graphs to generate possible health related information (e.g., tags) pertaining to the patient. The possible health related information may be associated with the indicia in the unstructured data. The one or more machine learning models may also identify, using the logical structure, a structural similarity of the possible health related information and a known predicate in the logical structure. The structural similarity between the possible health related information and the known predicate may enable identifying a pattern (e.g., treatment patterns, education and content patterns, order patterns, referral patterns, quality of care patterns, risk adjustment patterns, etc.). The one or more machine learning models may generate the cognified data based on the structural similarity and/or the pattern identified. Accordingly, the machine learning models may use a combination of knowledge graphs, logical structures, structural similarity comparison mechanisms, and/or pattern recognition to generate the cognified data. The cognified data may be output by the one or more trained machine learning models.

The cognified data may provide a summary of the medical condition of the patient. A diagnosis of the patient may be generated based on the cognified data. The summary of the medical condition may include one or more insights not present in the unstructured data. The summary may identify gaps in the unstructured data, such as treatment gaps (e.g., should prescribe medication, should provide different medication, should change dosage of medication, etc.), risk gaps (e.g., the patient is at risk for cancer based on familial history and certain lifestyle behaviors), quality of care gaps (e.g., need to check-in with the patient more frequently), and so forth. The summary of the medical condition may include one or more conclusions, recommendations, complications, risks, statements, causes, symptoms, etc. pertaining to the medical condition. In some embodiments, the summary of the medical condition may indicate another medical condition that the medical condition can lead to. Accordingly, the cognified data represents intelligence, knowledge, and logic cognified from unstructured data.

In some embodiments, the cognified data may be reviewed by physicians and the physicians may provide feedback pertaining to whether or not the cognified data is accurate. Also, the physicians may provide feedback pertaining to whether or not the diagnosis generated using the cognified data is accurate. This feedback may be used to update the one or more machine learning models to improve their accuracy.

The AI engine 109 may include machine learning models that are trained to schedule appointments for users, recommend appointments to users, determine costs of services, manage documents for users, extract data from images, provide curated content tailored for users, estimate wait times, perform natural language searching of curated content, and so forth.

The cognitive agent 110 represents a set of instructions executing within the cognitive intelligence platform 102 that implement a client-facing component of the cognitive intelligence platform 102. The cognitive agent 110 may be referred to as the autonomous multipurpose application interchangeably herein. The cognitive agent 110 is an interface between the cognitive intelligence platform 102 and the user device 104. And in some embodiments, the cognitive agent 110 includes a conversation orchestrator 124 that determines pieces of communication that are presented to the user device 104 (and the user). When a user of the user device 104 interacts with the cognitive intelligence platform 102, the user interacts with the cognitive agent 110. In some embodiments, the user of the user device 104 may be a patient. The several references herein, to the cognitive agent 110 performing a method, can implicate actions performed by the critical thinking engine 108, which accesses data in the knowledge cloud 106 and the natural language database 122.

Various user interfaces may be provided to computing devices communicating with the cognitive agent 110 executing in the cognitive intelligence platform 102. The user interfaces may be presented in a standalone application executing on the devices or in a web browser as website pages. In some embodiments, the cognitive agent 110 may be installed on a device of the user, the service provider 112, and/or the facility 114. In some embodiments, the devices of the user, the service provider 112, and/or the facility 114 may communicate with cognitive intelligence platform 102 in a client-server architecture. In some embodiments, the cognitive agent 110 may be implemented as computer instructions as an application programming interface.

In various embodiments, the several computing devices executing within the cognitive intelligence platform are communicably coupled by way of a network/bus interface. Furthermore, the various components (e.g., the knowledge cloud 106, the critical thinking engine 108, and the cognitive agent 110), are communicably coupled by one or more inter-host communication protocols 118. In one example, the knowledge cloud 106 is implemented using a first computing device, the critical thinking engine 108 is implemented using a second computing device, and the cognitive agent 110 is implemented using a third computing device, where each of the computing devices are coupled by way of the inter-host communication protocol 118. Although in this example, the individual components are described as executing on separate computing devices this example is not meant to be limiting, the components can be implemented on the same computing device, or partially on the same computing device, without departing from the scope of this disclosure.

The user device 104 represents any form of a computing device, or network of computing devices, e.g., a personal computing device, a smart phone, a tablet, a wearable computing device, a notebook computer, a media player device, and a desktop computing device. The user device 104 includes a processor, at least one memory, and at least one storage. A user uses the user device 104 to input a given text posed in natural language (e.g., typed on a physical keyboard, spoken into a microphone, typed on a touch screen, or combinations thereof) and interacts with the cognitive intelligence platform 102, by way of the cognitive agent 110.

The architecture 100 includes a network 120 that communicatively couples various devices, including the cognitive intelligence platform 102 and the user device 104. The network 120 can include local area network (LAN) and wide area networks (WAN). The network 102 can include wired technologies (e.g., Ethernet®) and wireless technologies (e.g., Wi-Fi®, code division multiple access (CDMA), global system for mobile (GSM), universal mobile telephone service (UMTS), Bluetooth®, and ZigBee®. For example, the user device 104 can use a wired connection or a wireless technology (e.g., Wi-Fi®) to transmit and receive data over the network 120.

Still referring to FIG. 1, the knowledge cloud 106 is configured to receive data from various sources and entities and integrate the data in a database. An example source that provides data to the knowledge could 106 is the service provider 112, an entity that provides a type of service to a user. For example, the service provider 112 can be a health service provider (e.g., a doctor's office, a physical therapist's office, a nurse's office, or a clinical social worker's office), and a financial service provider (e.g., an accountant's office). For purposes of this discussion, the cognitive intelligence platform 102 provides services in the health industry, thus the examples discussed herein are associated with the health industry. However, any service industry can benefit from the disclosure herein, and thus the examples associated with the health industry are not meant to be limiting.

Throughout the course of a relationship between the service provider 112 and a user (e.g., the service provider 112 provides healthcare to a patient), the service provider 112 collects and generates data associated with the patient or the user, including health records that include doctor's notes about the patient and prescriptions, billing records, and insurance records. The service provider 112, using a computing device (e.g., a desktop computer or a tablet), provides the data associated with the user to the cognitive intelligence platform 102, and more specifically the knowledge cloud 106.

Another example source that provides data to the knowledge cloud 106 is the facility 114. The facility 114 represents a location owned, operated, or associated with any entity including the service provider 112. As used herein, an entity represents an individual or a collective with a distinct and independent existence. An entity can be legally recognized (e.g., a sole proprietorship, a partnership, a corporation) or less formally recognized in a community. For example, the entity can include a company that owns or operates a gym (facility). Additional examples of the facility 114 include, but is not limited to, a hospital, a trauma center, a clinic, a dentist's office, a pharmacy, a store (including brick and mortar stores and online retailers), an out-patient care center, a specialized care center, a birthing center, a gym, a cafeteria, and a psychiatric care center.

As the facility 114 represents a large number of types of locations, for purposes of this discussion and to orient the reader by way of example, the facility 114 represents the doctor's office or a gym. The facility 114 generates additional data associated with the user such as appointment times, an attendance record (e.g., how often the user goes to the gym), a medical record, a billing record, a purchase record, an order history, and an insurance record. The facility 114, using a computing device (e.g., a desktop computer or a tablet), provides the data associated with the user to the cognitive intelligence platform 102, and more specifically the knowledge cloud 106.

An additional example source that provides data to the knowledge cloud 106 is the microsurvey 116. The microsurvey 116 represents a tool created by the cognitive intelligence platform 102 that enables the knowledge cloud 106 to collect additional data associated with the user. The microsurvey 116 is originally provided by the cognitive intelligence platform 102 (by way of the cognitive agent 110) and the user provides data responsive to the microsurvey 116 using the user device 104. Additional details of the microsurvey 116 are described below.

Yet another example source that provides data to the knowledge cloud 106, is the cognitive intelligence platform 102, itself. In order to address the care needs and well-being of the user, the cognitive intelligence platform 102 collects, analyzes, and processes information from the user, healthcare providers, and other eco-system participants, and consolidates and integrates the information into knowledge. For example, clinical-based evidence and guidelines may be obtained by the cognitive intelligence platform 102 and used as knowledge. The knowledge can be shared with the user and stored in the knowledge cloud 106.

In various embodiments, the computing devices used by the service provider 112 and the facility 114 are communicatively coupled to the cognitive intelligence platform 102, by way of the network 120. While data is used individually by various entities including: a hospital, practice group, facility, or provider, the data is less frequently integrated and seamlessly shared between the various entities in the current art. The cognitive intelligence platform 102 provides a solution that integrates data from the various entities. That is, the cognitive intelligence platform 102 ingests, processes, and disseminates data and knowledge in an accessible fashion, where the reason for a particular answer or dissemination of data is accessible by a user.

In particular, the cognitive intelligence platform 102 (e.g., by way of the cognitive agent 110 interacting with the user) holistically manages and executes a health plan for durational care and wellness of the user (e.g., a patient or consumer). The health plan includes various aspects of durational management that is coordinated through a care continuum.

The cognitive agent 110 can implement various personas that are customizable. For example, the personas can include knowledgeable (sage), advocate (coach), and witty friend (jester). And in various embodiments, the cognitive agent 110 persists with a user across various interactions (e.g., conversations streams), instead of being transactional or transient. Thus, the cognitive agent 110 engages in dynamic conversations with the user, where the cognitive intelligence platform 102 continuously deciphers topics that a user wants to talk about. The cognitive intelligence platform 102 has relevant conversations with the user by ascertaining topics of interest from a given text posed in a natural language input by the user. Additionally the cognitive agent 110 connects the user to healthcare service providers, hyperlocal health communities, and a variety of services and tools/devices, based on an assessed interest of the user.

As the cognitive agent 110 persists with the user, the cognitive agent 110 can also act as a coach and advocate while delivering pieces of information to the user based on tonal knowledge, human-like empathies, and motivational dialog within a respective conversational stream, where the conversational stream is a technical discussion focused on a specific topic. Overall, in response to a question—e.g., posed by the user in natural language—the cognitive intelligence platform 102 consumes data from and related to the user and computes an answer. The answer is generated using a rationale that makes use of common sense knowledge, domain knowledge, evidence-based medicine guidelines, clinical ontologies, and curated medical advice. Thus, the content displayed by the cognitive intelligence platform 102

(by way of the cognitive agent 110) is customized based on the language used to communicate with the user, as well as factors such as a tone, goal, and depth of topic to be discussed.

Overall, the cognitive intelligence platform 102 is accessible to a user, a hospital system, and physician. Additionally, the cognitive intelligence platform 102 is accessible to paying entities interested in user behavior—e.g., the outcome of physician-consumer interactions in the context of disease or the progress of risk management. Additionally, entities that provides specialized services such as tests, therapies, and clinical processes that need risk based interactions can also receive filtered leads from the cognitive intelligence platform 102 for potential clients.

Conversational Analysis

In various embodiments, the cognitive intelligence platform 102 is configured to perform conversational analysis in a general setting. The topics covered in the general setting is driven by the combination of agents (e.g., cognitive agent 110) selected by a user. In some embodiments, the cognitive intelligence platform 102 uses conversational analysis to identify the intent of the user (e.g., find data, ask a question, search for facts, find references, and find products) and a respective micro-theory in which the intent is logical.

For example, the cognitive intelligence platform 102 applies conversational analysis to decode what the user is asking or stated, where the question or statement is in free form language (e.g., natural language). Prior to determining and sharing knowledge (e.g., with the user or the knowledge cloud 106), using conversational analysis, the cognitive intelligence platform 102 identifies an intent of the user and overall conversational focus.

The cognitive intelligence platform 102 responds to a statement or question according to the conversational focus and steers away from another detected conversational focus so as to focus on a goal defined by the cognitive agent 110. Given an example statement of a user, "I want to fly out tomorrow," the cognitive intelligence platform 102 uses conversational analysis to determine an intent of the statement. Is the user aspiring to be bird-like or does he want to travel? In the former case, the micro-theory is that of human emotions whereas in the latter case, the micro-theory is the world of travel. Answers are provided to the statement depending on the micro-theory in which the intent logically falls.

The cognitive intelligence platform 102 utilize a combination of linguistics, artificial intelligence, and decision trees to decode what a user is asking or stating. The discussion includes methods and system design considerations and results from an existing embodiment. Additional details related to conversational analysis are discussed next.

Analyzing Conversational Context as Part of Conversational Analysis

For purposes of this discussion, the concept of analyzing conversational context as part of conversational analysis is now described. To analyze conversational context, the following steps are taken: 1) obtain text (e.g., receive a question) and perform translations; 2) understand concepts, entities, intents, and micro-theory; 3) relate and search; 4) ascertain the existence of related concepts; 5) logically frame concepts or needs; 6) understand the questions that can be answered from available data; and 7) answer the question. Each of the foregoing steps is discussed next, in turn.

Step 1: Obtain Text/Question and Perform Translations

In various embodiments, the cognitive intelligence platform 102 (FIG. 1) receives a text or question and performs translations as appropriate. The cognitive intelligence platform 102 supports various methods of input including text received from a touch interface (e.g., options presented in a microsurvey), text input through a microphone (e.g., words spoken into the user device), and text typed on a keyboard or on a graphical user interface. Additionally, the cognitive intelligence platform 102 supports multiple languages and auto translation (e.g., from English to Traditional/Simplified Chinese or vice versa).

The example text below is used to described methods in accordance with various embodiments herein:

"One day in January 1913. G. H. Hardy, a famous Cambridge University mathematician received a letter from an Indian named Srinivasa Ramanujan asking him for his opinion of 120 mathematical theorems that Ramanujan said he had discovered. To Hardy, many of the theorems made no sense. Of the others, one or two were already well-known. Ramanujan must be some kind of trickplayer, Hardy decided, and put the letter aside.

But all that day the letter kept hanging round Hardy. Might there by something in those wild-looking theorems?

That evening Hardy invited another brilliant Cambridge mathematician, J. E. Littlewood, and the two men set out to assess the Indian's worth. That incident was a turning point in the history of mathematics.

At the time, Ramanujan was an obscure Madras Port Trust clerk. A little more than a year later, he was at Cambridge University, and beginning to be recognized as one of the most amazing mathematicians the world has ever known. Though he died in 1920, much of his work was so far in advance of his time that only in recent years is it beginning to be properly understood.

Indeed, his results are helping solve today's problems in computer science and physics, problems that he could have had no notion of.

For Indians, moreover, Ramanujan has a special significance. Ramanujan, through born in poor and ill-paid accountant's family 100 years ago, has inspired many Indians to adopt mathematics as career.

Much of Ramanujan's work is in number theory, a branch of mathematics that deals with the subtle laws and relationships that govern numbers.

Mathematicians describe his results as elegant and beautiful but they are much too complex to be appreciated by laymen.

His life, though, is full of drama and sorrow. It is one of the great romantic stories of mathematics, a distressing reminder that genius can surface and rise in the most unpromising circumstances."

The cognitive intelligence platform 102 analyzes the example text above to detect structural elements within the example text (e.g., paragraphs, sentences, and phrases). In some embodiments, the example text is compared to other sources of text such as dictionaries, and other general fact databases (e.g., Wikipedia) to detect synonyms and common phrases present within the example text.

Step 2: Understand Concept, Entity, Intent, and Micro-Theory

In step 2, the cognitive intelligence platform 102 parses the text to ascertain concepts, entities, intents, and micro-theories. An example output after the cognitive intelligence platform 102 initially parses the text is shown below, where concepts, and entities are shown in bold.

"One day in January 1913. G. H. Hardy, a famous Cambridge University mathematician received a letter from an Indian named Srinivasa Ramanujan asking him for his opinion of 120 mathematical theorems that Ramanujan said he had discovered. To Hardy, many of the theorems made no sense. Of the others, one or two were already well-known.

Ramanujan must be some kind of trickplayer, Hardy decided, and put the letter aside. But all that day the letter kept hanging round Hardy. Might there by something in those wild-looking theorems?

That evening Hardy invited another brilliant Cambridge mathematician, J. E. Littlewood, and the two men set out to assess the Indian's worth.

That incident was a turning point in the history of mathematics.

At the time, Ramanujan was an obscure Madras Port Trust clerk. A little more than a year later, he was at Cambridge University, and beginning to be recognized as one of the most amazing mathematicians the world has ever known. Though he died in 1920, much of his work was so far in advance of his time that only in recent years is it beginning to be properly understood.

Indeed, his results are helping solve today's problems in computer science and physics, problems that he could have had no notion of.

For Indians, moreover, Ramanujan has a special significance.

Ramanujan, through born in poor and ill-paid accountant's family 100 years ago, has inspired many Indians to adopt mathematics as career.

Much of Ramanujan's work is in number theory, a branch of mathematics that deals with the subtle laws and relationships that govern numbers.

Mathematicians describe his results as elegant and beautiful but they are much too complex to be appreciated by laymen.

His life, though, is full of drama and sorrow. It is one of the great romantic stories of mathematics, a distressing reminder that genius can surface and rise in the most unpromising circumstances."

For example, the cognitive intelligence platform 102 ascertains that Cambridge is a university—which is a full understanding of the concept. The cognitive intelligence platform (e.g., the cognitive agent 110) understands what humans do in Cambridge, and an example is described below in which the cognitive intelligence platform 102 performs steps to understand a concept.

For example, in the context of the above example, the cognitive agent 110 understands the following concepts and relationships:

| | |
|---|---|
| Cambridge employed John Edensor Littlewood | (1) |
| Cambridge has the position Ramanujan's position at Cambridge University | (2) |
| Cambridge employed G. H. Hardy. | (3) |

The cognitive agent 110 also assimilates other understandings to enhance the concepts, such as:

| | |
|---|---|
| Cambridge has Trinity College as a suborganization. | (4) |
| Cambride is located in Cambridge. | (5) |
| Alan Turing is previously enrolled at Cambridge. | (6) |
| Stephen Hawking attended Cambridge. | (7) |

The statements (1)-(7) are not picked at random. Instead the cognitive agent 110 dynamically constructs the statements (1)-(7) from logic or logical inferences based on the example text above. Formally, the example statements (1)-(7) are captured as follows:

| | |
|---|---|
| (#$subOrganizations #$UniversityOfCambridge #$TrinityCollege-Cambridge-England) | (8) |
| (#$placeInCity #$UniversityOfCambridge #$Cityof CambridgeEngland) | (9) |
| (#$schooling #$AlanTuring #$UniversityOfCambridge #$PreviouslyEnrolled) | (10) |
| (#$hasAlumni #$UniversityOfCambridge #$StephenHawking) | (11) |

Step 3: Relate and Search

Next, in step 3, the cognitive agent 110 relates various entities and topics and follows the progression of topics in the example text. Relating includes the cognitive agent 110 understanding the different instances of Hardy are all the same person, and the instances of Hardy are different from the instances of Littlewood. The cognitive agent 110 also understands that the instances Hardy and Littlewood share some similarities—e.g., both are mathematicians and they did some work together at Cambridge on Number Theory. The ability to track this across the example text is referred to as following the topic progression with a context.

Step 4: Ascertain the Existence of Related Concepts

Next, in Step 4, the cognitive agent 110 asserts non-existent concepts or relations to form new knowledge. Step 4 is an optional step for analyzing conversational context. Step 4 enhances the degree to which relationships are understood or different parts of the example text are understood together. If two concepts appear to be separate—e.g., a relationship cannot be graphically drawn or logically expressed between enough sets of concepts—there is a barrier to understanding. The barriers are overcome by expressing additional relationships. The additional relationships can be discovered using strategies like adding common sense or general knowledge sources (e.g., using the common sense data 208) or adding in other sources including a lexical variant database, a dictionary, and a thesaurus.

One example of concept progression from the example text is as follows: the cognitive agent 110 ascertains the phrase "theorems that Ramanujan said he had discovered" is related to the phrase "his results", which is related to "Ramanujan's work is in number theory, a branch of mathematics that deals with the subtle laws and relationships that govern numbers."

Step 5: Logically Frame Concepts or Needs

In Step 5, the cognitive agent 110 determines missing parameters—which can include for example, missing entities, missing elements, and missing nodes—in the logical framework (e.g., with a respective micro-theory). The cognitive agent 110 determines sources of data that can inform the missing parameters. Step 5 can also include the cognitive agent 110 adding common sense reasoning and finding logical paths to solutions.

With regards to the example text, some common sense concepts include:

| | |
|---|---|
| Mathematicians develop Theorems. | (12) |
| Theorems are hard to comprehend. | (13) |
| Interpretations are not apparent for years. | (14) |
| Applications are developed over time. | (15) |
| Mathematicians collaborate and assess work. | (16) |

With regards to the example text, some passage concepts include:

| | |
|---|---|
| Ramanujan did Theorems in Early 20$^{th}$ Century. | (17) |
| Hardy assessed Ramanujan's Theorems. | (18) |
| Hardy collaborated with Littlewood. | (19) |
| Hardy and Littlewood assessed Ramanujan's work | (20) |

Within the micro-theory of the passage analysis, the cognitive agent 110 understands and catalogs available paths to answer questions. In Step 5, the cognitive agent 110 makes the case that the concepts (12)-(20) are expressed together.

Step 6: Understand the Questions that can be Answered from Available Data

In Step 6, the cognitive agent 110 parses sub-intents and entities. Given the example text, the following questions are answerable from the cognitive agent's developed understanding of the example text, where the understanding was developed using information and context ascertained from the example text as well as the common sense data 208 (FIG. 2):

| | |
|---|---|
| What situation causally contributed to Ramanujan's position at Cambridge? | (21) |
| Does the author of the passage regret that Ramanujan died prematurely? | (22) |
| Does the author of the passage believe that Ramanujan is a mathematical genius? | (23) |

Based on the information that is understood by the cognitive agent 110, the questions (21)-(23) can be answered.

By using an exploration method such as random walks, the cognitive agent 110 makes a determination as the paths that are plausible and reachable with the context (e.g., micro-theory) of the example text. Upon explorations, the cognitive agent 110 catalogs a set of meaningful questions. The set of meaningful questions are not asked, but instead explored based on the cognitive agent's understanding of the example text.

Given the example text, an example of exploration that yields a positive result is: "a situation X that caused Ramanujan's position." In contrast, an example of exploration that causes irrelevant results is: "a situation Y that caused Cambridge." The cognitive agent 110 is able to deduce that the latter exploration is meaningless, in the context of a micro-theory, because situations do not cause universities. Thus the cognitive agent 110 is able to deduce, there are no answers to Y, but there are answers to X.

Step 7: Answer the Question

In Step 7, the cognitive agent 110 provides a precise answer to a question. For an example question such as: "What situation causally contributed to Ramanujan's position at Cambridge?" the cognitive agent 110 generates a precise answer using the example reasoning:

| | |
|---|---|
| HardyandLittlewoodsEvaluatingOfRamanujansWork | (24) |
| HardyBeliefThatRamanujanIsAnExpertInMathematics | (25) |
| HardysBeliefThatRamanujanIsAnExpertInMathematicsAndAGenius | (26) |

In order to generate the above reasoning statements (24)-(26), the cognitive agent 110 utilizes a solver or prover in the context of the example text's micro-theory—and associated facts, logical entities, relations, and assertions. As an additional example, the cognitive agent 110 uses a reasoning library that is optimized for drawing the example conclusions above within the fact, knowledge, and inference space (e.g., work space) that the cognitive agent 110 maintains.

By implementing the steps 1-7, the cognitive agent 110 analyzes conversational context. The described method for analyzing conversation context can also be used for recommending items in conversations streams. A conversational stream is defined herein as a technical discussion focused on specific topics. As related to described examples herein, the specific topics relate to health (e.g., diabetes). Throughout the lifetime of a conversational stream, a cognitive agent 110 collect information over may channels such as chat, voice, specialized applications, web browsers, contact centers, and the like.

By implementing the methods to analyze conversational context, the cognitive agent 110 can recommend a variety of topics and items throughout the lifetime of the conversational stream. Examples of items that can be recommended by the cognitive agent 110 include: surveys, topics of interest, local events, devices or gadgets, dynamically adapted health assessments, nutritional tips, reminders from a health events calendar, and the like.

Accordingly, the cognitive intelligence platform 102 provides a platform that codifies and takes into consideration a set of allowed actions and a set of desired outcomes. The cognitive intelligence platform 102 relates actions, the sequences of subsequent actions (and reactions), desired sub-outcomes, and outcomes, in a way that is transparent and logical (e.g., explainable). The cognitive intelligence platform 102 can plot a next best action sequence and a planning basis (e.g., health care plan template, or a financial goal achievement template), also in a manner that is explainable. The cognitive intelligence platform 102 can utilize a critical thinking engine 108 and a natural language database 122 (e.g., a linguistics and natural language understanding system) to relate conversation material to actions.

For purposes of this discussion, several examples are discussed in which conversational analysis is applied within the field of durational and whole-health management for a user. The discussed embodiments holistically address the care needs and well-being of the user during the course of his life. The methods and systems described herein can also be used in fields outside of whole-health management, including: phone companies that benefits from a cognitive agent; hospital systems or physicians groups that want to coach and educate patients; entities interested in user behavior and the outcome of physician-consumer interactions in terms of a progress of disease or risk management; entities that provide specialized services (e.g., test, therapies, clinical processes) to filter leads; and sellers, merchants, stores and big box retailers that want to understand which product to sell.

In addition, the conversational analysis may include cognifying the text input by the user. For example, if the user states (e.g., text, voice) they have various symptoms, the cognification techniques disclosed herein may be performed to construct cognified data using the text input. The user may input text specifying that they have a level of 5.7 mmol/L blood sugar. The cognitive intelligence platform 102 may cognify the text to output that the level of blood sugar is within acceptable limits, and that blood sugar testing was used to measure the blood sugar level. In some embodiments, the cognification techniques may be performed to generate a diagnosis of a medical condition of the patient. Further, the cognitive intelligence platform 102 may provide information to the user pertaining to the medical condition at a regulated pace.

Figure 2:
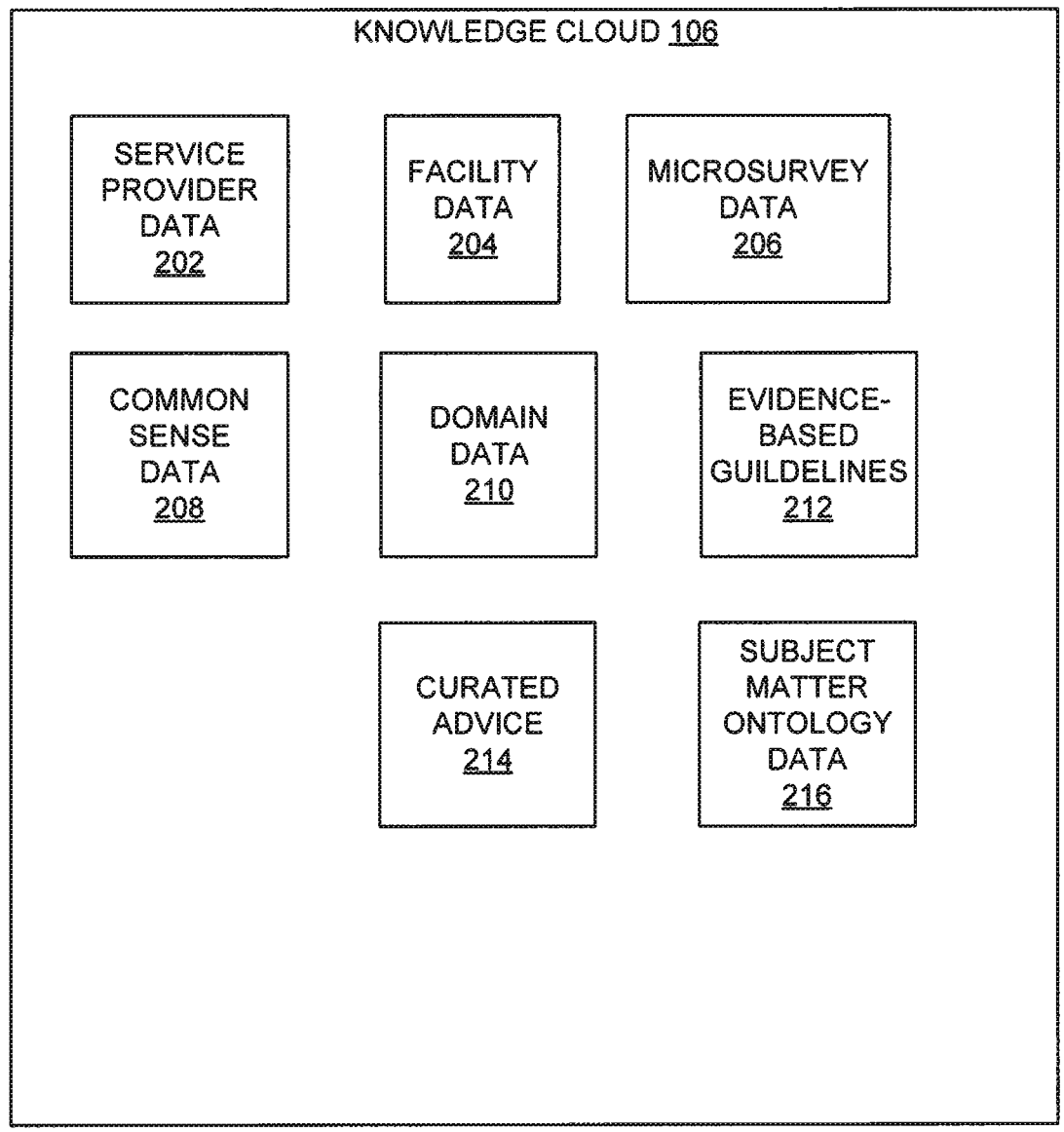
FIG. 2 shows additional details of a knowledge cloud, in accordance with various embodiments.

FIG. 2 shows additional details of a knowledge cloud, in accordance with various embodiments. In particular, FIG. 2 illustrates various types of data received from various sources, including service provider data 202, facility data 204, microsurvey data 206, commonsense data 208, domain data 210, evidence-based guidelines 212, subject matter ontology data 214, and curated advice 216. The types of data represented by the service provider data 202 and the facility data 204 include any type of data generated by the service provider 112 and the facility 114, and the above examples are not meant to be limiting. Thus, the example types of data are not meant to be limiting and other types of data can also be stored within the knowledge cloud 106 without departing from the scope of this disclosure.

The service provider data 202 is data provided by the service provider 112 (described in FIG. 1) and the facility data 204 is data provided by the facility 114 (described in FIG. 1). For example, the service provider data 202 includes medical records of a respective patient of a service provider 112 that is a doctor. In another example, the facility data 204 includes an attendance record of the respective patient, where the facility 114 is a gym. The microsurvey data 206 is data provided by the user device 104 responsive to questions presented in the microsurvey 116 (FIG. 1).

Common sense data 208 is data that has been identified as "common sense", and can include rules that govern a respective concept and used as glue to understand other concepts.

Domain data 210 is data that is specific to a certain domain or subject area. The source of the domain data 210 can include digital libraries. In the healthcare industry, for example, the domain data 210 can include data specific to the various specialties within healthcare such as, obstetrics, anesthesiology, and dermatology, to name a few examples. In the example described herein, the evidence-based guidelines 212 include systematically developed statements to assist practitioner and patient decisions about appropriate health care for specific clinical circumstances.

Curated advice 214 includes advice from experts in a subject matter. The curated advice 214 can include peer-reviewed subject matter, and expert opinions. Subject matter ontology data 216 includes a set of concepts and categories in a subject matter or domain, where the set of concepts and categories capture properties and relationships between the concepts and categories.

Figure 3:
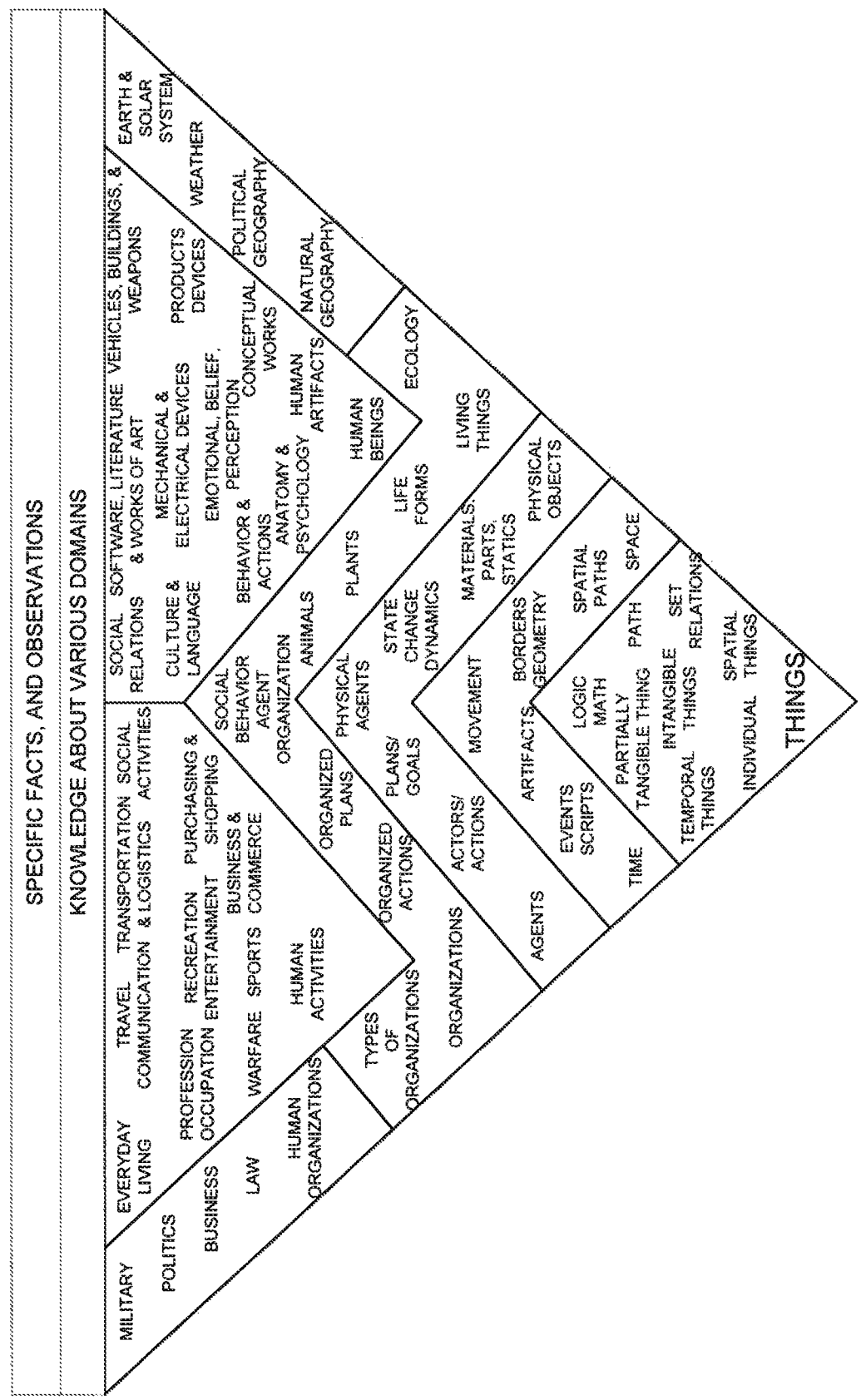
FIG. 3 shows an example subject matter ontology, in accordance with various embodiments.

In particular, FIG. 3 illustrates an example subject matter ontology 300 that is included as part of the subject matter ontology data 216.

Figure 4:
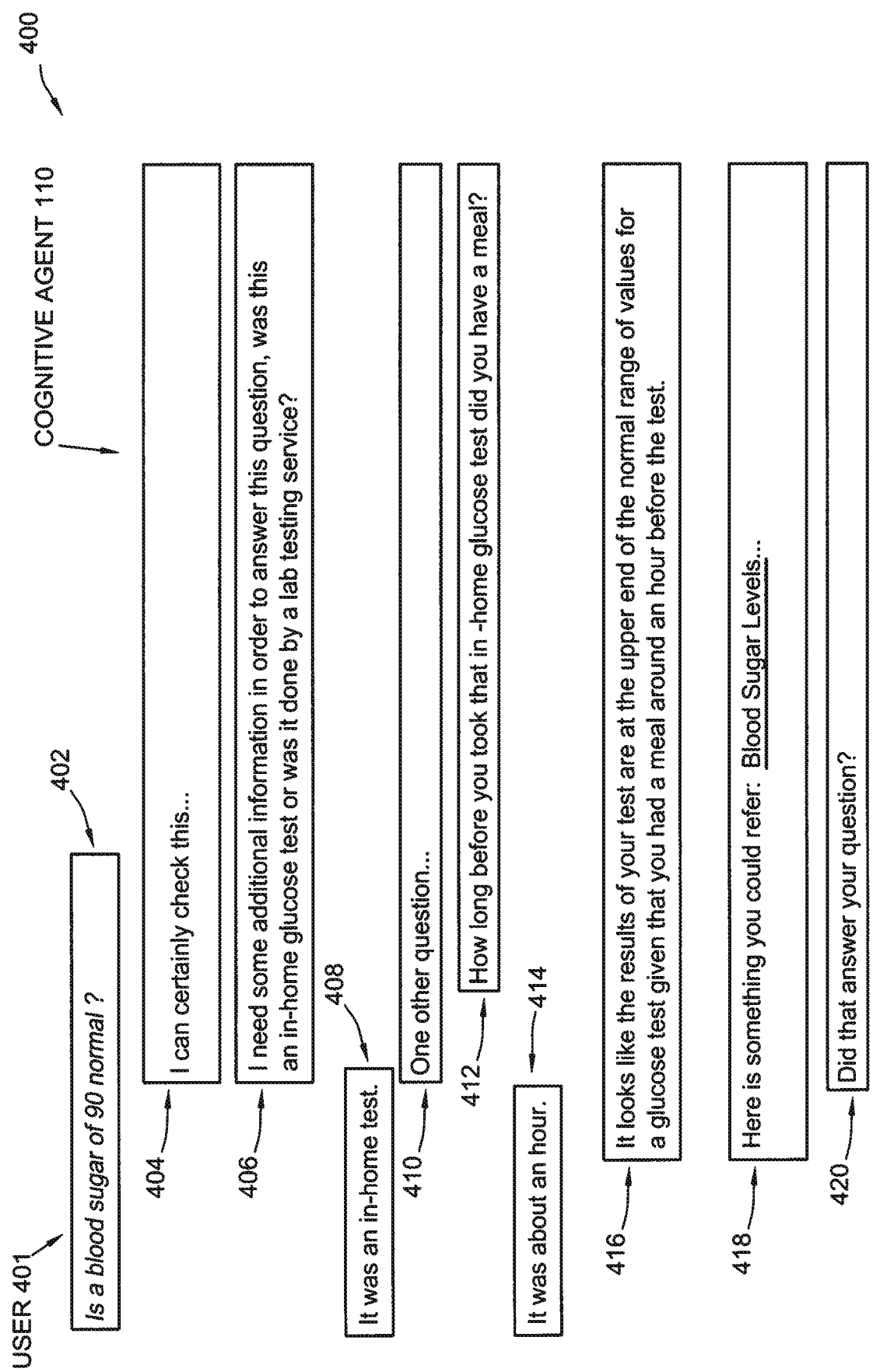
FIG. 4 shows aspects of a conversation, in accordance with various embodiments.

FIG. 4 illustrates aspects of a conversation 400 between a user and the cognitive intelligence platform 102, and more specifically the cognitive agent 110. For purposes of this discussion, the user 401 is a patient of the service provider 112. The user interacts with the cognitive agent 110 using a computing device, a smart phone, or any other device configured to communicate with the cognitive agent 110 (e.g., the user device 104 in FIG. 1). The user can enter text into the device using any known means of input including a keyboard, a touchscreen, and a microphone. The conversation 400 represents an example graphical user interface (GUI) presented to the user 401 on a screen of his computing device.

Initially, the user asks a general question, which is treated by the cognitive agent 110 as an "originating question." The originating question is classified into any number of potential questions ("pursuable questions") that are pursued during the course of a subsequent conversation. In some embodiments, the pursuable questions are identified based on a subject matter domain or goal. In some embodiments, classification techniques are used to analyze language (e.g., such as those outlined in HPS ID20180901-01_method for conversational analysis). Any known text classification technique can be used to analyze language and the originating question. For example, in line 402, the user enters an originating question about a subject matter (e.g., blood sugar) such as: "Is a blood sugar of 90 normal"? I In response to receiving an originating question, the cognitive intelligence platform 102 (e.g., the cognitive agent 110 operating in conjunction with the critical thinking engine 108) performs a first round of analysis (e.g., which includes conversational analysis) of the originating question and, in response to the first round of analysis, creates a workspace and determines a first set of follow up questions.

In various embodiments, the cognitive agent 110 may go through several rounds of analysis executing within the workspace, where a round of analysis includes: identifying parameters, retrieving answers, and consolidating the answers. The created workspace can represent a space where the cognitive agent 110 gathers data and information during the processes of answering the originating question. In various embodiments, each originating question corresponds to a respective workspace. The conversation orchestrator 124 can assess data present within the workspace and query the cognitive agent 110 to determine if additional data or analysis should be performed.

In particular, the first round of analysis is performed at different levels, including analyzing natural language of the text, and analyzing what specifically is being asked about the subject matter (e.g., analyzing conversational context). The first round of analysis is not based solely on a subject matter category within which the originating question is classified. For example, the cognitive intelligence platform 102 does not simply retrieve a predefined list of questions in response to a question that falls within a particular subject matter, e.g., blood sugar. That is, the cognitive intelligence platform 102 does not provide the same list of questions for all questions related to the particular subject matter. Instead, for example, the cognitive intelligence platform 102 creates dynamically formulated questions, curated based on the first round of analysis of the originating question.

In particular, during the first round of analysis, the cognitive agent 110 parses aspects of the originating question into associated parameters. The parameters represent variables useful for answering the originating question. For example, the question "is a blood sugar of 90 normal" may be parsed and associated parameters may include, an age of the inquirer, the source of the value 90 (e.g., in home test or a clinical test), a weight of the inquirer, and a digestive state of the user when the test was taken (e.g., fasting or recently eaten). The parameters identify possible variables that can impact, inform, or direct an answer to the originating question.

For purposes of the example illustrated in FIG. 4, in the first round of analysis, the cognitive intelligence platform 102 inserts each parameter into the workspace associated with the originating question (line 402). Additionally, based on the identified parameters, the cognitive intelligence platform 102 identifies a customized set of follow up questions ("a first set of follow-up questions). The cognitive intelligence platform 102 inserts first set of follow-up questions in the workspace associated with the originating question.

The follow up questions are based on the identified parameters, which in turn are based on the specifics of the originating question (e.g., related to an identified microtheory). Thus the first set of follow-up questions identified in response to, if a blood sugar is normal, will be different from a second set of follow up questions identified in response to a question about how to maintain a steady blood sugar.

After identifying the first set of follow up questions, in this example first round of analysis, the cognitive intelligence platform 102 determines which follow up question can be answered using available data and which follow-up question to present to the user. As described over the next few paragraphs, eventually, the first set of follow-up questions is reduced to a subset ("a second set of follow-up questions") that includes the follow-up questions to present to the user.

In various embodiments, available data is sourced from various locations, including a user account, the knowledge cloud 106, and other sources. Other sources can include a service that supplies identifying information of the user, where the information can include demographics or other characteristics of the user (e.g., a medical condition, a lifestyle). For example, the service can include a doctor's office or a physical therapist's office.

Another example of available data includes the user account. For example, the cognitive intelligence platform 102 determines if the user asking the originating question, is identified. A user can be identified if the user is logged into an account associated with the cognitive intelligence platform 102. User information from the account is a source of available data. The available data is inserted into the workspace of the cognitive agent 110 as a first data.

Another example of available data includes the data stored within the knowledge cloud 106. For example, the available data includes the service provider data 202 (FIG. 2), the facility data 204, the microsurvey data 206, the common sense data 208, the domain data 210, the evidence-based guidelines 212, the curated advice 214, and the subject matter ontology data 216. Additionally data stored within the knowledge cloud 106 includes data generated by the cognitive intelligence platform 102, itself.

Follow up questions presented to the user (the second set of follow-up questions) are asked using natural language and are specifically formulated ("dynamically formulated question") to elicit a response that will inform or fulfill an identified parameter. Each dynamically formulated question can target one parameter at a time. When answers are received from the user in response to a dynamically formulated question, the cognitive intelligence platform 102 inserts the answer into the workspace. In some embodiments, each of the answers received from the user and in response to a dynamically formulated question, is stored in a list of facts. Thus the list of facts include information specifically received from the user, and the list of facts is referred to herein as the second data.

With regards to the second set of follow-up questions (or any set of follow-up questions), the cognitive intelligence platform 102 calculates a relevance index, where the relevance index provides a ranking of the questions in the second set of follow-up questions. The ranking provides values indicative of how relevant a respective follow-up question is to the originating question. To calculate the relevance index, the cognitive intelligence platform 102 can use conversations analysis techniques described in HPS ID20180901-01_method. In some embodiments, the first set or second set of follow up questions is presented to the user in the form of the microsurvey 116.

In this first round of analysis, the cognitive intelligence platform 102 consolidates the first and second data in the workspace and determines if additional parameters need to be identified, or if sufficient information is present in the workspace to answer the originating question. In some embodiments, the cognitive agent 110 (FIG. 1) assesses the data in the workspace and queries the cognitive agent 110 to determine if the cognitive agent 110 needs more data in order to answer the originating question. The conversation orchestrator 124 executes as an interface For a complex originating question, the cognitive intelligence platform 102 can go through several rounds of analysis. For example, in a first round of analysis the cognitive intelligence platform 102 parses the originating question. In a subsequent round of analysis, the cognitive intelligence platform 102 can create a sub question, which is subsequently parsed into parameters in the subsequent round of analysis. The cognitive intelligence platform 102 is smart enough to figure out when all information is present to answer an originating question without explicitly programming or pre-programming the sequence of parameters that need to be asked about.

In some embodiments, the cognitive agent 110 is configured to process two or more conflicting pieces of information or streams of logic. That is, the cognitive agent 110, for a given originating question can create a first chain of logic and a second chain of logic that leads to different answers. The cognitive agent 110 has the capability to assess each chain of logic and provide only one answer. That is, the cognitive agent 110 has the ability to process conflicting information received during a round of analysis.

Additionally, at any given time, the cognitive agent 110 has the ability to share its reasoning (chain of logic) to the user. If the user does not agree with an aspect of the reasoning, the user can provide that feedback which results in affecting change in a way the critical thinking engine 108 analyzed future questions and problems.

Subsequent to determining enough information is present in the workspace to answer the originating question, the cognitive agent 110 answers the question, and additionally can suggest a recommendation or a recommendation (e.g., line 418). The cognitive agent 110 suggests the reference or the recommendation based on the context and questions being discussed in the conversation (e.g., conversation 400). The reference or recommendation serves as additional handout material to the user and is provided for informational purposes. The reference or recommendation often educates the user about the overall topic related to the originating question.

In the example illustrated in FIG. 4, in response to receiving the originating questions (line 402), the cognitive intelligence platform 102 (e.g., the cognitive agent 110 in conjunction with the critical thinking engine 108) parses the originating question to determine at least one parameter: location. The cognitive intelligence platform 102 categorizes this parameter, and a corresponding dynamically formulated question in the second set of follow-up questions. Accordingly, in lines 404 and 406, the cognitive agent 110 responds by notifying the user "I can certainly check this . . . " and asking the dynamically formulated question "I need some additional information in order to answer this question, was this an in-home glucose test or was it done by a lab or testing service?"

The user 401 enters his answer in line 408: "It was an in-home test," which the cognitive agent 110 further analyzes to determine additional parameters: e.g., a digestive state, where the additional parameter and a corresponding dynamically formulated question as an additional second set of follow-up questions. Accordingly, the cognitive agent 110 poses the additional dynamically formulated question in lines 410 and 412: "One other question . . . " and "How long before you took that in-home glucose test did you have a meal?" The user provides additional information in response "it was about an hour" (line 414).

The cognitive agent 110 consolidates all the received responses using the critical thinking engine 108 and the knowledge cloud 106 and determines an answer to the initial question posed in line 402 and proceeds to follow up with a final question to verify the user's initial question was answered. For example, in line 416, the cognitive agent 110 responds: "It looks like the results of your test are at the upper end of the normal range of values for a glucose test given that you had a meal around an hour before the test." The cognitive agent 110 provides additional information (e.g., provided as a link): "Here is something you could refer," (line 418), and follows up with a question "Did that answer your question?" (line 420).

As described above, due to the natural language database 108, in various embodiments, the cognitive agent 110 is able to analyze and respond to questions and statements made by a user 401 in natural language. That is, the user 401 is not restricted to using certain phrases in order for the cognitive agent 110 to understand what a user 401 is saying. Any phrasing, similar to how the user would speak naturally can be input by the user and the cognitive agent 110 has the ability to understand the user.

Figure 5:
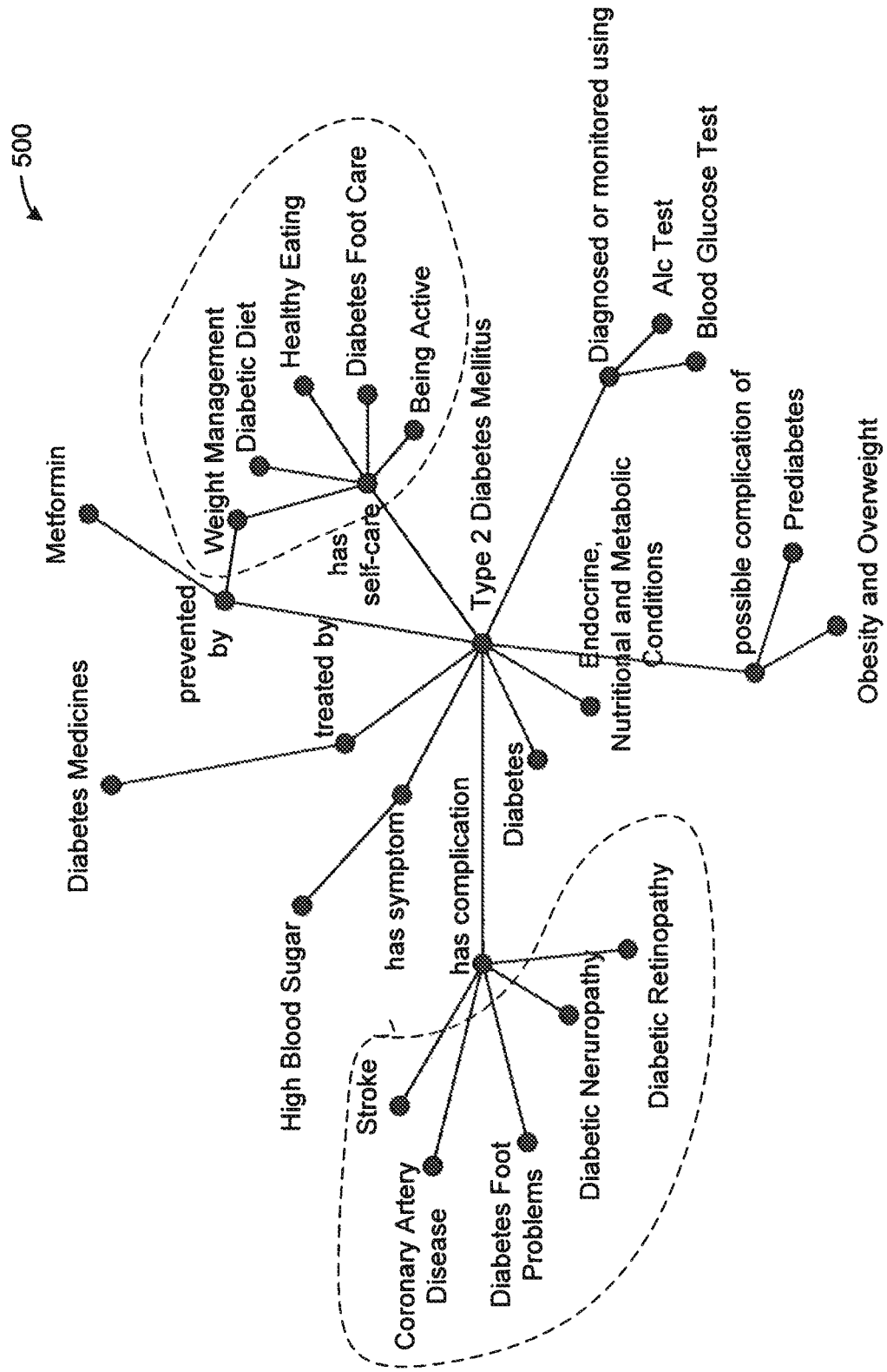
FIG. 5 shows a cognitive map or "knowledge graph", in accordance with various embodiments.

FIG. 5 illustrates a cognitive map or "knowledge graph" 500, in accordance with various embodiments. In particular, the knowledge graph represents a graph traversed by the cognitive intelligence platform 102, when assessing questions from a user with Type 2 diabetes. Individual nodes in the knowledge graph 500 represent a health artifact (health related information) or relationship (predicate) that is gleaned from direct interrogation or indirect interactions with the user (by way of the user device 104).

In one embodiment, the cognitive intelligence platform 102 identified parameters for an originating question based on a knowledge graph illustrated in FIG. 5. For example, the cognitive intelligence platform 102 parses the originating question to determine which parameters are present for the originating question. In some embodiments, the cognitive intelligence platform 102 infers the logical structure of the parameters by traversing the knowledge graph 500, and additionally, knowing the logical structure enables the cognitive agent 110 to formulate an explanation as to why the cognitive agent 110 is asking a particular dynamically formulated question.

In some embodiments, the individual elements or nodes are generated by the artificial intelligence engine based on input data (e.g., evidence-based guidelines, patient notes, clinical trials, physician research or the like). The artificial intelligence engine may parse the input data and construct the relationships between the health artifacts.

For example, a root node may be associated with a first health related information "Type 2 Diabetes Mellitus", which is a name of a medical condition. In some embodiments, the root node may also be associated with a definition of the medical condition. An example predicate, "has symptom", is represented by an individual node connected to the root node, and another health related information, "High Blood Sugar", is represented by an individual node connected to the individual node representing the predicate. A logical structure may be represented by these three nodes, and the logical structure may indicate that "Type 2 Diabetes Mellitus has symptom High Blood Sugar".

In some embodiments, the health related information may correspond to known facts, concepts, and/or any suitable health related information that are discovered or provided by a trusted source (e.g., a physician having a medical license and/or a certified/accredited healthcare organization), such as evidence-based guidelines, clinical trials, physician research, patient notes entered by physicians, and the like. The predicates may be part of a logical structure (e.g., sentence) such as a form of subject-predicate-direct object, subject-predicate-indirect object-direct object, subject-predicate-subject complement, or any suitable simple, compound, complex, and/or compound/complex logical structure. The subject may be a person, place, thing, health artifact, etc. The predicate may express an action or being within the logical structure and may be a verb, modifying words, phrases, and/or clauses. For example, one logical structure may be the subject-predicate-direct object form, such as "A has B" (where A is the subject and may be a noun or a health artifact, "has" is the predicate, and B is the direct object and may be a health artifact).

The various logical structures in the depicted knowledge graph may include the following: "Type 2 Diabetes Mellitus has symptom High Blood Sugar"; "Type 2 Diabetes Mellitus has complication Stroke"; "Type 2 Diabetes Mellitus has complication Coronary Artery Disease"; "Type 2 Diabetes Mellitus has complication Diabetes Foot Problems"; "Type 2 Diabetes Mellitus has complication Diabetic Neuropathy"; "Type 2 Diabetes Mellitus has complication Diabetic Retinopathy"; "Type 2 Diabetes Mellitus diagnosed or monitored using Blood Glucose Test"; just to name a few examples. It should be understood that there are other logical structures and represented in the knowledge graph 500.

In some embodiments, the information depicted in the knowledge graph may be represented as a matrix. The health artifacts may be represented as quantities and the predicates may be represented as expressions in a rectangular array in rows and columns of the matrix. The matrix may be treated as a single entity and manipulated according to particular rules.

The knowledge graph 500 or the matrix may be generated for each known medical condition and stored by the cognitive intelligence platform 102. The knowledge graphs and/or matrices may be updated continuously or on a periodic basis using subject data pertaining to the medical conditions received from the trusted sources. For example, additional clinical trials may lead to new discoveries about particular medical condition treatments, which may be used to update the knowledge graphs and/or matrices.

The knowledge graph 500 including the logical structures may be used to transform unstructured data (patient notes in an EMR entered by a physician) into cognified data. The cognified data may be used to generate a diagnosis of the patient. Also, the cognified data may be used to determine which information pertaining to the medical condition to provide to the patient and when to provide the information to the patient to improve the user experience using the computing device. The disclosed techniques may also save computing resources by providing the cognified data to the physician to review, improve diagnosis accuracy, and/or regulate the amount of information provided to the patient.

Figure 6:
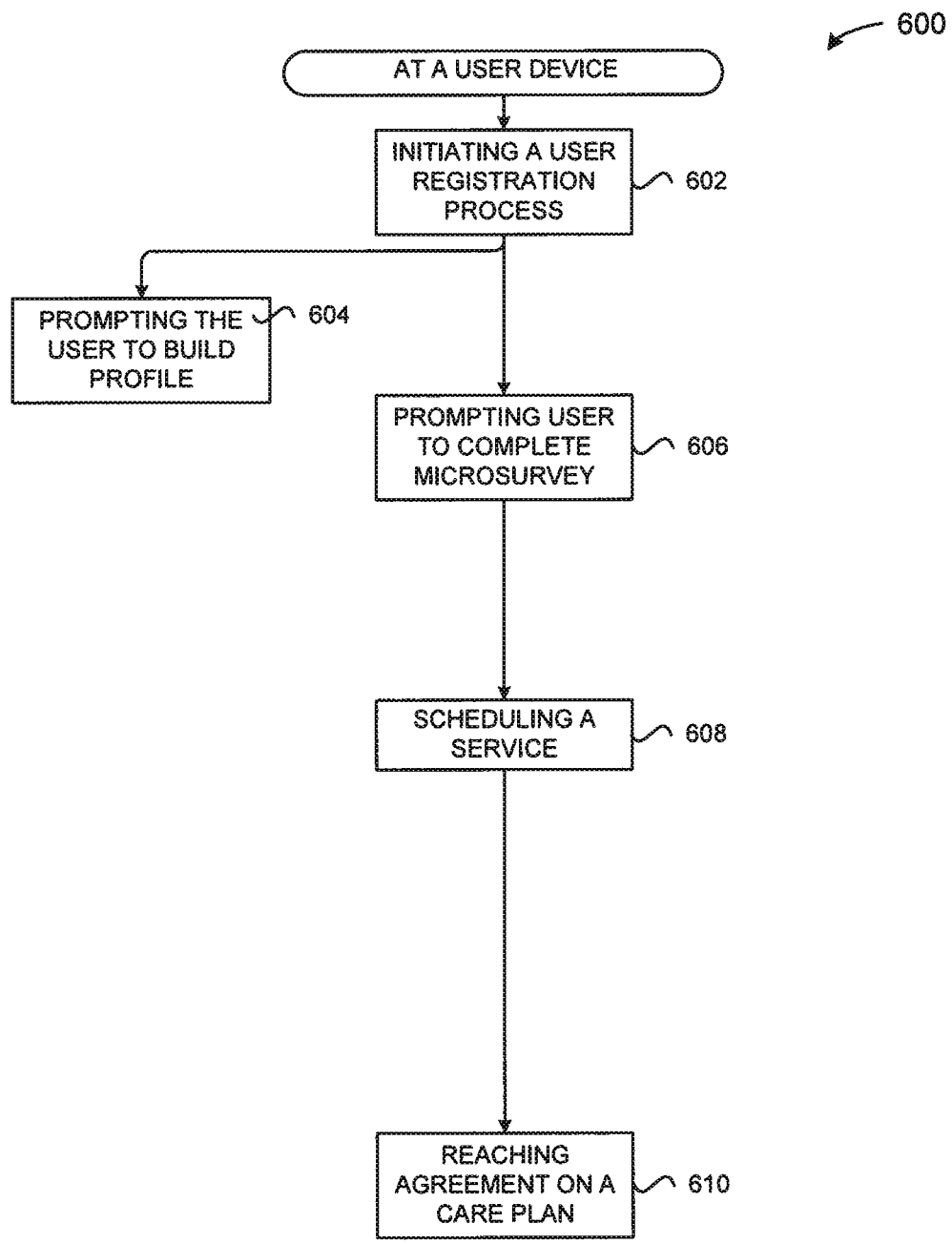
FIG. 6 shows a method, in accordance with various embodiments.

FIG. 6 shows a method, in accordance with various embodiments. The method is performed at a user device (e.g., the user device 102) and in particular, the method is performed by an application executing on the user device 102. The method begins with initiating a user registration process (block 602). The user registration can include tasks such as displaying a GUI asking the user to enter in personal information such as his name and contact information.

Next, the method includes prompting the user to build his profile (block 604). In various embodiments, building his profile includes displaying a GUI asking the user to enter in additional information, such as age, weight, height, and health concerns. In various embodiments, the steps of building a user profile is progressive, where building the user profile takes place over time. In some embodiments, the process of building the user profile is presented as a game. Where a user is presented with a ladder approach to create a "star profile". Aspects of a graphical user interface presented during the profile building step are additionally discussed in FIGS. 8A-8B.

The method contemplates the build profile (block 604) method step is optional. For example, the user may complete building his profile at this method step 604, the user may complete his profile at a later time, or the cognitive intelligence platform 102 builds the user profile over time as more data about the user is received and processed. For example, the user is prompted to build his profile, however, the user fails to enter in information or skips the step. The method proceeds to prompting a user to complete a microsurvey (block 606). In some embodiments, the cognitive agent 110 uses answers received in response to the microsurvey to build the profile of the user. Overall, the data collected through the user registration process is stored and used later as available data to inform answers to missing parameters.

Next, the cognitive agent 110 proceeds to scheduling a service (block 608). The service can be scheduled such that it aligns with a health plan of the user or a protocol that results in a therapeutic goal. Next, the cognitive agent 110 proceeds to reaching agreement on a care plan (block 610).

Figure 7A:
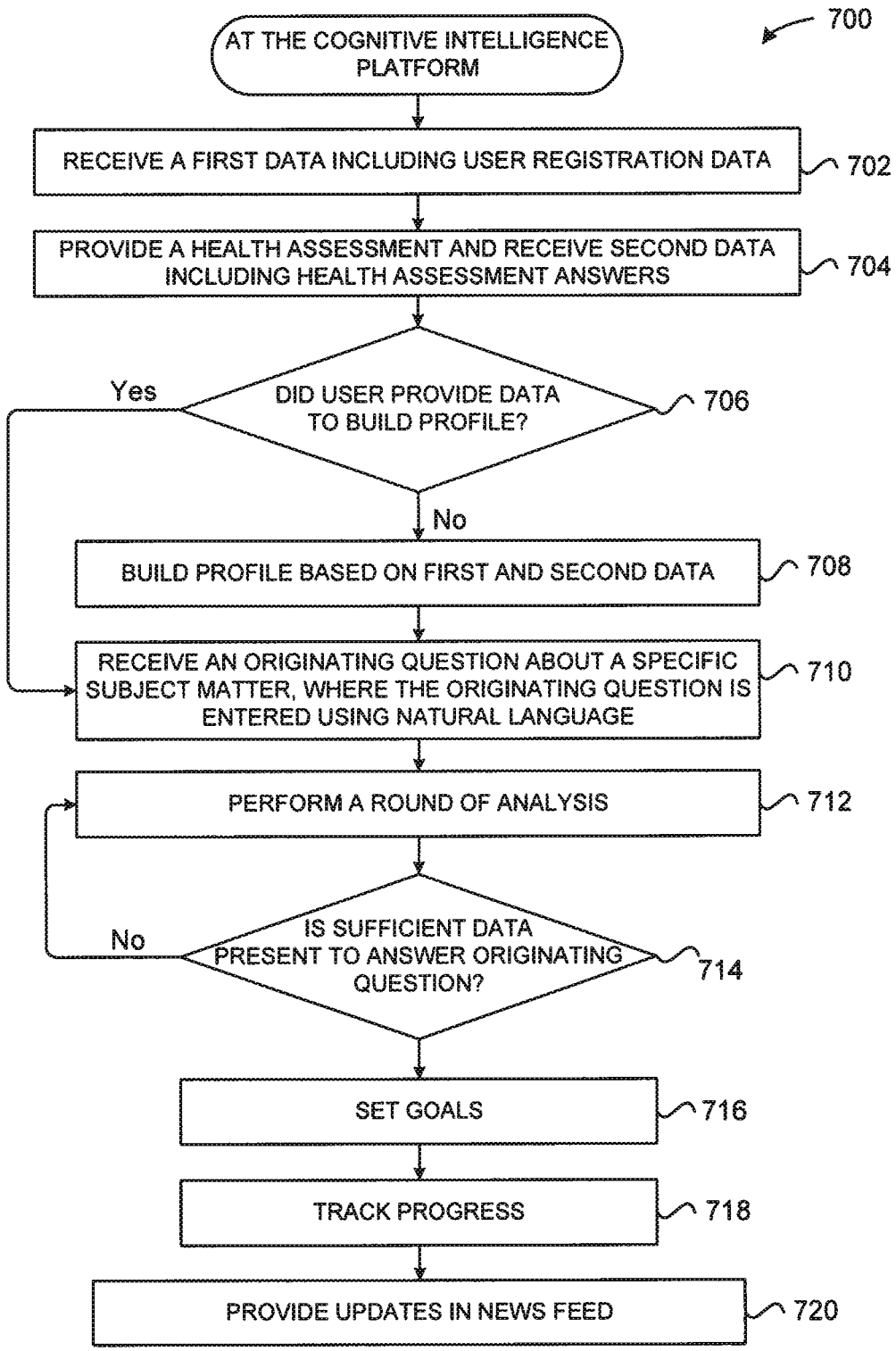
FIGS. 7A, 7B, and 7C show methods, in accordance with various embodiments.
Figure 7B:
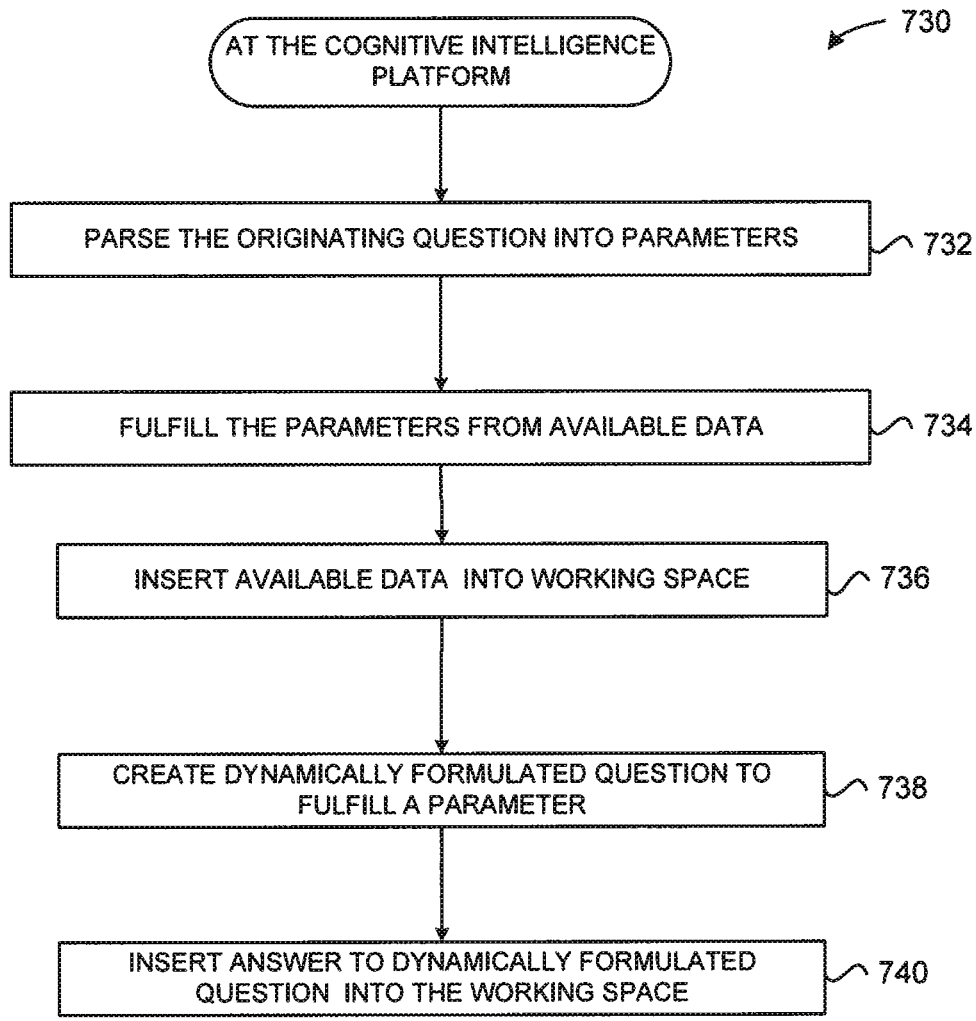
Figure 7C:
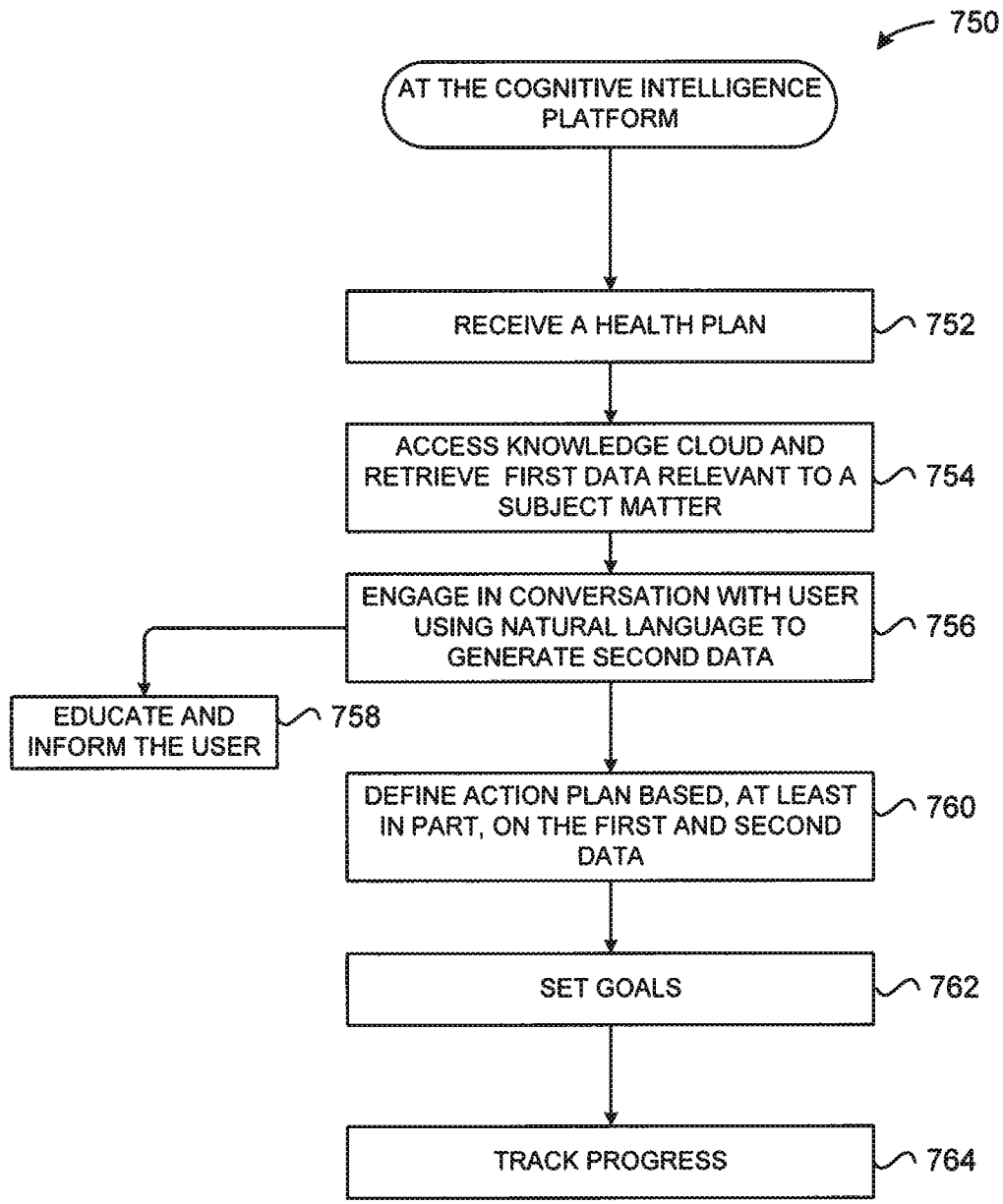

FIGS. 7A, 7B, and 7C, show methods, in accordance with various embodiments. The methods are performed at the cognitive intelligence platform. In particular, in FIG. 7A, the method begins with receiving a first data including user registration data (block 702); and providing a health assessment and receiving second data including health assessment answers (block 704). In various embodiments, the health assessment is a micro-survey with dynamically formulated questions presented to the user.

Next the method determine if the user provided data to build a profile (decision block 706). If the user did not provide data to build the profile, the method proceeds to building profile based on first and second data (block 708). If the user provided data to build the profile, the method proceeds to block 710.

At block 710, the method 700 proceeds to receiving an originating question about a specific subject matter, where the originating question is entered using natural language, and next the method proceeds to performing a round of analysis (block 712). Next, the method determines if sufficient data is present to answer originating questions (decision block 714). If no, the method proceeds to block 712 and the method performs another round of analysis. If yes, the method proceeds to setting goals (block 716), then tracking progress (block 718), and then providing updates in a news feed (block 720).

In FIG. 7B, a method 730 of performing a round of analysis is illustrated. The method begins with parsing the originating question into parameters (block 732); fulfilling the parameters from available data (block 734); inserting the parameters (first data) into a working space (block 736); creating a dynamically formulated question to fulfill a parameter (block 738); and inserting an answer to the dynamically formulated question into the working space (block 740).

In FIG. 7C, a method 750 is performed at the cognitive intelligence platform. The method begins with receiving a health plan (block 752); accessing the knowledge cloud and retrieving first data relevant to the subject matter (block 754); and engaging in conversation with the user using natural language to general second data (block 756). In various embodiments, the second data can include information such as a user's scheduling preferences, lifestyle choices, and education level. During the process of engaging in conversation, the method includes educating and informing the user (block 758). Next, the method includes defining an action plan based, at least in part, on the first and second data (block 760); setting goals (block 762); and tracking progress (block 764).

FIGS. 8A, 8B, 8C, and 8D illustrate aspects of interactions between a user and the cognitive intelligence platform 102, in accordance with various embodiments. As a user interacts with the GUI, the cognitive intelligence platform 102 continues to build a database of knowledge about the user based on questions asked by the user as well as answers provided by the user (e.g., available data as described in FIG. 4). In particular, FIG. 8A displays a particular screen shot 801 of the user device 104 at a particular instance in time. The screen shot 801 displays a graphical user interface (GUI) with menu items associated with a user's (e.g., Nathan) profile including Messages from the doctor (element 804), Goals (element 806), Trackers (element 808), Health Record (element 810), and Health Plans & Assessments (element 812). The menu item Health Plans & Assessments (element 812), additionally include child menu items: Health Assessments (element 812a), Health plans (812b).

The screen shot 803 displays the same GUI as in the screen shot 801, however, the user has scrolled down the menu, such that additional menu items below Health Plans & Assessments (element 812) are shown. The additional menu items include Reports (element 814), Health Team (element 816), and Purchases and Services (Element 818). Furthermore, additional menu items include Add your Health Team (element 820) and Read about improving your A1C levels (element 822).

Figure 8A:
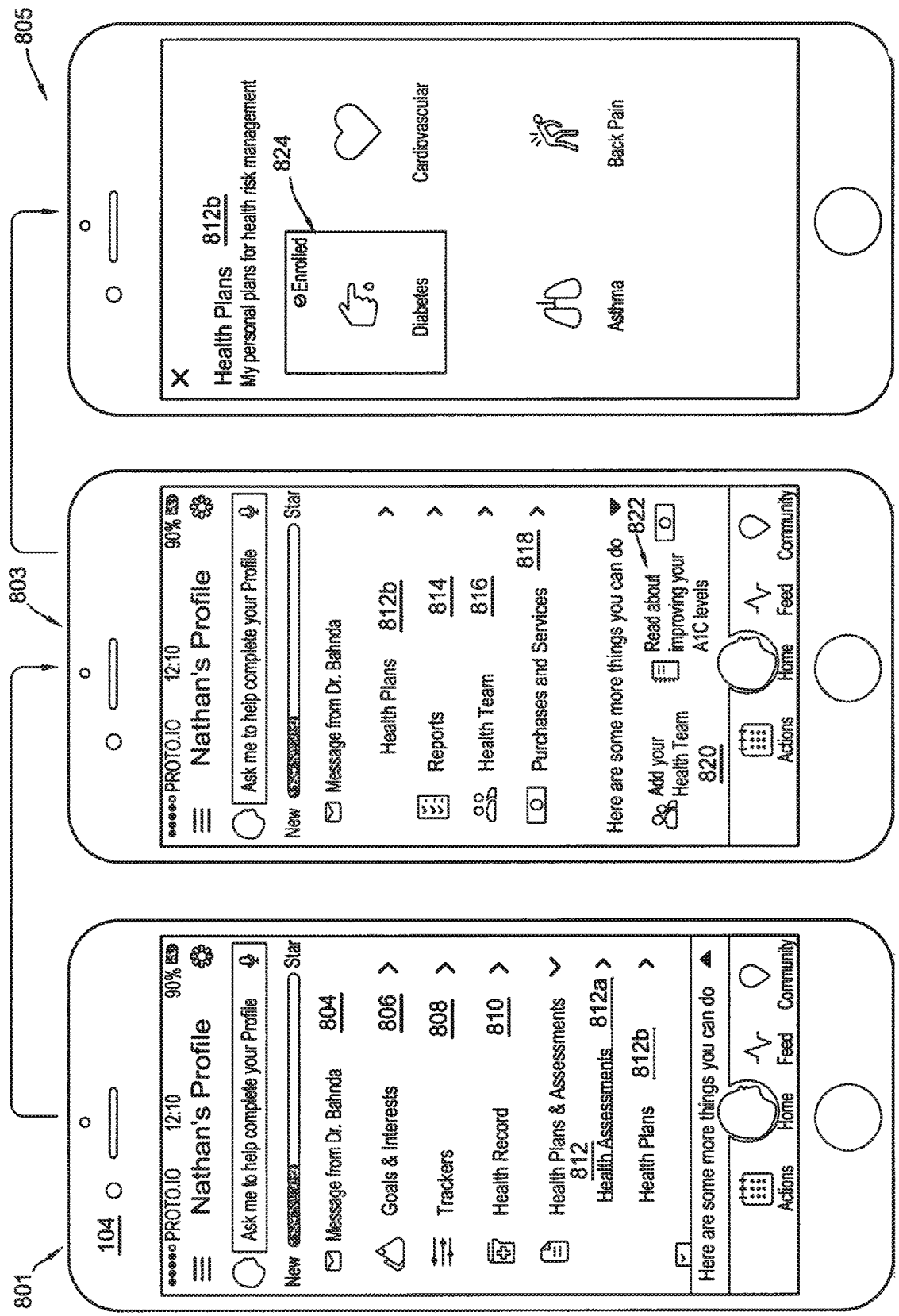

For purposes of the example in FIG. 8A, the user selects the menu item Health Plans (element 812b). Accordingly, in response to the receiving the selection of the menu item Health Plans, types of health plans are shown, as illustrated in screen shot 805. The types of health plans shown with respect to Nathan's profile include: Diabetes (element 824), Cardiovascular, Asthma, and Back Pain. Each type of health plan leads to separate displays. For purposes of this example in FIG. 8A, the user selects the Diabetes (element 824) health plan.

In FIG. 8B, the screenshot 851 is seen in response to the user's selection of Diabetes (element 824). Example elements displayed in screenshot 851 include: Know How YOUR Body Works (element 852); Know the Current Standards of Care (element 864); Expertise: Self-Assessment (element 866); Expertise: Self-Care/Treatment (element 868); and Managing with Lifestyle (element 870). Managing with Lifestyle (element 870) focuses and tracks actions and lifestyle actions that a user can engage in. As a user's daily routine helps to manage diabetes, managing the user's lifestyle is important. The cognitive agent 110 can align a user's respective health plan based on a health assessment at enrollment. In various embodiments, the cognitive agent 110 aligns the respective health plan with an interest of the user, a goal and priority of the user, and lifestyle factors of the user—including exercise, diet and nutrition, and stress reduction.

Each of these elements 852, 864, 866, 868, and 870 can display additional sub-elements depending on a selection of the user. For example, as shown in the screen shot 851, Know How YOUR Body Works (element 852) includes additional sub-elements: Diabetes Personal Assessment (854); and Functional Changes (856). Additional sub-elements under Functional Changes (856) include: Blood Sugar Processing (858) and Manageable Risks (860). Finally, the sub-element Manageable Risks (860) includes an additional sub-element Complications (862). For purposes of this example, the user selects the Diabetes Personal Assessment (854) and the screen shot 853 shows a GUI (872) associated with the Diabetes Personal Assessment.

The Diabetes Personal Assessment includes questions such as "Approximately what year was your Diabetes diagnosed" and corresponding elements a user can select to answer including "Year" and "Can't remember" (element 874). Additional questions include "Is your Diabetes Type 1 or Type 2" and corresponding answers selectable by a user include "Type 1," "Type 2," and "Not sure" (element 876). Another question includes "Do you take medication to manage your blood sugar" and corresponding answers selectable by a user include "Yes" and "No" (element 878). An additional question asks "Do you have a healthcare professional that works with you to manage your Diabetes" and corresponding answers selectable by the user include "Yes" and "No" (element 880).

In various embodiments, the cognitive intelligence platform 102 collects information about the user based on responses provided by the user or questions asked by the user as the user interacts with the GUI. For example, as the user views the screen shot 851, if the user asks if diabetes is curable, this question provides information about the user such as a level of education of the user.

Figure 8C:
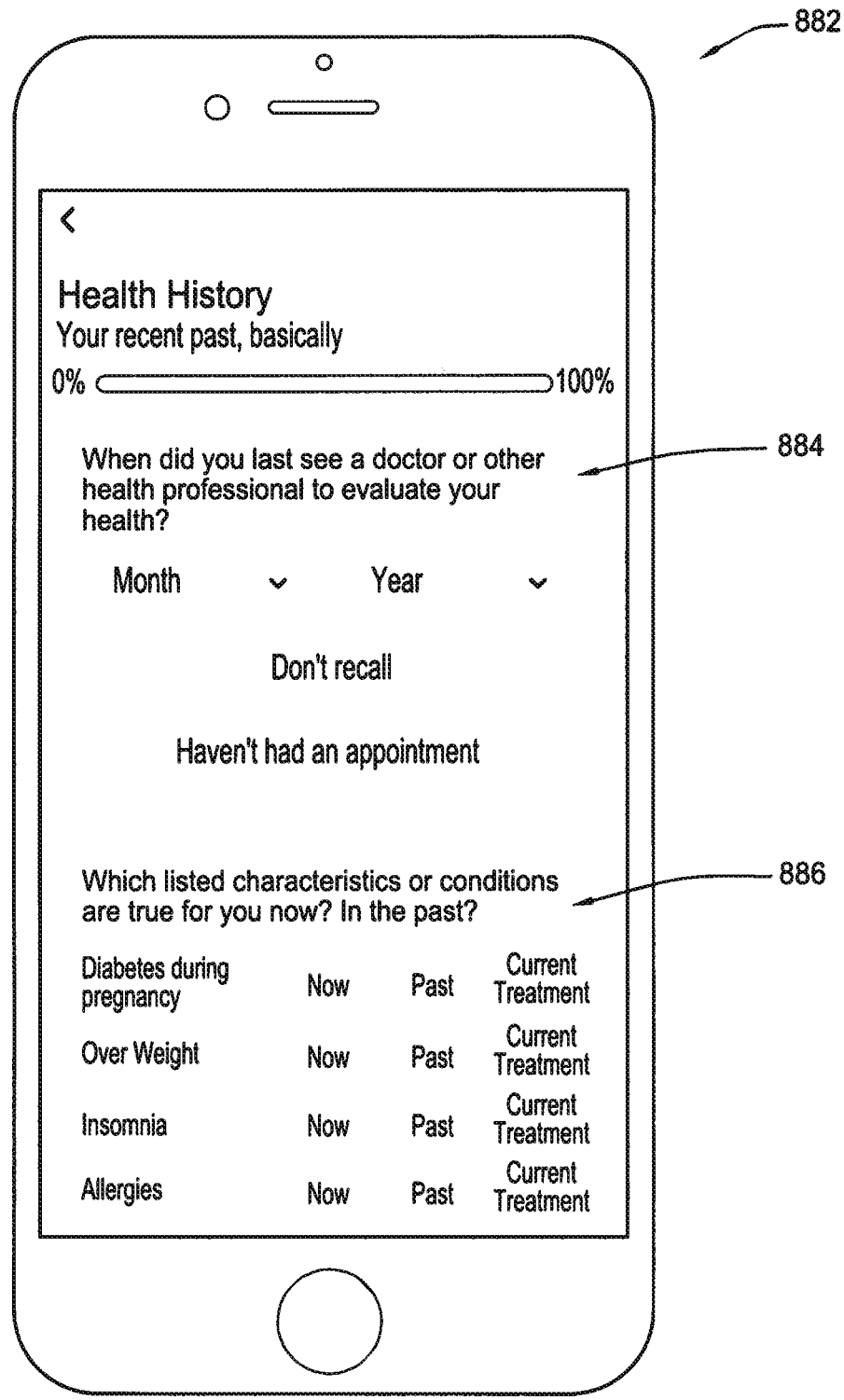

FIG. 8C illustrates aspects of an additional tool—e.g., a microsurvey—provided to the user that helps gather additional information about the user (e.g., available data). In various embodiments, a micro-survey represent a short targeted survey, where the questions presented in the survey are limited to a respective micro-theory. A microsurvey can be created by the cognitive intelligence platform 102 for several different purposes, including: completing a user profile, and informing a missing parameter during the process of answering an originating question.

In FIG. 8C, the microsurvey 882 gathers information related to health history, such as "when did you last see a doctor or other health professional to evaluate your health" where corresponding answers selectable by the user include specifying a month and year, "don't recall," and "haven't had an appointment" (element 884). An additional question asks "Which listed characteristics or conditions are true for you now? In the past?" where corresponding answers selectable by the user include "Diabetes during pregnancy," "Over Weight," "Insomnia," and "Allergies" (element 886). Each of the corresponding answer in element 886 also includes the option to indicate whether the characteristics or conditions are true for the user "Now", "Past," or "Current Treatment."

Figure 8D:
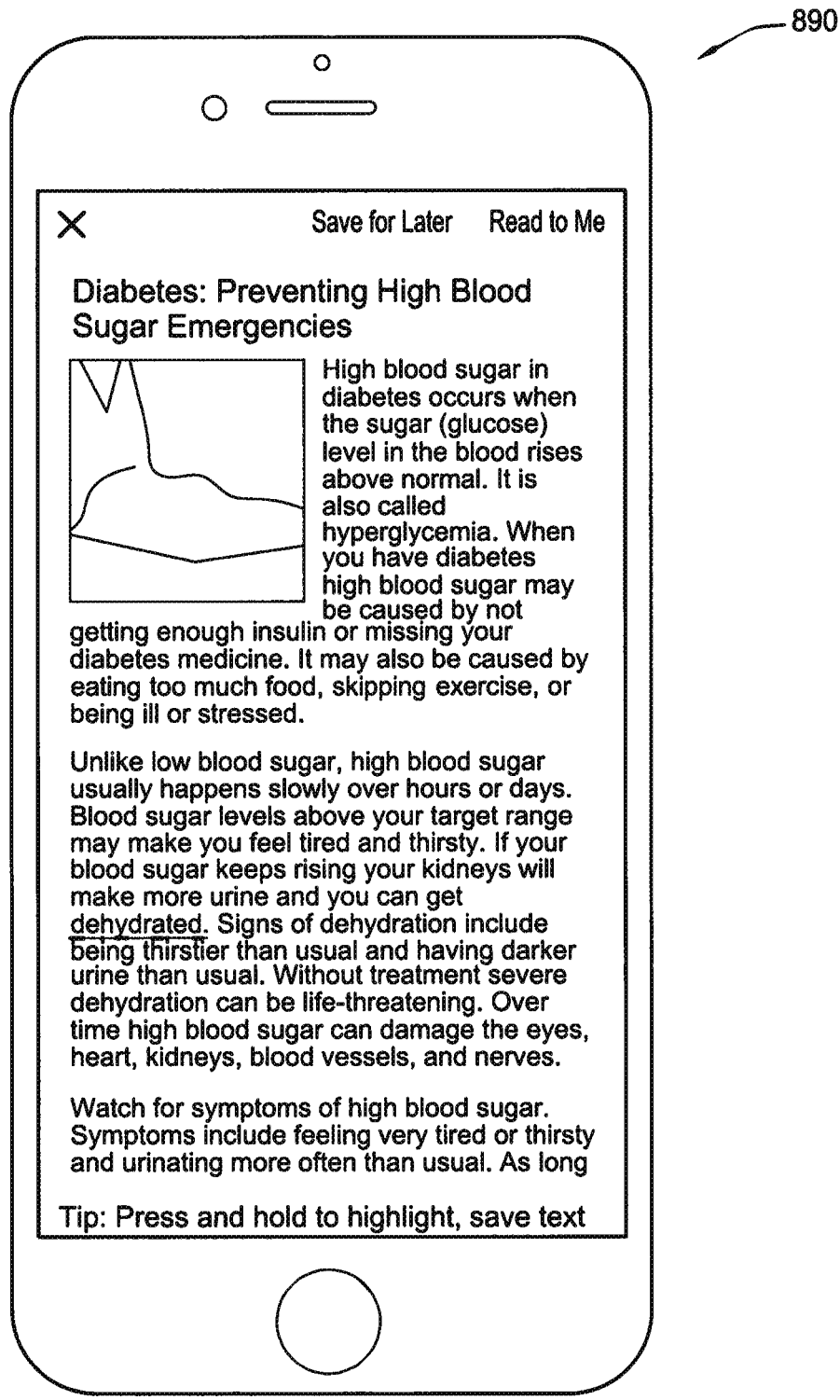

In FIG. 8D, aspects of educating a user are shown in the screen shot 890. The screen shot displays an article titled "Diabetes: Preventing High Blood Sugar Emergencies," and proceeds to describe when high blood sugar occurs and other information related to high blood sugar. The content displayed in the screen shot 890 is searchable and hearable as a podcast.

Accordingly, the cognitive agent 110 can answer a library of questions and provide content for many questions a user has as it related to diabetes. The information provided for purposes of educating a user is based on an overall health plan of the user, which is based on meta data analysis of interactions with the user, and an analysis of the education level of the user.

Figure 9A:
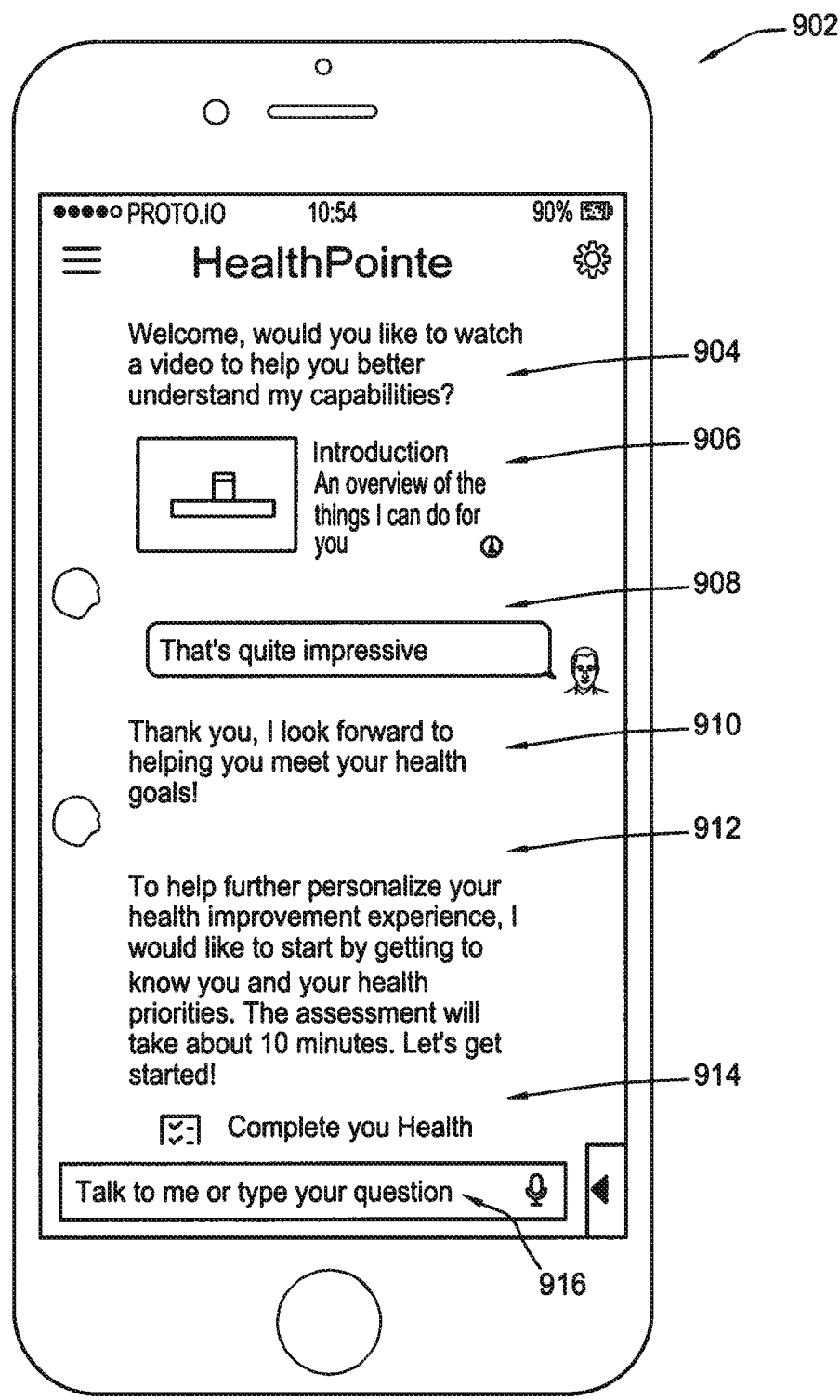
FIGS. 9A and 9B shows aspects of a conversational stream, in accordance with various embodiments.
Figure 9B:
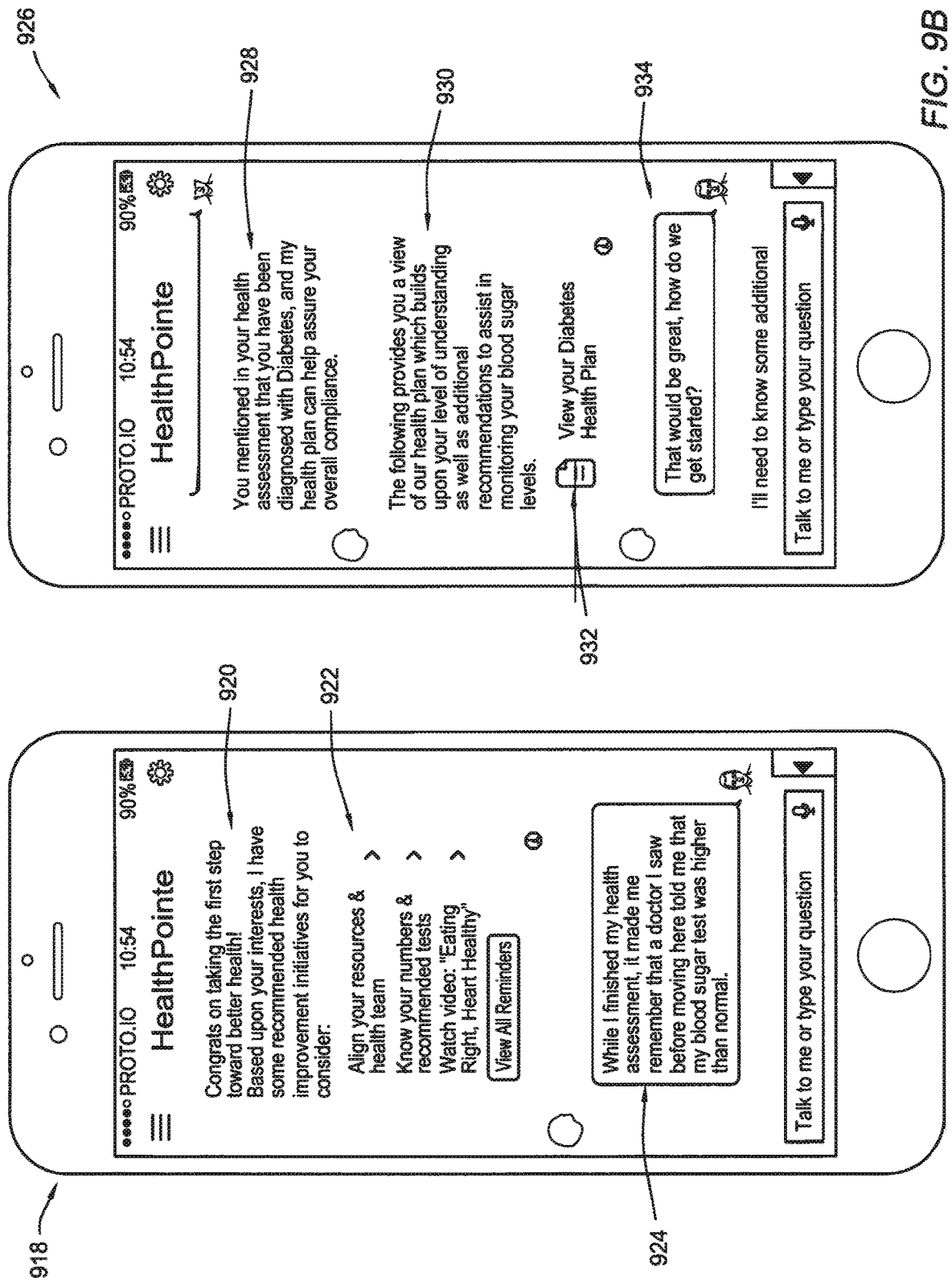

FIGS. 9A-9B illustrate aspects of a conversational stream, in accordance with various embodiments. In particular, FIG. 9A displays an example conversational stream between a user and the cognitive agent 110. The screen shot 902 is an example of a dialogue that unfolds between a user and the cognitive agent 110, after the user has registered with the cognitive intelligence platform 102. In the screen shot 902, the cognitive agent 110 begins by stating "Welcome, would you like to watch a video to help you better understand my capabilities" (element 904). The cognitive agent provides an option to watch the video (element 906). In response, the user inputs text "that's quite impressive" (element 908). In various embodiments, the user inputs text using the input box 916, which instructs the user to "Talk to me or type your question".

Next, the cognitive agent 110 says "Thank you. I look forward to helping you meet your health goals!" (element 910). At this point, the cognitive agent 110 can probe the user for additional data by offering a health assessment survey (e.g., a microsurvey) (element 914). The cognitive agent 110 prompts the user to fill out the health assessment by stating: "To help further personalize your health improvement experience, I would like to start by getting to know you and your health priorities. The assessment will take about 10 minutes. Let's get started!" (element 912).

In FIG. 9B, an additional conversational stream between the user and the cognitive agent 110 is shown. In this example conversational stream, the user previously completed a health assessment survey. The conversational stream can follow the example conversational stream discussed in FIG. 9A.

In the screen shot 918, the cognitive agent acknowledges the user's completion of the health assessment survey (element 920) and provides additional resources to the user (element 922). In element 920, the cognitive agent states: "Congrats on taking the first step toward better health! Based upon your interest, I have some recommended health improvement initiatives for you to consider," and presents the health improvement initiatives. In the example conversational stream, the user gets curious about a particular aspect of his health and states: "While I finished my health assessment, it made me remember that a doctor I saw before moving here told me that my blood sugar test was higher than normal." (element 924). After receiving the statement in element 924, the cognitive agent 110 treats the statement as an originating question and undergoes an initial round of analysis (and additional rounds of analysis as needed) as described above.

The cognitive agent 110 presents an answer as shown in screen shot 926. For example, the cognitive agent 110 states: "You mentioned in your health assessment that you have been diagnosed with Diabetes, and my health plan can help assure your overall compliance" (element 928). The cognitive agent further adds: "The following provides you a view of our health plan which builds upon your level of understanding as well as additional recommendations to assist in monitoring your blood sugar levels" (element 930). The cognitive agent 110 provides the user with the option to view his Diabetes Health Plan (element 932).

The user responds "That would be great, how do we get started" (element 934). The cognitive agent 110 receives the user's response as another originated question and undergoes an initial round of analysis (and additional rounds of analysis as needed) as described above. In the example screen shot 926, the cognitive agent 110 determines additional information is needed and prompts the user for additional information.

Figure 10:
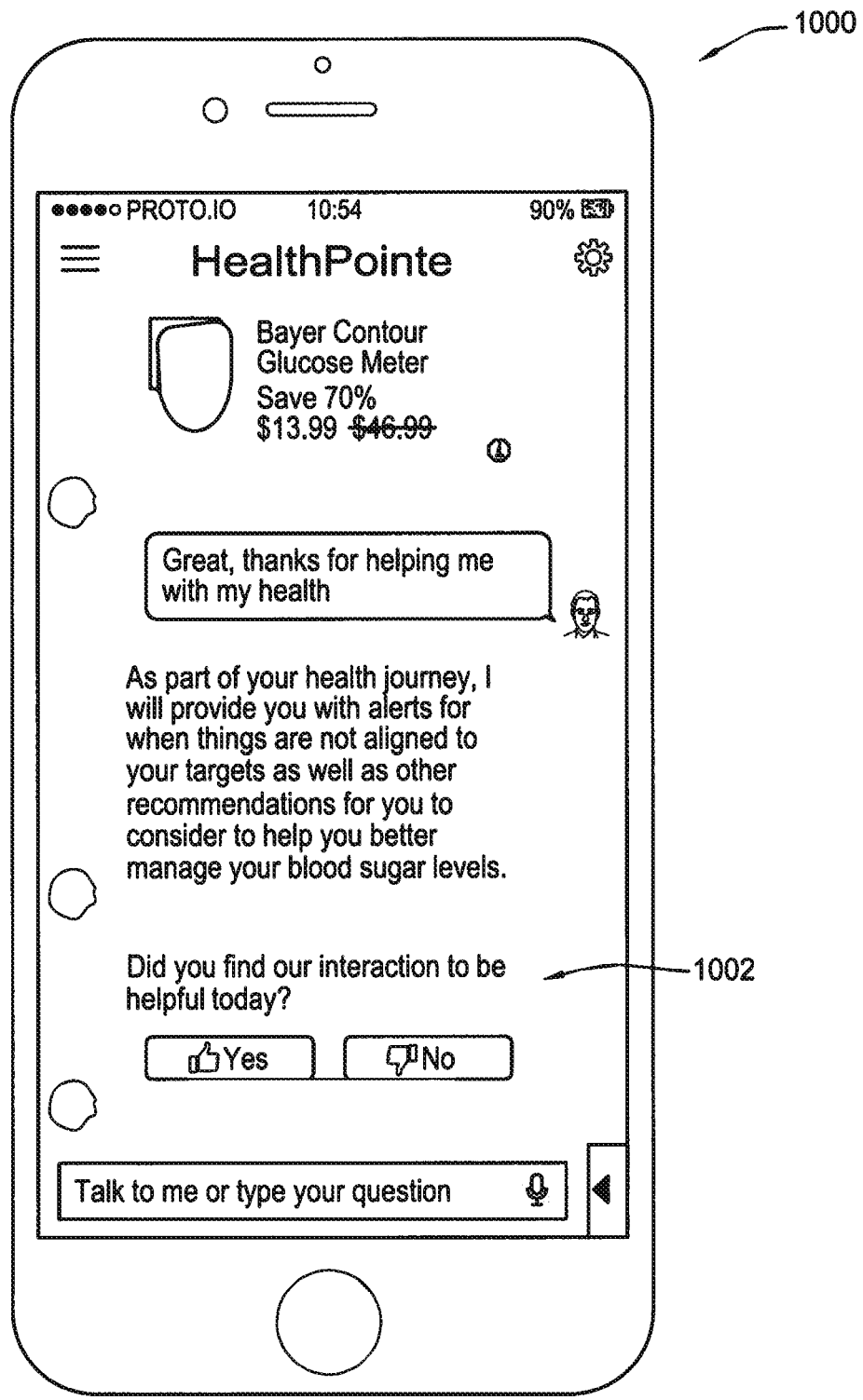
FIG. 10 shows aspects of a conversational stream, in accordance with various embodiments.

FIG. 10 illustrates an additional conversational stream, in accordance with various embodiments. In particular, in the screen shot 1000, the cognitive agent 110 elicit feedback (element 1002) to determine whether the information provided to the user was useful to the user.

FIG. 11 illustrates aspects of an action calendar, in accordance with various embodiments. The action calendar is managed through the conversational stream between the cognitive agent 110 and the user. The action calendar aligns to care and wellness protocols, which are personalized to the risk condition or wellness needs of the user. The action calendar is also contextually aligned (e.g., what is being required or searched by the user) and hyper local (e.g., aligned to events and services provided in the local community specific to the user).

Figure 12:
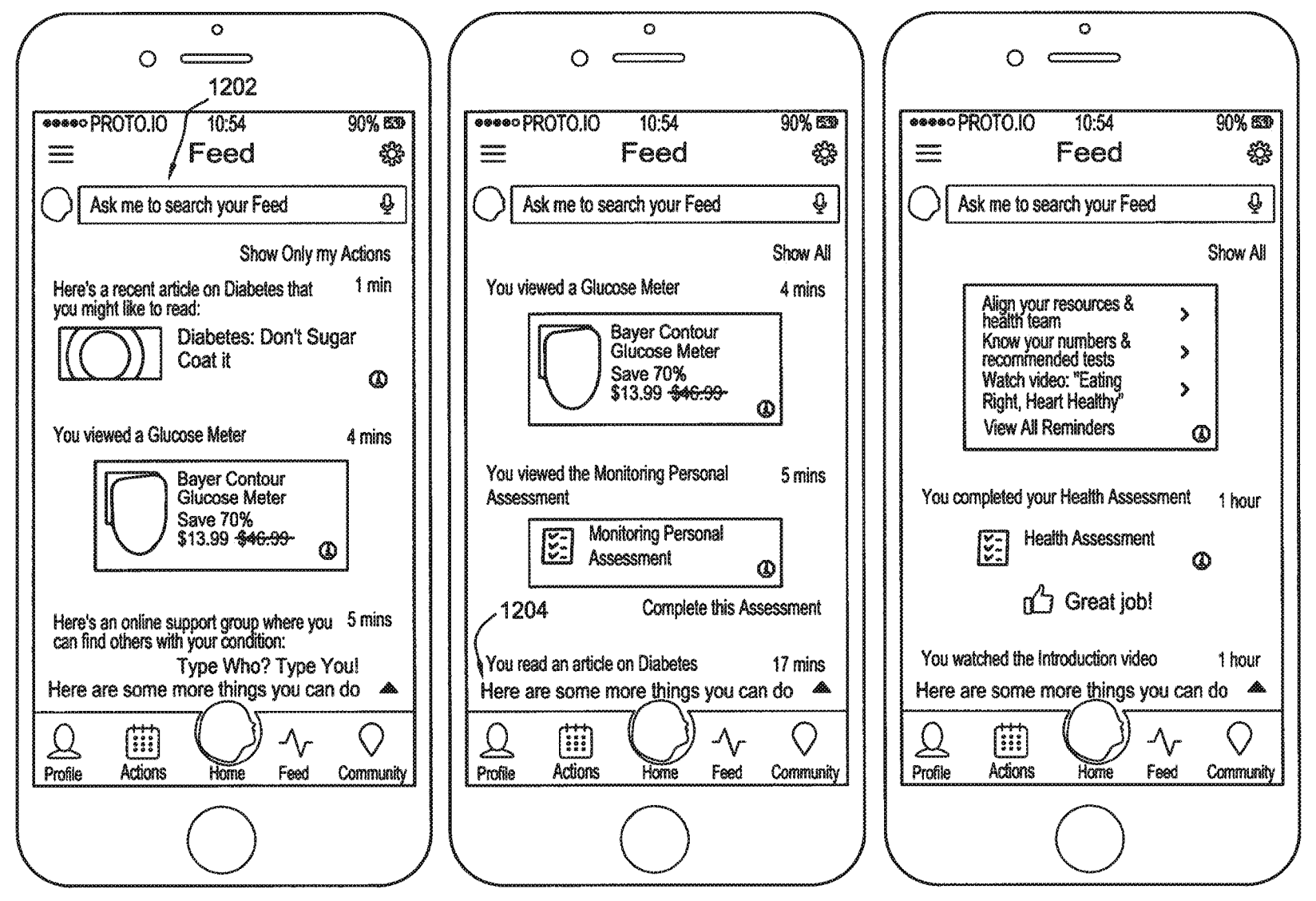

FIG. 12 illustrates aspects of a feed, in accordance with various embodiments. The feed allows a user to explore new opportunities and celebrate achieving goals (e.g., therapeutic or wellness goals). The feed provides a searchable interface (element 1202).

The feed provides an interface where the user accesses a personal log of activities the user is involved in. The personal log is searchable. For example, if the user reads an article recommended by the cognitive agent 110 and highlights passages, the highlighted passages are accessible through the search. Additionally, the cognitive agent 110 can initiate a conversational stream focused on subject matter related to the highlighted passages.

The feed provides an interface to celebrate mini achievements and successes in the user's personal goals (e.g., therapeutic or wellness goals). In the feed, the cognitive agent 110 is still available (ribbon 1204) to help search, guide, or steer the user toward a therapeutic or wellness goal.

Figure 13:
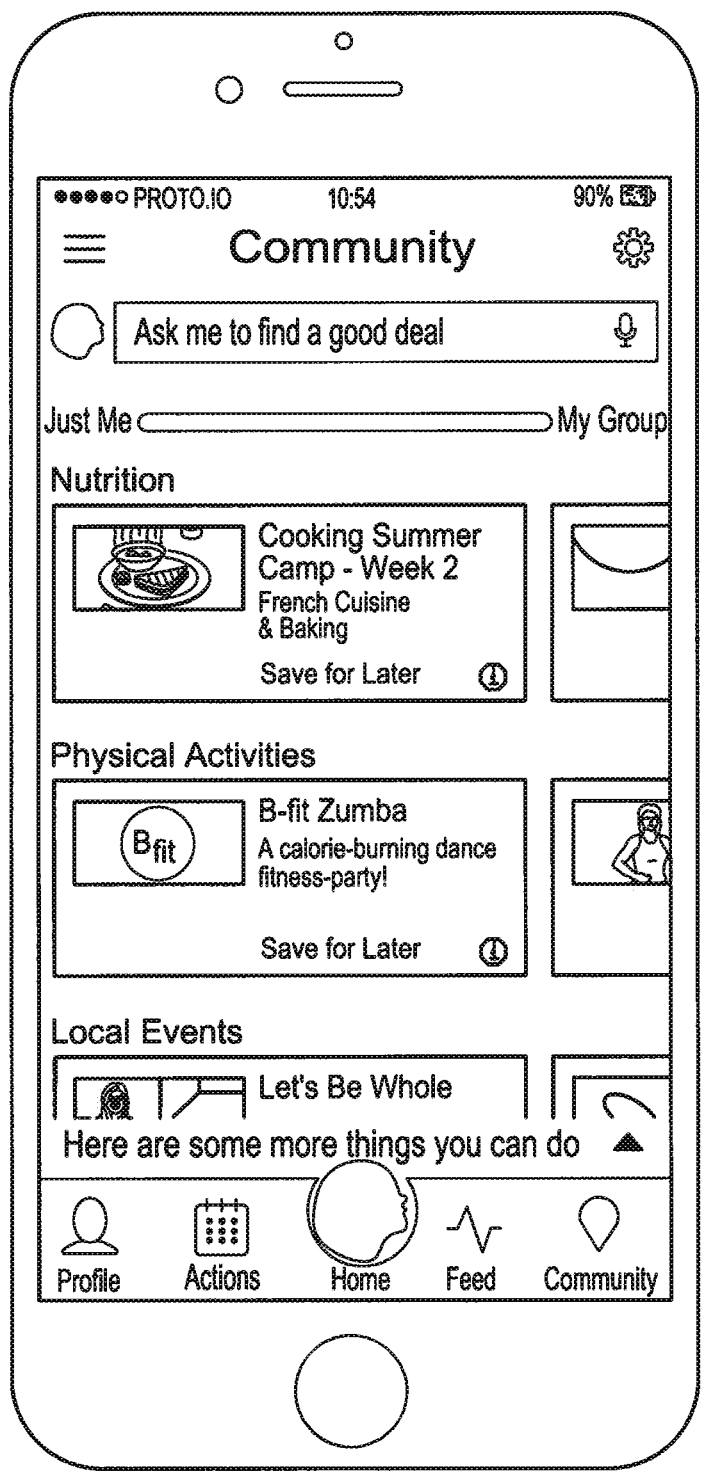
FIG. 13 shows aspects of a hyper-local community, in accordance with various embodiments.

FIG. 13 illustrates aspects of a hyper-local community, in accordance with various embodiments. A hyper-local community is a digital community that is health and wellness focused and encourages the user to find opportunities for themselves and get involved in a community that is physically close to the user. The hyper-local community allows a user to access a variety of care and wellness resources within his community and example recommendations include: Nutrition; Physical Activities; Healthcare Providers; Educations; Local Events; Services; Deals and Stores; Charities; and Products offered within the community. The cognitive agent 110 optimizes suggestions which help the user progress towards a goal as opposed to providing open ended access to hyper-local assets. The recommendations are curated and monitored for relevance to the user, based on the user's goals and interactions between the user and the cognitive agent 110.

Accordingly, the cognitive intelligence platform provides several core features including:
1) the ability to identify an appropriate action plan using narrative style interactions that generates data that includes intent and causation and using narrative style interactions;
2) monitoring: integration of offline to online clinical results across the functional medicine clinical standards;
3) the knowledge cloud that includes a comprehensive knowledge base of thousands of health related topics, an educational guide to better health aligned to western and eastern culture;
4) coaching using artificial intelligence; and
5) profile and health store that offers a holistic profile of each consumers health risks and interactions, combined with a repository of services, products, lab tests, devices, deals, supplements, pharmacy & telemedicine.

Figure 14:
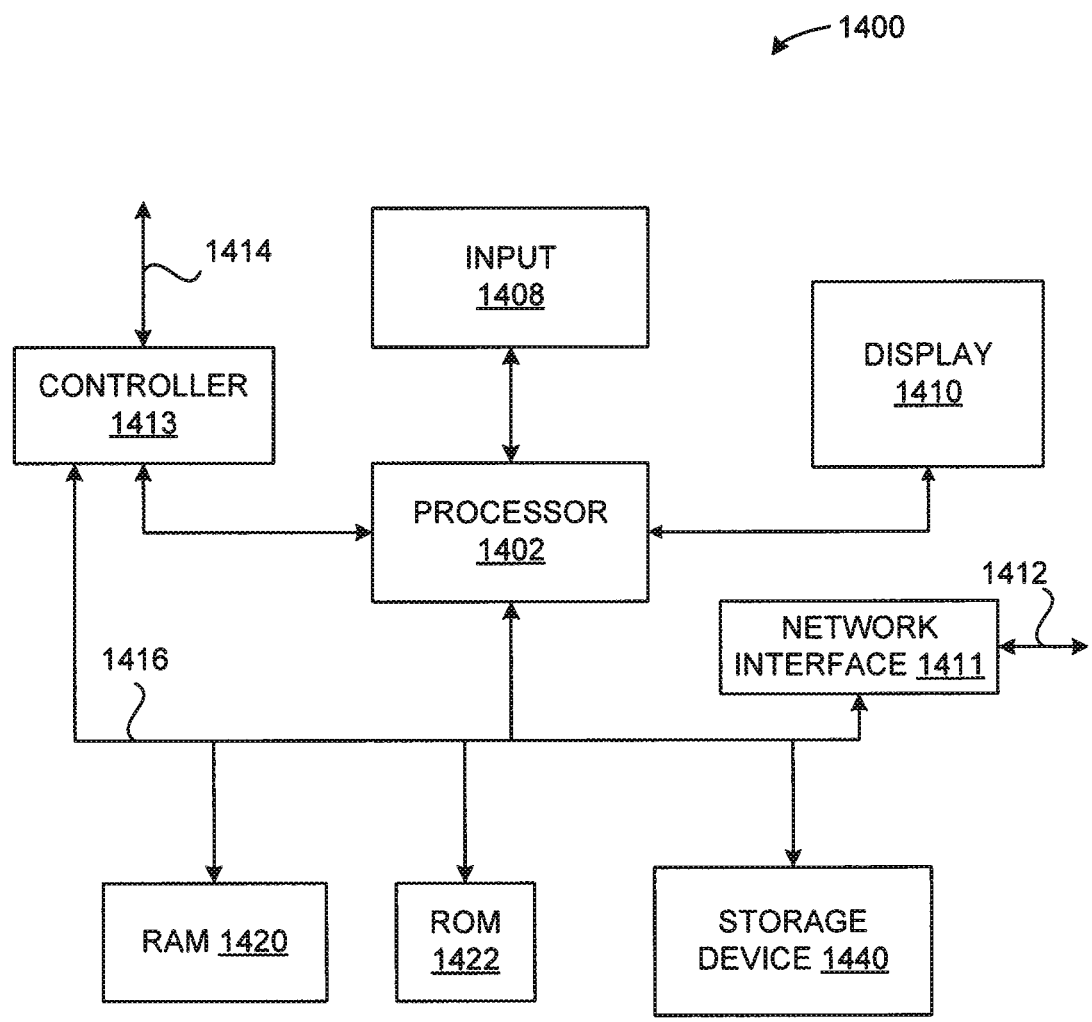
FIG. 14 illustrates a detailed view of a computing device that can represent the computing devices of FIG. 1 used to implement the various platforms and techniques described herein, according to some embodiments.

FIG. 14 illustrates a detailed view of a computing device 1400 that can be used to implement the various components described herein, according to some embodiments. In particular, the detailed view illustrates various components that can be included in the user device 104 illustrated in FIG. 1, as well as the several computing devices implementing the cognitive intelligence platform 102. Further, the computing device 1400 may include components that can be included in computing devices operated by the service provider 112 and/or the facility 114. As shown in FIG. 14, the computing device 1400 can include a processor 1402 that represents a microprocessor or controller for controlling the overall operation of the computing device 1400. The computing device 1400 can also include a user input device 1408 that allows a user of the computing device 1400 to interact with the computing device 1400. For example, the user input device 1408 can take a variety of forms, such as a button, keypad, dial, touch screen, audio input interface, visual/image capture input interface, input in the form of sensor data, and so on. Still further, the computing device 1400 can include a display 1410 that can be controlled by the processor 1402 to display information to the user. A data bus 1416 can facilitate data transfer between at least a storage device 1440, the processor 1402, and a controller 1413. The controller 1413 can be used to interface with and control different equipment through an equipment control bus 1414. The computing device 1400 can also include a network/bus interface 1411 that couples to a data link 1412. In the case of a wireless connection, the network/bus interface 1411 can include a wireless transceiver.

As noted above, the computing device 1400 also includes the storage device 1440, which can comprise a single disk or a collection of disks (e.g., hard drives), and includes a storage management module that manages one or more partitions within the storage device 1440. In some embodiments, storage device 1440 can include flash memory, semiconductor (solid-state) memory or the like. The computing device 1400 can also include a Random-Access Memory (RAM) 1420 and a Read-Only Memory (ROM) 1422. The ROM 1422 can store programs, utilities or processes to be executed in a non-volatile manner. The RAM 1420 can provide volatile data storage, and stores instructions related to the operation of processes and applications executing on the computing device.

Figure 15:
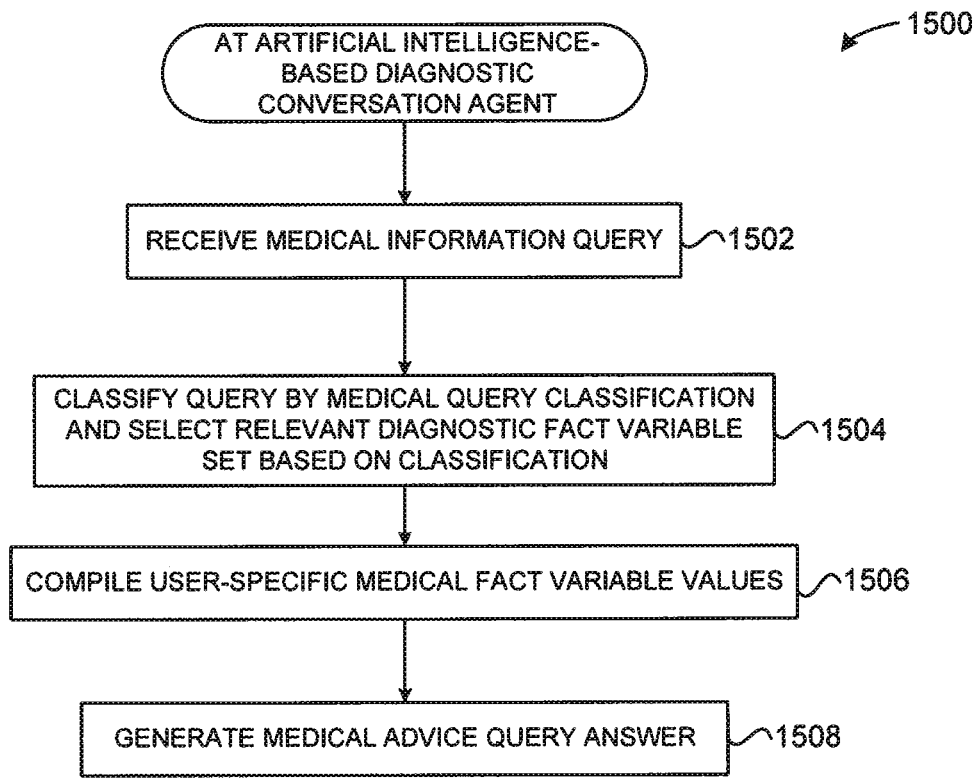
FIG. 15 shows a method, in accordance with various embodiments.

FIG. 15 shows a method (1500), in accordance with various embodiments, for answering a user-generated natural language medical information query based on a diagnostic conversational template.

In the method as shown in FIG. 15, an artificial intelligence-based diagnostic conversation agent receives a user-generated natural language medical information query as entered by a user through a user interface on a computer device (FIG. 15, block 1502). In some embodiments, the artificial intelligence-based diagnostic conversation agent is the conversation agent 110 of FIG. 1. In some embodiments the computer device is the mobile device 104 of FIG. 1. One example of a user-generated natural language medical information query as entered by a user through a user interface is the question "Is a blood sugar of 90 normal?" as shown in line 402 of FIG. 4. In some embodiments, receiving a user-generated natural language medical information query as entered by a user through a user interface on a computer device (FIG. 15, block 1502) is Step 1 as earlier discussed in the context of "Analyzing Conversational Context As Part of Conversational Analysis".

In response to the user-generated natural language medical information query, the artificial intelligence-based diagnostic conversation agent selects a diagnostic fact variable set relevant to generating a medical advice query answer for the user-generated natural language medical information query by classifying the user-generated natural language medical information query into one of a set of domain-directed medical query classifications associated with respective diagnostic fact variable sets (FIG. 15, block 1504). In some embodiments, the artificial intelligence-based diagnostic conversation agent selecting a diagnostic fact variable set relevant to generating a medical advice query answer for the user-generated natural language medical information query by classifying the user-generated natural language medical information query into one of a set of domain-directed medical query classifications associated with respective diagnostic fact variable sets (FIG. 15, block 1504) is accomplished through one or more of Steps 2-6 as earlier discussed in the context of "Analyzing Conversational Context As Part of Conversational Analysis".

FIG. 15 further shows compiling user-specific medical fact variable values for one or more respective medical fact variables of the diagnostic fact variable set (FIG. 15, block 1506). Compiling user-specific medical fact variable values for one or more respective medical fact variables of the diagnostic fact variable set (FIG. 15, block 1506) may include one or more of Steps 2-6 as earlier discussed in the context of "Analyzing Conversational Context As Part of Conversational Analysis".

In response to the user-specific medical fact variable values, the artificial intelligence-based diagnostic conversation agent generates a medical advice query answer in response to the user-generated natural language medical information query (FIG. 15, block 1508). In some embodiments, this is Step 7 as earlier discussed in the context of "Analyzing Conversational Context As Part of Conversational Analysis".

In some embodiments, compiling user-specific medical fact variable values (FIG. 15, block 1506) includes extracting a first set of user-specific medical fact variable values from a local user medical information profile associated with the user-generated natural language medical information query and requesting a second set of user specific medical fact variable values through natural-language questions sent to the user interface on the mobile device (e.g. the microsurvey data 206 of FIG. 2 that came from the microsurvey 116 of FIG. 1). The local user medical information profile can be the profile as generated in FIG. 7A at block 708.

In some embodiments, compiling user-specific medical fact variable values (FIG. 15, block 1506) includes extracting a third set of user-specific medical fact variable values that are lab result values from the local user medical information profile associated with the user generated natural language medical information query. The local user medical information profile can be the profile as generated in FIG. 7A at block 708.

In some embodiments, compiling user-specific medical fact variable values (FIG. 15, block 1506) includes extracting a fourth set of user-specific medical variable values from a remote medical data service profile associated with the local user medical information profile. The remote medical data service profile can be the service provider data 202 of FIG. 2, which can come from the service provider 112 of FIG. 1. The local user medical information profile can be the profile as generated in FIG. 7A at block 708.

In some embodiments, compiling user-specific medical fact variable values (FIG. 15, block 1506) includes extracting a fifth set of user-specific medical variable values from demographic characterizations provided by a remote data service analysis of the local user medical information profile. The remote demographic characterizations can be the service provider data 202 of FIG. 2, which can come from the service provider 112 of FIG. 1. The local user medical information profile can be the profile as generated in FIG. 7A at block 708.

In some embodiments, generating the medical advice query answer (FIG. 15, block 1508) includes providing a treatment action-item recommendation in response to user-specific medical fact values that may be non-responsive to the medical question presented in the user-generated natural language medical information query. Such an action could define an action plan based on the data compiled (FIG. 15, block 1506), as shown in FIG. 7C, block 758.

In some embodiments, generating the medical advice query answer (FIG. 15, block 1506) includes providing a medical education media resource in response to user-specific medical fact variable values that may be non-responsive to the medical question presented in the user-generated natural language medical information query. Such an action could serve to educate and inform the user, as in block 758 of FIG. 7C.

In some embodiments, selecting a diagnostic fact variable set relevant to generating a medical advice query answer for the user-generated natural language medical information query by classifying the user-generated natural language medical information query into one of a set of domain-directed medical query classifications associated with respective diagnostic fact variable sets (FIG. 15, block 1504) includes classifying the user-generated natural language medical information query into one of a set of domain-directed medical query classifications based on relevance to the local user medical information profile associated with the user-generated natural language medical information query. The local user medical information profile can be the profile as generated in FIG. 7A at block 708.

In some embodiments, the method (1500) for answering a user-generated natural language medical information query based on a diagnostic conversational template is implemented as a computer program product in a computer-readable medium.

In some embodiments, the system and method 1500 shown in FIG. 15 and described above is implemented on the computing device 1400 shown in FIG. 14.

Figure 16:
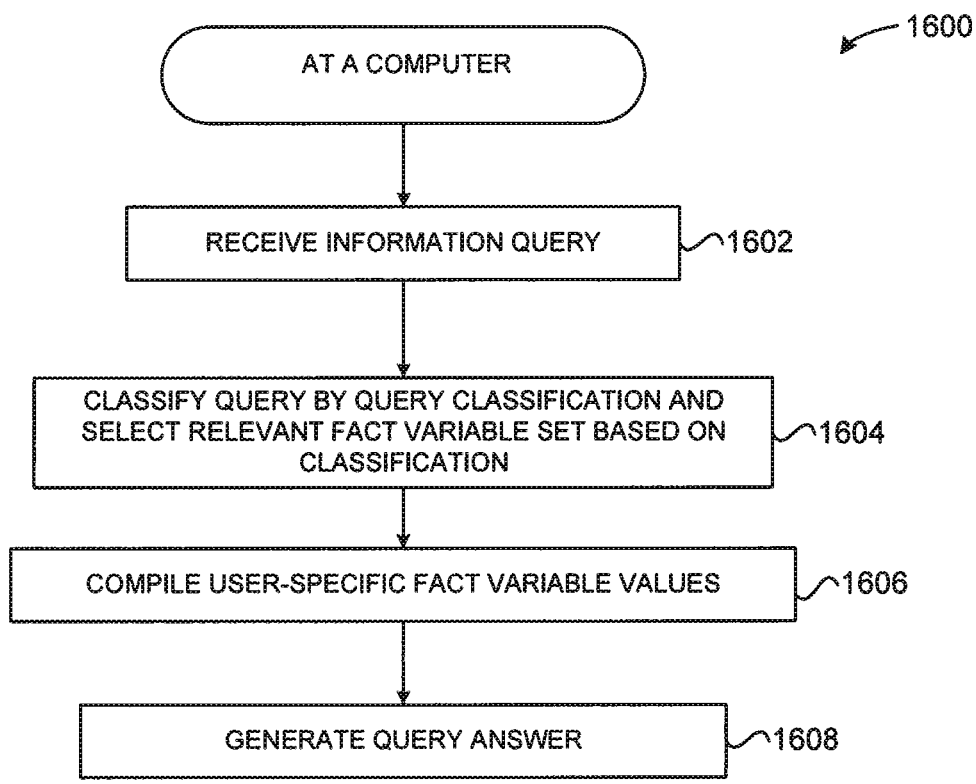
FIG. 16 shows a method, in accordance with various embodiments.

FIG. 16 shows a method (1600), in accordance with various embodiments, for answering a user-generated natural language query based on a conversational template.

In the method as shown in FIG. 16, an artificial intelligence-based conversation agent receives a user-generated natural language query as entered by a user through a user interface (FIG. 16, block 1602). In some embodiments, the artificial intelligence-based conversation agent is the conversation agent 110 of FIG. 1. In some embodiments, the user interface is on a computer device. In some embodiments the computer device is the mobile device 104 of FIG. 1. One example of a user-generated natural language query as entered by a user through a user interface is the question "Is a blood sugar of 90 normal?" as shown in line 402 of FIG. 4. In some embodiments, receiving a user-generated natural language query as entered by a user through a user interface on a computer device (FIG. 16, block 1602) is Step 1 as earlier discussed in the context of "Analyzing Conversational Context As Part of Conversational Analysis".

In response to the user-generated natural language query, the artificial intelligence-based conversation agent selects a fact variable set relevant to generating a query answer for the user-generated natural language query by classifying the user-generated natural language query into one of a set of domain-directed query classifications associated with respective fact variable sets (FIG. 16, block 1604). In some embodiments, the artificial intelligence-based conversation agent selecting a fact variable set relevant to generating a query answer for the user-generated natural language query by classifying the user-generated natural language query into one of a set of domain-directed query classifications associated with respective fact variable sets (FIG. 16, block 1604) is accomplished through one or more of Steps 2-6 as earlier discussed in the context of "Analyzing Conversational Context As Part of Conversational Analysis".

FIG. 16 further shows compiling user-specific variable values for one or more respective fact variables of the fact variable set (FIG. 16, block 1606). Compiling user-specific fact variable values for one or more respective fact variables of the fact variable set (FIG. 16, block 1606) may include one or more of Steps 2-6 as earlier discussed in the context of "Analyzing Conversational Context As Part of Conversational Analysis".

In response to the user-specific fact variable values, the artificial intelligence-based conversation agent generates a query answer in response to the user-generated natural language query (FIG. 16, block 1608). In some embodiments, this is Step 7 as earlier discussed in the context of "Analyzing Conversational Context As Part of Conversational Analysis".

In some embodiments, compiling user-specific fact variable values (FIG. 16, block 1606) includes extracting a first set of user-specific fact variable values from a local user profile associated with the user-generated natural language query and requesting a second set of user specific variable values through natural-language questions sent to the user interface on the mobile device (e.g. the microsurvey data 206 of FIG. 2 that came from the microsurvey 116 of FIG. 1). The local user profile can be the profile as generated in FIG. 7A at block 708. In some embodiments, the natural language questions sent to the user interface on the mobile device can be a part of a conversation template.

In some embodiments, compiling user-specific fact variable values (FIG. 16, block 1606) includes extracting a third set of user-specific fact variable values that are test result values from the local user profile associated with the user generated natural language query. The local user profile can be the profile as generated in FIG. 7A at block 708. In some embodiments, compiling user-specific fact variable values (FIG. 16, block 1606) includes extracting a fourth set of user-specific variable values from a remote data service profile associated with the local user profile. The remote data service profile can be the service provider data 202 of FIG. 2, which can come from the service provider 112 of FIG. 1. The local user profile can be the profile as generated in FIG. 7A at block 708.

In some embodiments, compiling user-specific fact variable values (FIG. 16, block 1606) includes extracting a fifth set of user-specific variable values from demographic characterizations provided by a remote data service analysis of the local user profile. The remote demographic characterizations can be the service provider data 202 of FIG. 2, which can come from the service provider 112 of FIG. 1. The local user profile can be the profile as generated in FIG. 7A at block 708.

In some embodiments, generating the query answer (FIG. 16, block 1608) includes providing an action-item recommendation in response to user-specific fact values that may be non-responsive to the question presented in the user-generated natural language query. Such an action could define an action plan based on the data compiled (FIG. 16, block 1606), as shown in FIG. 7C, block 758.

In some embodiments, generating the advice query answer (FIG. 16, block 1606) includes providing an education media resource in response to user-specific fact variable values that may be non-responsive to the question presented in the user-generated natural language query. Such an action could serve to educate and inform the user, as in block 758 of FIG. 7C.

In some embodiments, selecting a fact variable set relevant to generating a query answer for the user-generated natural language query by classifying the user-generated natural language query into one of a set of domain-directed query classifications associated with respective fact variable sets (FIG. 16, block 1604) includes classifying the user-generated natural language query into one of a set of domain-directed query classifications based on relevance to the local user profile associated with the user-generated natural language query. The local user profile can be the profile as generated in FIG. 7A at block 708.

In some embodiments, the method (1600) for answering a user-generated natural language query based on a conversational template is implemented as a computer program product in a computer-readable medium.

In some embodiments, the system and method shown in FIG. 16 and described above is implemented in the cognitive intelligence platform 102 shown in FIG. 1.

In the cognitive intelligence platform 102, a cognitive agent 110 is configured for receiving a user-generated natural language query at an artificial intelligence-based conversation agent from a user interface on a user device 104 (FIG. 16, block 1602).

A critical thinking engine 108 is configured for, responsive to content of the user-generated natural language query, selecting a fact variable set relevant to generating a query answer for the user-generated natural language query by classifying the user-generated natural language query into one of a set of domain-directed query classifications associated with respective fact variable sets (FIG. 16, block 1604).

Included is a knowledge cloud 106 that compiles user-specific fact variable values for one or more respective fact variables of the fact variable set (FIG. 16, block 1606).

Responsive to the fact variable values, the cognitive agent 110 is further configured for generating the query answer in response to the user-generated natural language query (FIG. 16, block 1606).

In some embodiments, the system and method 1600 shown in FIG. 16 and described above is implemented on the computing device 1400 shown in FIG. 14.

Figure 17:
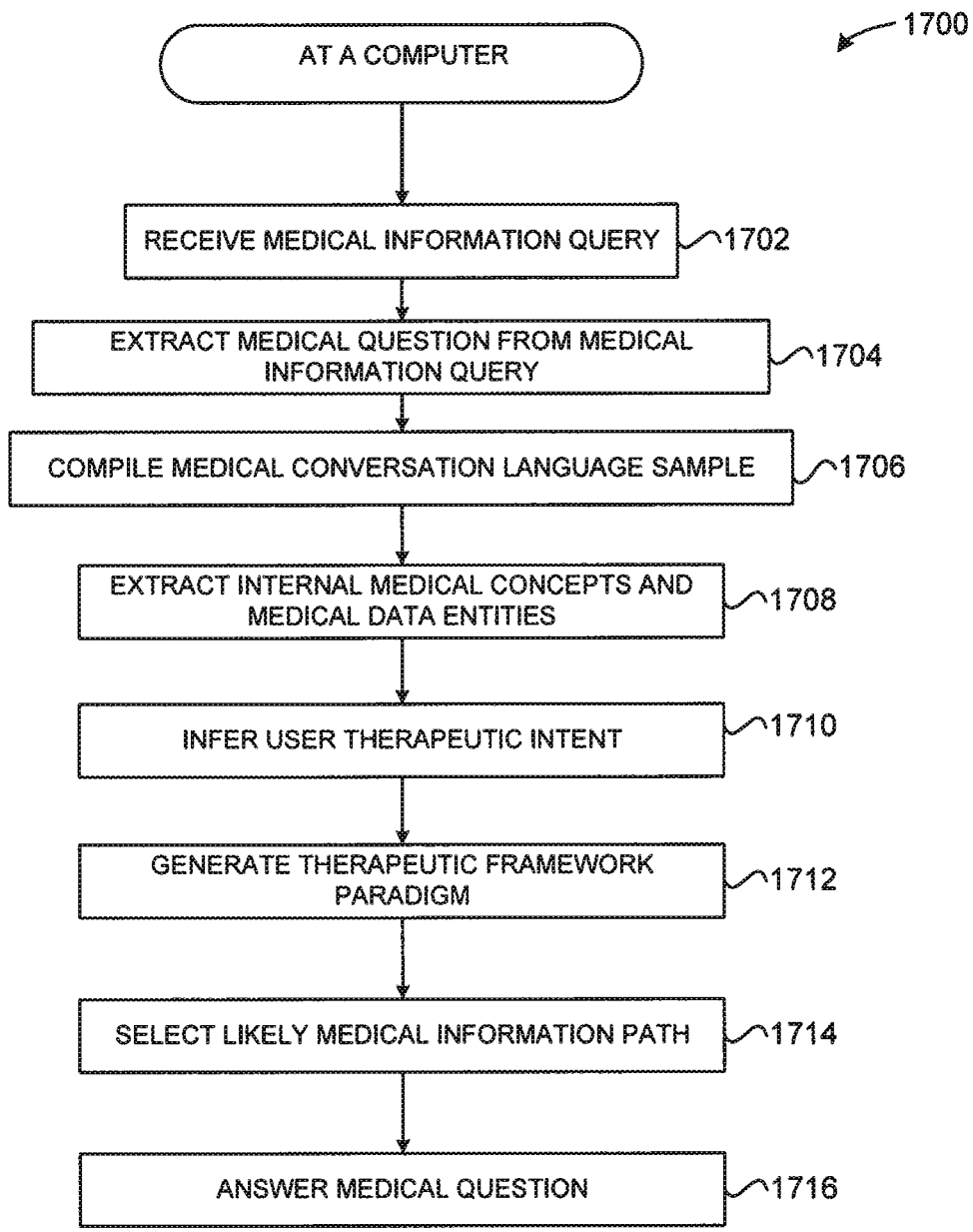
FIG. 17 shows a method, in accordance with various embodiments.

FIG. 17 shows a computer-implemented method 1700 for answering natural language medical information questions posed by a user of a medical conversational interface of a cognitive artificial intelligence system. In some embodiments, the method 1700 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14.

The method 1700 involves receiving a user-generated natural language medical information query from a medical conversational user interface at an artificial intelligence-based medical conversation cognitive agent (block 1702). In some embodiments, receiving a user-generated natural language medical information query from a medical conversational user interface at an artificial intelligence-based medical conversation cognitive agent (block 1702) is performed by a cognitive agent that is a part of the cognitive intelligence platform and is configured for this purpose. In some embodiments, the artificial intelligence-based diagnostic conversation agent is the conversation agent 110 of FIG. 1. One example of a user-generated natural language medical information query is "Is a blood sugar of 90 normal?" as shown in line 402 of FIG. 4. In some embodiments, the user interface is on the mobile device 104 of FIG. 1. In some embodiments, receiving a user-generated natural language medical information query from a medical conversational user interface at an artificial intelligence-based medical conversation cognitive agent (block 1702) is Step 1 as earlier discussed in the context of "Analyzing Conversational Context As Part of Conversational Analysis".

The method 1700 further includes extracting a medical question from a user of the medical conversational user interface from the user-generated natural language medical information query (block 1704). In some embodiments, extracting a medical question from a user of the medical conversational user interface from the user-generated natural language medical information query (block 1704) is performed by a critical thinking engine configured for this purpose. In some embodiments, the critical thinking engine is the critical thinking engine 108 of FIG. 1. In some embodiments, extracting a medical question from a user of the medical conversational user interface from the user-generated natural language medical information query (block 1704) is accomplished through one or more of Steps 2-6 as earlier discussed in the context of "Analyzing Conversational Context As Part of Conversational Analysis".

The method 1700 includes compiling a medical conversation language sample (block 1706). In some embodiments, compiling a medical conversation language sample (block 1706) is performed by a critical thinking engine configured for this purpose. In some embodiments, the critical thinking engine is the critical thinking engine 108 of FIG. 1. The medical conversation language sample can include items of health-information-related-text derived from a health-related conversation between the artificial intelligence-based medical conversation cognitive agent and the user. In some embodiments compiling a medical conversation language sample (block 1706) is accomplished through one or more of Steps 2-6 as earlier discussed in the context of "Analyzing Conversational Context As Part of Conversational Analysis".

The method 1700 involves extracting internal medical concepts and medical data entities from the medical conversation language sample (block 1708). In some embodiments, extracting internal medical concepts and medical data entities from the medical conversation language sample (block 1708) is performed by a critical thinking engine configured for this purpose. In some embodiments, the critical thinking engine is the critical thinking engine 108 of FIG. 1. The internal medical concepts can include descriptions of medical attributes of the medical data entities. In some embodiments, extracting internal medical concepts and medical data entities from the medical conversation language sample (block 1708) is accomplished through one or more of Steps 2-6 as earlier discussed in the context of "Analyzing Conversational Context As Part of Conversational Analysis".

The method 1700 involves inferring a therapeutic intent of the user from the internal medical concepts and the medical data entities (block 1710). In some embodiments, inferring a therapeutic intent of the user from the internal medical concepts and the medical data entities (block 1710) is performed by a critical thinking engine configured for this purpose. In some embodiments, the critical thinking engine is the critical thinking engine 108 of FIG. 1. In some embodiments, inferring a therapeutic intent of the user from the internal medical concepts and the medical data entities (block 1710) is accomplished as in Step 2 as earlier discussed in the context of "Analyzing Conversational Context As Part of Conversational Analysis".

The method 1700 includes generating a therapeutic paradigm logical framework 1800 for interpreting of the medical question (block 1712). In some embodiments, generating a therapeutic paradigm logical framework 1800 for interpreting of the medical question (block 1712) is performed by a critical thinking engine configured for this purpose. In some embodiments, the critical thinking engine is the critical thinking engine 108 of FIG. 1. In some embodiments, generating a therapeutic paradigm logical framework 1800 for interpreting of the medical question (block 1712) is accomplished as in Step 5 as earlier discussed in the context of "Analyzing Conversational Context As Part of Conversational Analysis".

Figure 18:
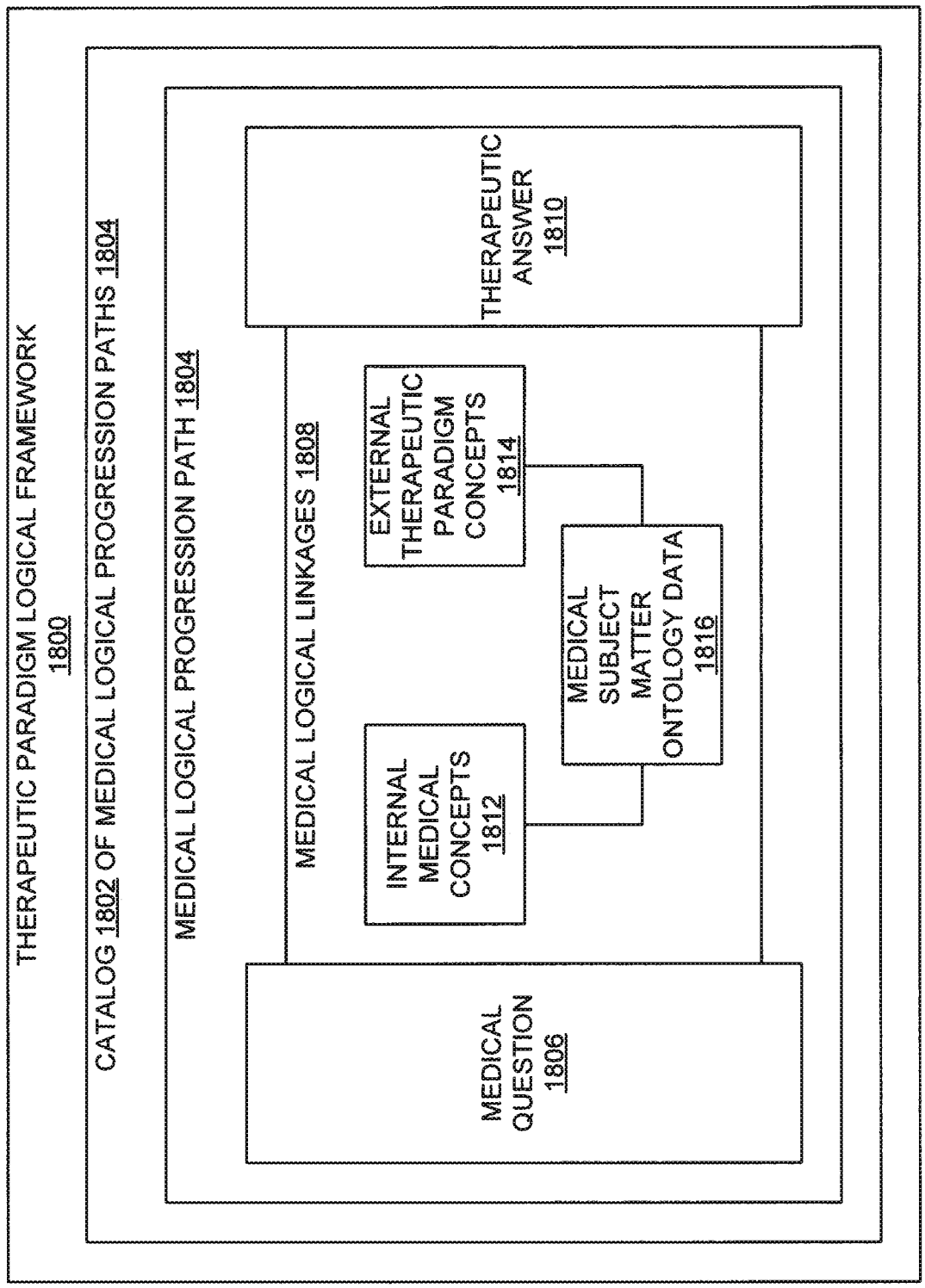
FIG. 18 shows a therapeutic paradigm logical framework, in accordance with various embodiments

FIG. 18 shows an example therapeutic paradigm logical framework 1800. The therapeutic paradigm logical framework 1800 includes a catalog 1802 of medical logical progression paths 1804 from the medical question 1806 to respective therapeutic answers 1810.

Each of the medical logical progression paths 1804 can include one or more medical logical linkages 1808 from the medical question 1806 to a therapeutic path-specific answer 1810.

The medical logical linkages 1808 can include the internal medical concepts 1812 and external therapeutic paradigm concepts 1814 derived from a store of medical subject matter ontology data 1816. In some embodiments, the store of subject matter ontology data 1816 is contained in a knowledge cloud. In some embodiments, the knowledge cloud is the knowledge cloud 102 of FIGS. 1 and 2. In some embodiments, the subject matter ontology data 1816 is the subject matter ontology data 216 of FIG. 2. In some embodiments, the subject matter ontology data 1816 includes the subject matter ontology 300 of FIG. 3.

The method 1700 shown in FIG. 17 further includes selecting a likely medical information path from among the medical logical progression paths 1804 to a likely path-dependent medical information answer based at least in part upon the therapeutic intent of the user (block 1714). In some embodiments, selecting a likely medical information path from among the medical logical progression paths 1804 to a likely path-dependent medical information answer based at least in part upon the therapeutic intent of the user (block 1714 is performed by a critical thinking engine configured for this purpose. In some embodiments, the critical thinking engine is the critical thinking engine 108 of FIG. 1. The selection can also be based in part upon the sufficiency of medical diagnostic data to complete the medical logical linkages 1808. In some embodiments, selection can also be based in part upon the sufficiency of medical diagnostic data to complete the medical logical linkages 1808 can be performed by a critical thinking engine that is further configured for this purpose. In some embodiments, the critical thinking engine is the critical thinking engine 108 of FIG. 1. The medical diagnostic data can include user-specific medical diagnostic data. The selection can also be based in part upon treatment sub-intents including tactical constituents related to the therapeutic intent of the user by the store of medical subject matter ontology data 1816. In some embodiments, selection based in part upon treatment sub-intents including tactical constituents related to the therapeutic intent of the user by the store of medical subject matter ontology data 1816 can be performed by a critical thinking engine further configured for this purpose. In some embodiments, the critical thinking engine is the critical thinking engine 108 of FIG. 1. The selection can further occur after requesting additional medical diagnostic data from the user. An example of requesting additional medical diagnostic data from the user is shown in FIG. 4 on line 406 "I need some additional information in order to answer this question, was this an in-home glucose test or was it done by a lab or testing service". In some embodiments, the process of selection after requesting additional medical diagnostic data from the user can be performed by a critical thinking engine further configured for this purpose. In some embodiments, the critical thinking engine is the critical thinking engine 108 of FIG. 1. In some embodiments, selecting a likely medical information path from among the medical logical progression paths 1804 to a likely path-dependent medical information answer based at least in part upon the therapeutic intent of the user (block 1714) is accomplished through one or more of Steps 5-6 as earlier discussed in the context of "Analyzing Conversational Context As Part of Conversational Analysis".

The method 1700 involves answering the medical question by following the likely medical information path to the likely path-dependent medical information answer (block 1716). In some embodiments, answering the medical question by following the likely medical information path to the likely path-dependent medical information answer (block 1716) is performed by a critical thinking engine configured for this purpose. In some embodiments, the critical thinking engine is the critical thinking engine 108 of FIG. 1. In some embodiments, answering the medical question by following the likely medical information path to the likely path-dependent medical information answer (block 1716) is accomplished as in Step 7 as earlier discussed in the context of "Analyzing Conversational Context As Part of Conversational Analysis".

The method 1700 can further include relating medical inference groups of the internal medical concepts. In some embodiments, relating medical inference groups of the internal medical concepts is performed by a critical thinking engine further configured for this purpose. In some embodiments, the critical thinking engine is the critical thinking engine 108 of FIG. 1. Relating medical inference groups of the internal medical concepts can be based at least in part on shared medical data entities for which each internal medical concept of a medical inference group of internal medical concepts describes a respective medical data attribute. In some embodiments, relating medical inference groups of the internal medical concepts based at least in part on shared medical data entities for which each internal medical concept of a medical inference group of internal medical concepts describes a respective medical data attribute can be performed by a critical thinking engine further configured for this purpose. In some embodiments, the critical thinking engine is the critical thinking engine 108 of FIG. 1.

In some embodiments, the method 1700 of FIG. 17 is implemented as a computer program product in a computer-readable medium.

Figure 19:
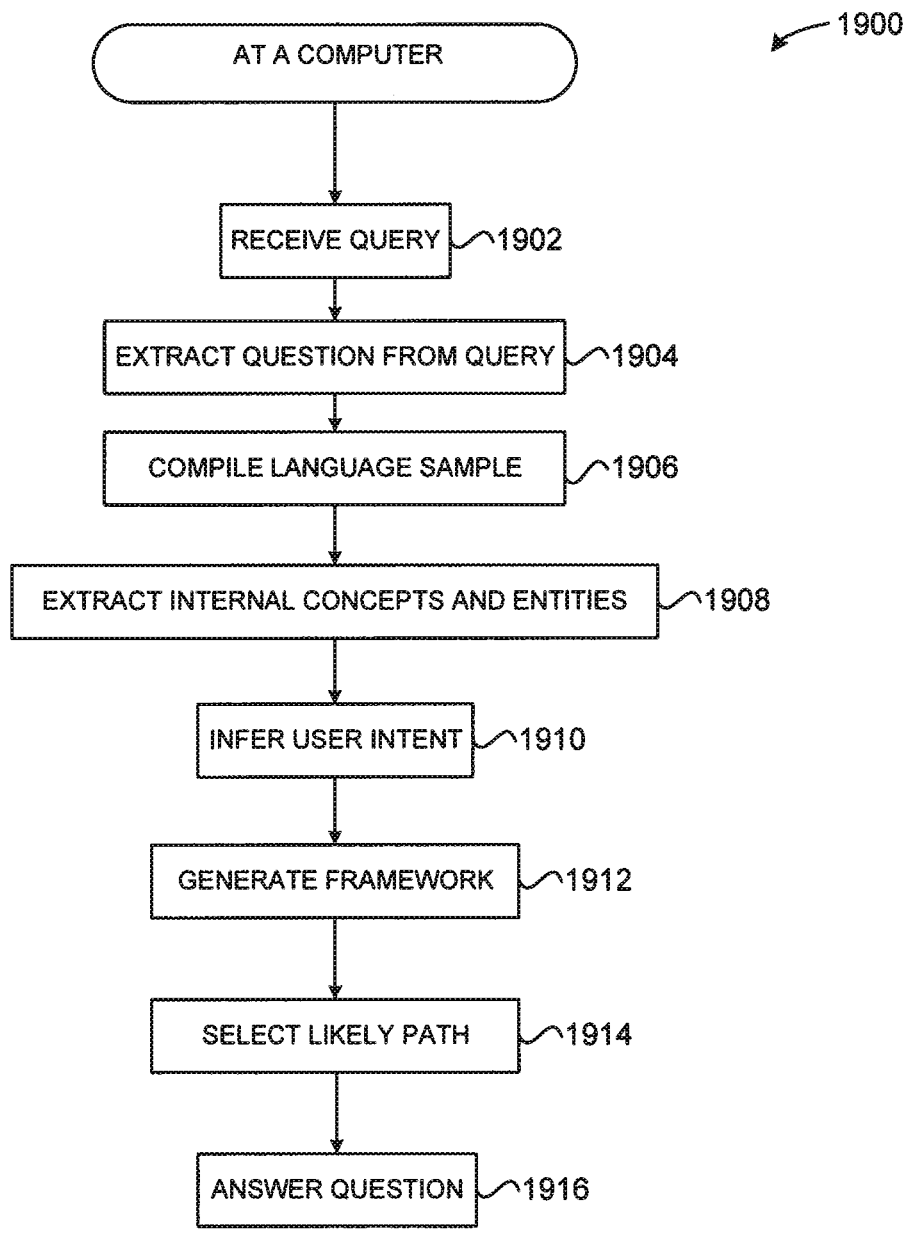
FIG. 19 shows a method, in accordance with various embodiments.

FIG. 19 shows a computer-implemented method 1900 for answering natural language questions posed by a user of a conversational interface of an artificial intelligence system. In some embodiments, the method 1900 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14.

The method 1900 involves receiving a user-generated natural language query at an artificial intelligence-based conversation agent (block 1902). In some embodiments, receiving a user-generated natural language query from a conversational user interface at an artificial intelligence-based conversation cognitive agent (block 1902) is performed by a cognitive agent that is a part of the cognitive intelligence platform and is configured for this purpose. In some embodiments, the artificial intelligence-based conversation agent is the conversation agent 110 of FIG. 1. One example of a user-generated natural language query is "Is a blood sugar of 90 normal?" as shown in line 402 of FIG. 4. In some embodiments, the user interface is on the mobile device 104 of FIG. 1. In some embodiments, receiving a user-generated natural language query from a conversational user interface at an artificial intelligence-based conversation cognitive agent (block 1902) is Step 1 as earlier discussed in the context of "Analyzing Conversational Context As Part of Conversational Analysis".

The method 1900 further includes extracting a question from a user of the conversational user interface from the user-generated natural language query (block 1904). In some embodiments, extracting a question from a user of the conversational user interface from the user-generated natural language query (block 1904) is performed by a critical thinking engine configured for this purpose. In some embodiments, the critical thinking engine is the critical thinking engine 108 of FIG. 1. In some embodiments, extracting a question from a user of the conversational user interface from the user-generated natural language query (block 1904) is accomplished through one or more of Steps 2-6 as earlier discussed in the context of "Analyzing Conversational Context As Part of Conversational Analysis".

The method 1900 includes compiling a language sample (block 1906). In some embodiments, compiling a language sample (block 1906) is performed by a critical thinking engine configured for this purpose. In some embodiments, the critical thinking engine is the critical thinking engine 108 of FIG. 1. The language sample can include items of health-information-related-text derived from a health-related conversation between the artificial intelligence-based conversation cognitive agent and the user. In some embodiments compiling a language sample (block 1906) is accomplished through one or more of Steps 2-6 as earlier discussed in the context of "Analyzing Conversational Context As Part of Conversational Analysis".

The method 1900 involves extracting internal concepts and entities from the language sample (block 1908). In some embodiments, extracting internal concepts and entities from the language sample (block 1908) is performed by a critical thinking engine configured for this purpose. In some embodiments, the critical thinking engine is the critical thinking engine 108 of FIG. 1. The internal concepts can include descriptions of attributes of the entities. In some embodiments, extracting internal concepts and entities from the language sample (block 1908) is accomplished through one or more of Steps 2-6 as earlier discussed in the context of "Analyzing Conversational Context As Part of Conversational Analysis".

The method 1900 involves inferring an intent of the user from the internal concepts and the entities (block 1910). In some embodiments, inferring an intent of the user from the internal concepts and the entities (block 1910) is performed by a critical thinking engine configured for this purpose. In some embodiments, the critical thinking engine is the critical thinking engine 108 of FIG. 1. In some embodiments, inferring an intent of the user from the internal concepts and the entities (block 1910) is accomplished as in Step 2 as earlier discussed in the context of "Analyzing Conversational Context As Part of Conversational Analysis".

The method 1900 includes generating a logical framework 2000 for interpreting of the question (block 1912). In some embodiments, generating a logical framework 2000 for interpreting of the question (block 1912) is performed by a critical thinking engine configured for this purpose. In some embodiments, the critical thinking engine is the critical thinking engine 108 of FIG. 1. In some embodiments, generating a logical framework 2000 for interpreting of the question (block 1912) is accomplished as in Step 5 as earlier discussed in the context of "Analyzing Conversational Context As Part of Conversational Analysis".

Figure 20:
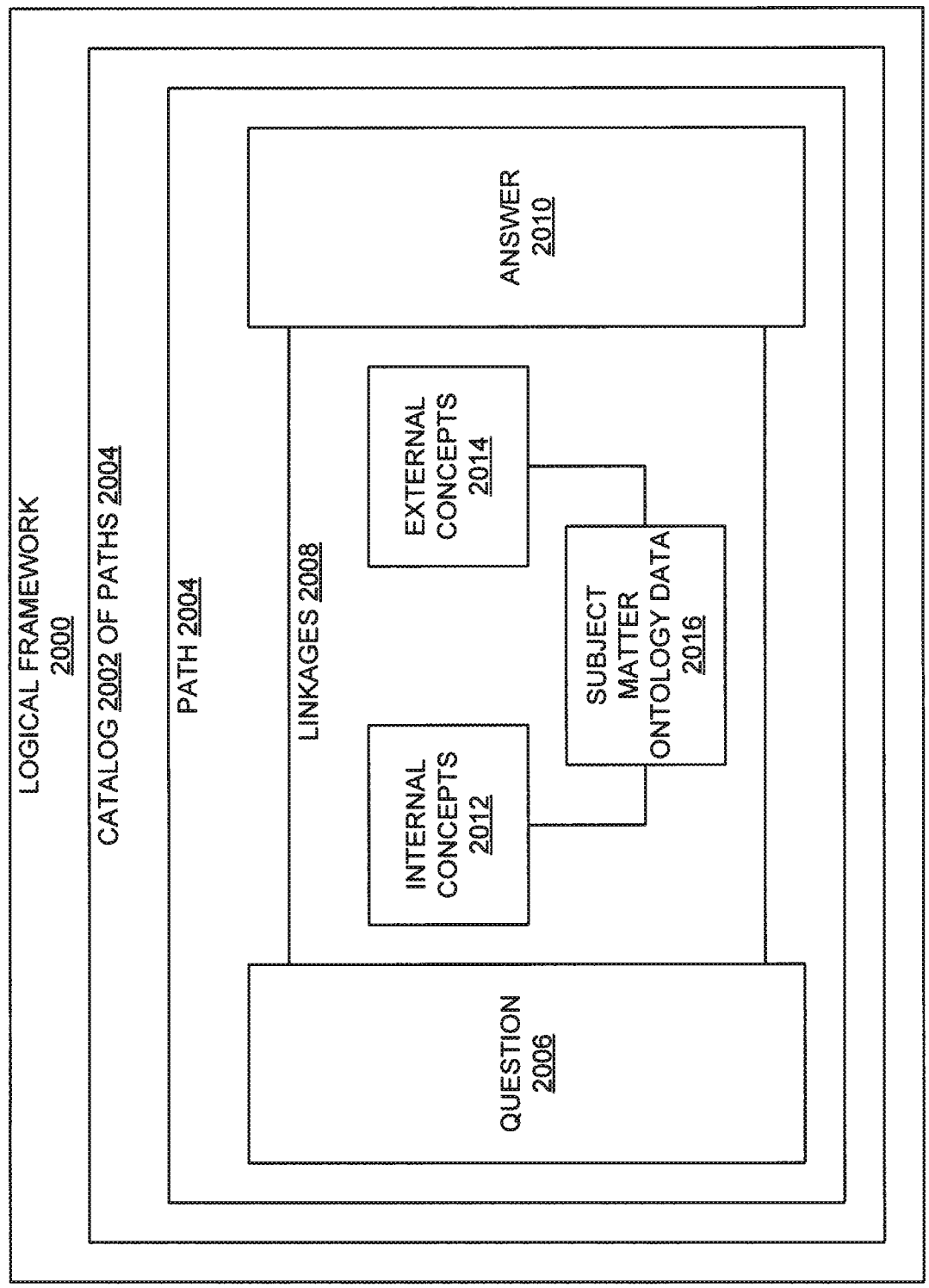
FIG. 20 shows a paradigm logical framework, in accordance with various embodiments.

FIG. 20 shows an example logical framework 2000. The logical framework 2000 includes a catalog 2002 of paths 2004 from the question 2006 to respective answers 2010.

Each of the paths 2004 can include one or more linkages 2008 from the question 2006 to a path-specific answer 2010.

The linkages 2008 can include the internal concepts 2012 and external concepts 2014 derived from a store of subject matter ontology data 2016. In some embodiments, the store of subject matter ontology data 2016 is contained in a knowledge cloud. In some embodiments, the knowledge cloud is the knowledge cloud 102 of FIGS. 1 and 2. In some embodiments, the subject matter ontology data 2016 is the subject matter ontology data 216 of FIG. 2. In some embodiments, the subject matter ontology data 2016 includes the subject matter ontology 300 of FIG. 3.

The method 1900 shown in FIG. 19 further includes selecting a likely path from among the paths 2004 to a likely path-dependent answer based at least in part upon the intent of the user (block 1914). In some embodiments, selecting a likely path from among the paths 2004 to a likely path-dependent answer based at least in part upon the intent of the user (block 1914 is performed by a critical thinking engine configured for this purpose. In some embodiments, the critical thinking engine is the critical thinking engine 108 of FIG. 1. The selection can also be based in part upon the sufficiency of data to complete the linkages 2008. In some embodiments, selection can also be based in part upon the sufficiency of data to complete the linkages 2008 can be performed by a critical thinking engine that is further configured for this purpose. In some embodiments, the critical thinking engine is the critical thinking engine 108 of FIG. 1. The data can include user-specific data. The selection can also be based in part upon treatment sub-intents including tactical constituents related to the intent of the user by the store of subject matter ontology data 2016. In some embodiments, selection based in part upon treatment sub-intents including tactical constituents related to the intent of the user by the store of subject matter ontology data 2016 can be performed by a critical thinking engine further configured for this purpose. In some embodiments, the critical thinking engine is the critical thinking engine 108 of FIG. 1. The selection can further occur after requesting additional data from the user. An example of requesting additional data from the user is shown in FIG. 4 on line 406 "I need some additional information in order to answer this question, was this an in-home glucose test or was it done by a lab or testing service". In some embodiments, the process of selection after requesting additional data from the user can be performed by a critical thinking engine further configured for this purpose. In some embodiments, the critical thinking engine is the critical thinking engine 108 of FIG. 1. In some embodiments, selecting a likely path from among the paths 2004 to a likely path-dependent answer based at least in part upon the intent of the user (block 1914) is accomplished through one or more of Steps 5-6 as earlier discussed in the context of "Analyzing Conversational Context As Part of Conversational Analysis".

The method 1900 involves answering the question by following the likely path to the likely path-dependent answer (block 1916). In some embodiments, answering the question by following the likely path to the likely path-dependent answer (block 1916) is performed by a critical thinking engine configured for this purpose. In some embodiments, the critical thinking engine is the critical thinking engine 108 of FIG. 1. In some embodiments, answering the question by following the likely path to the likely path-dependent answer (block 1916) is accomplished as in Step 7 as earlier discussed in the context of "Analyzing Conversational Context As Part of Conversational Analysis".

The method 1900 can further include relating inference groups of the internal concepts. In some embodiments, relating inference groups of the internal concepts is performed by a critical thinking engine further configured for this purpose. In some embodiments, the critical thinking engine is the critical thinking engine 108 of FIG. 1. Relating inference groups of the internal concepts can be based at least in part on shared entities for which each internal concept of an inference group of internal concepts describes a respective data attribute. In some embodiments, relating inference groups of the internal concepts based at least in part on shared entities for which each internal concept of an inference group of internal concepts describes a respective data attribute can be performed by a critical thinking engine further configured for this purpose. In some embodiments, the critical thinking engine is the critical thinking engine 108 of FIG. 1.

In some embodiments, the method 1900 of FIG. 19 is implemented as a computer program product in a computer-readable medium.

Figure 21:
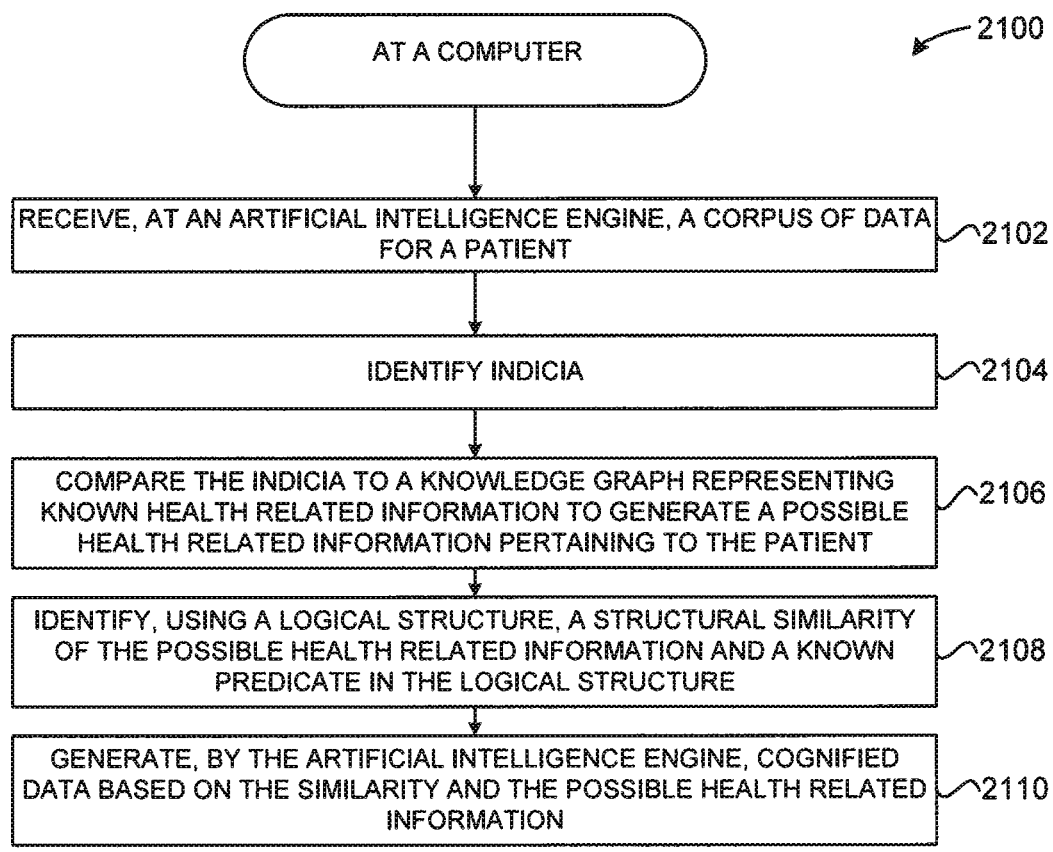
FIG. 21 shows a method for cognifying unstructured data, in accordance with various embodiments.

FIG. 21 shows a computer-implemented method 2100 for generated cognified data using unstructured data. In some embodiments, the method 2100 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 2100 may include operations that are implemented in computer instructions stored in a memory and executed by a processor of a computing device.

At block 2102, the processing device may receive, at an artificial intelligence engine, a corpus of data for a patient. The corpus of data may represent unstructured data. The corpus of data may include a set of strings of characters. The corpus of data may be patient notes in an electronic medical record entered by a physician. In some embodiments, an application programming interface (API) may be used to interface with an electronic medical record system used by the physician. The API may retrieve one or more EMRs of the patient and extract the patient notes. The artificial intelligence engine may include the one or more machine learning models trained to generate cognified data based on unstructured data.

At block 2104, the processing device may identify indicia. The indicia may be identified by processing the strings of characters. The indicia may include a phrase, a predicate, a subject, an object (e.g., direct, indirect), a keyword, a cardinal, a number, a concept, an objective, a noun, a verb, or some combination thereof.

At block 2106, the processing device may compare the indicia to a knowledge graph representing known health related information to generate a possible health related information pertaining to the patient. In some embodiments, the indicia may be compared to numerous knowledge graphs each representing a different medical conditions. As discussed herein, the knowledge graphs may include respective nodes that include different known health related information about the medical conditions, and a logical structure that includes predicates that correlate the information in the respective knowledge graphs. The knowledge graphs and the logical structures may be generated by the one or more trained machine learning models using the known health related information. The knowledge graph may represent knowledge of a disease and the knowledge graph may include a set of concepts pertaining to the disease obtained from the known health related information and also includes relationships between the set of concepts. The known health related information associated with the nodes may be facts, concepts, complications, risks, causal effects, etc. pertaining to the medical conditions (e.g., diseases) represented by the knowledge graphs. The processing device may codify evidence-based health related guidelines pertaining to the diseases to generate the logical structures. The generated possible health related information may be a tag that is associated with the indicia in the unstructured data.

At block 2108, the processing device may identify, using the logical structure, a structural similarity of the possible health related information and a known predicate in the logical structure. The structural similarity may be used to identify a certain pattern. The pattern may pertain to treatment, quality of care, risk adjustment, orders, referral, education and content patterns, and the like. The structural similarity and/or the pattern may be used to cognify the corpus of data.

At block 2110, the processing device may generate, by the artificial intelligence engine, cognified data based on the structural similarity. In some embodiments, the cognified data may include a health related summary of the possible health related information. The health related summary may include conclusions, concepts, recommendations, identified gaps in the treatment plan, identified gaps in risk analysis, identified gaps in quality of care, and so forth pertaining to one or more medical conditions represented by one or more knowledge graphs that include the logic structure having the known predicate that is structurally similar to the possible health related information.

In some embodiments, generating the cognified data may include generating at least one new string of characters representing a statement pertaining to the possible health related information. Also, the artificial intelligence engine executed by the processing device may include the at least one new string of characters in the health related summary of the possible health related information. The statement may include a concept, conclusion, and/or recommendation pertaining to the possible health related information. The statement may describe an effect that results from the possible health related information.

Figure 22:
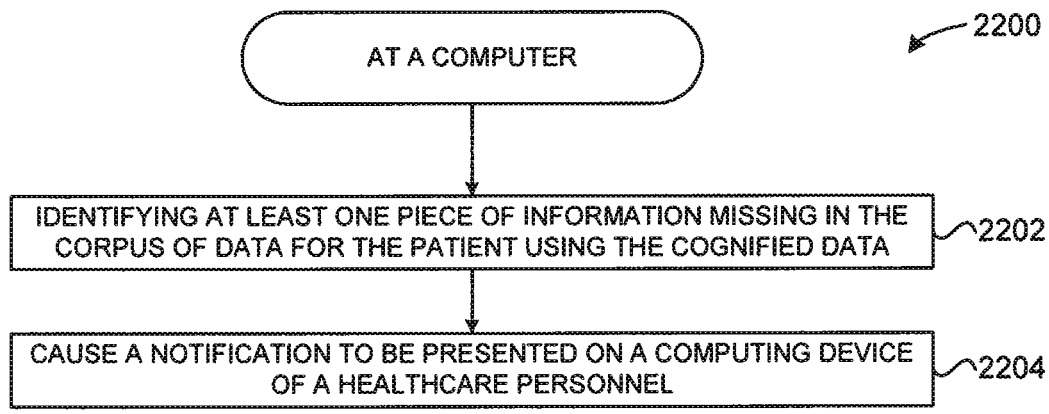
FIG. 22 shows a method for identifying missing information in a corpus of data, in accordance with various embodiments.

FIG. 22 shows a method 2200 for identifying missing information in a corpus of data, in accordance with various embodiments. In some embodiments, the method 2300 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 2200 may include operations that are implemented in computer instructions stored in a memory and executed by a processor of a computing device.

At block 2202, the processing device executing the artificial intelligence engine may identify at least one piece of information missing in the corpus of data for the patient using the cognified data. The at least one piece of information pertains to a treatment gap, a risk, gap, a quality of care gap, or some combination thereof.

At block 2204, the processing device may cause a notification to be presented on a computing device of a healthcare personnel (e.g., physician). The notification may instruct entry of the at least one piece of information into the corpus of data (e.g., patient notes in the EMR). For example, if certain symptoms are described for a patient in the corpus of data and those symptoms are known to result from a certain medication currently prescribed to the patient, but the corpus of data does not indicate switching medications, then the at least one piece of information may identify a treatment gap and recommend switching medications to one that does not cause those symptoms.

Figure 23:
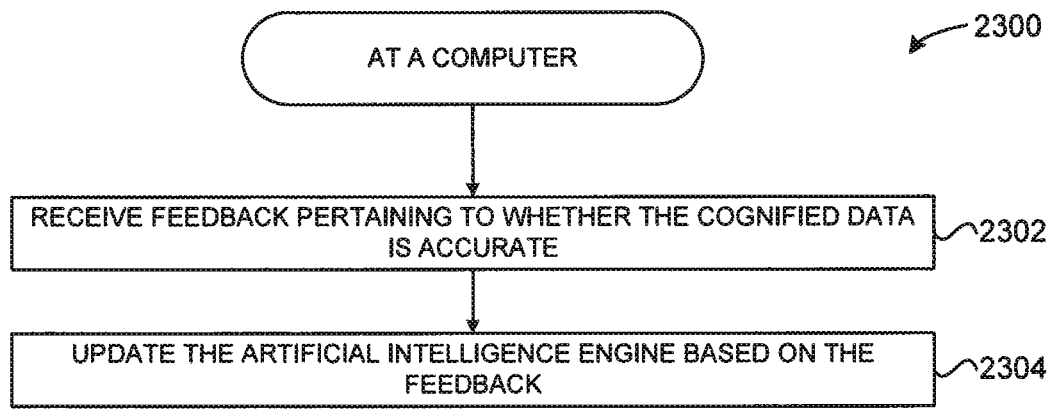
FIG. 23 shows a method for using feedback pertaining to the accuracy of cognified data to update an artificial intelligence engine, in accordance with various embodiments.

FIG. 23 shows a method 2300 for using feedback pertaining to the accuracy of cognified data to update an artificial intelligence engine, in accordance with various embodiments. In some embodiments, the method 2300 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 2300 may include operations that are implemented in computer instructions stored in a memory and executed by a processor of a computing device.

At block 2302, the processing device may receive feedback pertaining to whether the cognified data is accurate. For example, the physician may be presented with the cognified data on a computing device, and the physician may review the cognified data. The physician may be presented with options to verify the accuracy of portions or all of the cognified data for the particular patient. For example, the physician may select a first graphical element (e.g., button, checkbox, etc.) next to portions of the cognified data that are accurate and may select a second graphical element next to portions of the cognified data that are inaccurate. If the second graphical element is selected, an input box may appear and a notification may be presented to provide a reason why the portion is inaccurate and to provide corrected information. The feedback may be transmitted to the cognitive intelligence platform.

At block 2304, the processing device may update the artificial intelligence engine based on the feedback. A closed-loop feedback system may be implemented using these techniques. The feedback may enhance the accuracy of the cognified data as the artificial intelligence engine continues to learn and improve.

Figure 24A:
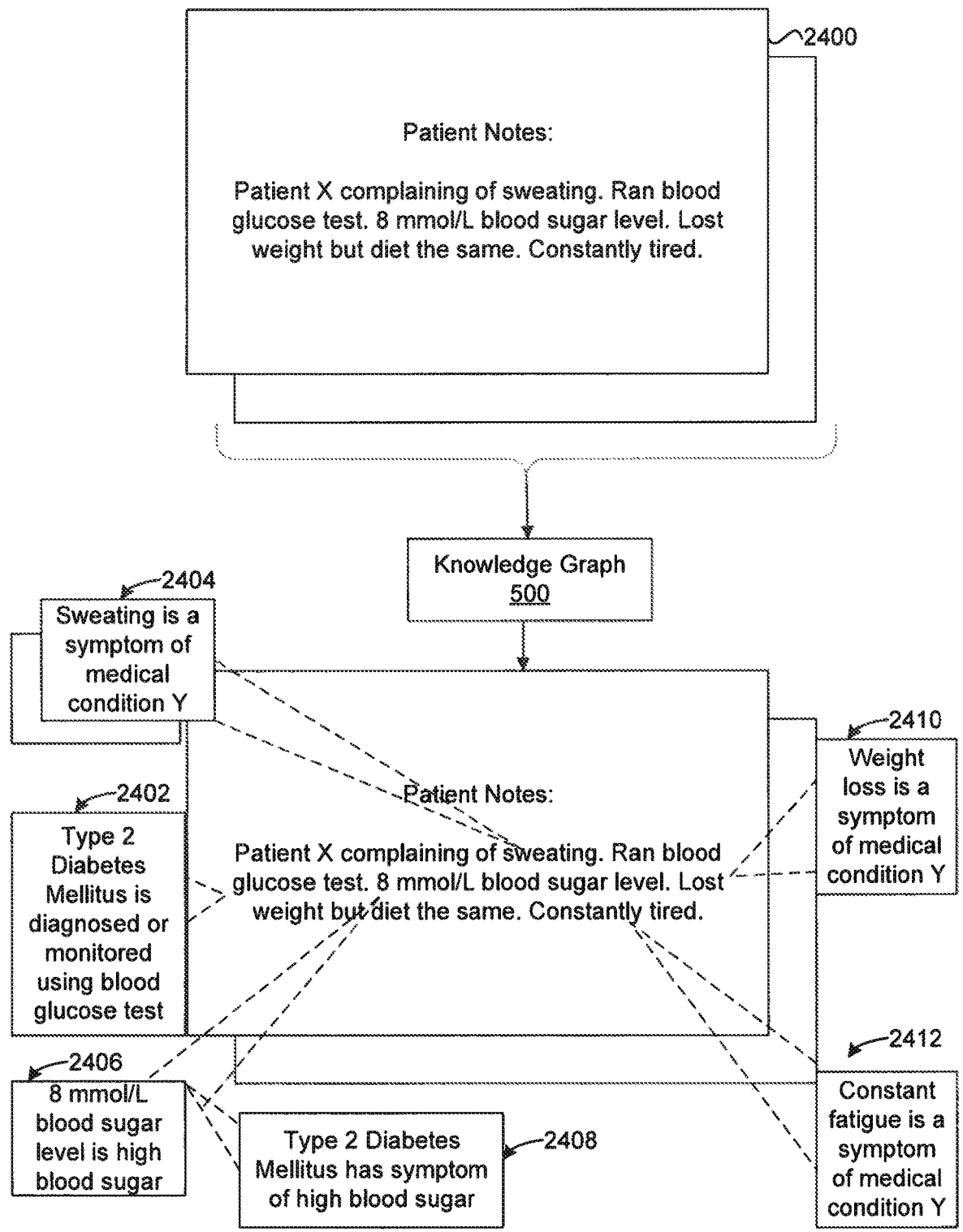
FIG. 24A shows a block diagram for using a knowledge graph to generate possible health related information, in accordance with various embodiments.

FIG. 24A shows a block diagram for using the knowledge graph 500 to generate possible health related information, in accordance with various embodiments. As depicted, a physician may have entered patient notes 2400 in one or more electronic medical records (EMRs). The EMRs may be provided directly to the cognitive intelligence engine 102 and/or retrieved using an application programming interface (API) from an EMR system used by the physician. The patient notes may be extracted from the EMRs. In some embodiments, numerous patient notes from numerous consultations may be processed, synthesized, and cognified using the disclosed techniques. In some embodiments, patient notes from a single consultation may be processed, synthesized, and cognified using the disclosed techniques. The patient notes may include a set of strings of characters that arranged in sentences, phrases, and/or paragraphs. The cognitive intelligence platform 102 may process the set of strings of characters to identify indicia comprising a phrase, a predicate, a keyword, a subject, an object, a cardinal, a number, a concept, or some combination thereof.

The cognitive intelligence platform 102, and in particular the artificial intelligence engine 109, may compare the indicia to numerous knowledge graphs 500 each representing a respective medical condition, such as diabetes, cancer, coronary artery disease, arthritis, just to name a few examples. The artificial intelligence engine 109 may be trained to generate possible health related information by constructing logical structures based on matched indicia and known health related information (health artifacts that are established based on information from a trusted source) represented in the knowledge graphs 500. The logical structures may be tagged to the indicia, as depicted in FIG. 24A.

The artificial intelligence engine 109 may identify the following example indicia: "Patient X", "sweating", "blood glucose test", "8 mmol/L blood sugar level", "lost weight", "diet the same", "constantly tired". The artificial intelligence engine 109 may match the indicia with known health related information in the knowledge graph 500. For example, in the knowledge graph 500 depicted in FIG. 5, "blood glucose test", is a known health related artifact that is used to test for Type 2 Diabetes Mellitus. Thus, various logical structures may be constructed by the artificial intelligence engine 109 that states "blood glucose test is used to test Type 2 Diabetes Mellitus", "Type 2 Diabetes Mellitus is diagnosed or monitored using blood glucose test" (tag 2402), "blood glucose test measures blood sugar level", and so forth.

The artificial intelligence engine 109 may generate other possible health related information for each of the indicia that matches known health related information in the knowledge graphs. For example, the artificial intelligence engine 109 generated example logical structure "Sweating is a symptom of medical condition Y" (tag 2404) for the indicia "sweating". The artificial intelligence engine 109 may generate other possible health related information for "sweating", such as "sweating is caused by running", "sweating is a symptom of fever". Further, the artificial intelligence engine 109 may elaborate on the generated possible health related information by generating further possible health related information. Based on generating "sweating is a symptom of medical condition Y" (where Y is the name of the medical condition), the artificial intelligence engine 109 may generate another logical structure "medical condition Y causes Z" (where Z is a health artifact such as another medical condition).

It should be understood that, although not shown, a logical structure may be included in the knowledge graph 500 that indicates "Type 2 Diabetes has normal blood sugar level 5-7 mmol/L". An example possible health related information generated by the artificial intelligence engine 109 for the indicia "8 mmol/L blood sugar level" is "8 mmol/L blood sugar level is high blood sugar" (tag 2406) based on comparing the indicia to the known health related information about acceptable blood sugar levels in the knowledge graph 500. The artificial intelligence engine 109 may generate an additional possible health information based on tag 2406, and the additional possible health information may state "Type 2 Diabetes Mellitus has symptom of high blood sugar" (tag 2408).

An example possible health related information generated by the artificial intelligence engine 109 for the indicia "lost weight" may be "Weight loss is a symptom of medical condition Y" (tag 2410) where medical condition Y is any medical condition that causes weight loss. For example, any knowledge graph that includes "weight loss", "loss of weight", or some variant thereof as a health artifact may be identified and one or more possible health related information may be generated indicating that weight loss is a symptom of the medical condition represented by that knowledge graph.

An example possible health related information generated by the artificial intelligence engine 109 for the indicia "constantly tired" may be "Constant fatigue is a symptom of medical condition Y" (tag 2412) where medical condition Y is any medical condition that causes constant fatigue. For example, any knowledge graph that includes "fatigue", "constant fatigue", or some variant thereof as a health artifact may be identified and one or more possible health related information may be generated indicating that constant fatigue is a symptom of the medical condition represented by that knowledge graph.

The knowledge graphs that include a threshold number of matches between the indicia and the known health related matches in the knowledge graphs may be selected for further processing. The threshold may be any suitable number of matches. For example, in the depicted example, the knowledge graph 500 representing Type 2 Diabetes Mellitus may be selected because 3 tags (2402, 2406, and 2408) relate to that medical condition represented in the knowledge graph 500.

Figure 24B:
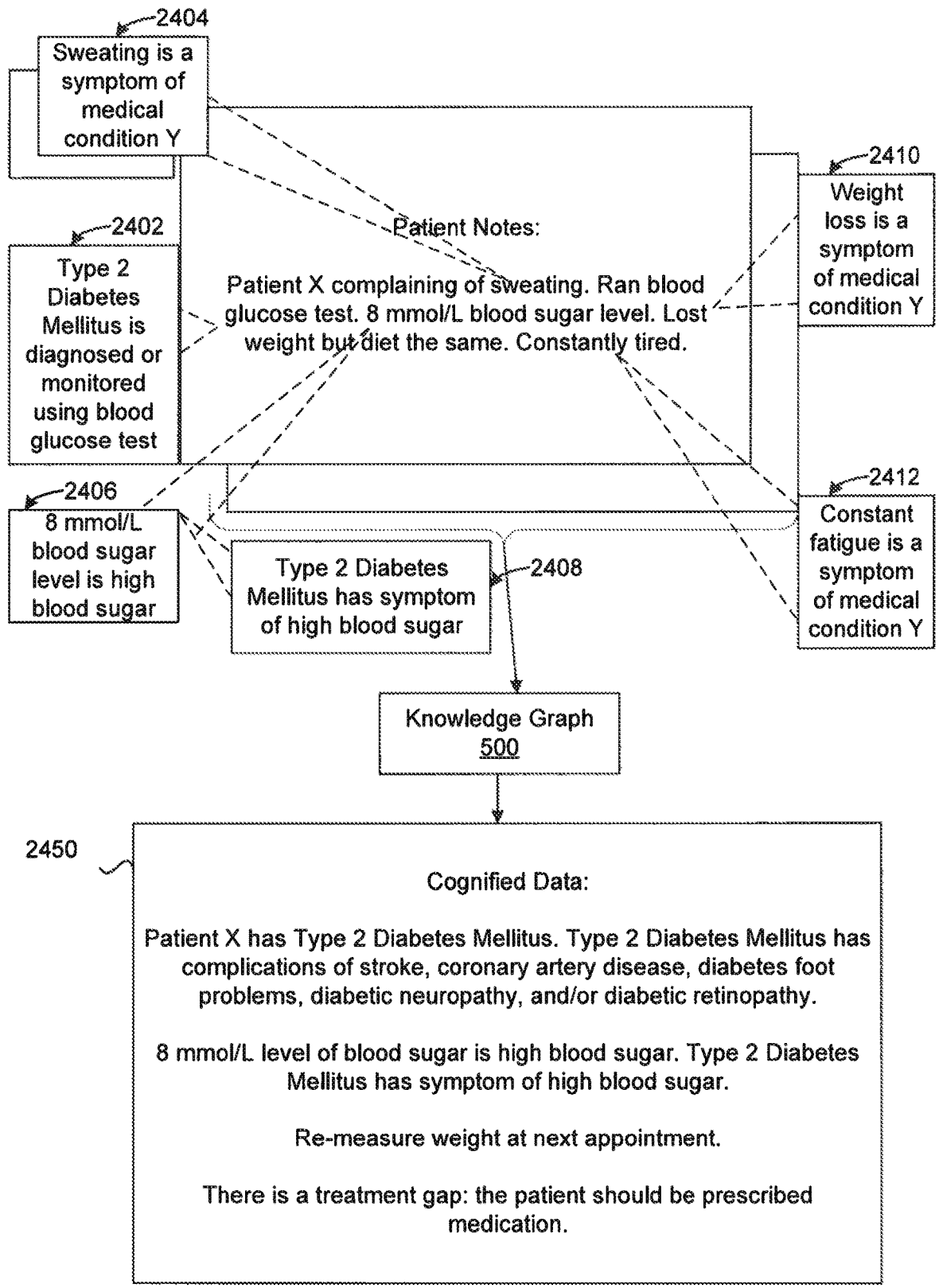
FIG. 24B shows a block diagram for using a logical structure to identify structural similarities with known predicates to generate cognified data, in accordance with various embodiments.

FIG. 24B shows a block diagram for using a logical structure to identify structural similarities with known predicates to generate cognified data, in accordance with various embodiments. The identification of structural similarities may be performed in parallel with the comparison of the indicia with the known health related information. In some embodiments, the generated possible health related information may be compared with the known predicates in the logical structures of the knowledge graphs. In some embodiments, predicates detected in the unstructured data may also be compared with the known predicates in the logical structures of the knowledge graphs. The artificial intelligence engine 500 may identify structural similarities between the possible health related information and the known predicates in the logical structures of the knowledge graphs. The artificial intelligence engine 500 may identify structural similarities between the detected predicates in the unstructured data and the known predicates in the logical structures of the knowledge graphs. In some embodiments, identifying structural similarities may refer to comparing the structure of the logical structure of the possible health related information to a known logical structure (known logical structure may refer to a logical structure established based on a trusted source), such as determining whether the subjects are the same or substantially similar, the predicates are the same or substantially similar, the objects are the same or substantially similar, and so forth.

For example, the knowledge graph 500 includes the logical structure "Type 2 Diabetes Mellitus has symptom high blood sugar". Comparing the possible health related information represented by tag 2408 "Type 2 Diabetes Mellitus has symptom of high blood sugar" to the known logical structure in the knowledge graph 500 results in identifying a structurally similarity between the two. Accordingly, the knowledge graph 500 may be selected for further processing.

In some embodiments, the structural similarities detected may be used to identify patterns. For example, a treatment pattern for diabetes may be detected if a blood glucose test is used, a patient is prescribed a certain medication, and the like. In some embodiments, gaps in the unstructured data may be identified based on the patterns detected. For example, if a person is determined to have a certain medical condition based on the treatment pattern identified, and it is known based on evidence-based guidelines that a certain medication should be prescribed for that treatment pattern, the artificial intelligence engine 109 may indicate there is a treatment gap if that medication has not been prescribed yet.

The knowledge graphs selected when comparing the indicia to the known health related information and the knowledge graphs selected when identifying structural similarities between the known logical structure and the possible health related information may be compared to determine whether there are overlaps. As discussed above, the knowledge graph 500 representing Type 2 Diabetes Mellitus overlaps as being selected during both operations. As a result, the knowledge graph 500 may be used for cognification. In some embodiments, any of the knowledge graphs selected during either operation may be used for cognification.

In some embodiments, the selected knowledge graphs may be used to generate cognified data 2450. Further, the possible health related information and the matching logical structures may be used to generate the cognified data 2450. The cognified data 2450 may include a health related summary of the possible health related information. In some embodiments, the cognified data 2450 may include conclusions, statements of facts, concepts, recommendations, identified gaps in the unstructured data that was processed, and the like.

In some embodiments, the cognified data 2450 may be used to generate a diagnosis of a medical condition for a patient. For example, if there are a threshold number of identified structural similarities between the known logical structures and the possible health related information and/or if there are a threshold number of matches between indicia and known health related information for a particular medical condition, a diagnosis may be generated for that particular medical condition. If there are numerous medical conditions identified after performing the cognification, the numerous medical conditions may be indicated as potential candidates for diagnosis. In the ongoing example, the knowledge graph 500 was selected as the overlapping knowledge graph and satisfies the threshold number of identified structural similarities and/or the threshold number of matches. Accordingly, a diagnosis that Patient X has Type 2 Diabetes Mellitus may be generated. The cognified data 2450 may include the diagnosis, as depicted.

When generating the cognified data, other health related information in the selected knowledge graph 500 that was not included in the unstructured data may be inserted. That is, sentences may be constructed using the known health related information and the predicates in the knowledge graph 50. For example, the unstructured data did not indicate any information pertaining to complications of Type 2 Diabetes Mellitus. However, as depicted in the knowledge graph 500 of FIG. 5, there is a logical structure that specifies "Type 2 Diabetes Mellitus has complications of stroke, coronary artery disease, diabetes foot problems, diabetic neuropathy, and/or diabetic retinopathy". As depicted, this construction of the logical structure is included in the cognified data 2450 by the artificial intelligence engine 109.

The cognified data 2450 may also include the tag 2406 ("8 mmol/L level of blood sugar is high blood sugar. Type 2 Diabetes Mellitus has symptom of high blood sugar") that was generated for the unstructured data based on the known health information in the knowledge graph 500. The artificial intelligence engine 109 may generate a recommendation based on the lost weight indicia indicated in the unstructured data. The recommendation may state "Re-measure weight at next appointment." In addition, as discussed above, the artificial intelligence engine 109 may identify certain gaps. For example, the diagnosis that is generated indicates that the patient has Type 2 Diabetes Mellitus. The unstructured data does not indicate that medication is prescribed. However, the knowledge graph 500 specifies that Type 2 Diabetes Mellitus is treated by "Diabetes Medicines". Accordingly, a treatment gap may be identified by the artificial intelligence engine 109 based on treatment patterns codified in the knowledge graph 500, and a statement may be constructed and inserted in the cognified data 2450. The statement may state "There is a treatment gap: the patient should be prescribed medication."

The cognified data 2450 may be transmitted by the cognitive intelligence platform 102 to a computing device of the service provider 112, such as the physician who entered the unstructured data. As depicted, the cognified data 2450 may be instilled with intelligence, knowledge, and logic using the disclosed cognification techniques. The physician may quickly review the cognified data 2450 without having to review numerous patient notes from various EMRs. In some embodiments, the physician may be presented with options to verify portions or all of the cognified data 2450 is accurate. The feedback may be transmitted to the cognitive intelligence platform 102 and the artificial intelligence engine 109 may update its various machine learning models using the feedback.

Figure 25:
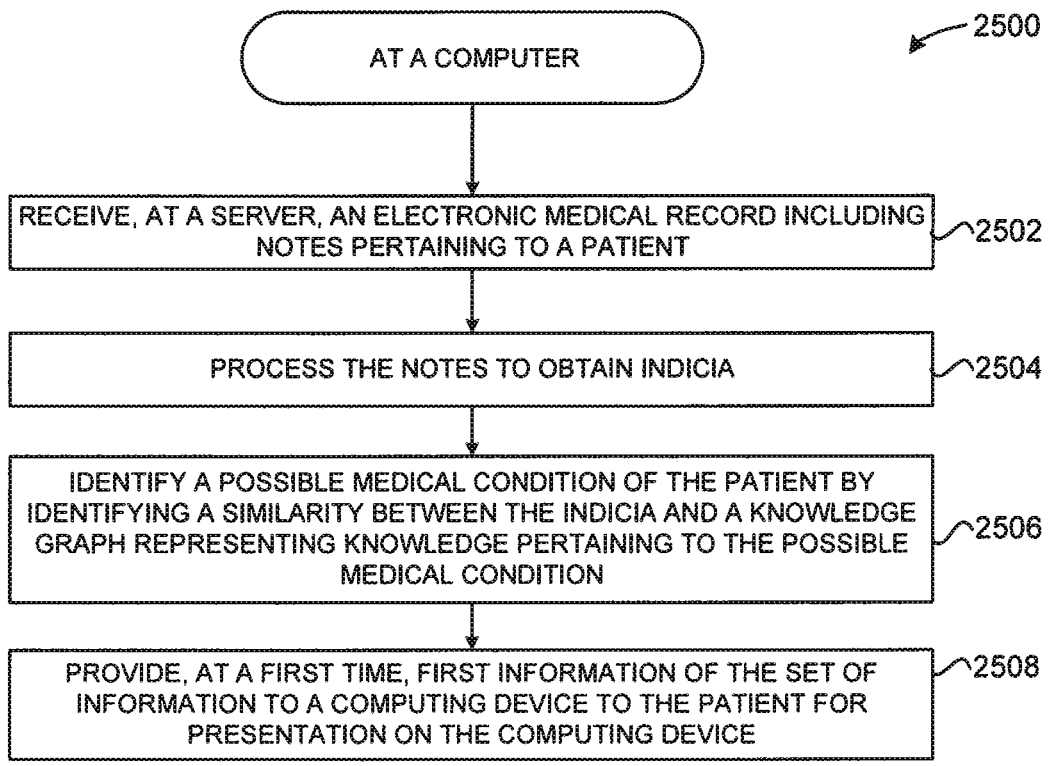
FIG. 25 shows a method for providing first information pertaining to a possible medical condition of a patient to a computing device, in accordance with various embodiments.

FIG. 25 shows a method 2500 for providing first information pertaining to a possible medical condition of a patient to a computing device, in accordance with various embodiments. In some embodiments, the method 2500 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 2500 may include operations that are implemented in computer instructions stored in a memory and executed by a processor of a computing device.

At block 2502, the processing device of a server may receive an electronic medical record (EMR) including notes pertaining to a patient. The EMR may be transmitted directly to the server from a computing device of the physician that entered the notes, and/or the EMR may be obtained using an application programming interface (API) interfacing with an EMR system used by the physician that entered the notes. In some embodiments, the server may receive text input by the patient. For example, the text input by the user may include symptoms the patient is experiencing and ask a question pertaining to what medical condition the patient may have. The operations of method 2500 may be used to similarly provide information to the patient based on identifying the possible medical condition using the cognification techniques.

At block 2504, the processing device may process the notes to obtain indicia including a subject, an object, a word, a cardinal, a phrase, a concept, a sentence, a predicate, or some combination thereof. Textual analysis may be performed to extract the indicia. Processing the patient notes to obtain the indicia may further include inputting the notes into an artificial intelligence engine 109 trained to identify the indicia in text based on commonly used indicia pertaining to the possible medical condition. The artificial intelligence engine 109 may determine commonly used indicia for various medical conditions based on evidence-based guidelines, clinical trial results, physician research, or the like that are input to one or more machine learning models.

At block 2506, the processing device may identify a possible medical condition of the patient by identifying a similarity between the indicia and a knowledge graph representing knowledge pertaining to the possible medical condition. The knowledge graph may include a set of nodes representing the set of information pertaining to the possible medical condition. The set of nodes may also include relationships (e.g., predicates) between the set of information pertaining to the possible medication condition. In some embodiments, identifying the possible medical condition may include using a cognified data structure generated from the notes of the patient. The cognified data structure may include a conclusion based on a logic structure representing evidence-based guidelines pertaining to the possible medical condition.

In some embodiments, the similarity may pertain to a match between the indicia and a health artifact (known health related information) included in the knowledge graph 500. For example, "high blood pressure" may be extracted as indicia from the sentence "Patient X has high blood pressure", and "high blood pressure" is a health artifact at a node in the knowledge graph 500 representing Type 2 Diabetes Mellitus.

In some embodiments, the similarity may pertain to a structural similarity between the logical structure (e.g., "Type 2 Diabetes has symptoms of High Blood Pressure) and the indicia (e.g., "Patient X has symptoms of High Blood Pressure") that is included in the unstructured data. If the subject, predicates, and/or objects of the logical structure and the indicia match or substantially match (e.g., "has symptoms of High Blood Pressure" match between the logical structure and the indicia, also "Type 2 Diabetes has symptoms of High Blood Pressure" and "Patient X has symptoms of High Blood Pressure" substantially match), then the knowledge graph 500 including the logical structure is a candidate for a possible medical condition. In some embodiments, a combination of similarities identified between the match between the indicia and the health artifact and between the logical structure and the indicia may be used to identify a possible medical condition and/or cognify the unstructured data.

An artificial intelligence engine 109 may be used to identify the possible medical condition by identifying the similarity between the indicia and the knowledge graph. The artificial intelligence engine 109 may be trained using feedback from medical personnel. The feedback may pertain to whether output regarding the possible medical conditions from the artificial intelligence engine 109 are accurate for input including notes of patients.

At block 2508, the processing device may provide, at a first time, first information of the set of information to a computing device of the patient for presentation of the computing device, the first information being associated with a root node of the set of nodes. In some embodiments, the first information may pertain to a name of the possible medical condition. As depicted in the knowledge graph 500 of FIG. 5, the root node is associated with the name of the medical condition "Type 2 Diabetes Mellitus". In some embodiments, the first information may pertain to a definition of the possible medical condition, instead of or in addition to the name of the possible medical condition.

Figure 26:
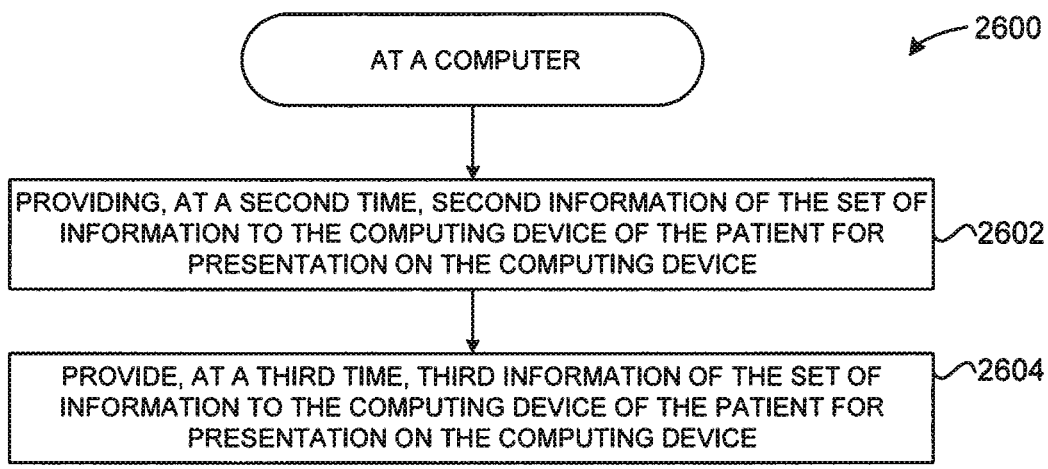
FIG. 26 shows a method for providing second and third information pertaining to a possible medical condition of a patient to a computing device, in accordance with various embodiments.

FIG. 26 shows a method 2600 for providing second and third information pertaining to a possible medical condition of a patient to a computing device, in accordance with various embodiments. In some embodiments, the method 2600 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 2600 may include operations that are implemented in computer instructions stored in a memory and executed by a processor of a computing device.

At block 2602, the processing device may provide, at a second time, second information of the set of information to the computing device of the patient for presentation on the computing device. The second information may be associated with a second node of the set of nodes, and the second time may be after the first time. The second information may be different than the first information. The second information may pertain to how the possible medical condition affects people, signs and symptoms of the possible medical condition, a way to treat the possible medical condition, a progression of the possible medical condition, complications of the possible medical condition, or some combination thereof. The second time may be selected based on when the second information is relevant to a stage of the possible medical condition. The second time may be preconfigured based on an amount of time elapsed since the first time.

At block 2604, the processing device may provide, at a third time, third information of the set of information to the computing device of the patient for presentation on the computing device of the patient. The third information may be associated with a third node of the set of nodes, and the third time may be after the second time. The third information may be different than the first information and the second information. The third information may pertain to how the possible medical condition affects people, signs and symptoms of the possible medical condition, a way to treat the possible medical condition, a progression of the possible medical condition, complications of the possible medical condition, or some combination thereof. The third time may be selected based on when the third information is relevant to a stage of the possible medical condition. The third time may be preconfigured based on an amount of time elapsed since the second time.

This process may continue until each node of the knowledge graph 500 are traversed to provide relevant information to the patient at relevant times until all information associated with the set of nodes has been delivered to the computing device of the patient. In this way, the patient may not be overwhelmed with a massive amount of information at once. Further, memory resources of the computing device of the patient may be saved by regulating the amount of information that is provided.

Figure 27:
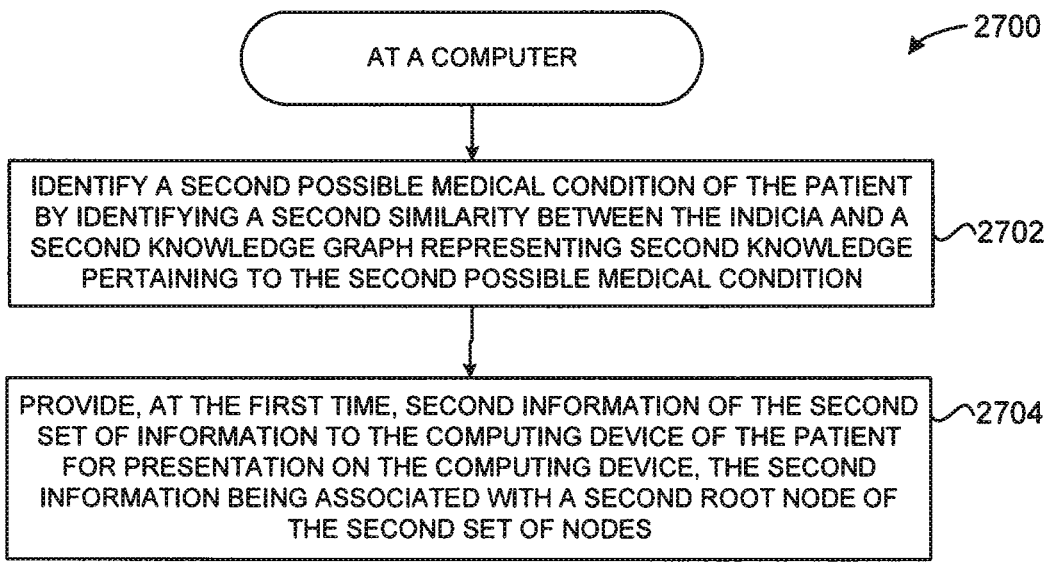
FIG. 27 shows a method for providing second information pertaining to a second possible medical condition of the patient, in accordance with various embodiments.

FIG. 27 shows a method 2700 for providing second information pertaining to a second possible medical condition of the patient, in accordance with various embodiments. In some embodiments, the method 2700 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 2700 may include operations that are implemented in computer instructions stored in a memory and executed by a processor of a computing device.

At block 2702, the processing device may identify a second possible medical condition of the patient by identifying a second similarity between the indicia and a second knowledge graph representing second knowledge pertaining to the second possible medical condition. In some embodiments, the second similarity may pertain to a match between the indicia and a health artifact (known health related information) included in the second knowledge graph. For example, "vomiting" may be extracted as indicia from the sentence "patient has symptom of vomiting", and "vomiting" is a health artifact at a node in the second knowledge graph representing the flu. In some embodiments, the second similarity may pertain to a second structural similarity between a second logical structure (e.g., "Flu has symptom of vomiting) and the possible health information (e.g., "has symptom of vomiting") that is included in the unstructured data. In some embodiments a combination of the similarities between the indicia and the health artifact and between the logical structure and the possible health information may be used to identify the second possible medical condition and/or cognify the unstructured data.

At block 2704, the processing device may provide, at the first time, second information of the second set of information to the computing device of the patient for presentation on the computing device, the second information being associated with a second root node of the second set of nodes. The second information may be provided with the first information at the first time. In some embodiments, a user interface on the computing device of the patient may present the first information and the second information concurrently on the same screen. For example, the user interface may present that the possible medical conditions include "Type 2 Diabetes Mellitus" and the "flu". It should be understood that any suitable number of possible medical conditions may be identified using the cognification techniques and the information related to those medical conditions may be provided to the computing device of the patient on a regulated basis.

In some embodiments, the patient may be presented with options to indicate whether the information provided at the various times was helpful. The feedback may be provided to the artificial intelligence engine 109 to update one or more machine learning models to improve the information that is provided to the patients.

Figure 28:
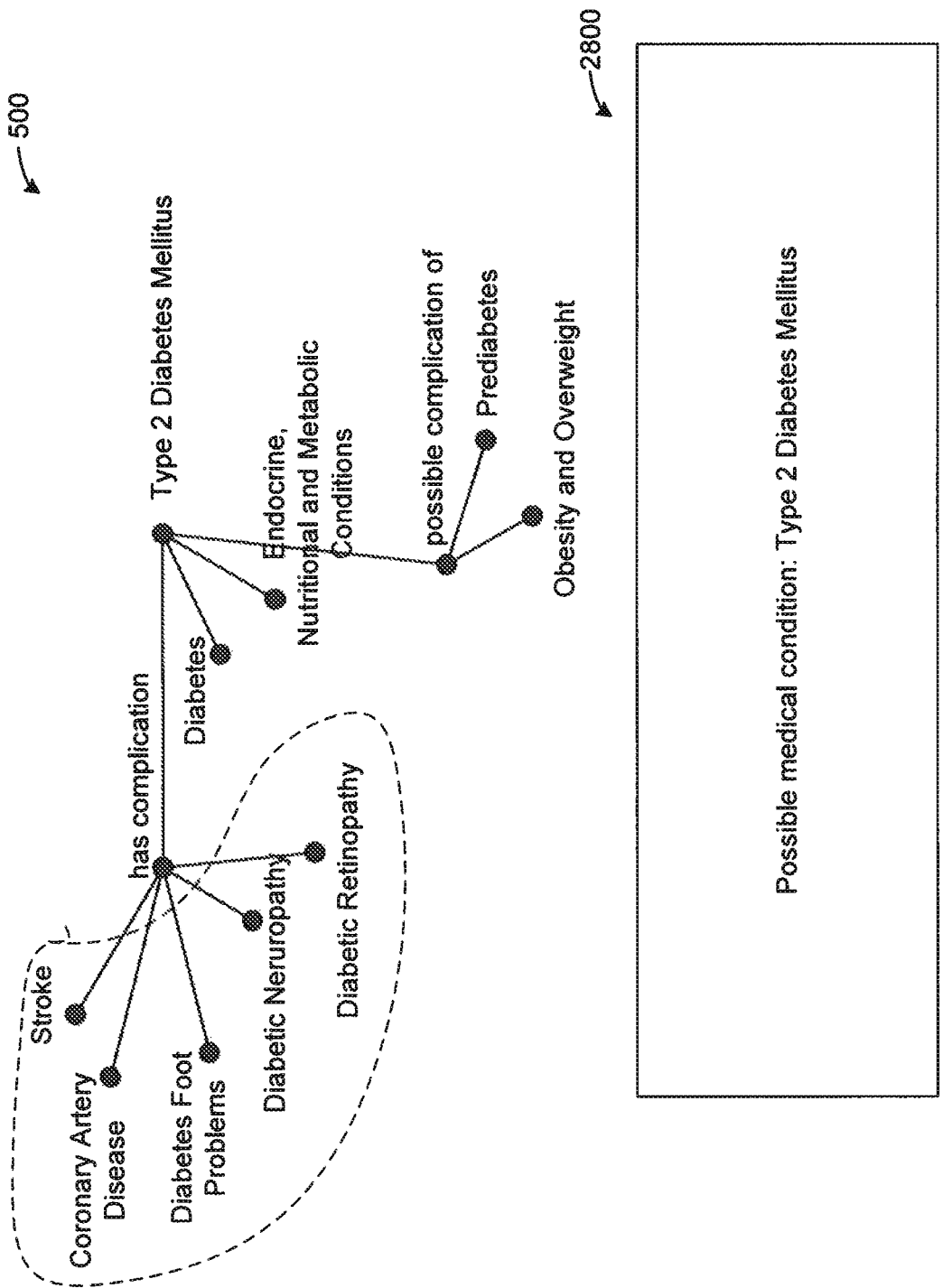
FIG. 28 shows an example of providing first information of a knowledge graph representing a possible medical condition, in accordance with various embodiments.

FIG. 28 shows an example of providing first information of a knowledge graph 500 representing a possible medical condition, in accordance with various embodiments. In the depicted example, just a portion of the knowledge graph 500 representing Type 2 Diabetes Mellitus is depicted. Based on the patient notes entered by the physician and/or the text input by the patient, the artificial intelligence engine 109 may extract indicia. Using the indicia, the artificial intelligence engine 109 may identify a possible medical condition of the patient by identifying at least one similarity between the indicia and the knowledge graph 500. It should be understood that the artificial intelligence engine 109 identified Type 2 Diabetes Mellitus as the possible medical condition based on the similarity between the indicia and the knowledge graph 500 using the cognification techniques described herein.

Accordingly, at a first time, the cognitive intelligence platform 102 may provide first information associated with the root node of the knowledge graph 500. The root node may be associated with the name "Type 2 Diabetes Mellitus" of the medical condition. A user interface 2800 of the computing device of the patient may present the first information "Possible medical condition: Type 2 Diabetes Mellitus" at the first time.

Figure 29:
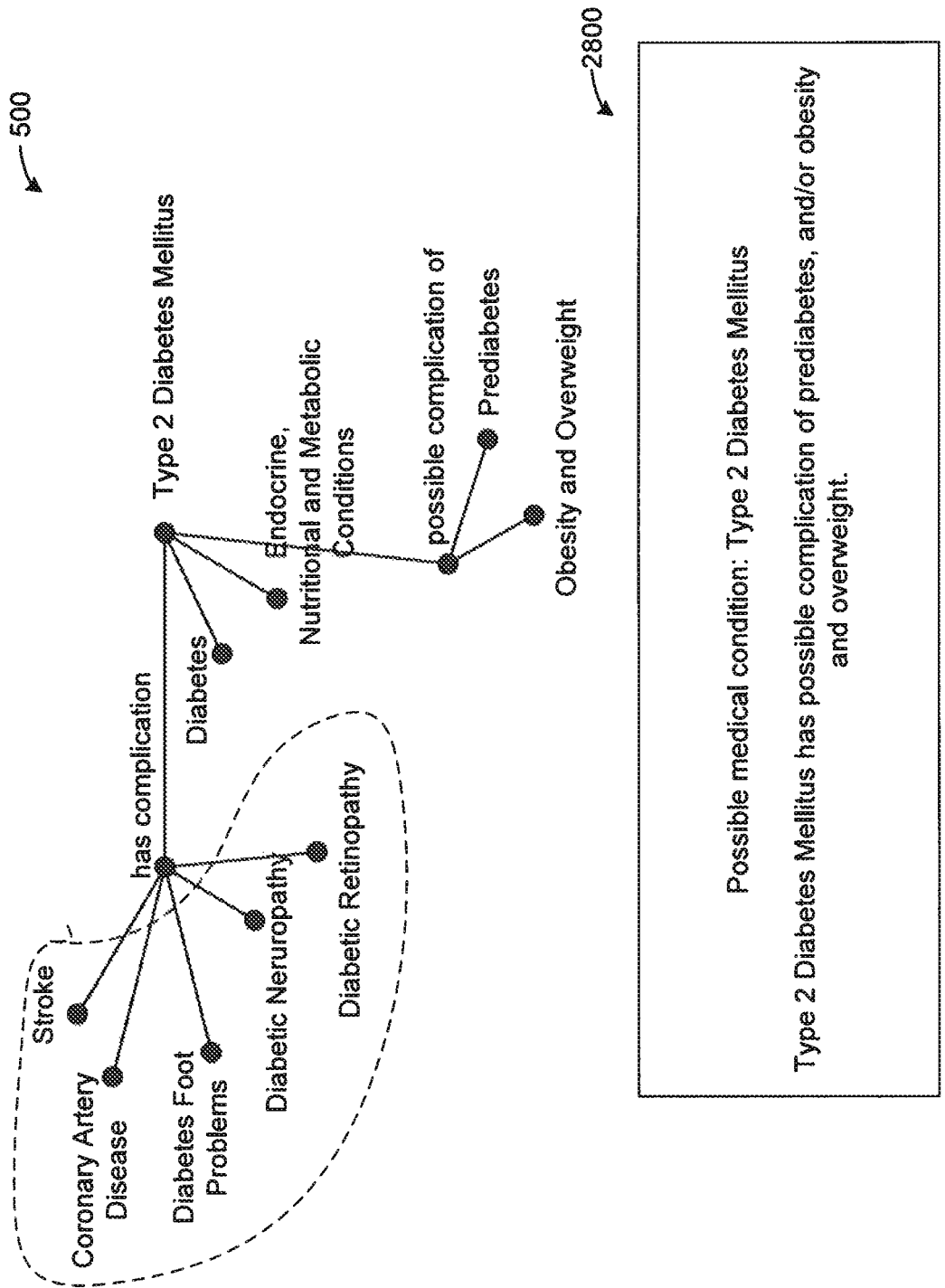
FIG. 29 shows an example of providing second information of the knowledge graph representing the possible medical condition, in accordance with various embodiments.

FIG. 29 shows an example of providing second information of the knowledge graph 500 representing the possible medical condition, in accordance with various embodiments. The second information may be provided at a second time subsequent to the first time the first information was provided. The second information may be associated with at least a second node representing a health artifact of the knowledge graph 500. The second information may be different than the first information. The second information may combine a predicate of a node that connects the second node representing the health artifact to the root node. For example, the second information may include "Type 2 Diabetes Mellitus has possible complication of prediabetes, or obesity and overweight." The second information may be presented on the user interface 2800 with the first information, as depicted. In some embodiments, just the second information may be presented on the user interface 2800 and the first information may be deleted from the user interface 2800.

Figure 30:
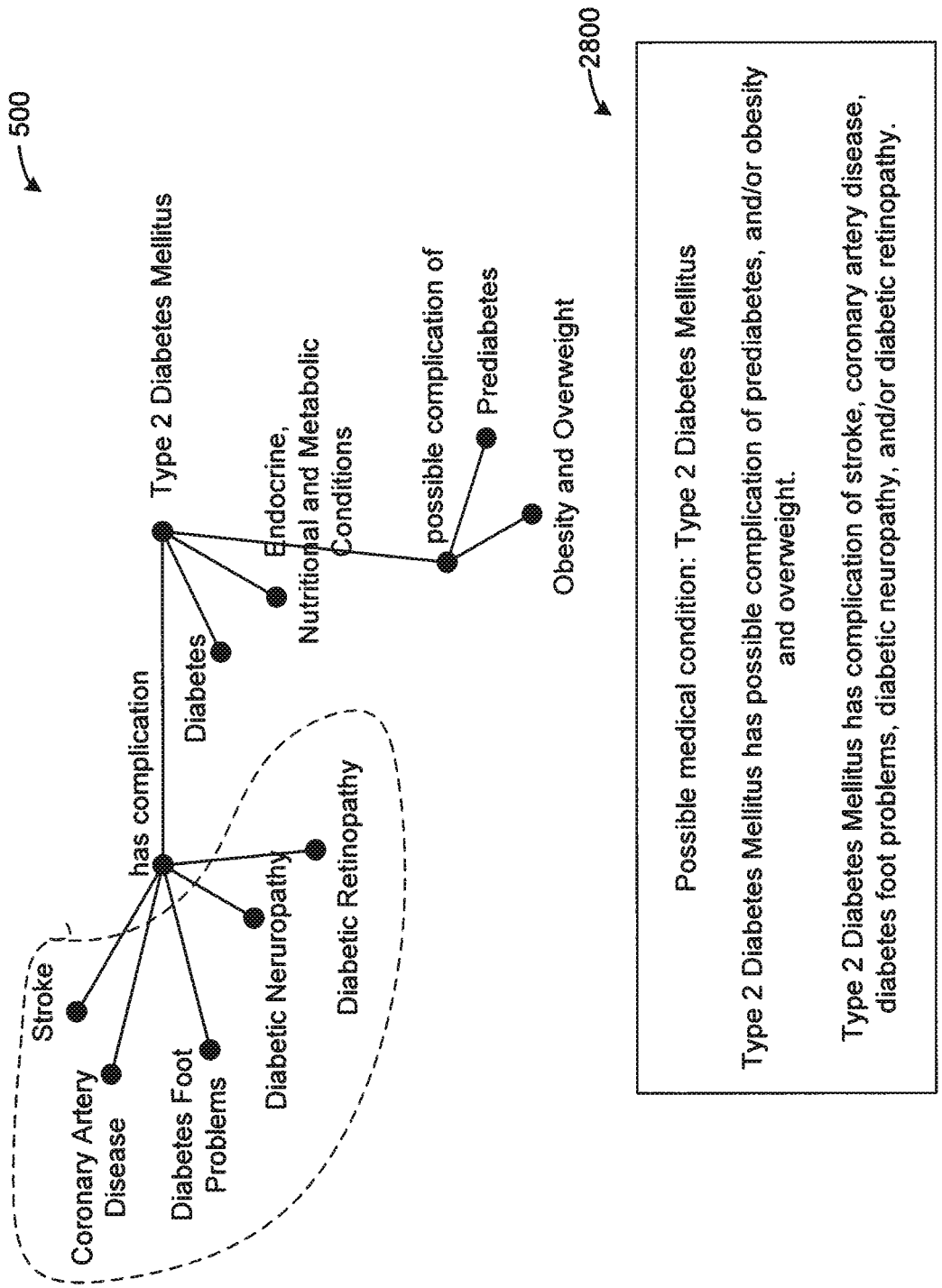
FIG. 30 shows an example of providing third information of the knowledge graph representing the possible medical condition, in accordance with various embodiments.

FIG. 30 shows an example of providing third information of the knowledge graph representing the possible medical condition, in accordance with various embodiments. The third information may be provided at a third time subsequent to the second time the second information was provided. The third information may be associated with at least a third node representing a health artifact of the knowledge graph 500. The third information may be different than the first information and the second information. The third information may combine a predicate of a node that connects the third node representing the health artifact to the root node. For example, the third information may include "Type 2 Diabetes Mellitus has complication of stroke, coronary artery disease, diabetes foot problems, diabetic neuropathy, and/or diabetic retinopathy." The third information may be presented on the user interface 2800 with the first information and/or the second information, as depicted. In some embodiments, just the third information may be presented on the user interface 2800, and the first information and the second information may be deleted from the user interface 2800. In some embodiments, any combination of the first, second, and third information may be presented on the user interface 2800.

In some embodiments, the various health artifacts represented by each node in the knowledge graph 500 may be provided to the computing device of the patient until all of the information in the knowledge graph 500 is provided. Additionally, if the knowledge graph 500 contains a link to another knowledge graph representing a related medical condition, the information included in that other knowledge graph may be provided to the patient. At any time, the patient may request to stop receiving information about the possible medical condition and no additional information will be provided. If the patient desires additional information faster, the patient may be presented with an option to obtain the next set of information at any time.

Figure 31:
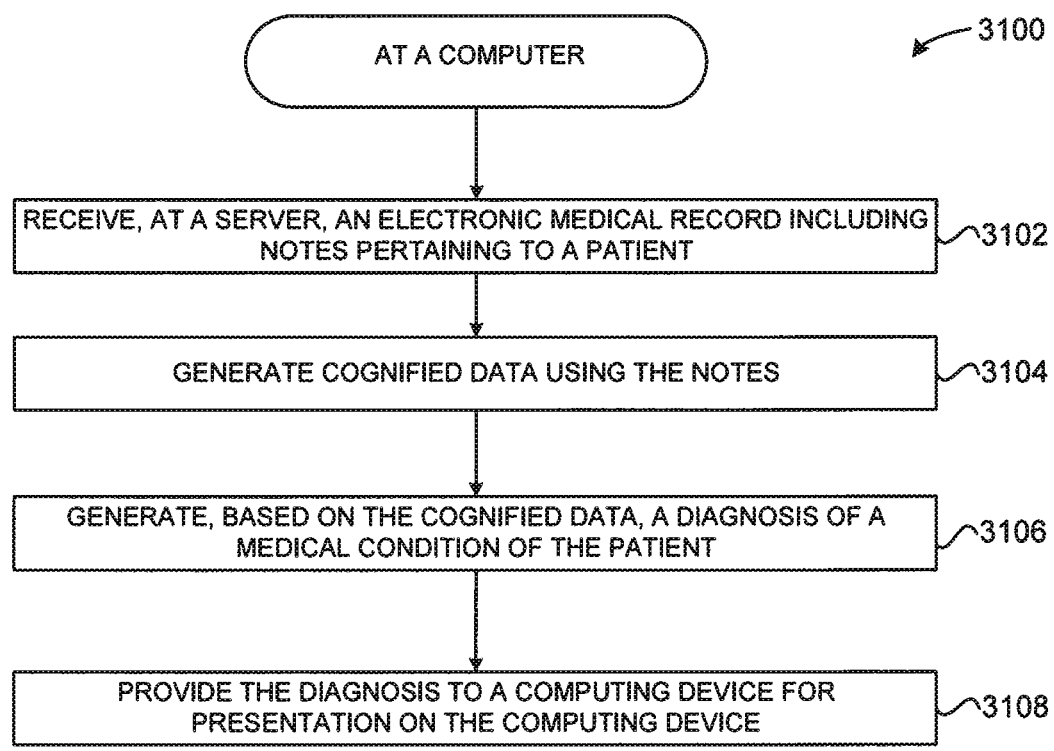
FIG. 31 shows a method for using cognified data to diagnose a patient, in accordance with various embodiments.

FIG. 31 shows a method 3100 for using cognified data to diagnose a patient, in accordance with various embodiments. In some embodiments, the method 3100 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 3100 may include operations that are implemented in computer instructions stored in a memory and executed by a processor of a computing device.

At block 3102, the processing device of a server may receive an electronic medical record including notes pertaining to a patient. The notes may include strings of characters arranged in sentences and/or paragraphs. The processing device may process the strings of characters and identify, in the notes, indicia including a phrase, a predicate, a subject, an object, a cardinal, a number, a concept, or some combination thereof. In some embodiments, the notes may be processed to obtain the indicia by inputting the notes into the artificial intelligence engine 109 trained to identify the indicia in text based on commonly used indicia pertaining to the medical condition.

At block 3104, the processing device may generate cognified data using the notes. The cognified data may include a health summary of a medical condition. Generating the cognified data may further include detecting the medical condition by identifying a similarity between the indicia and a knowledge graph. For example, in some embodiments, the similarity may pertain to a match between the indicia and a health artifact (known health related information) included in the knowledge graph 500. For example, "high blood pressure" may be extracted as indicia from the sentence "Patient X has high blood pressure", and "high blood pressure" is a health artifact at a node in the knowledge graph 500 representing Type 2 Diabetes Mellitus. In some embodiments, the similarity may pertain to a structural similarity between the logical structure (e.g., "Type 2 Diabetes has symptoms of High Blood Pressure) and possible health related information generated using the identified indicia or subjects, predicates, and/or objects (e.g., "Patient X has symptoms of High Blood Pressure") that is included in the unstructured data. In some embodiments, a combination of similarities between the indicia and the health artifact, and between the logical structure and the indicia/possible health related information may be used to detect the medical condition.

At block 3106, the processing device may generate, based on the cognified data, a diagnosis of the medical condition of the patient. The diagnosis may at least identify a type of the medical condition that is detected using the cognified data. The diagnosis may be generated if a threshold number of matches between the indicia and health artifacts in the knowledge graph are identified, and/or if a threshold number of structural similarities are identified between logical structures of the knowledge graph and indicia/possible health information generated for the unstructured data. For example, the threshold numbers may be configurable and set based on a confidence level that the health artifacts that match the indicia and/or the logical structures that are similar to the indicia/possible health related information are correlated with the particular medical condition. The threshold numbers may be based on information from trusted sources, such as physicians having medical licenses.

In some embodiments, the processing device may use an artificial intelligence engine 109 that is trained using feedback from medical personnel. The feedback may pertain to whether output regarding diagnoses from the artificial intelligence engine 109 are accurate for input including notes of patients. The cognified data may include a conclusion that is identified based on a logical structure in the knowledge graph 500, where the logical structure represents codified evidence-based guidelines pertaining to the medical condition.

At block 3108, the processing device may provide the diagnosis to a computing device of a patient and/or a physician for presentation on the computing device. The diagnosis may be included in the cognified data. The physician may review the diagnosis and may provide feedback via graphical element(s) whether the diagnosis is accurate. The feedback may be received by the artificial intelligence engine 109 and used to update the one or more machine learning models used by the artificial intelligence engine 109 to cognify data and generate diagnoses.

Figure 32:
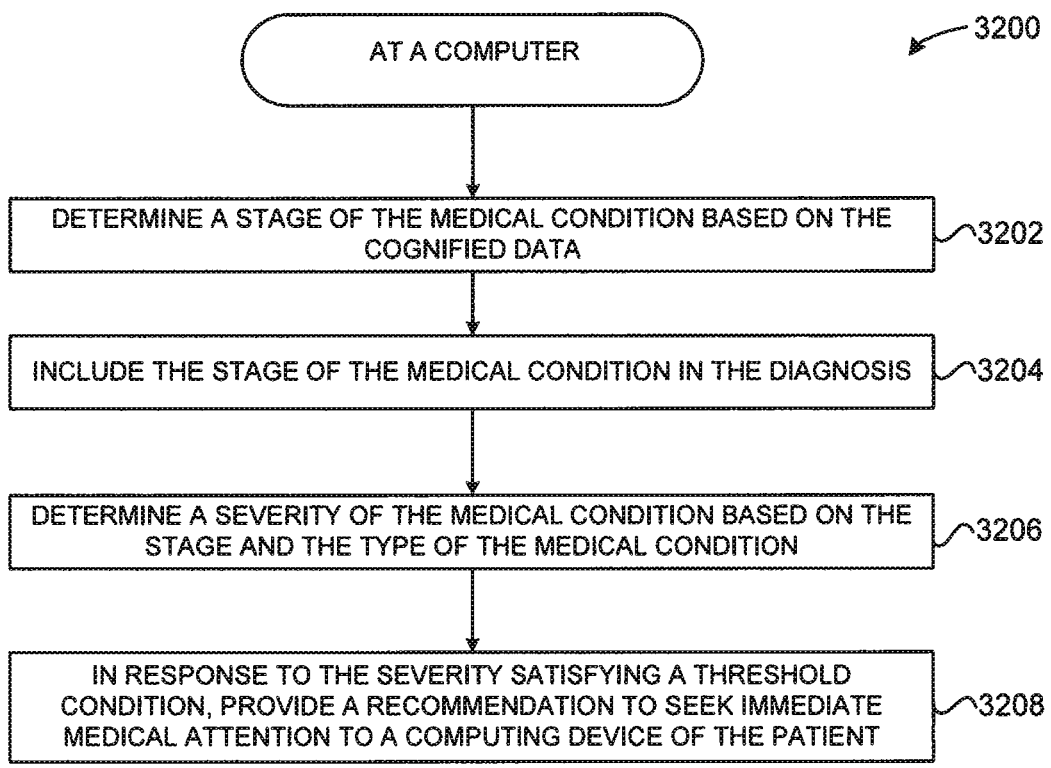
FIG. 32 shows a method for determining a severity of a medical condition based on a stage and a type of the medical condition, in accordance with various embodiments.

FIG. 32 shows a method 3200 for determining a severity of a medical condition based on a stage and a type of the medical condition, in accordance with various embodiments. In some embodiments, the method 3200 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 3200 may include operations that are implemented in computer instructions stored in a memory and executed by a processor of a computing device.

At block 3202, the processing device may determine a stage of the medical condition diagnosed based on the cognified data. The stage of the medical condition may be determined based on information included in the cognified data. For example, the information in the cognified data may be indicative of the particular stage of the medical condition. Such stages may include numerical values (e.g., 1, 2, 3, 4, etc.), descriptive terms (e.g., chronic, acute, etc.), or any suitable representation capable of indicating different progressions in a range (e.g., from low to high, or from mild to severe, etc.).

The artificial intelligence engine 109 may be trained to identify the stage based on the information in the cognified data. For example, if certain symptoms are present, certain blood levels are present, certain vital signs are present, or the like for a particular medical condition, the artificial intelligence engine 109 may determine that the medical condition has reached a certain stage. The artificial intelligence engine 109 may be trained on evidence-based guidelines that correlate the various information with the particular stages. For example, it may be known that a particular stage of cancer involves symptoms such as weight loss, lack of appetite, bone pain, dry cough or shortness of breath, or some combination thereof. If those symptoms are identified for the medical condition diagnosed (cancer) for the patient, then that particular stage may be determined.

At block 3204, the processing device may include the stage of the medical condition in the diagnosis. For example, the processing device may indicate the diagnosis is the "Patient X has stage 4 breast cancer". At block 3206, the processing device may determine a severity of the medical condition based on the stage and the type of the medical condition. If the stage is relatively low and the medical condition is easily treatable, then the severity may be low. If the stage is relatively high (chronic) and the medical condition is difficult to treat (cancer), then the severity may be high.

At block 3208, in response to the severity satisfying a threshold condition, the processing device may provide a recommendation to seek immediate medical attention to a computing device of the patient. The threshold condition may be configurable. In some embodiments, the threshold condition may be set based on information from a trusted source (e.g., evidence-based guidelines, clinical trial results, physician research, and the like).

Figure 33:
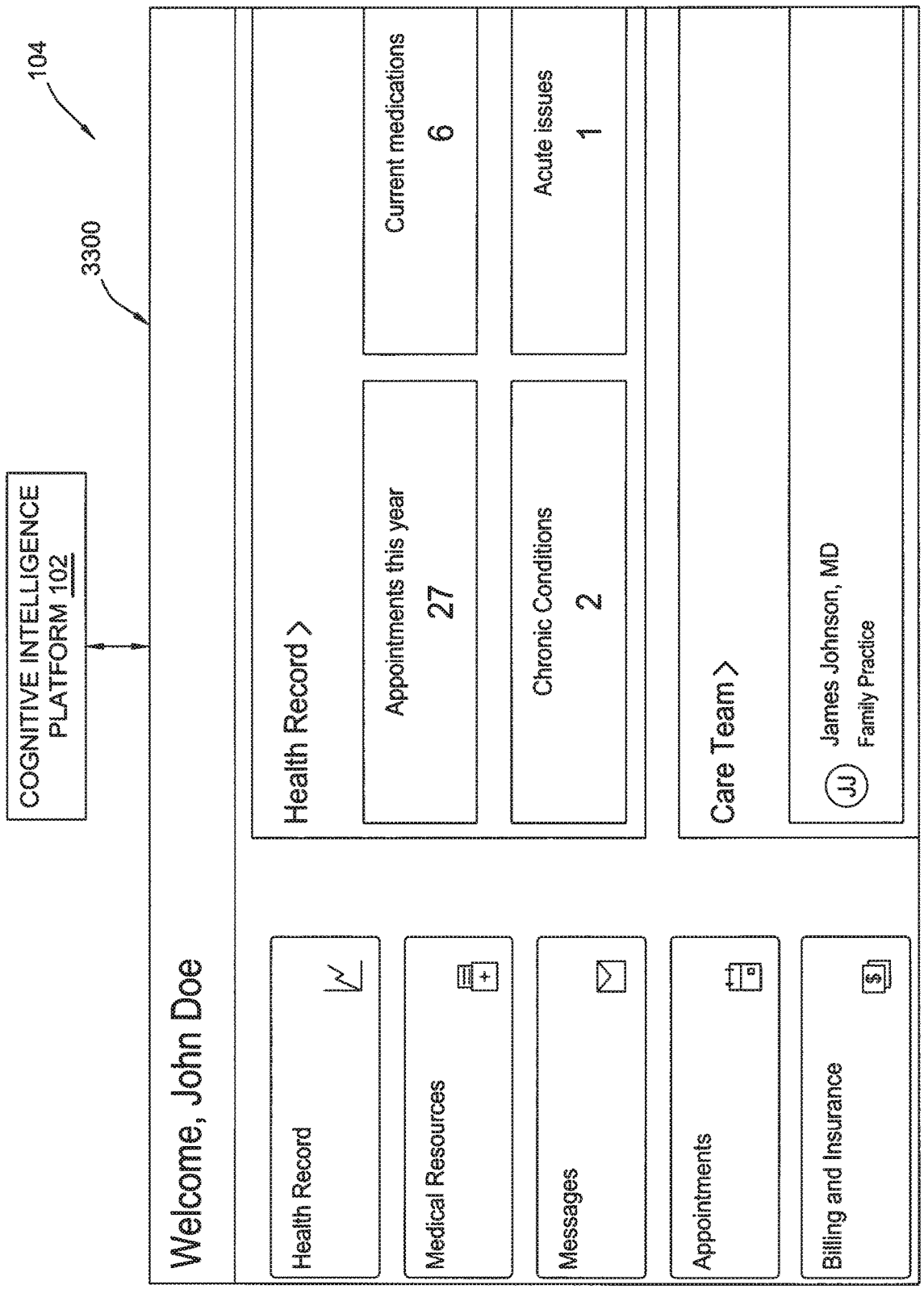
FIG. 33 shows an example of providing a home user interface for an autonomous multipurpose application, in accordance with various embodiments.

FIG. 33 shows an example of providing a home user interface 3300 for an autonomous multipurpose application, in accordance with various embodiments. It should be noted that the user interfaces of the autonomous multipurpose application presented on the user device 104 of a patient may be referred to as a patient viewer herein. The home user interface 3300 is presented on a display of the user device 104. The user device 104 is communicatively coupled with the cognitive intelligence platform 102 that may execute the autonomous multipurpose application. The user can manage their healthcare using the home user interface 3300. There are various options for "Health Record", "Medical Resources", "Messages", "Appointments", and "Billing and Insurance". The health record section may include information pertaining to the health of the user, such as conditions the user has, vital signs, weight, height, medications, and so forth. The medical resources section may include curated content that is tailored based on the conditions the user has and allows the user to search for any desired content using natural language processing. The messages section may enable a user to send messages to anyone on their care team, such as doctors, nurses, clinician, administrators, and so forth. The appointments section may enable a user to schedule an appointment with a person having a specialty, among other things.

A summary of the health record is presented and includes "Appointments this year", "Current medications", "Chronic conditions", and "Acute issues". Further, the home user interface 3300 includes a "Care Team" section that presents the care providers from whom the user receives services. As depicted, "James Johnson, MD—Family Practice" is on the care team for user John Doe.

Figure 34:
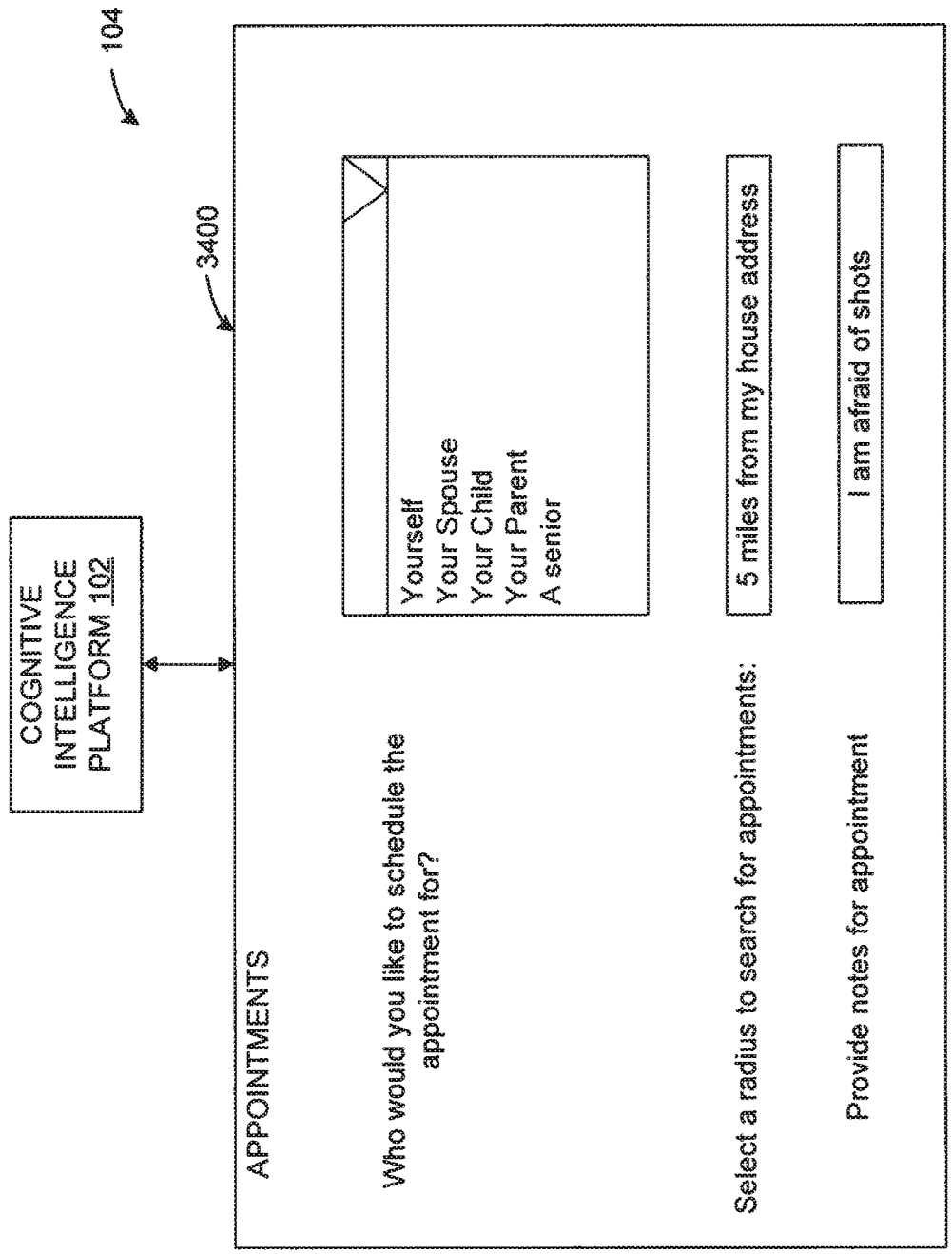
FIG. 34 shows an example of providing a user interface for selecting which person to schedule an appointment for, in accordance with various embodiments.

FIG. 34 shows an example of providing a user interface 3400 for selecting which person to schedule an appointment for, in accordance with various embodiments. The user interface 3400 is presented on a display of the user device 104. The user device 104 is communicatively coupled with the cognitive intelligence platform 102 that may execute the autonomous multipurpose application. The user interface 3400 may be presented when the user selects the "Appointments" button on the home user interface 3300. Such a user interface 3400 may also be presented on a computing device of the service provider 112 and/or the facility 114. For example, an administrator of a doctor's office may use the user interface 3400 on a computing device.

The user interface 3400 presents an option to select which individual for which to schedule an appointment. The options include, for example, "Yourself", "Your Spouse", "Your Child", "Your Parent", and "A Senior". Accordingly, using the user interface 3400, the user may schedule an appointment for multiple-family members. In some embodiments, the user interface 3400 may include an option to select a radius to search for appointments. The user entered "5 miles from my house address". The house address of the user may be stored in a profile maintained by the cognitive intelligence platform 102. In some embodiments, the user may enter an address and a radius to search around that address. Further, as depicted, the user interface 3400 may include an option to provide notes for appointments. The user entered "I am afraid of shots". These notes may be presented to the care provider and/or an administrator at the office of the care provider prior to or during the appointment. Further, the notes may be maintained and presented during subsequent appointments, as well.

Figure 35:
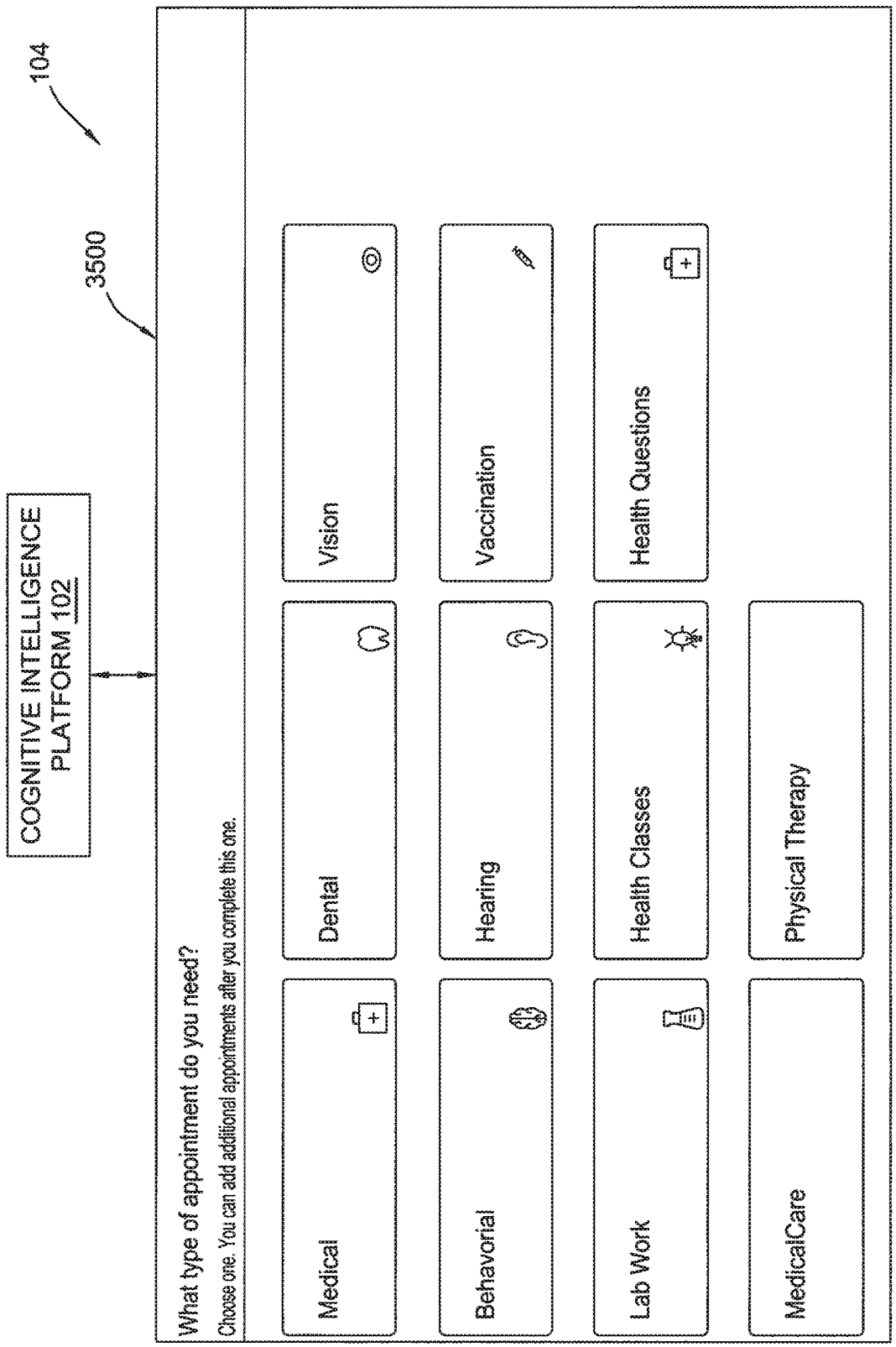
FIG. 35 shows an example of providing a user interface for selecting a specialty for an appointment, in accordance with various embodiments.

FIG. 35 shows an example of providing a user interface 3500 for selecting a specialty for an appointment, in accordance with various embodiments. The user interface 3500 is presented on a display of the user device 104. The user device 104 is communicatively coupled with the cognitive intelligence platform 102 that may execute the autonomous multipurpose application. The user interface 3500 presents numerous specialties from which the user may select. For example, the specialties include "Medical", "Dental", "Vision", "Behavioral", "Hearing", "Vaccination", "Lab Work", "Health Classes", "Health Questions", "MedicalCare", and "Physical Therapy". Any suitable specialty may be included in the user interface 3500, such that the user interface 3500 is not limited to a particular type of specialty.

Figure 36:
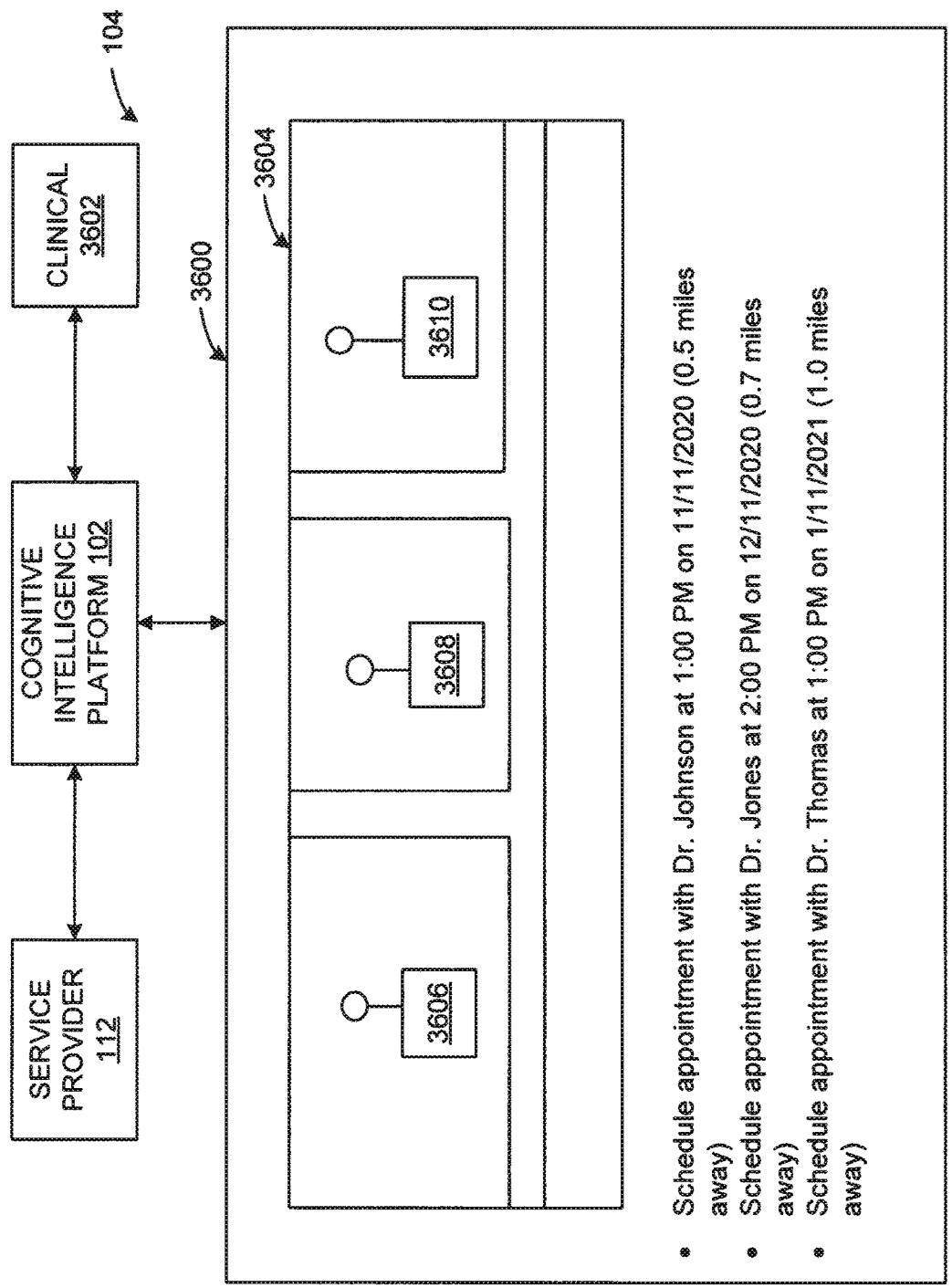
FIG. 36 shows an example of providing a user interface for displaying locations of people and recommended appointment times with the people, in accordance with various embodiments.

FIG. 36 shows an example of providing a user interface 3600 for displaying locations of people and recommended appointment times with the people, in accordance with various embodiments. The user interface 3600 is presented on a display of the user device 104. The user device 104 is communicatively coupled with the cognitive intelligence platform 102 that may execute the autonomous multipurpose application. The user interface 3600 may be presented based on the selection of the specialty or specialties.

The cognitive intelligence platform 102 may be communicatively coupled with systems (e.g., clinical 3602, patient management system, EMR system, scheduling system, etc.) of the service provider 112 having the specialties. In some embodiments, the schedule of the user may be considered when searching for available appointments. The schedules of care providers within the radius specified and matching the specialty or specialties selected may be retrieved from the systems by the cognitive intelligence platform 102. For example, different service providers 112 having available appointments and different specialties may be presented.

As depicted, three appointments are found and recommended. Also, a map 3604 may present the locations 3606, 3608, and 3610 of the offices at which the service providers 112 work. The user interface 3600 presents "Schedule appointment with Dr. Johnson at 1:00 PM on Nov. 11, 2020 (0.5 miles away)", "Schedule appointment with Dr. Jones at 2:00 PM on Dec. 11, 2020 (0.7 miles away)", and "Schedule appointment with Dr. Thomas at 1:00 PM on Jan. 11, 2021 (1.0 miles away)". Thus, multiple service providers 112 at different locations may be recommended for scheduling an appointment. The order of appointments may be configured to depend on distance away from the user device 104 or address, the date and time the appointments are available, a service cost based on the insurance of the user, and so forth. In some embodiments, the specialties of the service providers 112 with recommended appointments may vary based on which specialties the user selected. For example, Dr. Johnson may be a medical doctor, and Dr. Jones may be a dentist.

FIG. 37 shows an example of providing a user interface 3700 for presenting a profile of a person, in accordance with various embodiments. The user interface 3700 is presented on a display of the user device 104. The user device 104 is communicatively coupled with the cognitive intelligence platform 102 that may execute the autonomous multipurpose application. The user interface 3700 may be presented when the user selects to view more details of one of the people associated with the recommended appointments.

For example, the information in the profile of "Jame Johnson, MD" includes the type of practice "Family Practice" and a brief description of Dr. Johnson. The profile also includes his education, services he performs, and languages he speaks. The profile may include other information, as well, and the presented information is for illustration purposes and is not to limit the disclosure. In some embodiments, the profile may include the types of insurance accepted by Dr. Johnson and/or the clinic/hospital at which he works.

Figure 38:
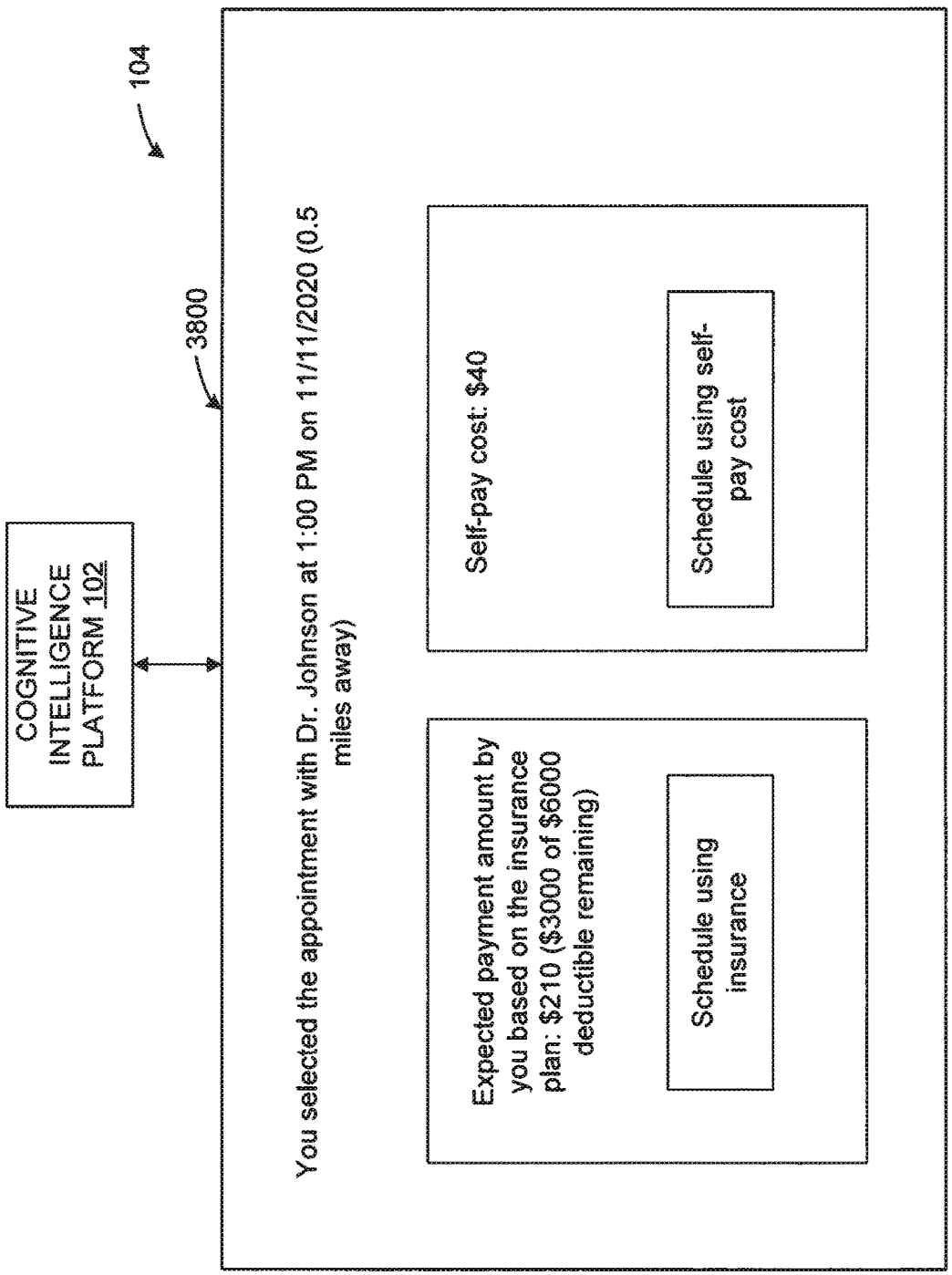
FIG. 38 shows an example of providing a user interface that shows various payment options for the selected appointment, in accordance with various embodiments.

FIG. 38 shows an example of providing a user interface 3800 that shows various payment options for the selected appointment, in accordance with various embodiments. The user interface 3800 is presented on a display of the user device 104. The user device 104 is communicatively coupled with the cognitive intelligence platform 102 that may execute the autonomous multipurpose application. The user interface 3800 may be presented when the user selects one of the recommended appointments presented in the user interface 3600 of FIG. 36.

The user interface 3800 may present information indicating that "You selected the appointment with Dr. Johnson at 1:00 PM on Nov. 11, 2020 (0.5 miles away)". The cognitive intelligence platform 102 may retrieve the insurance plan for the user of the user device 104 that selected the appointment. The cognitive intelligence platform 102 may determine the deductible and/or co-pay for the insurance plan, and determine an expected payment that the user will be expected to pay based on the deductible and/or co-pay. The autonomous multipurpose application may perform one or more function calls to an application programming interface of a system associated with the insurance provider to determine what the user is expected to pay, an amount the insurance provider may cover, a deductible amount, a co-pay, and the like. For example, if the deductible for the insurance plan is $6,000, the user has paid $3,000 toward the deductible, and the service to be performed by Dr. Johnson costs $210, then the user may be expected to pay the $210 out of pocket that will apply towards the deductible because the deductible has not been met yet. In some instances, the entity (e.g., clinic, hospital, office, etc.) at which the service provider performs the service may offer a self-pay cost for particular services. In the depicted example, a self-pay costs of $40 is presented for Dr. Johnson to perform the service.

In the depicted example, electronic scheduling is not enabled, and thus, the user was allowed to select which appointment they wanted to schedule, and the user interface 3800 is presented that allows the user to select how to pay for the service to be provided at the scheduled appointment. Accordingly, the autonomous multipurpose application provides cost transparency and the ability to choose different options for paying for the service via the user interface 3800.

Figure 39:
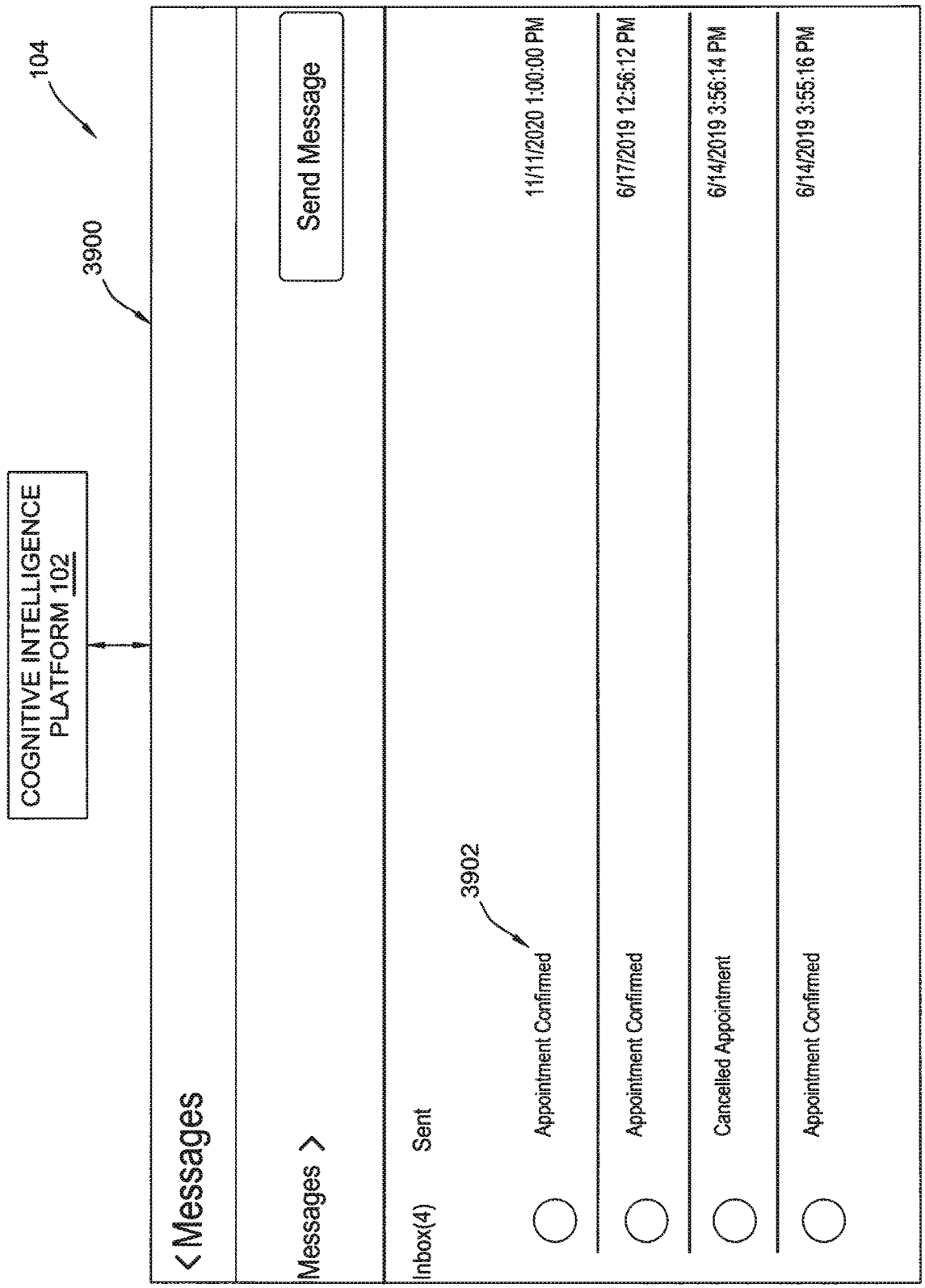
FIG. 39 shows an example of providing a user interface that shows messages pertaining to appointments for a user, in accordance with various embodiments.

FIG. 39 shows an example of providing a user interface 3900 that shows messages pertaining to appointments for a user, in accordance with various embodiments. The user interface 3900 is presented on a display of the user device 104. The user device 104 is communicatively coupled with the cognitive intelligence platform 102 that may execute the autonomous multipurpose application. The user interface 3900 may be presented when the user selects the Messages tab on the home user interface 3300 of FIG. 33.

As depicted, an inbox of the user presents 4 messages. A first message 3902 indicates that the appointment was confirmed with Dr. Johnson on Nov. 11, 2020 at 1:00:00 PM. This confirmation message 3902 may be received in response to the user selecting the particular appointment and the user device transmitting a message to the cognitive intelligence platform 102. The cognitive intelligence platform 102 may communicate via APIs with a system (e.g., EMR) associated with Dr. Johnson to send the appointment request to the system. If the appointment is still available, the system may book the appointment as a booked appointment and transmit the message 3902 back to the cognitive intelligence platform 102 and/or the user device 104.

The messages may use cryptography and be presented by the user interface 3900 after decryption. In some embodiments, public key—private key encryption may be used to encrypt and decrypt the messages. In some embodiments, the messages may be transmitted via text messaging, emails, and/or voicemail. Thus, omni-channel messaging may be implemented by the cognitive intelligence platform 102.

FIG. 40A shows an example of a cognitive intelligence platform 102 receiving an image 4000 of an insurance card 4002, in accordance with various embodiments. The image 4000 may be captured by a camera of the user device 104. The image 4000 may be a file that is emailed to an email account of the user and accessed on the user device 104. The image 4000 may be obtained in any suitable manner. The image 4000 may be transmitted to the cognitive intelligence platform 102.

The cognitive intelligence platform 102 may perform imaging extraction techniques, such as optical character recognition and/or use a machine learning model trained to identify and extract certain information. The cognitive intelligence platform 102 may use the critical thinking engine 108 that executes artificial intelligence techniques pertaining to natural language processing. For example, optical character recognition may refer to electronic conversion of an image of printed text (e.g., a driver's license, an insurance plan, a certification, etc.) into machine-encoded text. OCR may be used to digitize information include on various cards, documents, and the like. In some embodiments, pattern recognition and/or computer vision may be used to extract information form the cards, documents, and the like. Computer vision may involve image understanding by processing symbolic information from image data using models constructed with the aid of geometry, physics, statistics, and/or learning theory. Pattern recognition may refer to electronic discovery of regularities in data through the use of computer algorithms and with the use of these regularities to take actions such as classifying the data into different categories and/or determining what the symbols represent in the image (e.g., words, sentences, names, numbers, identifiers, etc.).

Further, natural language understanding (NLU) may be performed on the image of the cards, documents, or the like. The NLU techniques may process unstructured data using text analytics to extract entities, relationships, keywords, semantic roles, and so forth. The NLU may extract the text from the images received by the cognitive intelligence platform 102.

For example, FIG. 40B shows an example of the cognitive intelligence platform 102 extracting insurance plan information and causing it to be presented on a user device 104, in accordance with various embodiments. The insurance plan information presented on the user device 104 includes "Your insurance plan is: Bluecross Blueshield (BCBS)®", "Your dependents are: Spouse, Child", "Your insurance expires on: 1/1/2021", "Your deductible is: $6000", and "You have paid $3000 of the $6000 deductible."

FIG. 40C shows an example of the cognitive intelligence platform 102 extracting driver's license information and causing it to be presented on the user device 104, in accordance with various embodiments. User interface 4010 is presented on the user device 104. As depicted, the information extracted from an image 4012 of the driver's license includes First Name ("Regina b"), Last Name ("ranoa"), Sex ("Female"), Date of Birth ("06/21/1961"), Address ("655 12 S 224, Oakland CA 94607"), Issue Date ("09/30/2011"), Expiration Date ("10/31/2016"), and ID number ("B82364178"). Also, an image 4014 of a face of the person on the image 4012 of the driver's license may be extracted and used for a profile picture of the user. Other information that may be extracted may include the Eye Color, Height, Weight, and so forth. The information extracted from the image 4012 may be associated with the user and stored in the cognitive intelligence platform 102.

Figure 40D:
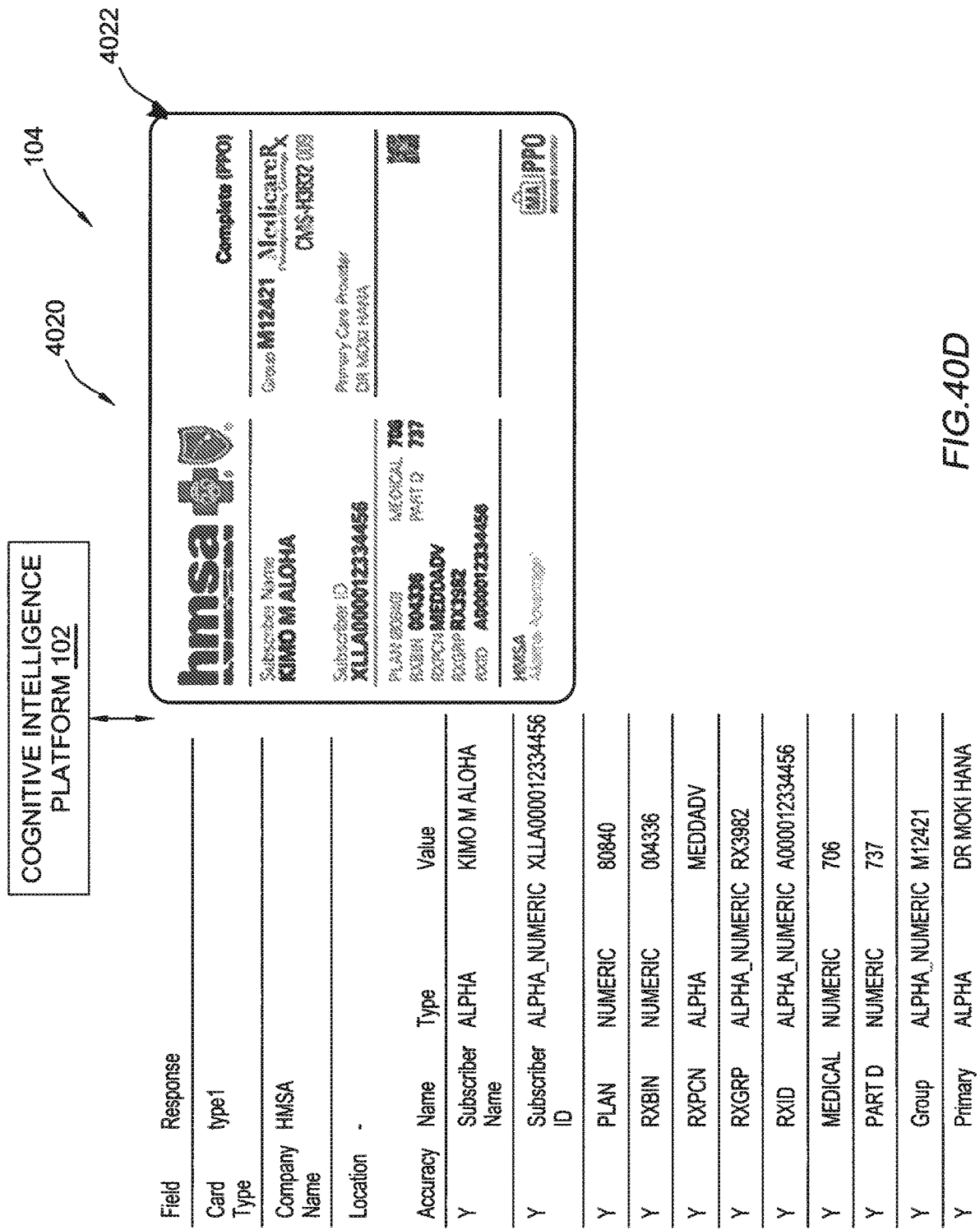
FIG. 40D shows another example of the cognitive intelligence platform extracting insurance plan information and causing it to be presented on a user device, in accordance with various embodiments.

FIG. 40D shows another example of the cognitive intelligence platform 102 extracting insurance plan information and causing it to be presented on the user device 104, in accordance with various embodiments. User interface 4020 is presented on the user device 104. As depicted, the information extract from an image 4022 of the insurance card may include various columns for "Accuracy", "Name", "Type", and "Value". The Accuracy column refers to whether the information extracted is accurate. For example, a service (application programming interface) associated with the insurance provider (HMSA) may be called and provided with the information extracted from the image 4022. The service may determine whether the information is accurate for the insurance plan of the user and return a response indicated "Y" or "N". The Name column refers to the name of the data. The Type column refers to the data type of the information. The Value column refers to the value of the data extracted from the image 4022.

In the depicted example, the following information may be extracted and presented in the user interface 4020: Company Name ("HMSA"), Subscriber Name ("KIMO M ALOHA"), Subscriber ID ("LLA000012334456""), PLAN ("80840"), RXBIN ("004336"), RXPCN ("MEDDADV"), RXGRP ("RX3982"), RXID ("A000012334456"), MEDICAL ("706"), PART D ("737"), Group ("M12421"), Primary ("DR MOKI HANA"). The cognitive intelligence platform 102 validated that each value of data is accurate and presents "Y" in the Accuracy column for each row of data. The information extracted from the image 4022 may be associated with the user and stored in the cognitive intelligence platform 102.

Figure 41:
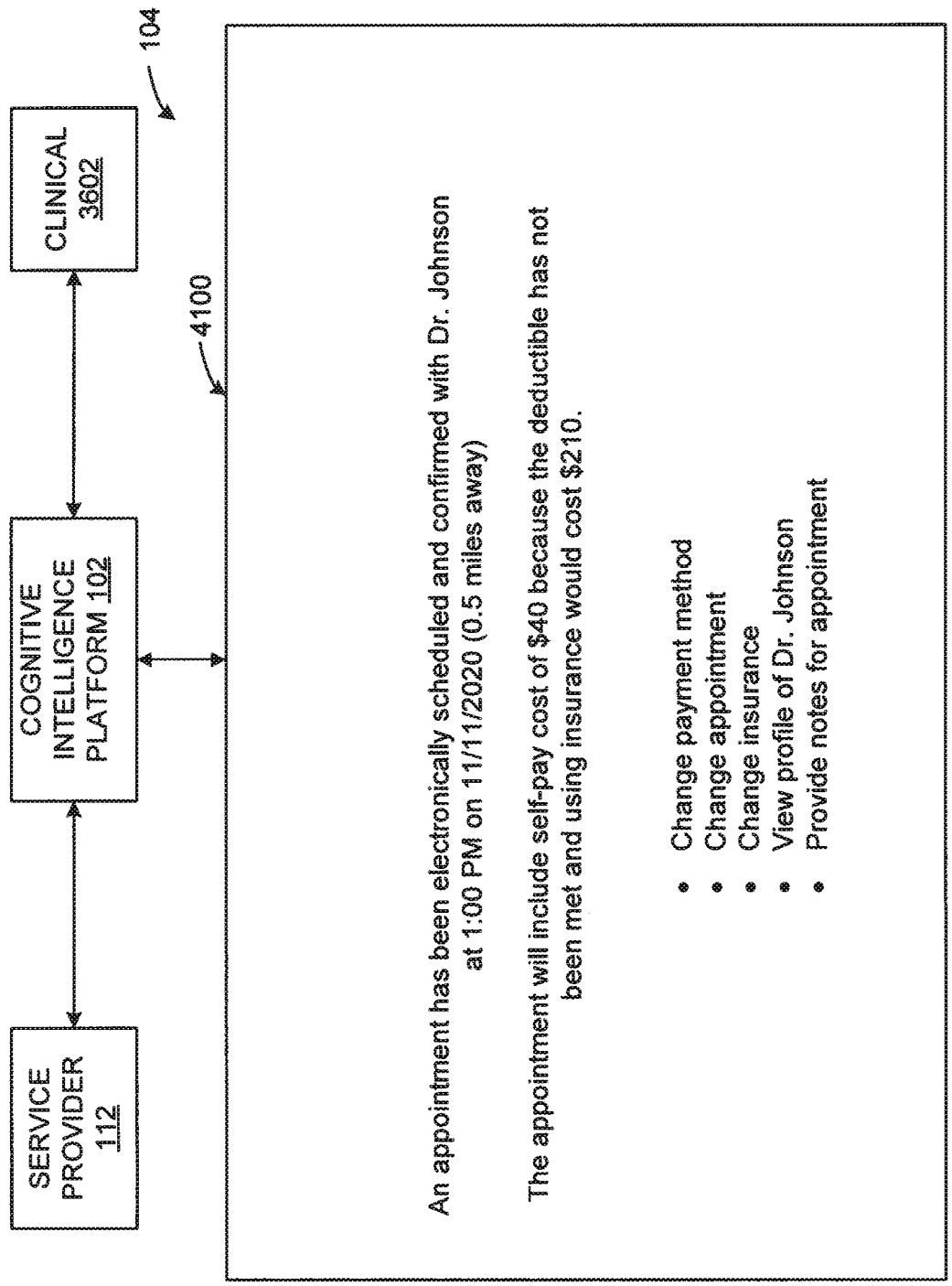
FIG. 41 shows an example of providing a user interface that shows an appointment has been electronically scheduled, in accordance with various embodiments.

FIG. 41 shows an example of providing a user interface 4100 that shows an appointment has been electronically scheduled, in accordance with various embodiments. The user device 104 presents the user interface 4100 of the autonomous multipurpose application. The user may have elected to enable electronic scheduling via an option presented on the user device 104. The autonomous multipurpose application may be capable of allowing the user to enable or disable the electronic scheduling at any time.

In the depicted example, the user elected to enable electronic scheduling. Accordingly, when the user requests to schedule an appointment for a selected user (e.g., their self, a dependent, etc.) and a specialty of a person to perform a service at the appointment, the cognitive intelligence platform 102 may obtain the schedules of people having the specialty within a geolocation radius of the user. For example, the cognitive intelligence platform 102 may retrieve the schedules from systems (e.g., EMRs) of the service provider 112 and/or a clinical system 3602. The cognitive intelligence platform 102 (e.g., autonomous multipurpose application) may analyze multiple factors when selecting which appointment to schedule. The multiple factors may include availability of the people having the specialty, availability of the user, ratings of the people having the specialty, proximity to the user of the people having the specialty, insurance considerations, and the like. For example, the cognitive intelligence platform 102 may determine an expected payment amount the selected user will be expected to pay for the service to be performed based on a deductible and/or co-pay specified in the insurance plan of the selected user. The cognitive intelligence platform 102 may also determine a self-pay cost that the selected user will be expected to pay without using insurance.

The cognitive intelligence platform 102 may select the appointment with Dr. Johnson based on the factors described above. Accordingly, the user interface 4100 presents "An appointment has been electronically scheduled and confirmed with Dr. Johnson at 1:00 PM on 11/11/2020 (0.5 miles away). Further, the cognitive intelligence platform 102 may select the option for the self-pay cost for the appointment without using insurance because the self-pay cost is cheaper than the expected payment amount using insurance. Accordingly, the user interface 4100 presents "The appointment will include self-pay cost of $40 because the deductible has not been met and using insurance would cost $210." Further, the user interface 4100 may present options to allow the user to "Change payment method", "Change appointment", "Change insurance", "View profile of Dr. Johnson", and "Provide notes for appointment". Other options may include "Schedule another appointment".

Figure 42:
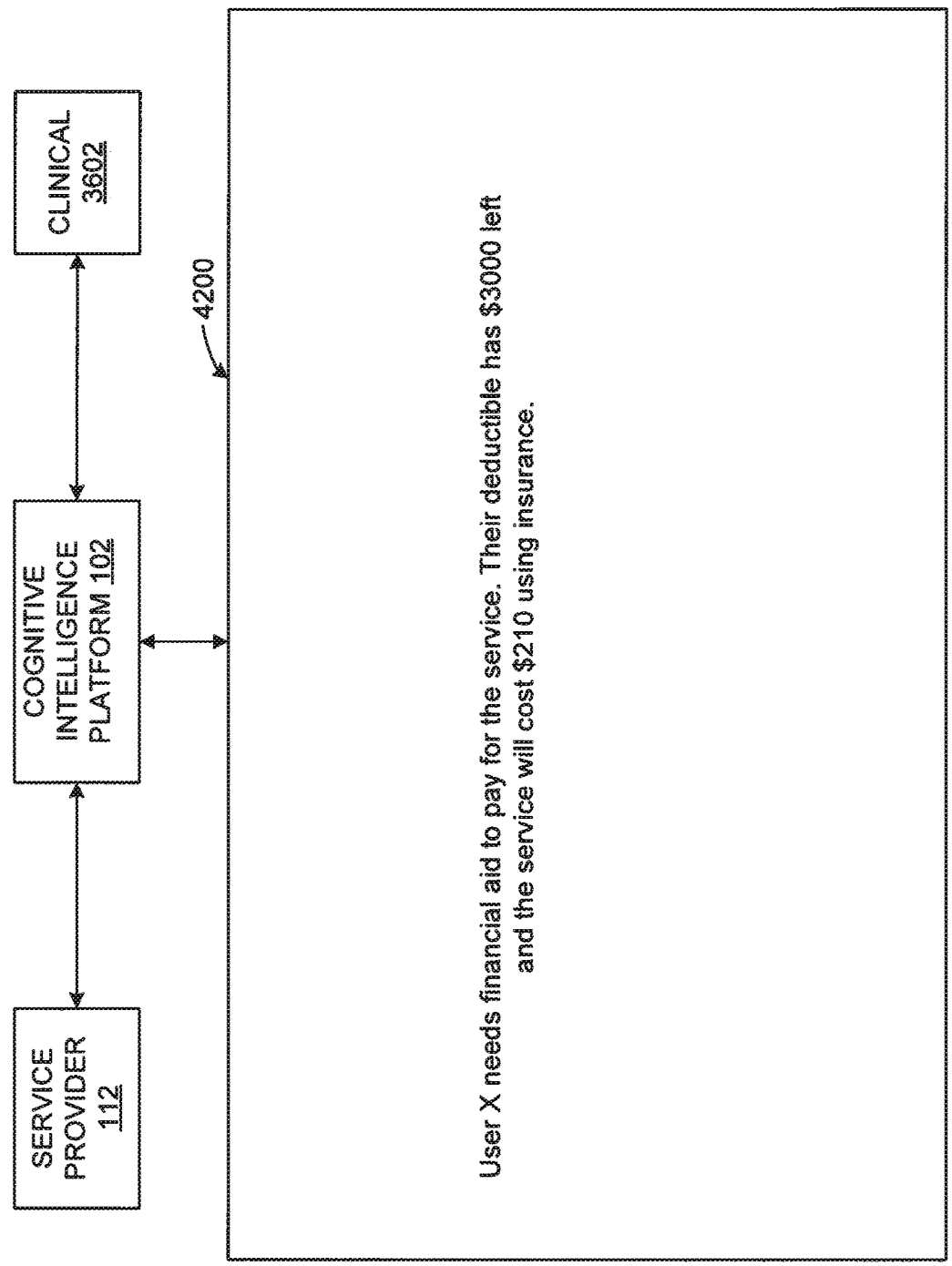
FIG. 42 shows an example of providing a user interface that shows a user needs financial aid for a particular service, in accordance with various embodiments.

FIG. 42 shows an example of providing a user interface 4200 that shows a user needs financial aid for a particular service, in accordance with various embodiments. The user interface 4200 may be presented on a device of the service provider 112. The service provider 112 may be the physician, administrator, or the like. The cognitive intelligence platform 102 may determine, based on the insurance plan of the user, that the user may need financial aid to pay for the service. For example, if the insurance is a high deductible and the service cost is expensive, then the cognitive intelligence platform 102 may determine the user may want financial aid. The user interface 4200 presents "User X needs financial aid to pay for the service. Their deductible has $3000 left and the service will cost $210 using insurance." In such a scenario, the service provider 112 may discuss financial aid with the user prior to the user coming in for the appointment, during the appointment, and/or after the appointment.

Figure 43:
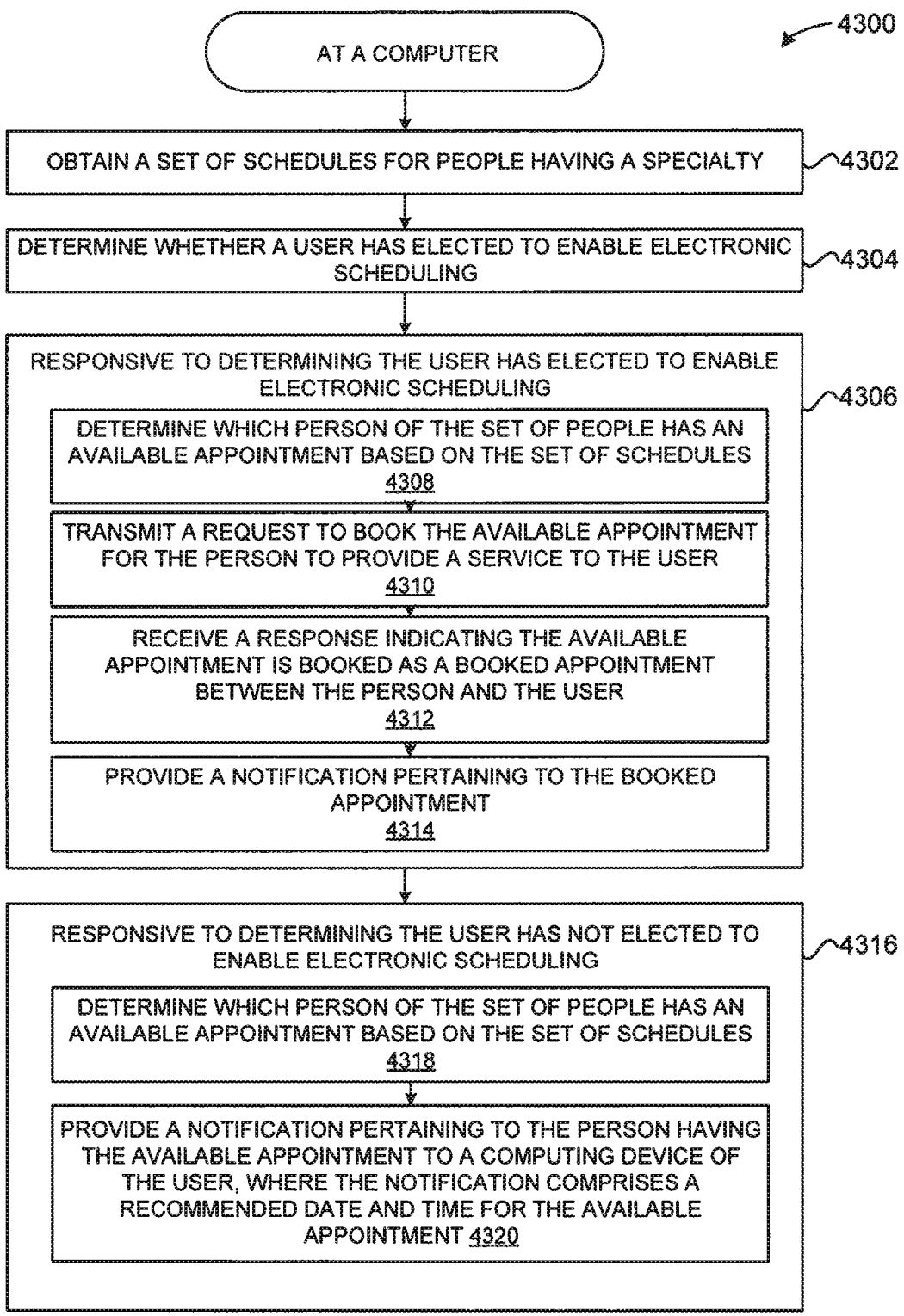
FIG. 43 shows a method for scheduling an appointment based on whether a user has elected to enable electronic scheduling, in accordance with various embodiments.
Figure 44:
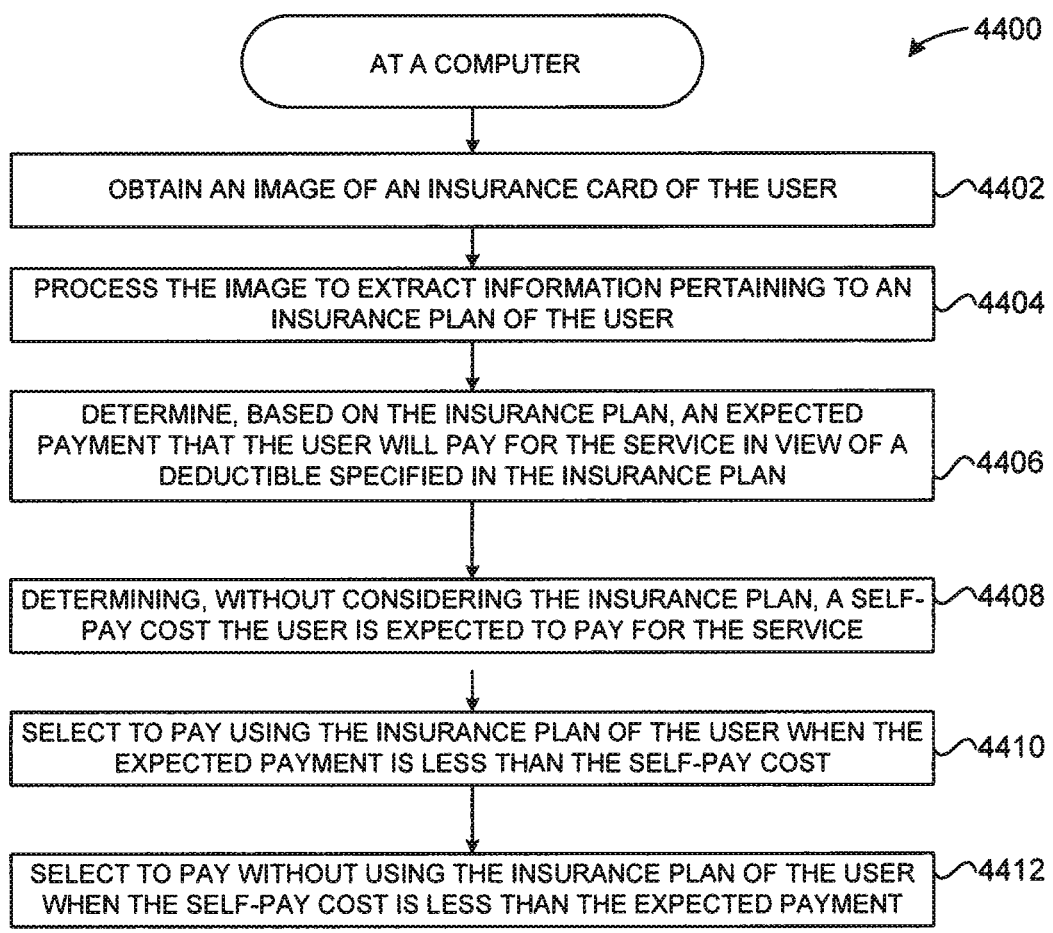
FIG. 44 shows a method for selecting a payment option between a co-pay cost and a self-pay cost, in accordance with various embodiments.
Figure 45:
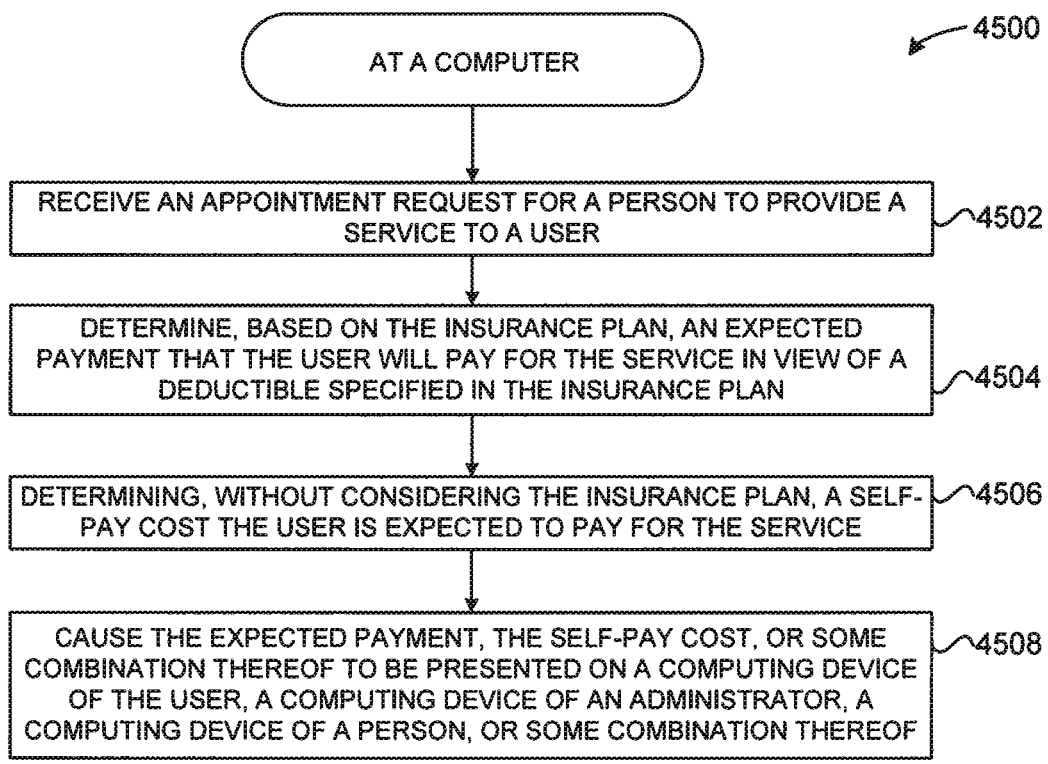
FIG. 45 shows providing various costs associated with a service to a computing device of a user, in accordance with various embodiments.
Figure 52:
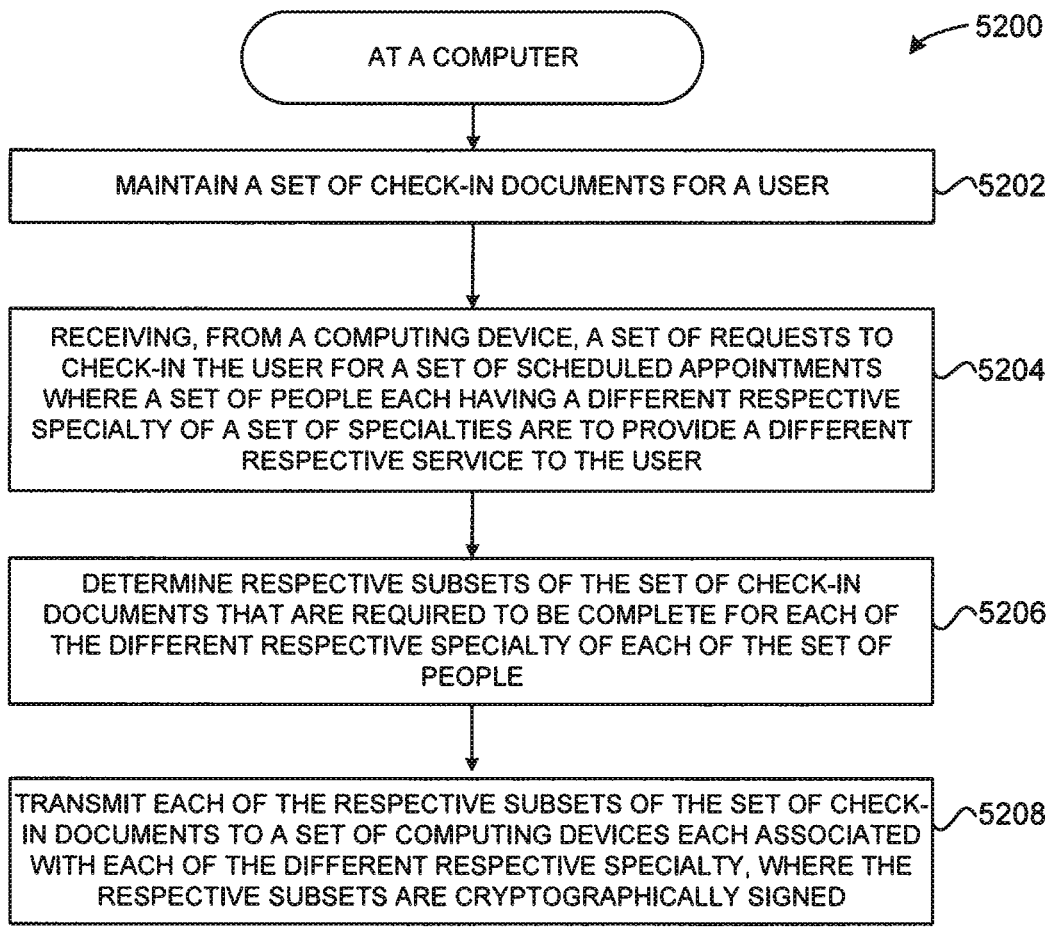
FIG. 52 shows a method of maintaining and transmitting check-in documents for a user to numerous different computing devices associated with people performing different specialties, in accordance with various embodiments.
Figure 53:
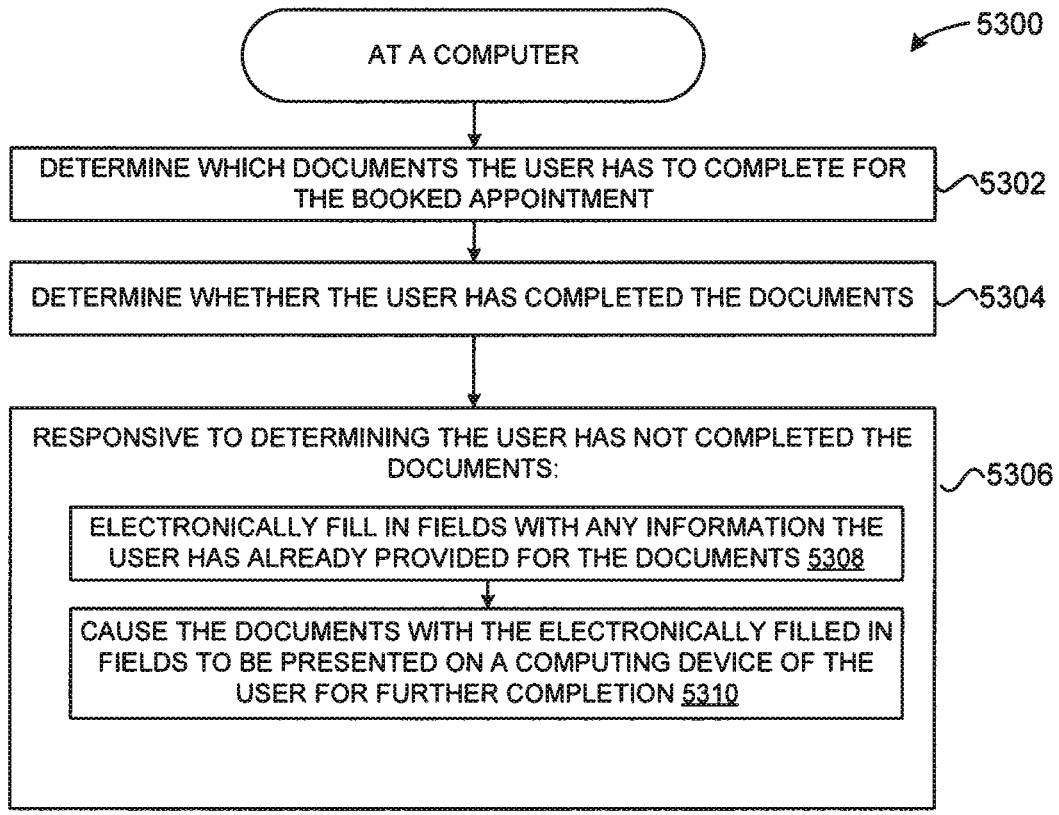
FIG. 53 shows a method of determining whether the user has completed certain check-in documents required for a booked appointment, in accordance with various embodiments.
Figure 54:
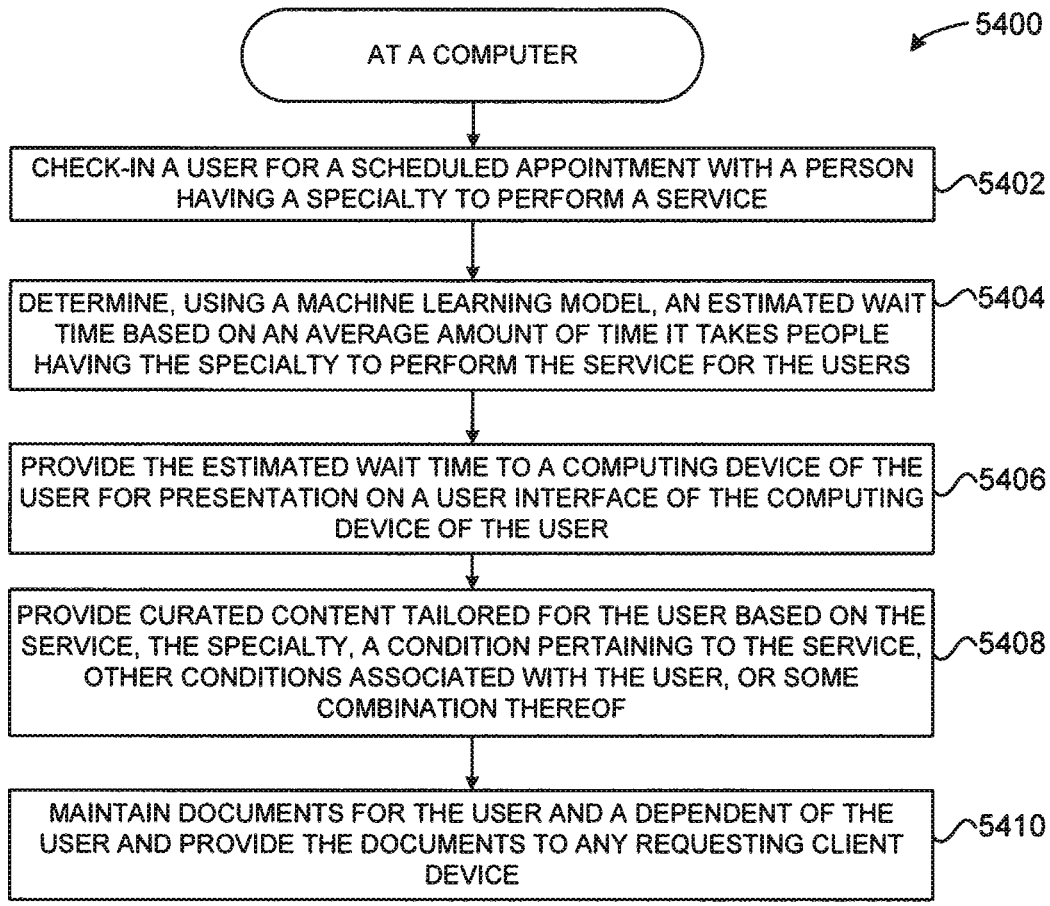
FIG. 54 shows a method of providing an estimated wait time to a computing device of the user, in accordance with various embodiments.

FIGS. 43-45 show methods 4300, 4400, and 4500 for scheduling an appointment between a person having a specialty and a user, FIGS. 52-54 show methods 5200, 5300, and 5400 for checking-in a user for a scheduled appointment. In some embodiments, various of the operations in the methods 4300, 4400, 4500, 5200, 5300, and/or 5400 may be performed in combination.

FIG. 43 shows a method for scheduling an appointment based on whether a user has elected to enable electronic scheduling, in accordance with various embodiments. In some embodiments, the method 4300 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 4300 may include operations that are implemented in computer instructions stored in a memory and executed by a processor of a computing device. In some embodiments, the method 4300 includes operations performed by the cognitive agent 110 (autonomous multipurpose application), the knowledge cloud 106, and/or the critical thinking engine 108 of the cognitive intelligence platform 102 as shown in FIG. 1.

At block 4302, the processing device may obtain a set of schedules for people having a specialty. The processing device may obtain the set of schedules for the set of people having the specialty from at least an electronic medical record system, a patient management system, a scheduling management system, or the like. In some embodiments, the set of schedules may be obtained for people within a geographic radius of a location of the user (e.g., home address of the user) or computing device of the user. The specialty may be selected by the user of the user device 104. For example, the user may desire to go to a dentist for a teeth cleaning or problem they are experiencing with a tooth, the user may desire to go to a medical doctor for certain symptoms they are experiencing, and so forth. To that end, a set of specialties to be selected from may include at least two of a dentist, a medical doctor, an optometrist, a behavioral psychologist, a chiropractor, a physician's assistant, and a masseuse.

At block 4304, the processing device may determine whether a user has elected to enable electronic scheduling. A user interface of the autonomous multipurpose application may be presented on the user device 104 and may present an option to enable or disable electronic scheduling of appointments.

At block 4306, responsive to determining the user has elected to enable electronic scheduling, the processing device may determine (block 4308) which person of the set of people has an available appointment based on the set of schedules, transmit (block 4310) a request to book the available appointment for the person to provide a service to the user, receive (block 4312) a response indicating the available appointment is booked as a booked appointment between the person and the user, and provide (block 4314) a notification pertaining to the booked appointment.

At block 4316, responsive to determining the user has not elected to enable electronic scheduling, the processing device may determine (block 4318) which person of the set of people has an available appointment based on the set of schedules, and provide (block 4320) a notification pertaining to the person having the available appointment to a computing device of the user, where the notification includes a recommended date and time for the available appointment. For example, multiple recommended available appointments may be provided for presentation on a user interface on the user device 104. The recommended available appointments and the locations of the service providers 112 associated with the recommended available appointments may be presented in text form (e.g., a list) on the user interface and/or in a map. The recommended available appointments may each provide a date and time of the appointment, an identity of the service provider 112 to perform the service, a distance from the user or the user device 104, or some combination thereof. The distance from the user device 104 may be determined using global positioning system (GPS) coordinates of the user device 104 and the location of the service provider 112.

In some embodiments, determining which person of the set of people has the available appointment may be based on the available appointment having a future date and time that is closest to a current date and time the request was received. Further, the determination of which person of the set of people has the available appointment may be based on a schedule of the user, insurance considerations (e.g., whether a deductible has been met, and/or a co-pay cost) for the service, and the like.

In some embodiments, the notification pertaining to the booked appointment may be provided to the user device 104, a computing device of the service provider 112, a computing device of an administrator of the service provider 112, and/or a computing device of a facility 114. The notification may be a secure message displayed by a user interface of the autonomous multipurpose application, a secure text message, a secure email, and/or a secure voicemail/telephone call.

FIG. 44 shows a method 4400 for selecting a payment option between a co-pay cost and a self-pay cost, in accordance with various embodiments. In some embodiments, the method 4400 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 4400 may include operations that are implemented in computer instructions stored in a memory and executed by a processor of a computing device. In some embodiments, the method 4400 includes operations performed by the cognitive agent 110 (autonomous multipurpose application), the knowledge cloud 106, and/or the critical thinking engine 108 of the cognitive intelligence platform 102 as shown in FIG. 1.

At block 4402, the processing device may obtain an image of an insurance card of the user. The image may be captured using a camera of the user device 104 and may be transmitted to the processing device of the cognitive intelligence engine 102 from the user device 104.

At block 4404, the processing device may process the image to extract information pertaining to an insurance plan of the user. The processing device may use various artificial intelligence techniques to extract the information, such as optical character recognition, pattern recognition, or the like. One or more machine learning models may be trained to identify the text included at portions of the insurance card based on training data that uses labels. For example, supervised training using training data including numerous images of insurance cards with labels identifying pertinent text and identifiers. The trained machine learning models may identify the pertinent text and extract the text from the image by processing pixels and/or using object character recognition.

At block 4406, the processing device may determine, based on the insurance plan, an expected payment that the user will pay for the service in view of a deductible and/or co-pay specified in the insurance plan. The processing device may be communicatively coupled with a system of the insurance provider. The processing device may verify the information extracted from the insurance card with the system of the insurance provider. Further, the processing device may obtain the amount of the deductible, an amount already paid towards the deductible, a co-pay, and the like. In one example, if the user has paid $3000 towards a $6000 deductible, and a service costs $210, then the user may be responsible for the $210 since the deductible is not satisfied. However, in some instances, the deductible may be satisfied and the user may be expected to pay a lower amount (e.g., co-pay of $20).

At block 4408, the processing device may determine, without considering the insurance plan, a self-pay cost the user is expected to pay for the service. Some entities may provide flat fees for certain services performed by the service providers 112 without considering insurance. For example, a service may include a routine physical and may be a flat fee of $40.

At block 4410, the processing device may select to pay using the insurance plan of the user when the expected payment is less than the self-pay cost. At block 4412, the processing device may select to pay without using the insurance plan of the user when the self-pay cost is less than the expected payment. If payment information for the user is stored in a profile of the user, the selected payment option may be paid prior to the appointment, during the appointment, or after completion of the appointment via electronic communication with a system of the service provider 112 or a financial institution associated with the service provider 112. For example, when the user checks-in for the scheduled appointment, the selected payment option may be electronically paid by the autonomous multipurpose application. In some embodiments, the user may pay when they check-in for the appointment at the location of the scheduled appointment.

FIG. 45 shows providing various costs associated with a service to a computing device of a user, in accordance with various embodiments. In some embodiments, the method 4500 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 4500 may include operations that are implemented in computer instructions stored in a memory and executed by a processor of a computing device. In some embodiments, the method 4500 includes operations performed by the cognitive agent 110 (autonomous multipurpose application), the knowledge cloud 106, and/or the critical thinking engine 108 of the cognitive intelligence platform 102 as shown in FIG. 1.

Method 4500 may be performed when the user has elected to disable electronic scheduling.

At block 4502, the processing device may receive an appointment request for a person to provide a service to a user. The appointment request may include a specialty of the person to provide the service to the user. The appointment request may specify an address and a radius around the address from which to search for available appointments. In some embodiments, the appointment request may specify using a geolocation of the user device 104 and a radius around the geolocation from which to search for available appointments. In some embodiments, the appointment request may specify an identity of the person to provide the service to the user. The cognitive intelligence platform 102 may provide recommended available appointments with the person having the specialty.

At block 4504, the processing device may determine, based on the insurance plan, an expected payment that the user will pay for the service in view of a deductible specified and/or co-pay in the insurance plan.

At block 4506, the processing device may determine, without considering the insurance plan, a self-pay cost the user is expected to pay for the service. The self-pay cost may be obtained from a system associated with the facility 114, clinic, or entity at which the service provider 112 is providing the service for the appointment. For example, an entity (e.g., company) may be a store that includes a clinic and there may be fixed self-pay costs for various services, such as vaccines, physicals, consultations, etc.

At block 4508, the processing device may cause the expected payment, the self-pay cost, or some combination thereof to be presented on a computing device of the user (user device 104), a computing device of an administrator, a computing device of a person having the specialty (e.g., service provider 112), or some combination thereof. The user may select the payment option that is preferred and a request to book the selected appointment with the selected payment option may be transmitted to a system (e.g., EMR, scheduling management system, patient management system, etc.) associated with the person having the specialty and/or the facility 114 at which the person having the specialty will perform the service for the selected appointment. If the selected appointment is confirmed, a response may be transmitted to the cognitive intelligence platform 102 and a message may be sent to the user device 104 confirming the appointment.

Figure 46:
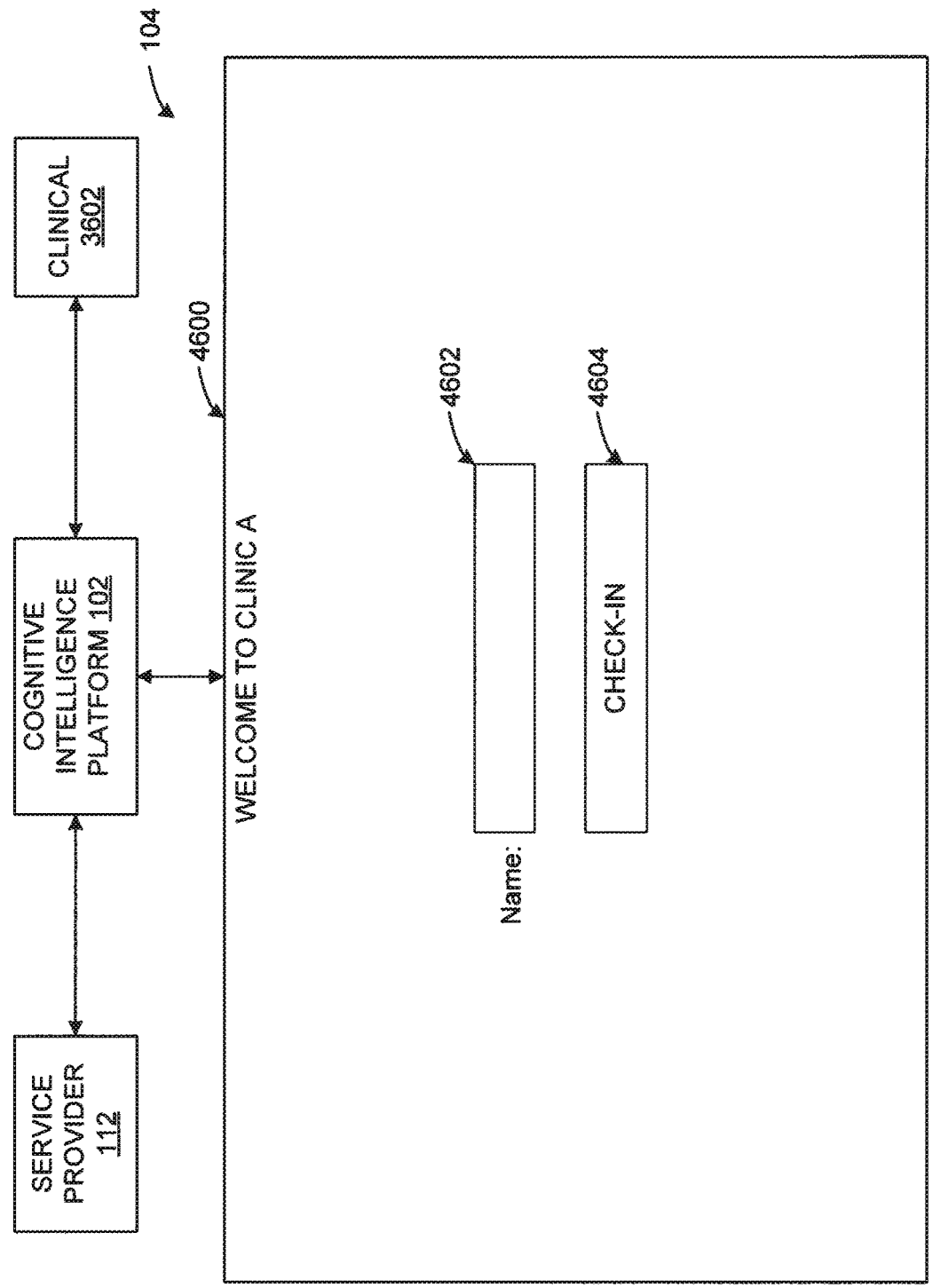
FIG. 46 shows an example of providing a user interface for checking-in a user for service, in accordance with various embodiments.

FIG. 46 shows an example of providing a user interface 4600 for checking-in a user for a service, in accordance with various embodiments. The user device 104 presents the user interface 4100 of the autonomous multipurpose application. As depicted, an option 4602 (e.g., input box) may be presented for the user to enter their name, and another option 4604 (e.g., button) be presented to allow the user to begin the check-in process. When the user selects the option 4604, a check-in request may be transmitted to the cognitive intelligence platform 102. The check-in request may include the name the user provided, or any suitable identifier for the user. The cognitive intelligence platform 102 may retrieve any check-in documents (e.g., consents, medical history, any suitable check-in document, etc.) associated with the name or identifier of the user. The cognitive intelligence platform 102 may store any check-in documents the user has completed at any service provider 112 that has a system (e.g., EMR) communicatively coupled with the cognitive intelligence platform 102. That is, the cognitive intelligence platform 102 may function as a centralized repository for any check-in documents such that the user does not to refill the same check-in documents if they go to a different service provider 112.

Instead, if the check-in documents required for a new service provider 112 are complete, the cognitive intelligence platform 102 may transmit those check-in documents to the system (e.g., EMR) associated with the new service provider 112, and the user will be checked-in without having to refill out the check-in documents. If the check-in documents are not complete, the cognitive intelligence platform 102 may cause the user device 104 to present the incomplete check-in documents for the user to complete.

Figure 47:
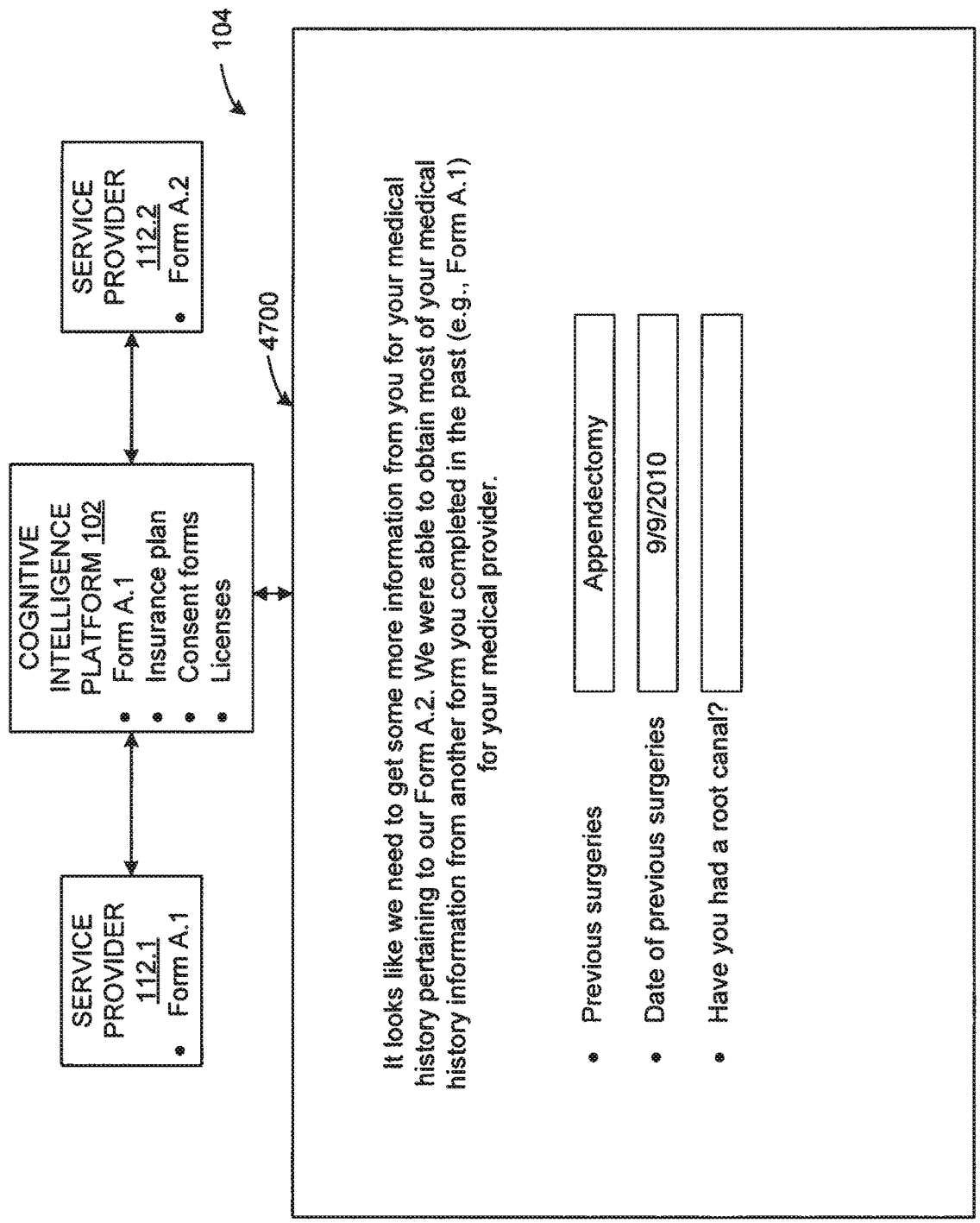
FIG. 47 shows an example of providing a user interface that shows additional required information is needed for a check-in document, in accordance with various embodiments.

For example, FIG. 47 shows an example of providing a user interface 4700 that shows additional required information is needed for a check-in document, in accordance with various embodiments. The user interface 4700 may be presented on the user device 104 and/or a computing device of an administrator. In the depicted example, the user is checking-in for an appointment scheduled with service provider 112.2 (e.g., a dentist). Service provider 112.2 requires completion of check-in document "Form A.2". The user previously went to an appointment with service provider 112.1 (e.g., medical provider), where the user completed check-in document "Form A.1". The cognitive intelligence platform 102 received the completed check-in document "Form A.1", associated it with the identity of the user, and stored it in a database. As depicted, the cognitive intelligence platform 102 is storing Form A.1, Insurance plan, Consent forms, and Licenses for the user.

Form A.2 includes most of the same information as Form A.1, but Form A.2 includes a new field of information that was not included in Form A.1. Accordingly, the user interface 4700 indicates "It looks like we need to get some more information from you for your medical history pertaining to our Form A.2. We were able to obtain most of your medical history information from another form you completed in the past (e.g., Form A.1) for your medical provider."

Accordingly, as depicted, the fields in Form A.2 for "Previous surgeries" ("Appendectomy") and "Date of previous surgeries" ("9/9/2010") is prefilled with the information obtained from Form A.1. The new field "Have you had a root canal?" is specific to the service provider 112.2 and is incomplete. The user may enter yes or no in the field and submit the Form A.2 to the cognitive intelligence platform 102 to maintain for future reference.

Figure 48A:
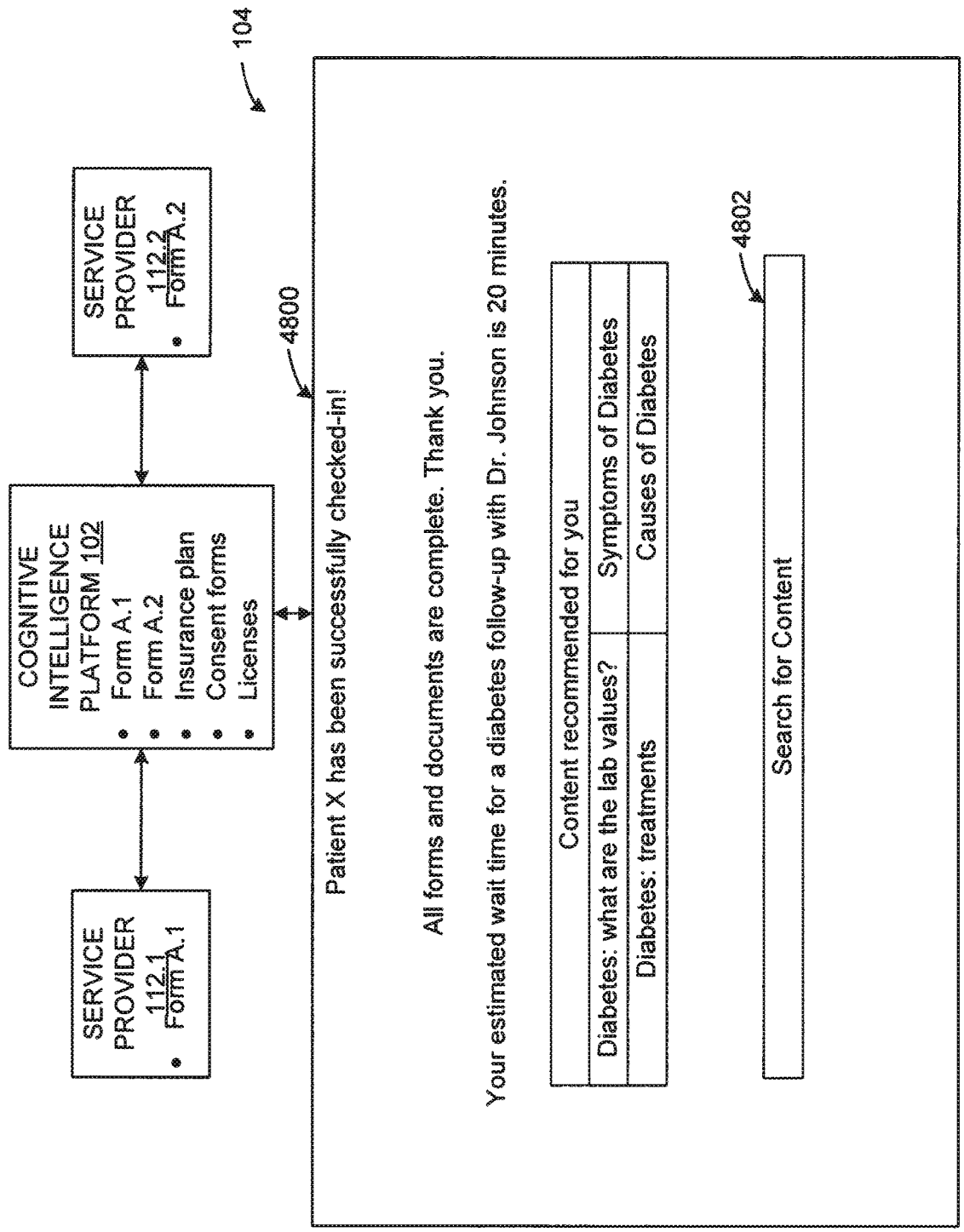
FIG. 48A shows an example of providing a user interface that shows check-in is complete, an estimated wait time, and curated content tailored for a condition of the user, in accordance with various embodiments.

For example, FIG. 48A shows an example of providing a user interface 4800 that shows check-in is complete, an estimated wait time, and curated content tailored for a condition of the user, in accordance with various embodiments. The Form A.2 is now stored in the cognitive intelligence platform 102, as depicted. The user interface 4800 of the autonomous multipurpose application may be presented on the user device 104 and/or a computing device of an administrator of the service provider 112.

The user interface 4800 indicates "Patient X has been successfully checked-in! All forms and documents are complete. Thank you." Further, the cognitive intelligence platform may estimate the wait time using one or more machine learning models and/or artificial intelligence techniques. The estimation at the patient level may be based on the time of check-in and how many patients are waiting in various specialty queues. The estimation may also account for multiple physicians having the same specialty that are working the day of the appointment. In some instances, patients may check-in randomly, may have multiple appointments, and/or arrive late. These scenarios may be accounted for to provide the estimated wait time. In some embodiments, the wait time may be estimated based on the average wait time for a given specialty at a particular facility 114. In some embodiments, the wait time may be estimated based on historical information for the service provider 112 with which the patient has the appointment. The historical information may include an average amount of time it takes the service provider 112 to perform the particular services for patients that are in the wait queue in front of the patient waiting. As depicted, the user interface 4800 presents "Your estimated wait time for a diabetes follow-up with Dr. Johnson is 20 minutes."

In addition, the cognitive intelligence platform 102 may use the knowledge cloud 106 to retrieve curated content associated with a condition for which the patient is seeking treatment at the appointment. For example, the user may have scheduled the appointment for the condition Diabetes. As depicted, the user interface 4800 presents content recommended for the user, such as "Diabetes: what are the lab values?", "Diabetes: treatments", "Symptoms of Diabetes", and "Causes of Diabetes". The content may be links that the user may select to read and/or view the content. The content may include articles, videos, documents, pictures, etc. that are reviewed, curated, and/or approved by licensed medical professionals. In some embodiments, the cognitive intelligence platform 102 may also retrieve curated content for any condition of the patient that the cognitive intelligence platform 102 is aware of. For example, if the patient has asthma, content pertaining to asthma may be provided. As such, the amount of information presented to a user may not overwhelm the user and may provide an enhanced experience because the content is tailored to their conditions. Further, computing resources (processing, memory) and network bandwidth may be reduced because the user may not perform searches for information pertaining to their conditions since content pertaining to their conditions is presented on the user interface 4800. This may enable educating the user about their conditions while the user waits.

Further, in some embodiments, if the user desires to search for additional content, the user may select an option 4802 and enter a natural language search query into an input box. Natural language processing may be used as described herein to obtain content pertaining to the search query.

FIG. 48B shows an example of providing a user interface 4810 that shows an estimated wait time for a scheduled appointment, in accordance with various embodiments. The user interface 4810 of the autonomous multipurpose application may be presented on the user device 104 and/or a computing device of an administrator of the service provider 112. As depicted, the user may have scheduled two appointments for May 30. The first appointment is for a first person "Adrian Smith" and the second appointment is for a second person "Zahra Smith". The user interface 4810 indicates the wait time for a first appointment is 20 minutes. The user interface 4810 also presents a self-pay estimate of $45 for each medical appointment with the same medical doctor. Further, an estimated total ($90.00) for the scheduled appointments is presented. Options 4812 and 4812 may also be presented. Option 4812 may allow the user to add another appointment for their self or any dependent. Option 4814 may allow the user to check-in for the appointments for each user. Further, the user may cancel and/or reschedule any appointments presented on user interface 4810.

Accordingly, the user interface 4810 enables a user to manage multiple appointments for multiple different users in a single user interface 4810. Thus, the user does not have to log into different systems or user interfaces to view their scheduled appointments for different users. As a result, computing resources may be saved using the disclosed techniques, and the user experience may be enhanced using the user interface 4810.

Figure 49:
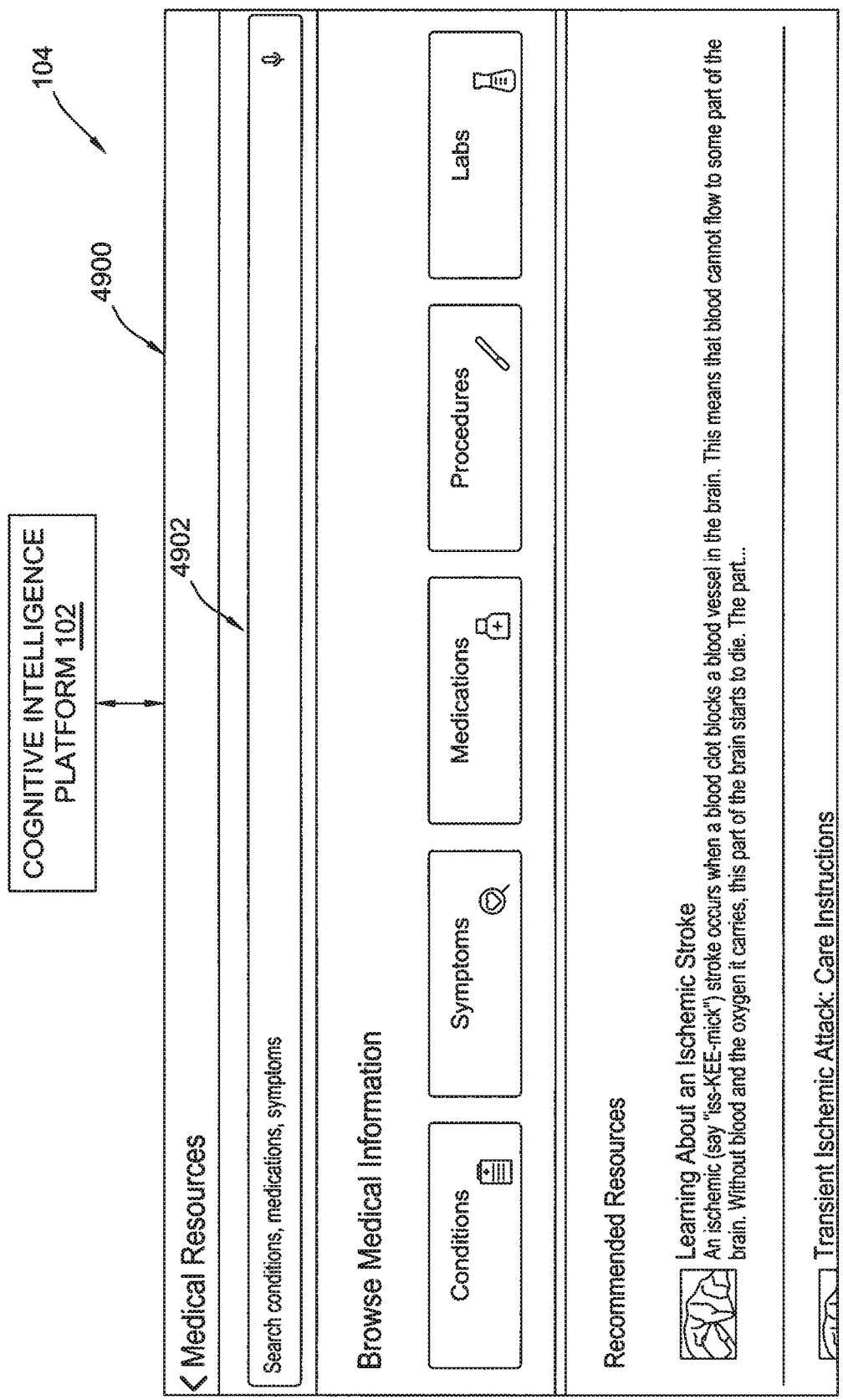
FIG. 49 shows an example of providing a user interface that allows searching for content and provides recommended content based on a condition of the user, in accordance with various embodiments.

FIG. 49 shows an example of providing a user interface 4900 that allows searching for content and provides recommended content based on a condition of the user, in accordance with various embodiments. The user interface 4900 of the autonomous multipurpose application may be presented on the user device 104. The user interface 4900 may be accessed by the user selecting the "Medical Resources" tab on the home user interface 3300 in FIG. 33. The cognitive intelligence platform 102 may store information pertaining to the user that indicates the user has a certain condition (e.g., "Ischemic Stroke"). Accordingly, the cognitive intelligence platform 102 may cause curated content ("Learning About an Ischemic Stroke" and "Transient Ischemic Attach: Care Instructions") to be presented on the user interface 4900 using artificial intelligence. Also, input box 4902 may enable a user to search for conditions, medications, symptoms, and so forth. The cognitive intelligence platform 102 may process the natural language as described herein to provide the content associated with the entered search query.

In addition, graphical elements (e.g., buttons) may be presented for the user to browse medical information. The medical information to be browsed may include conditions, symptoms, medications, procedures, labs, and so forth. When a graphical element is selected, content associated with the medical information may be retrieved from the knowledge cloud 106 and presented on the user interface 4900.

Figure 50:
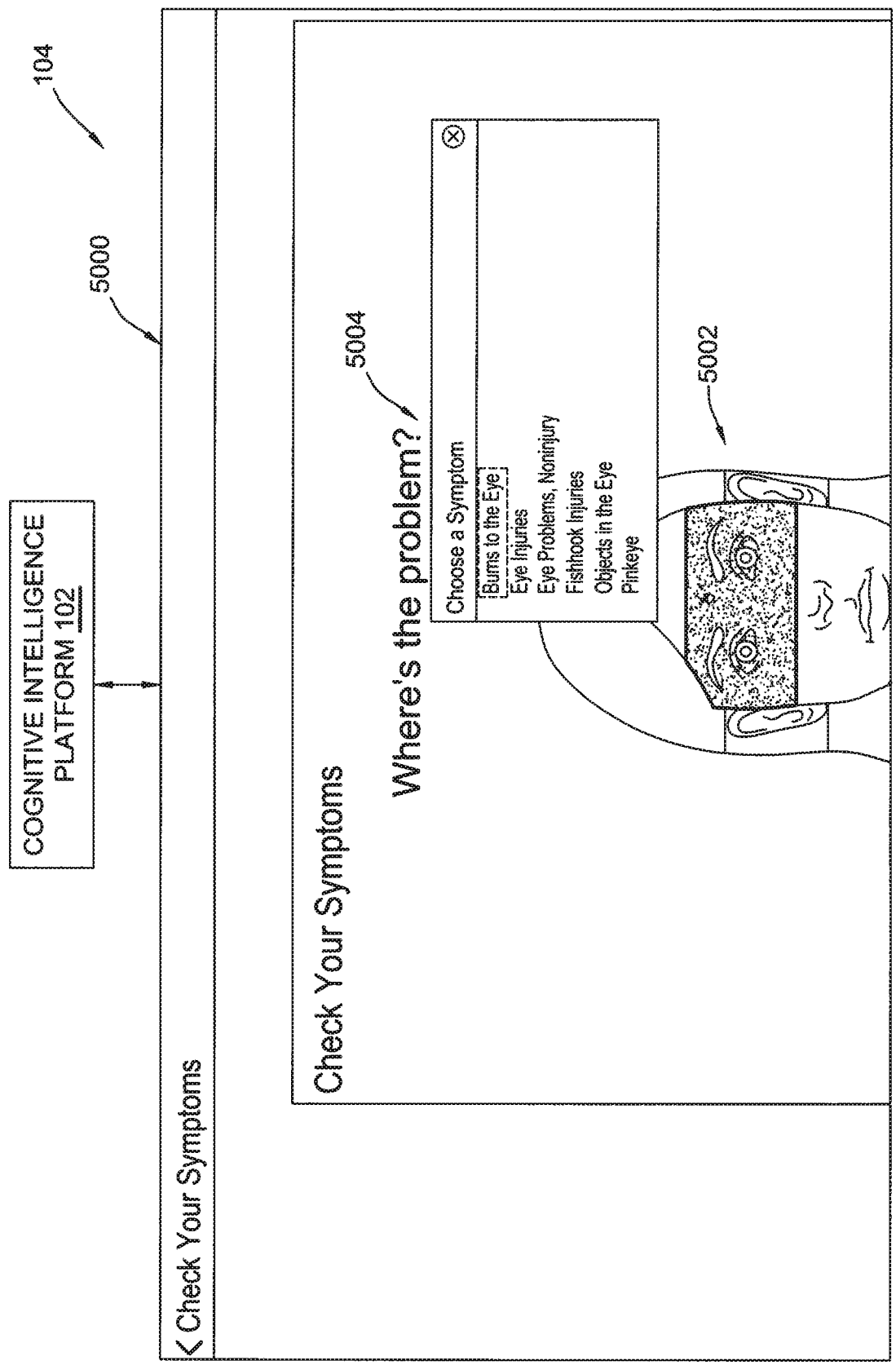
FIG. 50 shows an example of providing a user interface to check symptoms, in accordance with various embodiments.

FIG. 50 shows an example of providing a user interface 5000 to check symptoms, in accordance with various embodiments. The user interface 5000 of the autonomous multipurpose application may be presented on the user device 104. The user interface 5000 may include a graphical representation 5002 of a human body (e.g., male and/or female). The graphical representation 5002 may include different portions that are selectable by clicking on the portions (using a mouse and/or a finger on a touchscreen) or mousing-over the portions to highlight the portions. As depicted, the user selected a portion corresponding to eyes. A pop-up menu 5004 may appear that includes a list of symptoms to select from. As depicted, the symptoms in the pop-up menu 5004 include "Burns to the Eye", "Eye Injuries", "Eye Problems, Noninjury", "Fishhook Injuries", "Objects in the Eye", "Pinkeye". The user may select "Burns to the Eye".

Figure 51:
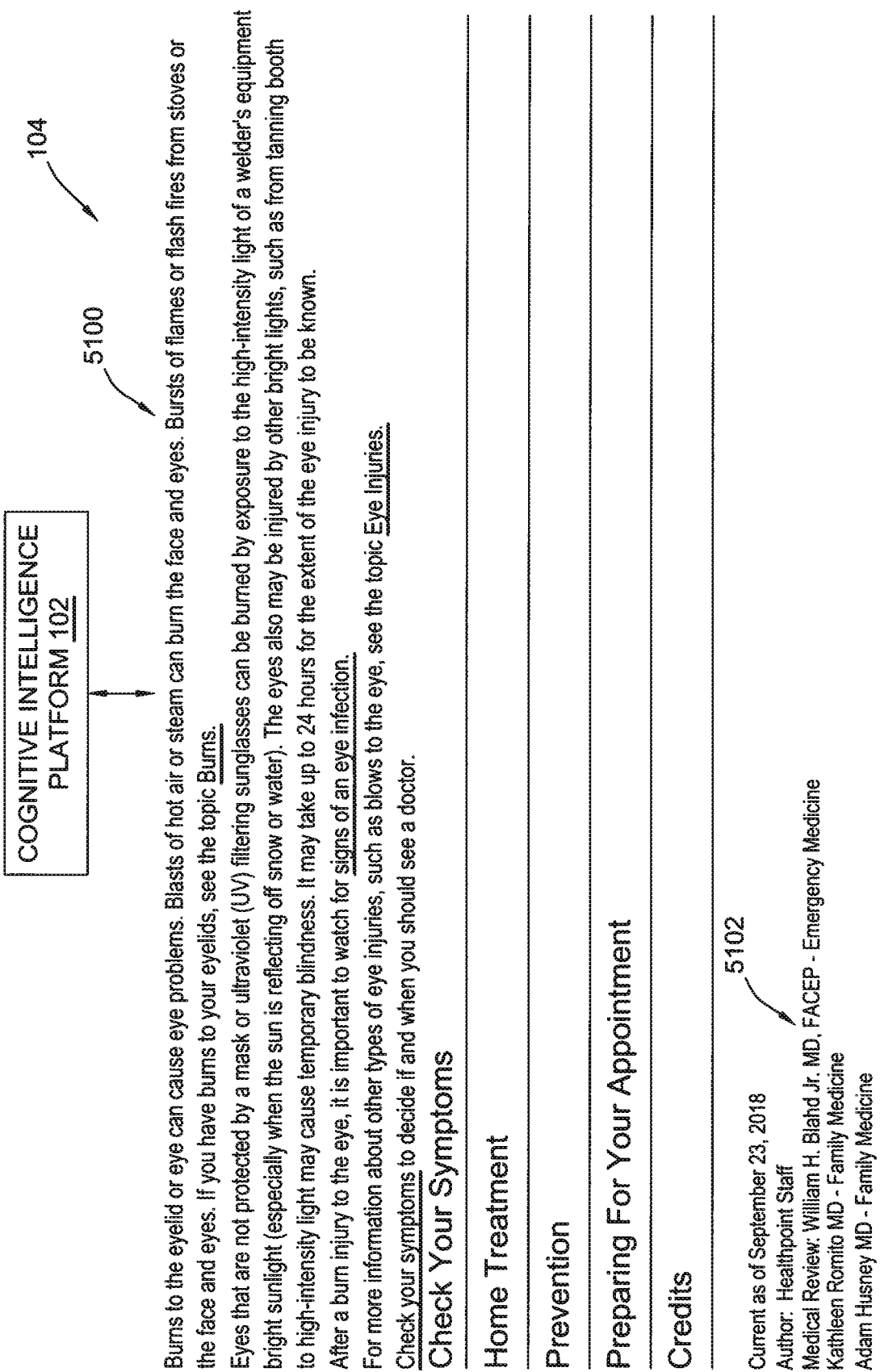
FIG. 51 shows an example of providing a user interface that provides details about symptoms that have been authored and reviewed by medical doctors, in accordance with various embodiments.

Accordingly, FIG. 51 shows an example of providing a user interface 5100 that provides details about symptoms that have been authored and reviewed by medical doctors, in accordance with various embodiments. The user interface 5100 of the autonomous multipurpose application may be presented on the user device 104. The user interface 5100 may present content retrieved from the knowledge cloud 106 pertaining to the symptoms "Burns to the Eye". As depicted, the user interface 5100 includes a section 5102 that presents information pertaining to the content, such as the content is "Current as of Sep. 23, 2018", "Author: Healthpoint Staff", "Medical Review: William H. Bland Jr. MD, FACEP—Emergency Medicine, Kathleen Romito MD—Family Medicine, Adam Husney MD—Family Medicine". Accordingly, the user may verify that the content presented is current and has been reviewed by people having medical licenses. Such content may provide comfort to the user that the user can trust the content they are presented.

FIG. 52 shows a method 5200 of maintaining and transmitting check-in documents for a user to numerous different computing devices associated with people performing different specialties, in accordance with various embodiments. In some embodiments, the method 5200 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 5200 may include operations that are implemented in computer instructions stored in a memory and executed by a processor of a computing device. In some embodiments, the method 5200 includes operations performed by the cognitive agent 110 (autonomous multipurpose application), the knowledge cloud 106, and/or the critical thinking engine 108 of the cognitive intelligence platform 102 as shown in FIG. 1.

At block 5202, the processing device may maintain a set of check-in documents for a user. For example, the cognitive intelligence platform 102 may retrieve the check-in documents that are required to be filled out for each service provider 112 for appointments with the service providers. The check-in documents may be consent forms for distributing health information, consent forms for procedures, consent forms for minors, medical history documents, and so forth. There may be overlap between information that is requested amongst the set of check-in documents. For example, the medical history document for a first specialty of a service provider 112.1 (medical doctor) may require the user to enter their previous surgeries and the medical history document for a second specialty of a second service provider 112.2 (dentist) may also require the user to enter their previous surgeries. This information may be stored the first time the user enters the information in the medical history document at a first appointment and prefilled if the user needs to add other information to the medical history document for a subsequent appointment. Accordingly, the cognitive intelligence platform 102 may function as a central repository of check-in documents for multiple specialties and for multiple users.

At block 5204, the processing device may receive, from the user device 104, a set of requests to check-in the user for a set of scheduled appointments where a set of people each having a different respective specialty of a set of specialties are to provide a different respective service to the user. The set of specialties may include medical doctors, dentists, optometrists, ophthalmologists, chiropractors, masseuses, orthodontists, behavioral specialists, therapists, physical therapists, clinicians, or some combination thereof. In some embodiments, the set of requests may be received over a period of time and each of the set of scheduled appointments may be scheduled at different dates, times, or both.

At block 5206, the processing device may determine respective subsets of the set of check-in documents that are required to be complete for each of the different respective specialty of each of the set of people. In some instances, the respective subsets of the set of check-in documents may include the same check-in documents (e.g., medical history form, consent form). In some instances, the respective subsets of the set of check-in documents may include one or more different check-in documents and/or one or more different information to be provided by the user.

In some embodiments, for each of the set of scheduled appointments, the processing device may determine whether check-in requirements are satisfied. The check-in requirements may be satisfied when required information in each of the respective subsets of the set of check-in documents has already been provided. In some embodiments, responsive to determining the check-in requirements for one of the set of scheduled appointments is satisfied, the processing device may check-in the user for the one of the scheduled appointments.

In some embodiments, responsive to determining the check-in requirements for one of the set of scheduled appointments is not satisfied because one of the respective subsets of the set of check-in documents is lacking a portion of the required information, the processing device may cause the computing device to present a notification that the portion of the required information is lacking. The processing device may receive the portion of the required information and update the one of the respective subsets of the set of check-in documents with the portion of the required information. Further, the processing device may check-in the user for the one of the set of schedule appointments once the update is complete.

At block 5208, the processing device may transmit each of the respective subsets of the set of check-in documents to a set of computing devices each associated with each of the different respective specialty. The respective subsets of the check-in documents may be cryptographically signed. For example, public key and private key encryption may be used to cryptographically sign the respective subsets of the check-in documents.

In some embodiments, the processing device may update the set of check-in documents based on input from the user, input from the set of people having the specialties, output from a machine learning model trained to determine when certain information needs to be updated, information obtained from a third-party source (e.g., information about a child dependent entered by a parent), or some combination thereof. In some embodiments, the machine learning model may be trained to determine when the insurance plan is about to expire and cause a notification to be presented on the user device 104 indicating that the insurance plan information should be updated.

The disclosed techniques may eliminate manual or paper check in. The disclosed techniques may Maintain and satisfy all check-in requirements from a multi-specialty perspective and electronically transmitting up-to-date and sending cryptographically signed check-in documents to the doctor's office/practice management software/electronic health record software instead of paper.

FIG. 53 shows a method of determining whether the user has completed certain check-in documents required for a booked appointment, in accordance with various embodiments. In some embodiments, the method 5300 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 5300 may include operations that are implemented in computer instructions stored in a memory and executed by a processor of a computing device. In some embodiments, the method 5300 includes operations performed by the cognitive agent 110 (autonomous multipurpose application), the knowledge cloud 106, and/or the critical thinking engine 108 of the cognitive intelligence platform 102 as shown in FIG. 1.

At block 5302, the processing device may determine which documents the user has to complete for a booked appointment or scheduled appointment. This determination may be made when the user requests to check-in for the booked appointment.

At block 5304, the processing device may determine whether the user has completed the documents.

At block 5306, responsive to determining the user has not completed the documents, the processing device may electronically fill in (block 5308) fields with any information the user has already provided for the documents, and cause (block 5310) the documents with the electronically filled in fields to be presented on a computing device of the user (user device 104) for further completion. Responsive to determining the documents are complete, the processing device may check-in the user and provide an estimated wait time for presentation on the user device 104. Further, the processing device may cause curated content tailored for one or more conditions of the user to be presented on the user device 104.

FIG. 54 shows a method 5400 of providing an estimated wait time to a computing device of the user, in accordance with various embodiments. In some embodiments, the method 5400 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 5400 may include operations that are implemented in computer instructions stored in a memory and executed by a processor of a computing device. In some embodiments, the method 5400 includes operations performed by the cognitive agent 110 (autonomous multipurpose application), the knowledge cloud 106, and/or the critical thinking engine 108 of the cognitive intelligence platform 102 as shown in FIG. 1.

At block 5402, the processing device may check-in a user for a scheduled appointment with a person having a specialty to perform a service. The checking-in may be completed when the user has provided the information in the check-in documents for the specialty of the person to perform a service at the scheduled appointment.

At block 5404, the processing device may determine, using a machine learning model, an estimated wait time based on an average amount of time it takes people having the specialty to perform the service for the users. In some embodiments, the estimation at the patient level may be based on the time of check-in and how many patients are waiting in various specialty queues. The estimation may also account for multiple physicians having the same specialty that are working the day of the scheduled appointment. In some instances, patients may check-in randomly, may have multiple appointments, and/or arrive late. These scenarios may be accounted for to provide the estimated wait time. In some embodiments, the wait time may be estimated based on historical information for the service provider 112 with which the patient has the appointment. The historical information may include an average amount of time it takes the person having the specialty to perform the particular services for patients that are in the wait queue in front of the patient waiting.

At block 5406, the processing device may provide the estimated wait time to a computing device of the user for presentation on a user interface of the computing device of the user (user device 104).

At block 5408, the processing device may provide curated content tailored for the user based on the service, the specialty, a condition pertaining to the service, other conditions associated with the user, or some combination thereof. Accordingly, the disclosed techniques educate the user with pertinent information while the user waits in a lobby or waiting room to be called back to an office for the scheduled appointment.

At block 5410, the processing device may maintain documents for the user and a dependent of the user and provide the documents to any requesting client device. The documents may be check-in documents described above. The cognitive intelligence platform 102 may maintain the check-in documents for each person of a family. A request client device may include a system (e.g., EMR) of a new service provider 112 that the user has not been to yet and/or a system (e.g., EMR) of a previous service provider 112 that requests updated information.

Figure 55:
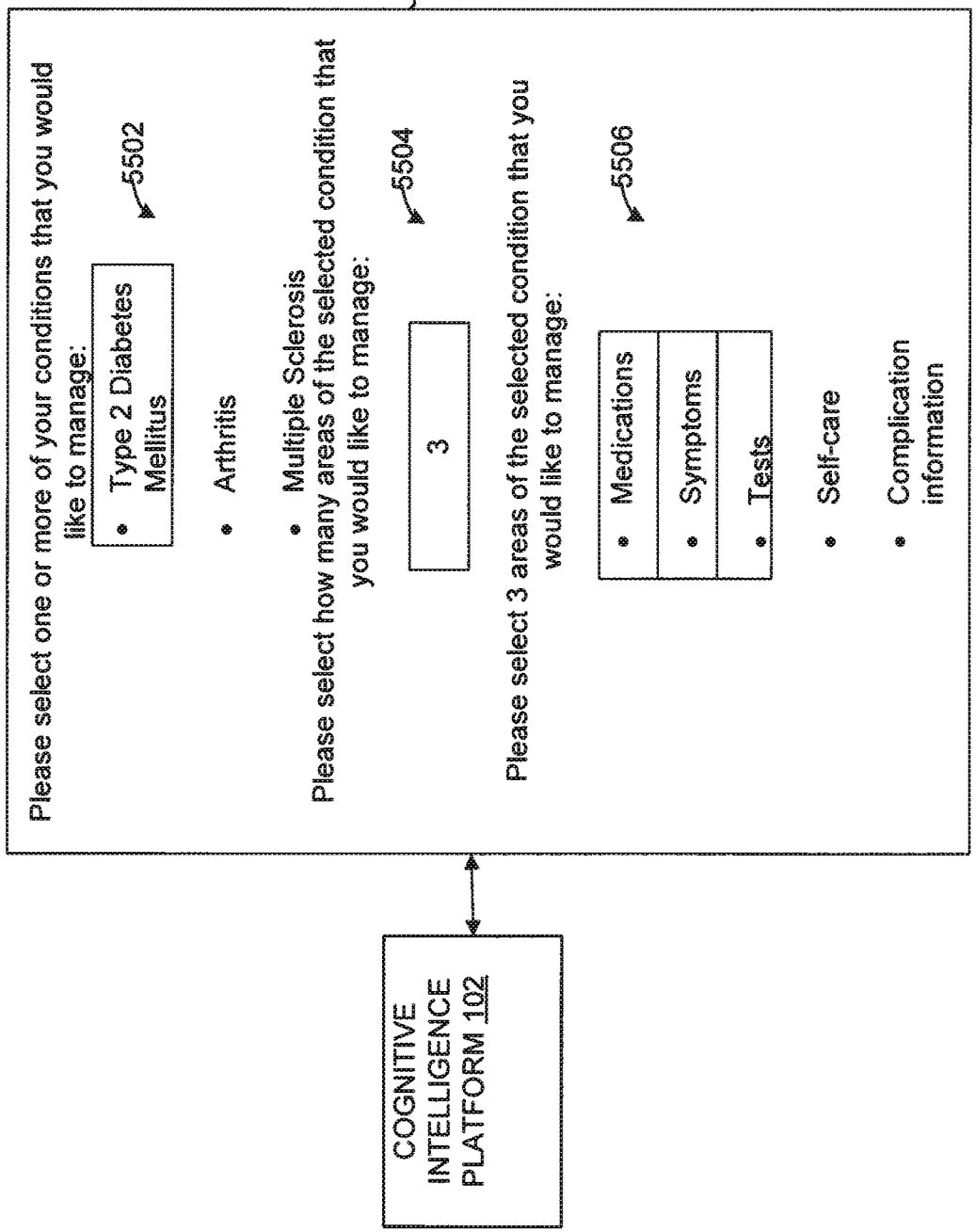
FIG. 55 shows an example of providing a user interface that includes options to select a condition, a number of areas of the condition to manage, and which areas of the condition to manage, in accordance with various embodiments.

FIG. 55 shows an example of providing a user interface 5500 that includes options to select a condition, a number of areas of the condition to manage, and which areas of the condition to manage, in accordance with various embodiments. The options are depicted in section 5502, 5504, and 5506, respectively. The user may have logged into, using the user device 104, the autonomous multipurpose application with credentials associated with a patient/user role. As such, the user interface 5500 of the patient viewer may be provided by the autonomous multipurpose application and presented on the user device 104.

As depicted, section 5502 presents text "Please select one of your conditions that you would like to manage". The conditions that are presented in section 5502 may be conditions diagnosed for the user logged into the patient viewer (e.g., via 2-factor authentication) having the user interface 5500. For example, the cognitive intelligence platform 102 may maintain a data structure for each patient that stores each condition diagnosed for the patient. In section 5502, the conditions associated with the logged-in user are "Type 2 Diabetes Mellitus", "Arthritis", "Multiple Sclerosis". The user selected "Type 2 Diabetes Mellitus", which may cause a knowledge graph representing Type 2 Diabetes Mellitus to be accessed in the knowledge cloud 106. Further, a patient graph for Type 2 Diabetes Mellitus of the user may be accessed in the knowledge cloud 106 as a result of the selection. It should be noted that more than one condition may be selected by the user to manage, and the patient viewer may present a care plan for each respective condition selected. If the user does not select one or more conditions, a default selection may be made, such as selecting all of the conditions of the user.

Different respective data structures (e.g., patient graphs) pertaining to each condition of the user may be maintained by the cognitive intelligence platform 102. In some embodiments, the patient graphs may include elements (e.g., health artifacts) represented by nodes that are linked based on relationships. The elements included in the patient graph may represent content consumed by, actions performed by, and/or interactions performed by the user.

A root node of a patient graph for a condition may include a type of the condition with which the user is diagnosed. If the user is recently diagnosed, the patient graph for the condition of the user may just include the root node, since the user has not performed any actions and/or interactions, or consumed content. As described further below, the disclosed techniques may compare the patient graph for a condition with a knowledge graph for that condition and generate a care plan. The care plan may include various action instructions for a patient, a medical personnel, and/or an administrator.

In section 5504, the user interface 5500 presents an option to "Please select how many areas of the selected condition that you would like to manage". The user entered "3" into the input text box on the user interface 5500. It should be understood that the user may choose any suitable number of areas to manage. In some embodiments, if the user does not input a number, a default number may be used.

In section 5506, the user interface 5500 presents the various areas of the selected condition. The areas for Type 2 Diabetes Mellitus may include "Medications", "Symptoms", "Tests", "Self-care", "Complication information", etc. These areas may correspond to elements in the knowledge graph for the condition Type 2 Diabetes Mellitus. In the depicted example, the user selected "Medications", "Symptoms", and "Tests". If the user does not make a selection of the areas, then a default selection may be made, such as all of the areas of the condition. The selections of the condition(s), the number of areas of the condition, and/or the areas of the condition may be transmitted to the cognitive intelligence platform 102.

Figure 56:
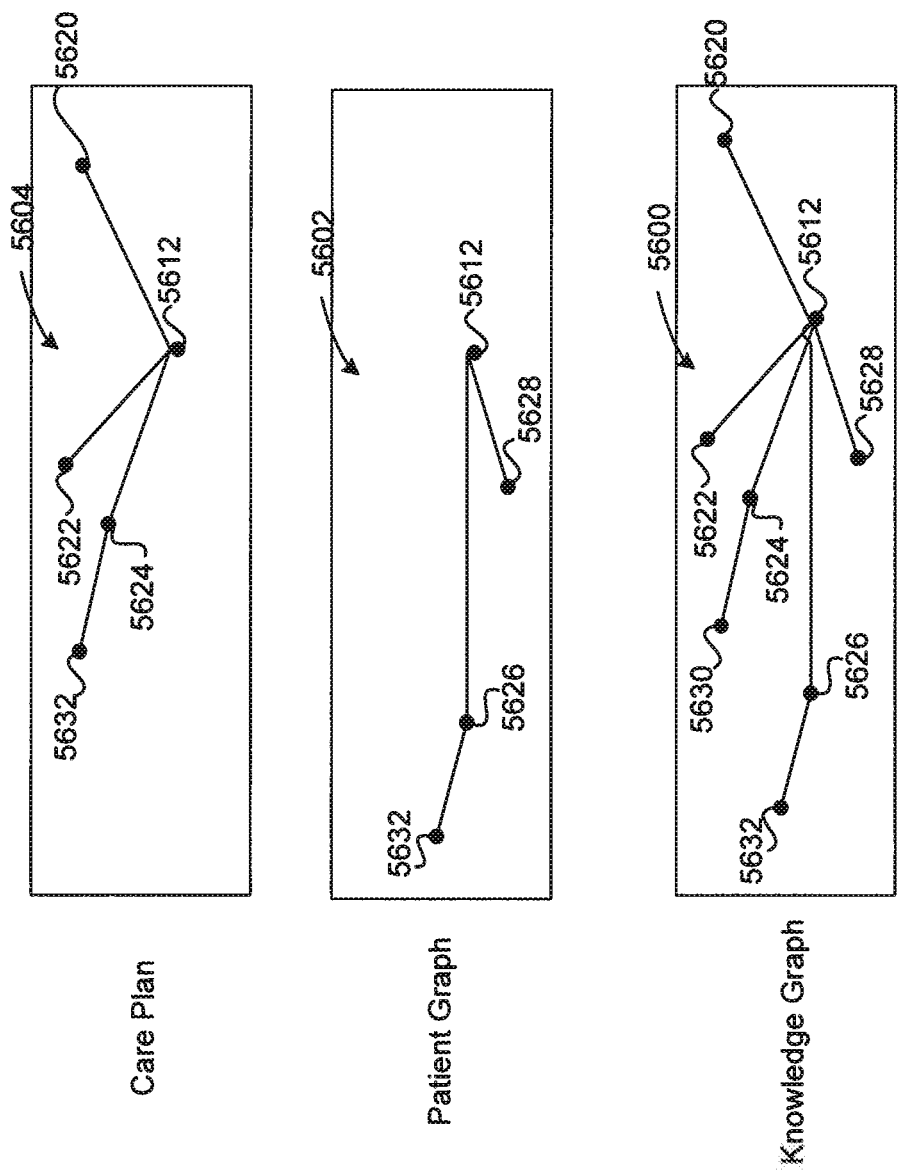
FIG. 56 shows an example of a knowledge graph, a patient graph, and a care plan, in accordance with various embodiments.

FIG. 56 shows an example of a knowledge graph 5600, a patient graph 5602, and a care plan 5604, in accordance with various embodiments. The knowledge graph 5600 may pertain to any suitable medical condition and include numerous elements (e.g., health artifacts) represented by nodes and relationships between the nodes represented by edges. For example, the knowledge graph 5600 includes a root node 5612; a first layer of nodes 5620, 5622, 5624, 5626, and 5628; and a second layer of nodes 5630, and 5632. The root node 5612 may include information pertaining to a type of the medical condition, such as "Multiple Sclerosis". The edges connecting the root node 5612 to the first layer of nodes 5620, 5622, 5624,5626, and 5628 may represent a relationship between the root node 5612 and the first layer of nodes 5620, 5622, 5624,5626, and 5628. For example, the edge connecting the root node 5612 and 5620 may represent a relationship "has symptoms of" and the node 5620 may represent a health artifact "tingling and numbness". The knowledge graph 5600 may include a superset of curated medical knowledge of the medical condition represented by the nodes and relationships pertaining to the medical condition.

The patient graph 5602 may be tailored for a particular user and may correspond to the condition represented by the knowledge graph 5600. For example, the patient graph 5602 may correspond to the medical condition "Multiple Sclerosis". In some embodiments, the nodes in the patient graph 5602 may represent the health artifacts (e.g., actions, interactions, content, concepts, facts, protocols, evidence-based guidelines, etc.) which the user has performed, interacted, experienced, reported, consumed, been treated for, been diagnosed, and/or been prescribed. For example, the node 5628 may represent a particular test for Multiple Sclerosis. The user may have performed the particular test for Multiple Sclerosis. As such, the node 5628 is included in the patient graph 5602. The node 5628 may include a type of the particular test, a timestamp of the particular test, a result of the particular test, and the like.

Nodes 5626 and 5632 may correspond to other health artifacts which the user has performed, interacted, consumed, been treated for, been diagnosed, and/or been prescribed. As such, the nodes 5626 and 5632 are included in the patient graph 5602.

In the depicted example, the user may not have interacted with and/or performed the health artifacts associated with the nodes 5620, 5622, 5624, and 5630 in the knowledge graph for Multiple Sclerosis. Accordingly, the nodes 5620, 5622, 5624, and 5630 are not included in the patient graph 5602 for Multiple Sclerosis for the user. For example, the user may not have performed the action of performing a disease-modify therapy technique for treating Multiple Sclerosis. The health artifact for the disease-modifying therapy technique may be represented by node 5622, and thus, node 5622 is not included in the patient graph 5602.

The cognitive intelligence platform 102 may compare the patient graph 5602 to the knowledge graph 5600 to determine which areas of the condition Multiple Sclerosis to manage to generate the care plan 5604. Further, the cognitive intelligence platform 102 may consider the areas the user selected to manage when generating the care plan 5604. The patient graph 5602 may be projected onto the knowledge graph 5600. Overlapping nodes that are included in both the patient graph 5602 and the knowledge graph 5600 may be identified (e.g., highlighted in a first color). Further, nodes that are included in the knowledge graph 5600 and not included in the patient graph 5602 may also be identified (e.g., highlighted in a second color).

In some embodiments, the nodes that are present in the knowledge graph 5600 and not present in the patient graph 5602 may be selected to include in the care plan 5604. As depicted, nodes 5620, 5622, 5624, and 5632 are present in the knowledge graph 5600 and not in the patient graph 5602. Accordingly, the care plan 5604 may be generated to include the root node 5612 and the nodes 5620, 5622, 5624, and 5632. One or more action instructions may be generated and associated with each of the nodes 5620, 5622, 5624, and 5632.

For example, node 5620 may represent medications to take for the condition, and an action instruction may be generated to recommend the user discuss being prescribed a different medication for the condition. Other action instructions pertaining to various health artifacts may include scheduling a follow-up appointment, performing a certain test for the condition, reading certain recommended curated medical content pertaining to the condition, performing certain self-care treatments, and the like. In some embodiments, nodes may be selected to include in the care plan 5604 based on the areas of the condition the user selected to manage as well as the number of the areas of the condition the user selected to manage.

The care plan 5604 may be converted into natural language for each particular role. For example, the natural language representing the care plan 5604 may be tailored for providing action instructions to a user, the natural language representing the care plan 5604 may be tailored for providing action instructions to a medical personnel, and the natural language representing the care plan 5604 may be tailored for providing action instructions to an administrator. For example, the natural language conversion of the care plan 5604 may include an action instruction for the patient that specifies "Discuss changing medications with your physician". In another example, the natural language conversion of the care plan 5604 may include an action instruction for the medical personnel that specifies "Discuss changing medications with the patient". Each respective natural language conversion representing the care plan 5604 may be presented on the respective patient viewer, clinic viewer, and administrator viewer. The natural language conversion may be in text format and presented on the various viewers and/or may be in audio format and may be output by a speaker of a computing device.

Figure 57A:
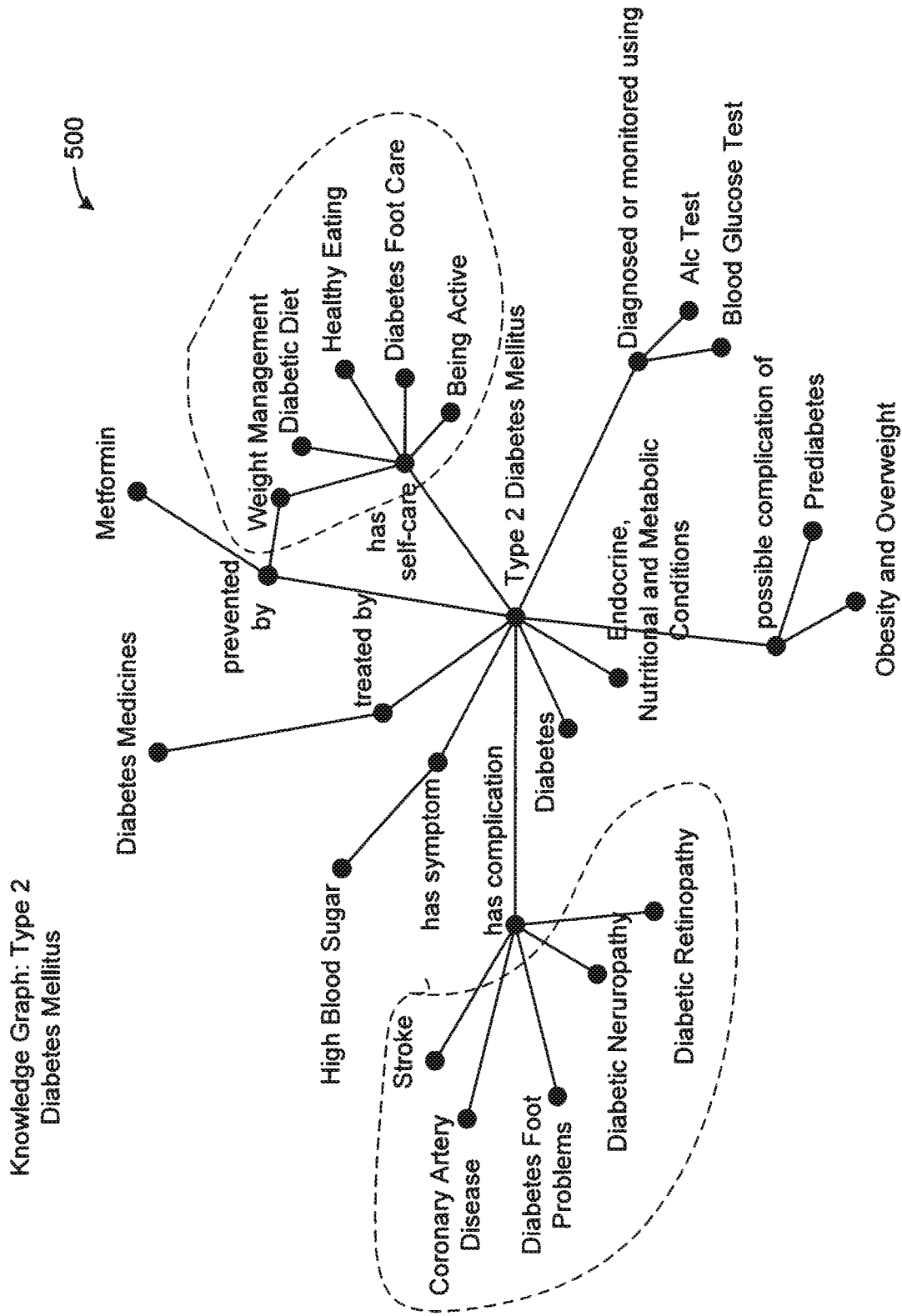

FIGS. 57A-57D show examples for generating a care plan 5750 using a knowledge graph 500 and a patient graph 5700, in accordance with various embodiments. In particular, FIG. 57A depicts the knowledge graph 500 (first data structure) for the medical condition "Type 2 Diabetes Mellitus". For purposes of explanation, it should be understood that the knowledge graph 500 includes a superset of health artifacts (e.g., elements represented by nodes) pertaining to Type 2 Diabetes Mellitus. The ontological medical data included in the knowledge graph 500 may be maintained by the knowledge cloud 106 and updated based on any changes and/or discoveries regarding medical knowledge of Type 2 Diabetes Mellitus.

Figure 57B:
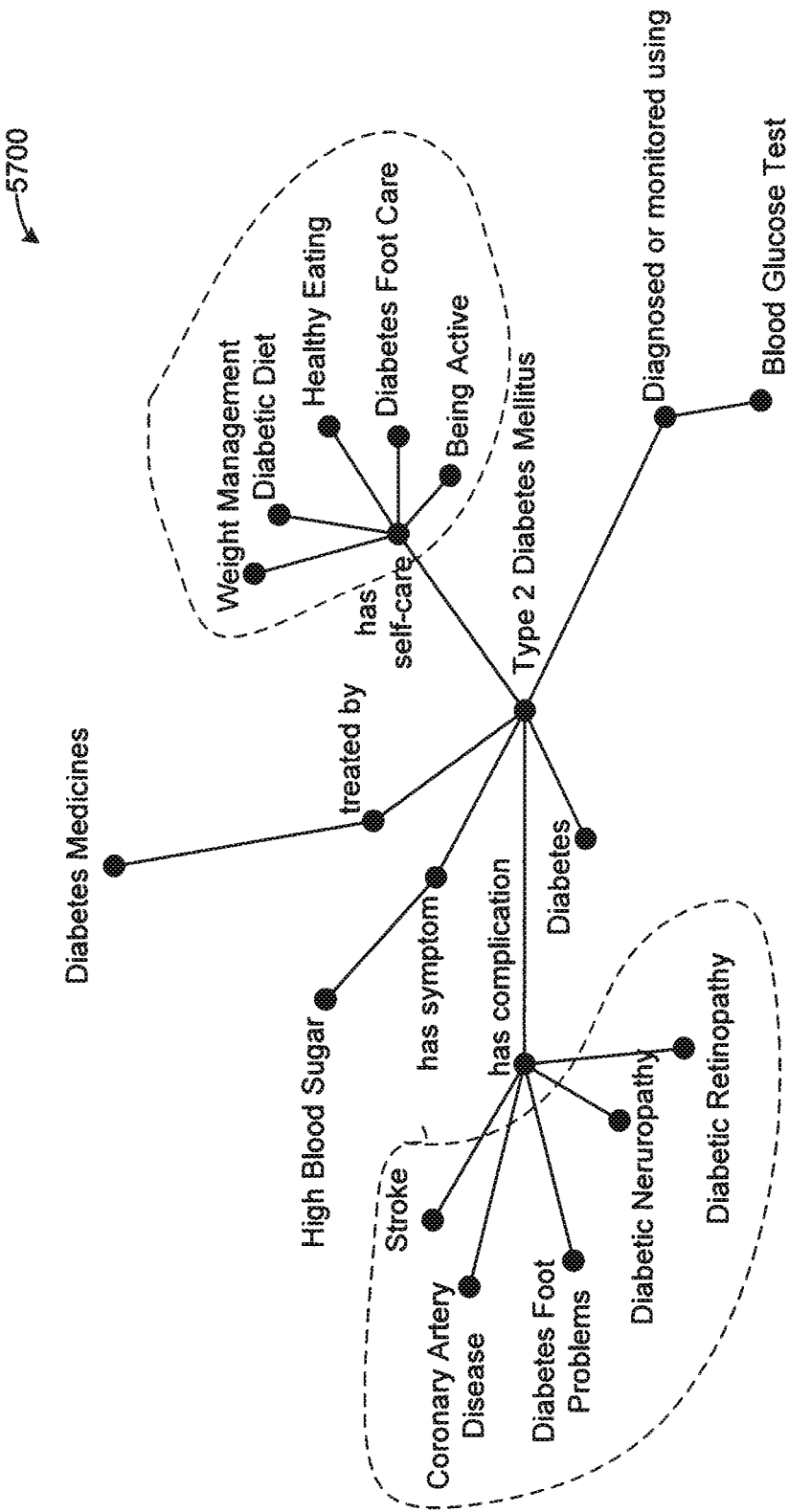

FIG. 57B depicts the patient graph 5700 (second data structure) for a particular user having the condition Type 2 Diabetes Mellitus. The patient graph 5700 may also include an engagement profile as metadata that stores interactions of the patient with the various health artifacts presented in a care plan for the user. The interactions may be used to track a level of compliance with the care plan for the user. In some embodiments, the health artifacts represented by the nodes may be added to the patient graph as the patient interacts with the health artifacts. In some embodiments, the health artifacts may be added to the patient graph 5700 if the patient interacts with the health artifact to a threshold level.

As depicted, the patient graph 5700 includes a subset of the superset of health artifacts included in the knowledge graph 500. For example, the patient graph 5700 includes a node representing a "Blood Glucose Test" health artifact that the patient performed. Various information (e.g., result, timestamp, etc.) pertaining to the blood glucose test may be associated with the node. However, the patient graph 5700 does not include a node representing the "A1c" health artifact that is included in the knowledge graph 500 because the patient has not interacted with that health artifact yet. In other words the patient has not performed the A1c test yet.

Other nodes representing health artifacts that are included in the knowledge graph 500 and not in the patient graph 5700 (e.g., due to the patient not interacting with those health artifacts yet) are a node representing "Endocrine, Nutritional and Metabolic Conditions", a node representing "possible complication of" connected to nodes representing "Prediabetes" and "Obesity and Overweight", and a node representing "prevented by" connected to a node representing "Metformin".

Figure 57C:
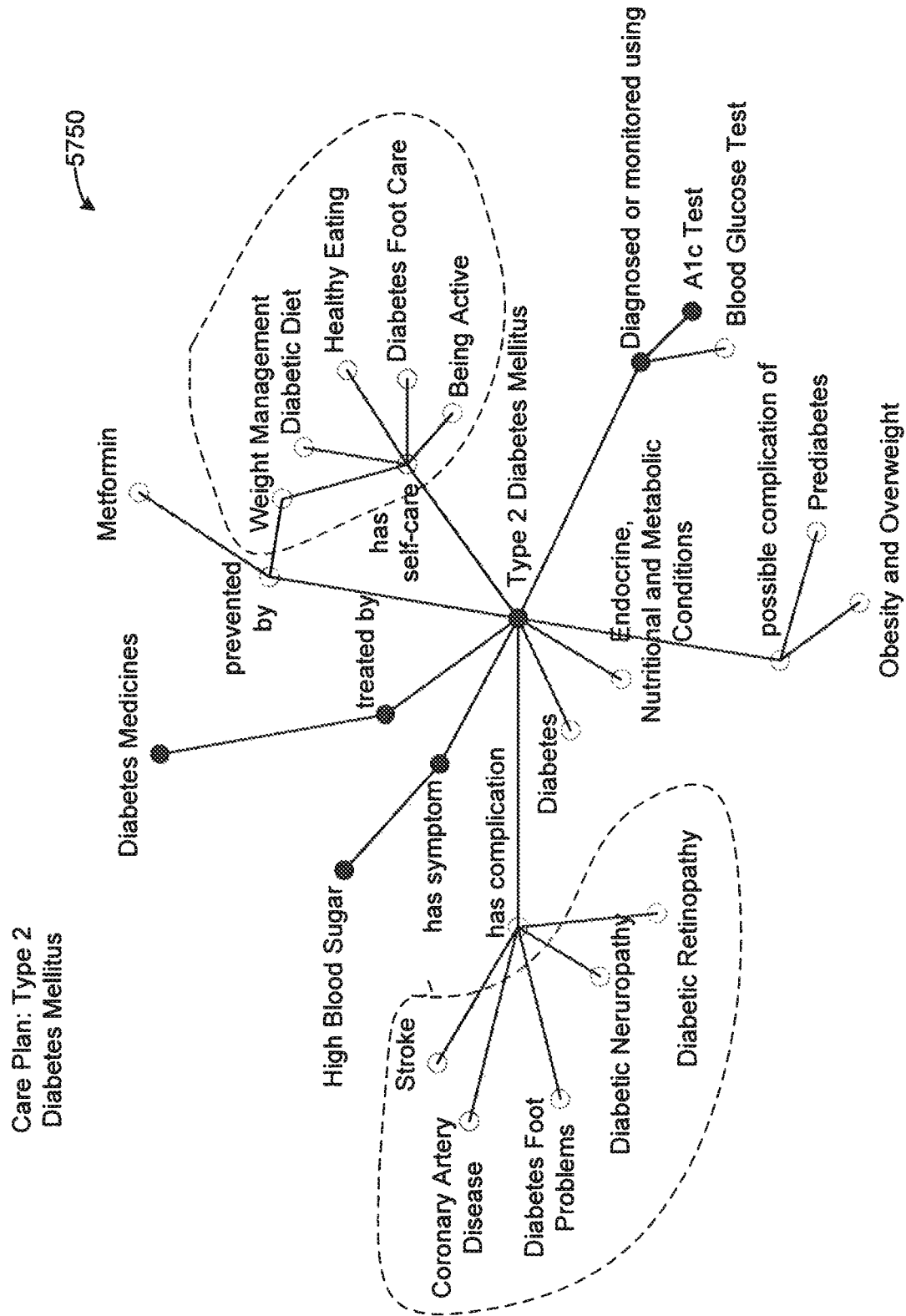

To generate the care plan 5750 depicted in FIG. 57C, the cognitive intelligence platform 102 (e.g., the autonomous multipurpose application, the critical thinking engine 108, and/or the knowledge cloud 106) may compare the patient graph 5700 to the knowledge graph 500. Comparing the patient graph 5700 to the knowledge graph 500 may include projecting the patient graph 5700 onto the knowledge graph 500. In some embodiments, projecting the patient graph 5700 onto the knowledge graph 500 may include overlaying the patient graph 500 on the knowledge graph 500, and/or plotting the patient graph 5700 in a same space as the knowledge graph 500. Based on the comparing, the cognitive intelligence platform 102 may select a subset of the superset of health artifacts in the knowledge graph 500. The selecting may be based on identifying nodes representing health artifacts that are included in the knowledge graph 500 and not the patient graph 5700, and/or on areas of the condition the patient selected to manage in FIG. 55. Continuing the example in FIG. 55, the patient selected to manage the areas of "Medications", "Symptoms", and "Tests".

As depicted in FIG. 57C, the care plan 5750 represents the patient graph 5700 projected onto the knowledge graph 500. The nodes that are filled in (black circles) represent health artifacts that are included in the care plan based on the selecting described above. The nodes that are not filled in (empty circles) represent health artifacts that are not included in the care plan 5750. The cognitive intelligence platform 102 selected the node representing "A1c" test to include in the care plan 5750 because the patient graph 5700 included a node representing the blood glucose test and did not include a node representing the A1c test that is included in the knowledge graph 500. Further, the patient selected to manage "Tests", so including the health artifact A1c test fits that area.

The patient also selected to manage the areas of "Medications" and "Symptoms". Accordingly, the cognitive intelligence platform 102 included nodes representing health artifacts pertaining to those areas. In particular, the nodes included for the "Symptoms" area are "has symptom" connected to "High Blood Sugar" and the nodes included for the "Medicines" area are "treated by" connected to "Diabetes Medicines".

Although some nodes are included in the knowledge graph 500 and not in the patient graph 5700, such as the "possible complication of" connected to "Prediabetes" and "Obesity and Overweight" health artifacts, they may not be included in the care plan 5750 because those nodes are associated with areas the patient did not select to manage.

The care plan 5750 may be converted into natural language text by the critical thinking engine 108 using the natural language database 122 according to the techniques disclosed herein. The cognitive intelligence platform 102 may generate action instructions pertaining to the health artifacts included in the care plan 5750. FIG. 57D depicts the care plan 5750 in the natural language text presented in a user interface 5700 of the patient viewer on the user device 104. Although the depicted natural language text is tailored for the patient, in some embodiments, the natural language text may be tailored for the medical personnel or the administrator when presented in the clinic viewer or the administrator viewer respectively.

It should be noted that the natural language text of the care plan 5750 depicted is an example and is for explanatory purposes. Any suitable variation of the natural language text is envisioned in this disclosure. The natural language text in the user interface 5700 presents "Please find information and/or action instructions pertaining to the 3 areas you selected relating to Type 2 Diabetes Mellitus below:".

For the "Medications" area, the natural language text presents information about types of medications for the condition: "The types of medication available to treat Type 2 Diabetes Mellitus include: medication A, medication B, and medication C." Further, the natural language text presents an action instruction for the patient: "You are currently prescribed medication A. If it is not working as desired, discuss medication change with your physician".

Further, the cognitive intelligence platform 102 may compare the patient graphs of each condition of the patient to determine if there are conflicts, redundancy, and the like. For example, natural language text presents another action instruction based on artificial-intelligence analysis performed by the cognitive intelligence platform 102: "We see that you are also prescribed medication D for condition Y. Medication B and medication D are not compatible and may cause issues. Be sure to discuss this with your physician."

For the "Symptoms" area, the natural language text presents information about types of symptoms for the condition: "Type 2 Diabetes Mellitus has the following symptoms: High Blood Sugar." Further, the natural language text presents an action instruction for the patient: "If you have high blood sugar, contact your physician".

For the "Tests" area, the natural language text presents information about types of tests for the condition: "The types of tests for Type 2 Diabetes Mellitus include: A1c Test and Blood Glucose Test." Further, the natural language text presents an action instruction for the patient: "You have already had an A1c Test. You can take an A1c test to get additional results, or you can retake the Blood Glucose Test".

Figure 58:
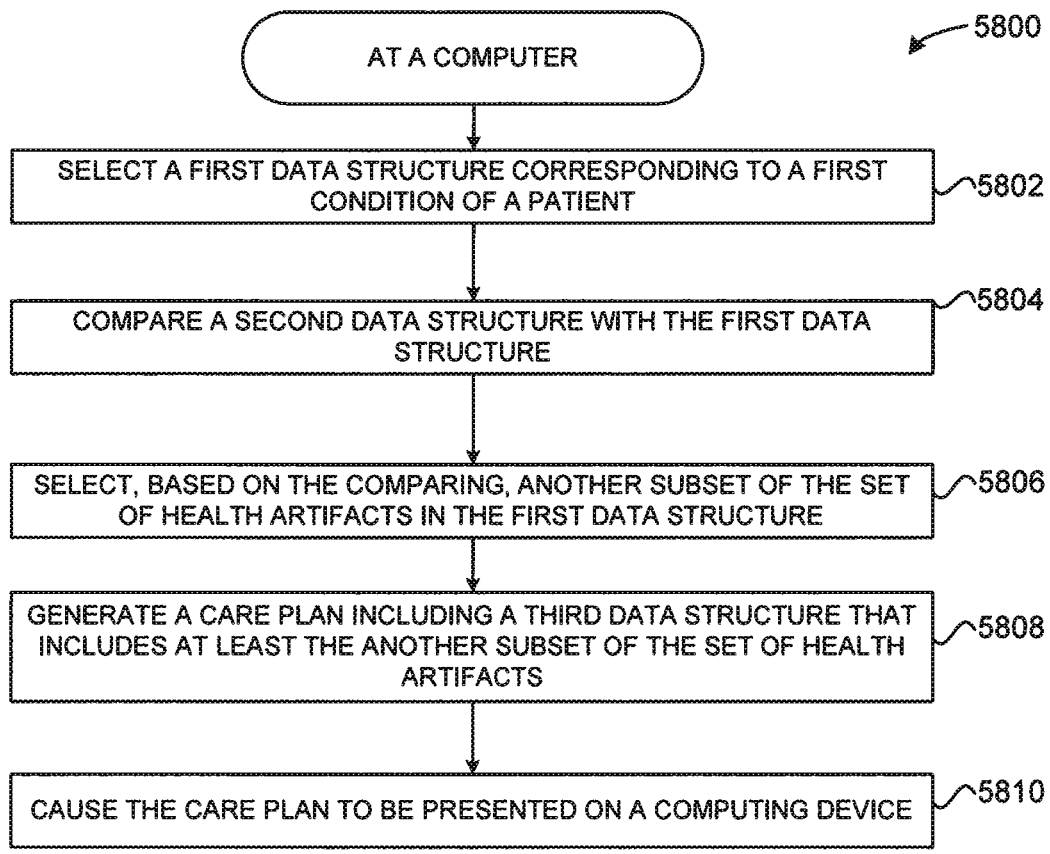
FIG. 58 shows a method for generating a care plan using a knowledge graph and a patient graph, in accordance with various embodiments.

FIG. 58 shows a method 5800 for generating a care plan using a knowledge graph and a patient graph, in accordance with various embodiments. In some embodiments, the method 5800 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 5800 may include operations that are implemented in computer instructions stored in a memory and executed by a processor of a computing device. In some embodiments, the method 5800 includes operations performed by the cognitive agent 110 (autonomous multipurpose application), the knowledge cloud 106, and/or the critical thinking engine 108 of the cognitive intelligence platform 102 as shown in FIG. 1.

At block 5802, the processing device may select a first data structure corresponding to a first condition of a patient. The first data structure may be a knowledge graph of medical ontological data of the condition. The first data structure may include a set of health artifacts pertaining to the first condition and the set of health artifacts may be connected via relationships between the health artifacts.

At block 5804, the processing device may compare a second data structure with the first data structure. The second data structure may be a patient graph of the patient. The second data structure corresponds to the patient and the first condition of the patient, and the second data structure may include a subset of the set of health artifacts. If the second data structure includes the set of health artifacts of the first data structure, then a determination may be made by the processing device that the patient is managing the condition as desired.

At block 5806, the processing device may select, based on the comparing, another subset of the set of health artifacts in the first data structure. The processing device may receive input from the computing device (user device 104), and the input may specify an area of the condition the patient selects to manage. The area may include a type (e.g., Medications, Symptoms, Tests, etc.) of health artifacts in the set of the health artifacts. The processing device may select, based on the comparing, the another subset of the set of health artifacts in the first data structure by selecting the another subset based on the number and the type of health artifacts specified by the patient. In some embodiments, the processing device may select the another subset of the set of health artifacts based on which health artifacts are included in the first data structure and that are not included in the second data structure. The subset of the set of health artifacts may correspond with interactions already performed by the patient, and the another subset of the set of health artifacts may correspond with interactions that have not yet been performed by the patient.

At block 5808, the processing device may generate a care plan including a third data structure that includes at least the another subset of the set of health artifacts. The third data structure may be a graph structure and include nodes representing the another subset of the set of health artifacts and relationships between the nodes.

At block 5810, the processing device may cause the care plan to be presented on a computing device. The processing device may include, in the care plan, action an instruction pertaining to the another subset of the set of health artifacts. In some embodiments, the care plan is tailored based on the role of the user logged into the autonomous multipurpose application. For example, a care plan may be tailored for a patient/user role, for a care provider (e.g., medical personnel) role, for an administrator role, and the like. The action instruction may be directed toward the role of the person to receive the care plan. Each respective tailored plan may be presented on a respective computing device of the person having the respective role.

In some embodiments, the processing device may generate natural language representing the another subset of the set of health artifacts included in the third data structure. The processing device may cause the natural language to be presented on the computing device.

In some embodiments, the processing device may determine a value of patient compliance with the care plan based on tracked interactions of the patient and the another subset of the set of health artifacts. The tracked interactions may include activity of the patient using the computing device. The activity may include a selection using an input peripheral of the computing device, an amount of time the patient actively uses an application, an amount of time the patient spends viewing a particular user interface, a search query entered by the patient, or some combination thereof. The tracked interactions may include an indication from an external system that the patient has interacted with the health artifact of the another subset of the set of health artifacts. For example, the indication may be an EMR record from an EMR system of a care provider of the patient. The EMR record may indicate the user had a test performed by the care provider. The test (e.g., A1c) may be for a condition (e.g., Diabetes) and the health artifact in the patient graph of the user may be updated.

In some embodiments, the processing device may select a fourth data structure (e.g., a knowledge graph) corresponding to a second condition of the patient. The fourth data structure may include a second set of health artifacts pertaining to the second condition, and the first (e.g., Type 2 Diabetes Mellitus) and second condition (e.g., Multiple Sclerosis) are different. The processing device may compare a fifth data structure (e.g., a patient graph) with the fourth data structure. The fifth data structure pertains to the patient and the second condition of the patient, and the fifth data structure may include a second subset of the second set of health artifacts. The processing device may select, based on the comparing, a third subset of the set of health artifacts in the fourth data structure. The processing device may generate the care plan including the third data structure that includes at least the another subset of the set of health artifacts and the third subset of the set of health artifacts. In this way, the care plan may include health artifacts pertaining to two different conditions of the patient. It should be understood that the care plan may be generated to include the health artifacts of any suitable number of conditions of the patient. The care plan may include action instructions pertaining to each condition represented in the care plan for the patient.

Figure 59:
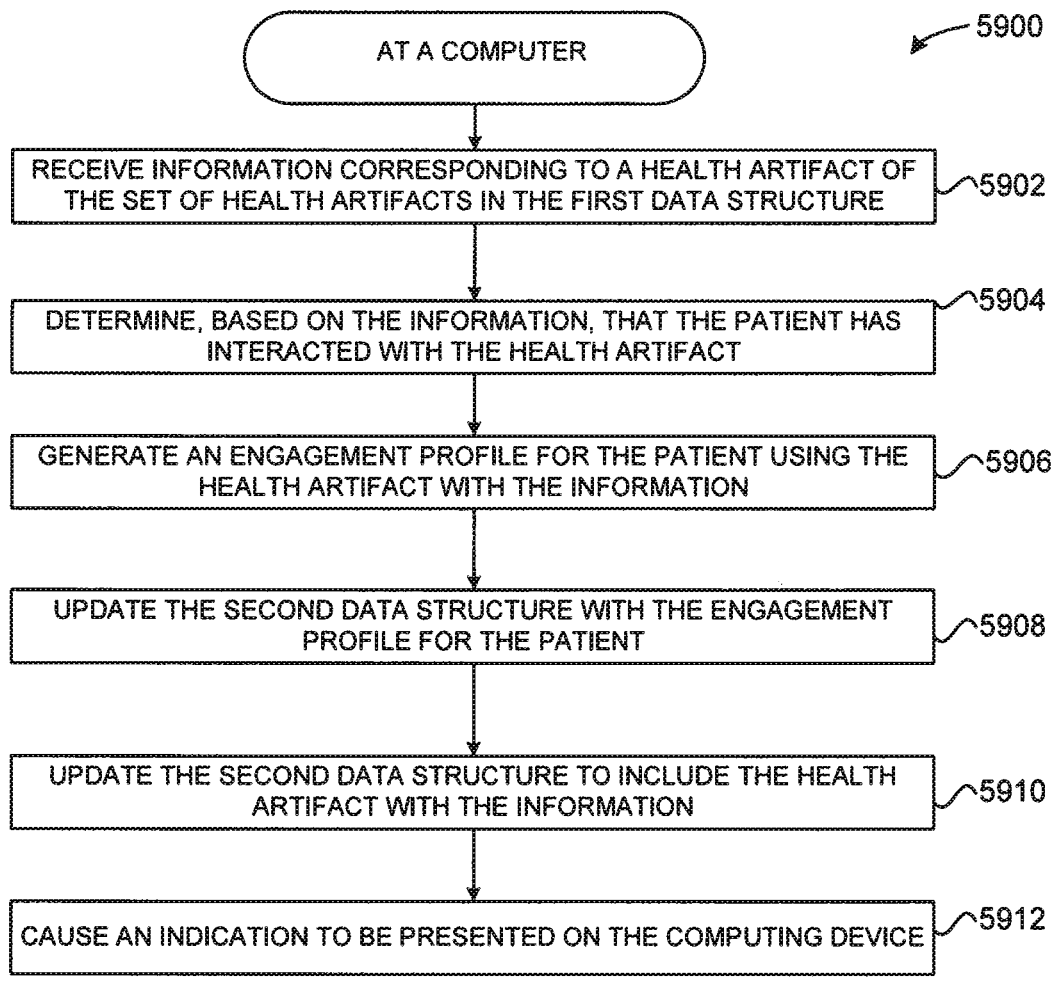
FIG. 59 shows a method for updating a patient graph based on an interaction with a health artifact by the patient, in accordance with various embodiments.

FIG. 59 shows a method 5900 for updating a patient graph based on an interaction with a health artifact by the patient, in accordance with various embodiments. In some embodiments, the method 5900 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 5900 may include operations that are implemented in computer instructions stored in a memory and executed by a processor of a computing device. In some embodiments, the method 5900 includes operations performed by the cognitive agent 110 (autonomous multipurpose application), the knowledge cloud 106, and/or the critical thinking engine 108 of the cognitive intelligence platform 102 as shown in FIG. 1. The operations of the method 5900 in FIG. 59 may be performed in some combination with the operations of the method 5800 in FIG. 58.

At block 5902, the processing device may receive information corresponding to a health artifact of the set of health artifacts in the first data structure. The information may pertain to an interaction with a user interface of the patient viewer, to an appointment for a condition, to an interaction with a browser, to any interaction on the user device 104, to a medical test being performed, to exercise performed by the user, to familial medical history of the user, to a diet of the user, to scheduling an appointment, to consuming recommended curated content, and so forth. In some embodiments the information may be received from a source including an electronic medical records system, an application programming interface, a claims system, an electronic health virtual assistant, an application executing on the user device 104, a data store, or some combination thereof.

At block 5904, the processing device may determine, based on the information, that the patient has interacted with the health artifact.

At block 5906, the processing device may generate an engagement profile for the patient using the health artifact with the information. In some embodiments, if an engagement profile is already generated, the processing device may update the engagement profile for the patient in the patient graph.

At block 5908, the processing device may update the second data structure with the engagement profile for the patient. Updating the second data structure with the engagement profile for the patient may refer to storing metadata including the engagement profile with the second data structure and/or correlating the metadata and the second data structure.

At block 5910, the processing device may update the second data structure (the patient graph) to include the health artifact with the information.

At block 5912, the processing device may cause an indication to be presented on the computing device. The indication may include an updated care plan that indicates the interaction with the health artifact. For example, if the interaction with the health artifact is the patient performing a test pertaining to the condition, the updated care plan may present an indication that the test results are normal, abnormal, etc. and may include an action instruction pertaining to the test (e.g., "discuss the test results with your physician").

Figure 60A:
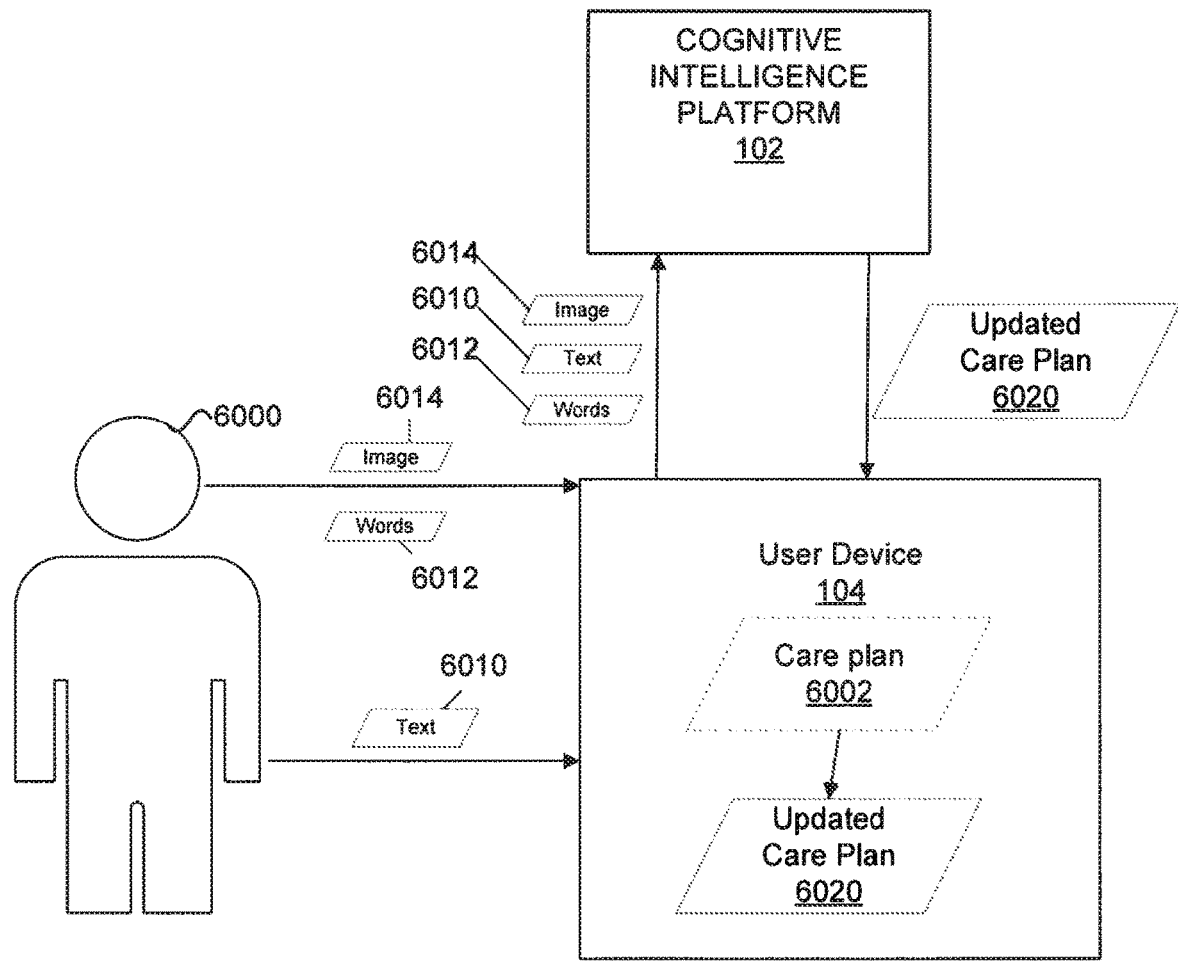
Figure 60B:
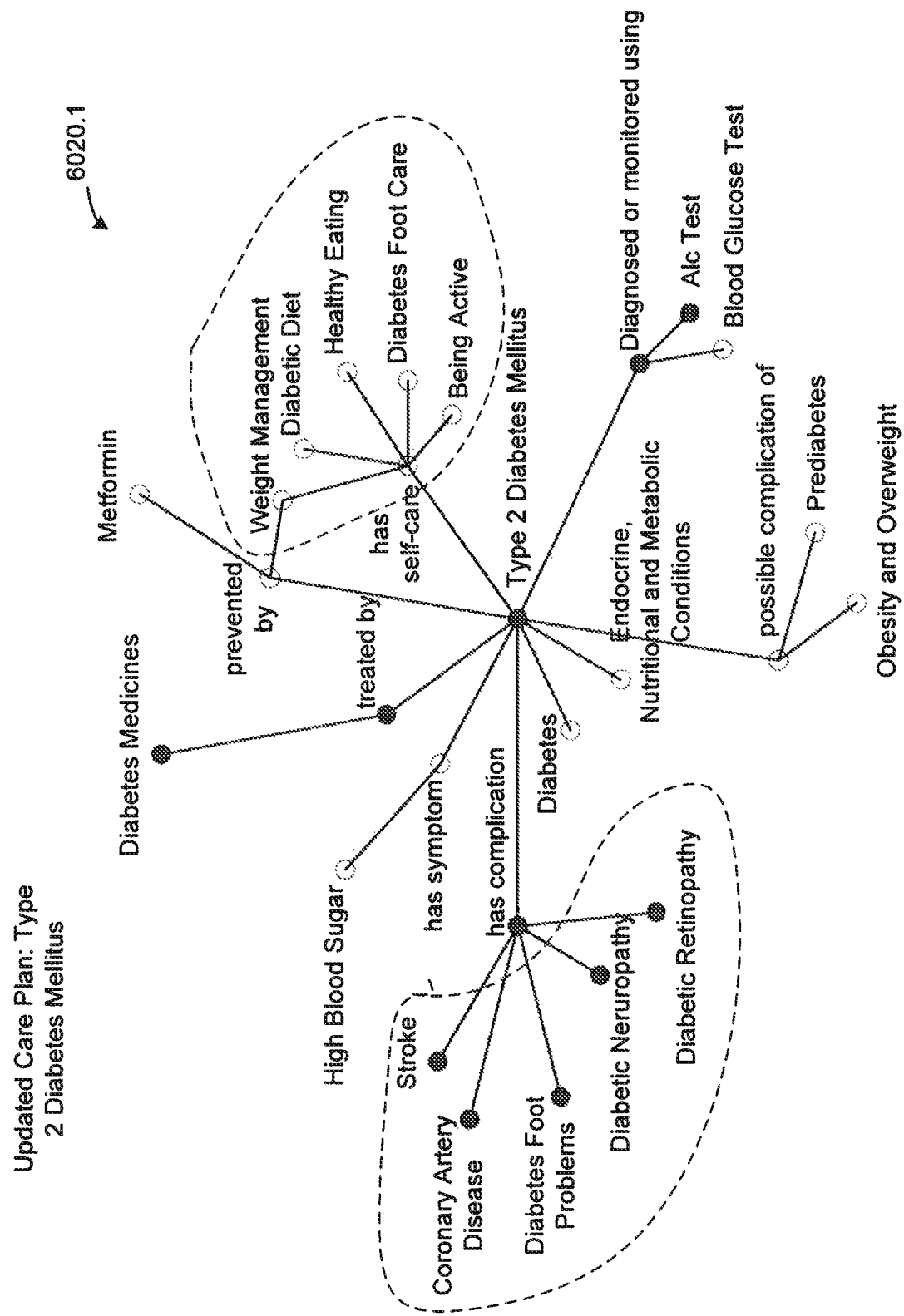
Figure 60C:
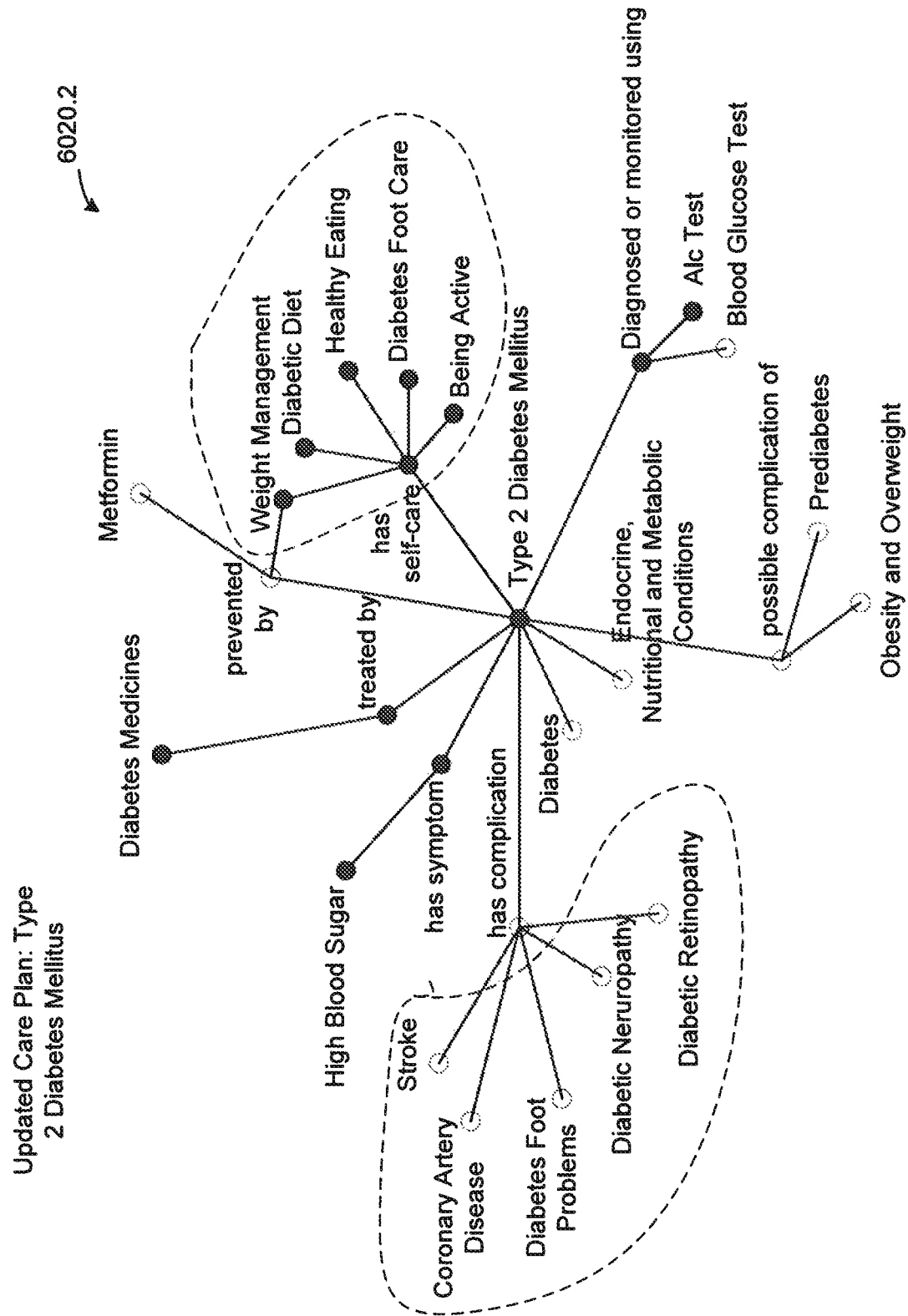

FIG. 60A-E show examples of modifying a care plan based on a detected emotion of the patient, a detected tone of the patient, a different medical outcome entered by a physician, or some combination thereof, in accordance with various embodiments. FIG. 60A depicts a user 6000 (e.g., patient) using the user device 104. The cognitive intelligence platform 102 provided a care plan 6002 that was originally generated for the patient for a medical condition of the patient. The care plan 6002 may include an action instruction pertaining to the medical condition of the user 6000, such as an instruction to read certain recommended content for the medical condition, schedule an appointment with a physician, etc. In some embodiments, the care plan 6002 may include a natural language result or answer based on a natural language query entered in the patient viewer by the user 6000.

Figure 61:
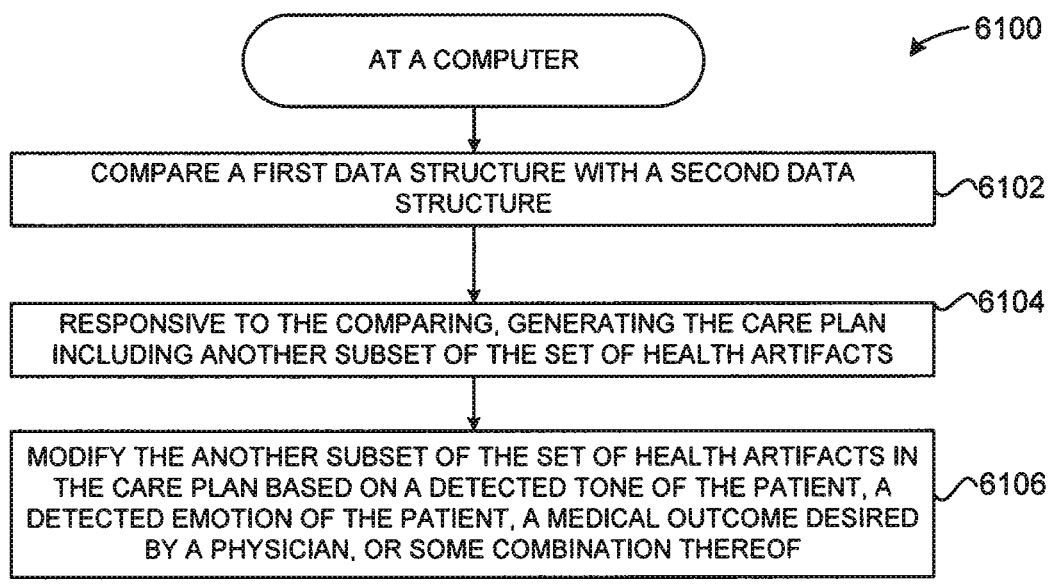
FIG. 61 shows a method for modifying a care plan based on a detected emotion of the patient, a detected tone of the patient, a different medical outcome entered by a physician, or some combination thereof, in accordance with various embodiments.

FIG. 61 shows a method 6100 for modifying a care plan based on a detected emotion of the patient, a detected tone of the patient, a different medical outcome entered by a physician, or some combination thereof, in accordance with various embodiments. In some embodiments, the method 6100 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 6100 may include operations that are implemented in computer instructions stored in a memory and executed by a processor of a computing device. In some embodiments, the method 6100 includes operations performed by the cognitive agent 110 (autonomous multipurpose application), the knowledge cloud 106, and/or the critical thinking engine 108 of the cognitive intelligence platform 102 as shown in FIG. 1.

At block 6102, the processing device may compare a first data structure with a second data structure. The first data structure (e.g., knowledge graph) includes a set of health artifacts pertaining to a first condition of the patient. The second data structure (e.g., patient graph) pertains to the patient and the first condition of the patient, and the second data structure includes a subset of the set of health artifacts.

At block 6104, responsive to the comparing, the processing device may generate the care plan including another subset of the set of health artifacts. The subset of the health artifacts may correspond with actions already performed by the patient, and the another subset of the set of the health artifacts may correspond with actions that have not yet been performed by the patient. The comparing may include projecting the second data structure onto the first data structure. The processing device may include, in the care plan, action instructions pertaining to the another subset of the set of the health artifacts. The action instructions may be directed toward a medical personnel, the patient, and/or an administrator depending on the role to which the care plan is tailored.

At block 6106, the processing device may modify the another subset of the set of health artifacts in the care plan based on a detected tone of the patient, a detected emotion of the patient, a medical outcome desired by a physician, or some combination thereof. In some embodiments, the processing may modify the another subset of the set of the health artifacts in real-time or near real-time. Real-time or near real-time may refer to performing an action in 2 seconds or less.

In some embodiments, the processing device may detect the tone of the patient based on spoken words by the patient, text entered by the patient, or some combination thereof. In some embodiments, the processing device may detect the emotion of the patient based on words spoken by the patient, text entered by the patient, a detected facial expression of the patient, or some combination thereof.

In some embodiments, the processing device may cause the care plan including the modifications to the another subset of the set of the health artifacts to be presented on a computing device. The care plan may be converted into natural language and may be tailored based on role of the person logged into the autonomous multipurpose application at the computing device. For example, the natural language may be tailored for the patient/user role, the care provider (e.g., medical personnel) role, and/or the administrator role.

In some embodiments, the processing device may modify the another set of the set of the health artifacts in the care plan based on the medical outcome desired by the physician by receiving instructions from a computing device of a physician to select a health artifact that corresponds to the medical outcome and to include the health artifact in the another subset of the set of the health artifacts. For example, the physician may select to include in the care plan health artifacts pertaining to self-care treatment for Type 2 Diabetes Mellitus when the care plan originally generated is lacking those health artifacts. The physician may be attempting to reduce the effects of the condition faster as the desired medical outcome of the inclusion of the health artifacts by the physician.

In some embodiments, the processing device may receive input from a computing device (user device 104). The input may specify a number and an area of the first condition the patient desires to manage. The area may include a type of health artifacts in the set of the health artifacts the patient selects to manage for the first condition. The processing device may select, based on the comparing, the another subset of the set of the health artifacts in the first data structure by selecting the another subset based on the number and the type of health artifacts specified by the patient.

Figure 62:
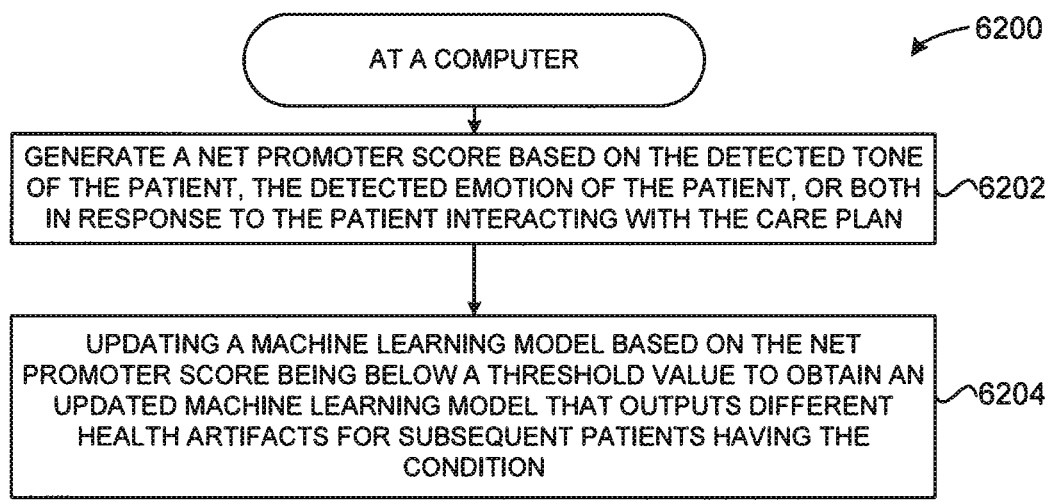
FIG. 62 shows a method for using a net promoter score to update a machine learning model to output different health artifacts, in accordance with various embodiments.

FIG. 62 shows a method 6200 for using a net promoter score to update a machine learning model to output different health artifacts, in accordance with various embodiments. In some embodiments, the method 6200 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 6200 may include operations that are implemented in computer instructions stored in a memory and executed by a processor of a computing device. In some embodiments, the method 6200 includes operations performed by the cognitive agent 110 (autonomous multipurpose application), the knowledge cloud 106, and/or the critical thinking engine 108 of the cognitive intelligence platform 102 as shown in FIG. 1. The operations of the method 6200 in FIG. 62 may be performed in some combination with the operations of the method 6100 in FIG. 61.

At block 6202, the processing device may generate a net promoter score based on the detected tone of the patient, the detected emotion of the patient, or both in response to the patient interacting with the care plan. A net promoter score may be used to gauge the loyalty of a customer and an entity providing the care plan. The net promoter score may be generated based on feedback received from patients, medical personnel, and/or administrators that use the care plan. The feedback may specify how likely the patients, medical personnel, and/or administrators are to recommend the cognitive intelligence platform 102, the features (e.g., generation of useful care plans and modifying the care plans based on tone, emotion, and/or medical outcome) of the cognitive intelligence platform 102, and the like. The net promoter score may be generated by subtracting the percentage of customers who respond between a first range (e.g., scores from 0 and 6) from the percentage of customers who respond with a score between a second range (e.g., scores from 9 to 10).

At block 6204, the processing device may update a machine learning model based on the net promoter score being below a threshold value to obtain an updated machine learning model that outputs different health artifacts for subsequent patients having the condition. For example, training data may be generated by collecting the care plans for medical conditions that received scores in the second range (high scores, positive feedback) and the care plans for medical conditions that received scores in the first range (low scores, positive feedback), and determining the differences in the care plans that resulted in the scores in the first range and the second range. The training data may include input data of the condition and output data of the care plans based on the differences.

Figure 63:
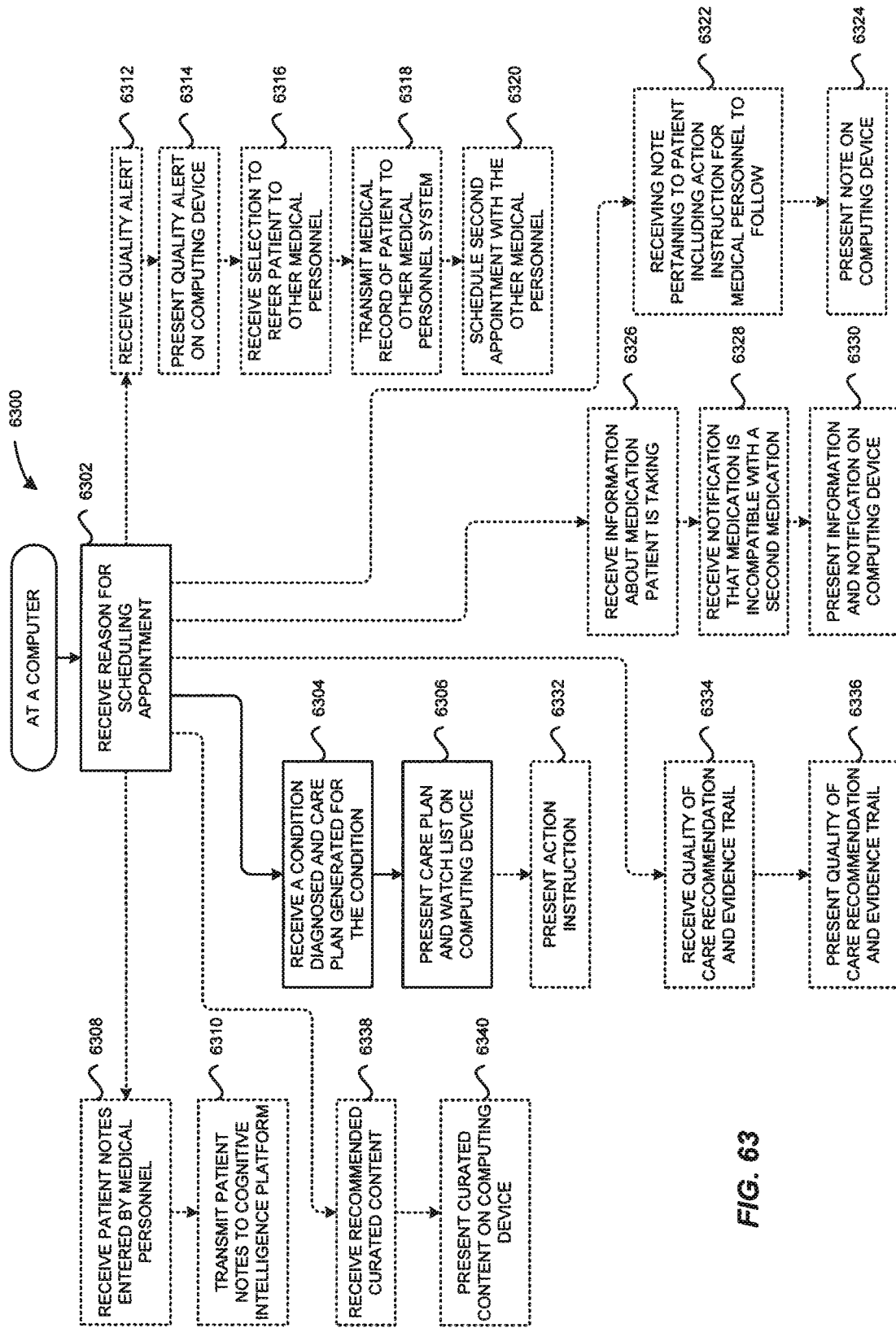
FIG. 63 shows a method for operating a clinic viewer on a computer device.

An aspect of the disclosure includes a clinic viewer on a computing device. FIG. 63 shows a method 6300 for operating the clinic viewer on the computing device of a medical personnel. The computing device may be the computing device 1400 of FIG. 14. The clinic viewer may be displayed on a display such as the display 1410 of FIG. 14.

Figure 64:
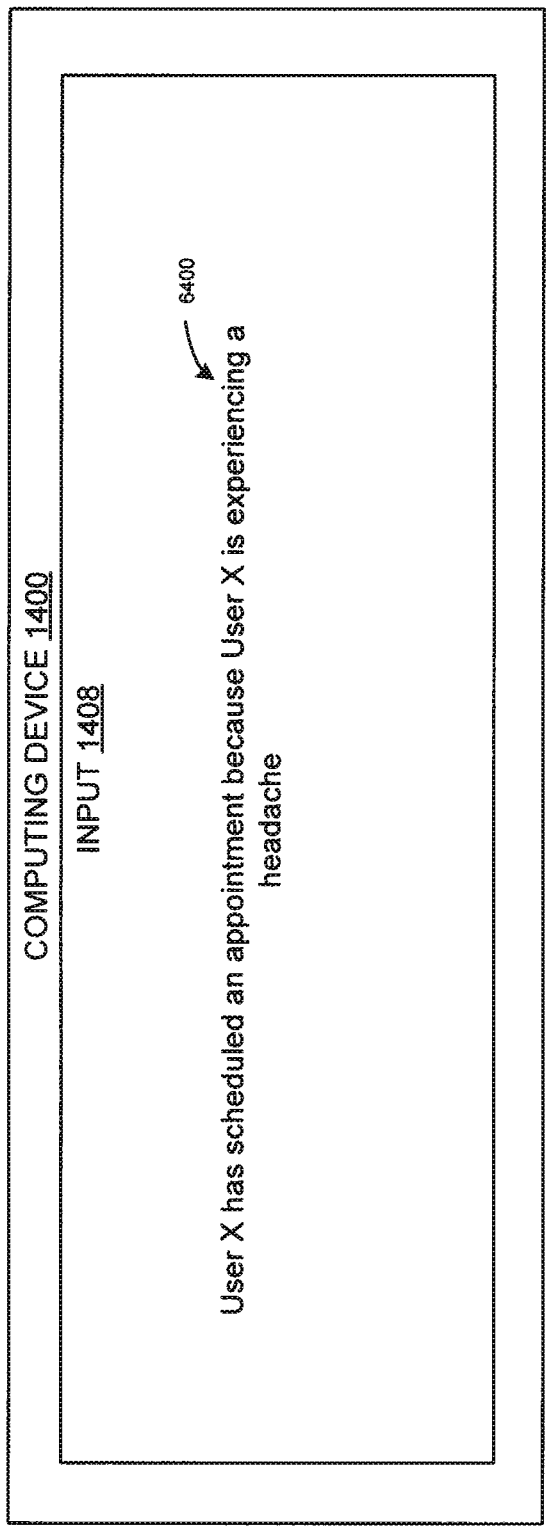
FIG. 64 shows a computing device receiving a reason that a patient scheduled an appointment with medical personnel as an example of a step of the method of FIG. 63.

The method 6300 includes receiving a reason that a patient scheduled an appointment with the medical personnel (block 6302). In some embodiments, the reason that a patient scheduled an appointment with the medical personnel is received at an input (e.g., a keyboard, a mouse, a touchscreen, etc.) of the computing device, such as the input 1408 of the computing device 1400 in FIG. 14. FIG. 64 shows an example of the computing device 1400 receiving a reason 6400 that a patient scheduled an appointment with the medical personnel. In some embodiments, a tangible, non-transitory computer-readable medium stores instructions that, when executed, cause a processing device, such as the processor 1402 shown in FIG. 14 to execute the step of block 6302.

Figure 65:
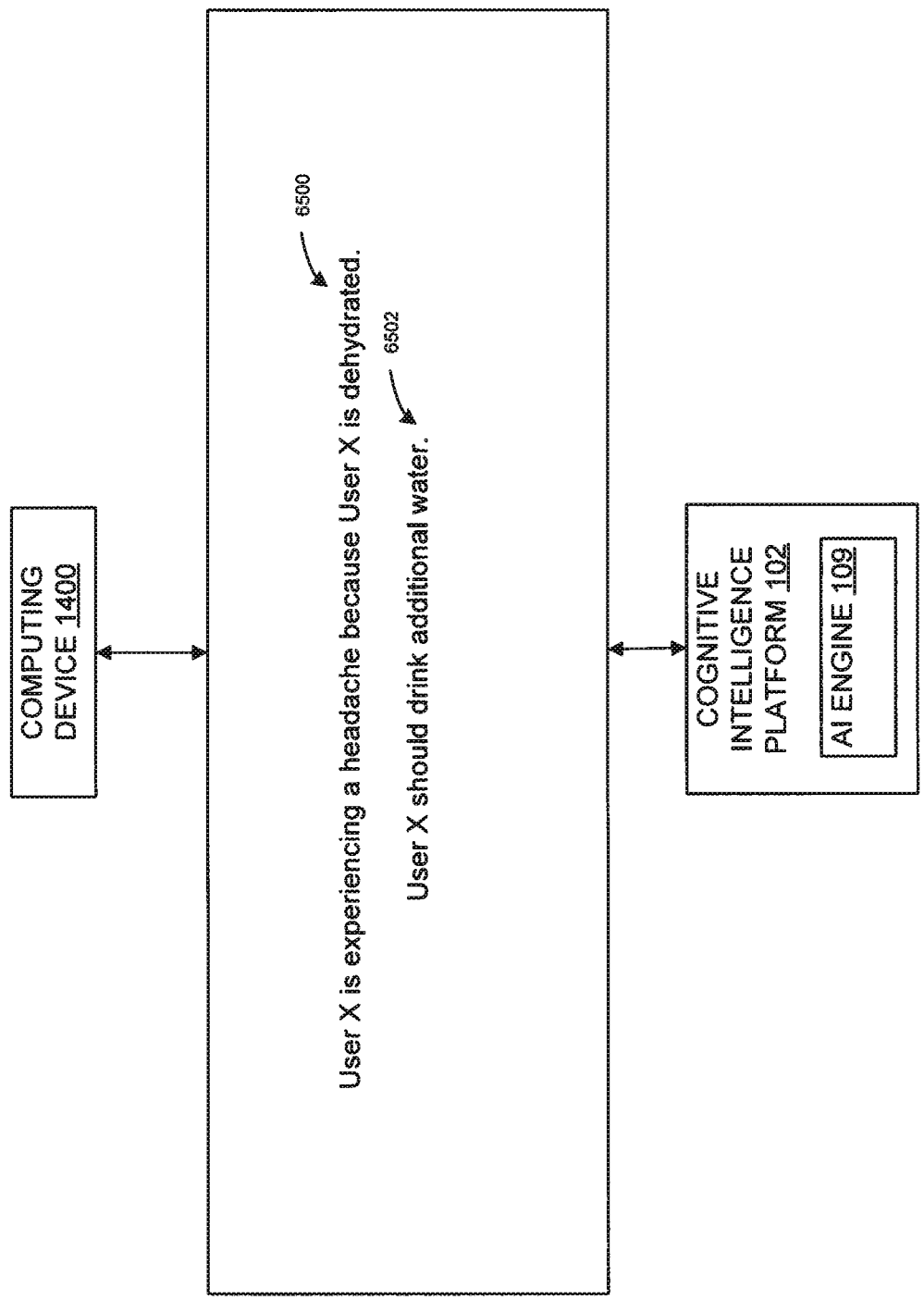
FIG. 65 a condition diagnosed for a patient and a care plan generated by an artificial intelligence engine as an example of a step of the method of FIG. 63.

The method 6300 further includes receiving a condition diagnosed for the patient and a care plan generated for the condition, wherein the care plan is generated by an artificial intelligence engine, such as the AI engine 109 of FIG. 1, of a cognitive intelligence platform, such as the cognitive intelligence platform 102 shown in FIG. 1 (block 6304). FIG. 65 shows a condition diagnosed for the patient 6500 and a care plan 6502 generated by the cognitive intelligence platform 102 (e.g., artificial intelligence engine 109, cognitive agent 110, and/or knowledge cloud 106). In some embodiments, a tangible, non-transitory computer-readable medium stores instructions that, when executed, cause a processing device, such as the processor 1402 shown in FIG. 14 to execute the step of block 6304.

In some embodiments, the care plan is generated based on a knowledge graph pertaining to the condition and information pertaining to the patient, and the information includes any action the patient has performed pertaining to the condition. In some embodiments, the knowledge graph is the knowledge graph 500 of FIG. 5. The information pertaining to the patient may be included in a patient graph tailored for the patient and the particular condition. As described herein, there may be a patient graph generated for each condition of each patient.

Figure 66:
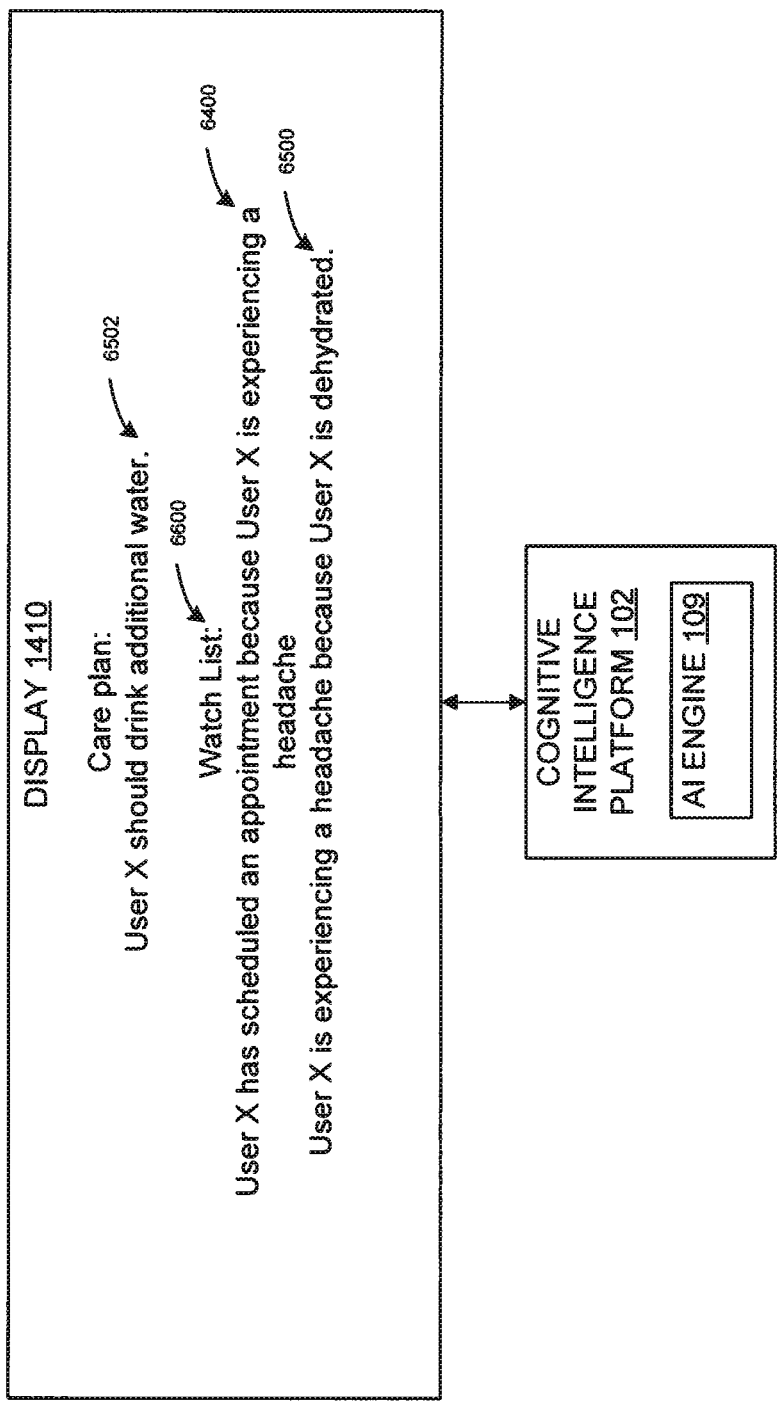
FIG. 66 shows a display showing a care plan and a watch list including a reason for a patient visit and a condition diagnosed for the patient as an example of a step of the method of FIG. 63.

The method 6300 further includes presenting, on the clinic viewer, the care plan and a watch-list including the reason, the condition, or some combination thereof (block 6306). FIG. 66 shows an example of the display 1410 showing a care plan 6502 and a watch list 6600 including the reason 6400 and the condition 6500. As discussed herein, the care plan 6502 and the watch list 6600 may be generated by the cognitive intelligence platform 102 (e.g., artificial intelligence engine 109, cognitive agent 110, and/or knowledge cloud 106). In some embodiments, a tangible, non-transitory computer-readable medium stores instructions that, when executed, cause a processing device, such as the processor 1402 shown in FIG. 14 to execute the step of block 6306.

Figure 67:
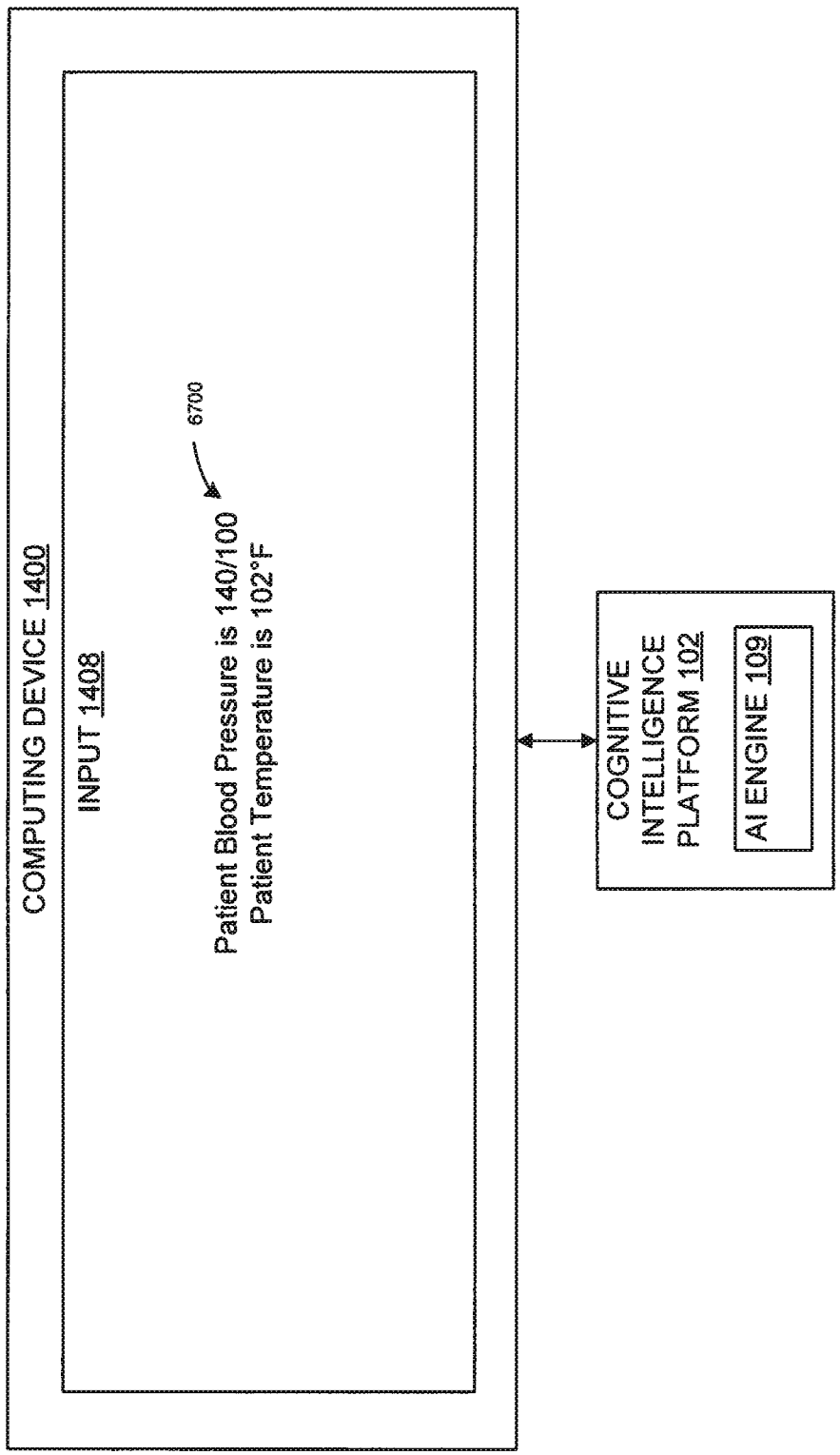
FIG. 67 shows patient notes received at an input of a computing device as an example of a step of the method of FIG. 63.

In some embodiments, the method 6300 further includes receiving patient notes entered by the medical personnel, wherein the patient notes pertain to a symptom of the patient, a vital sign of the patient, a characteristic of the patient, a diagnosis for the patient, or some combination thereof (block 6308). In some embodiments, the patient notes are received at an input of the computing device, such as the input 1408 of the computing device 1400 in FIG. 14. FIG. 67 shows patient notes 6700, in this case, a patient blood pressure and body temperature, received at the input 1408 of the computing device 1400. In some embodiments, a tangible, non-transitory computer-readable medium stores instructions that, when executed, cause a processing device, such as the processor 1402 shown in FIG. 14 to execute the step of block 6308.

Figure 68:
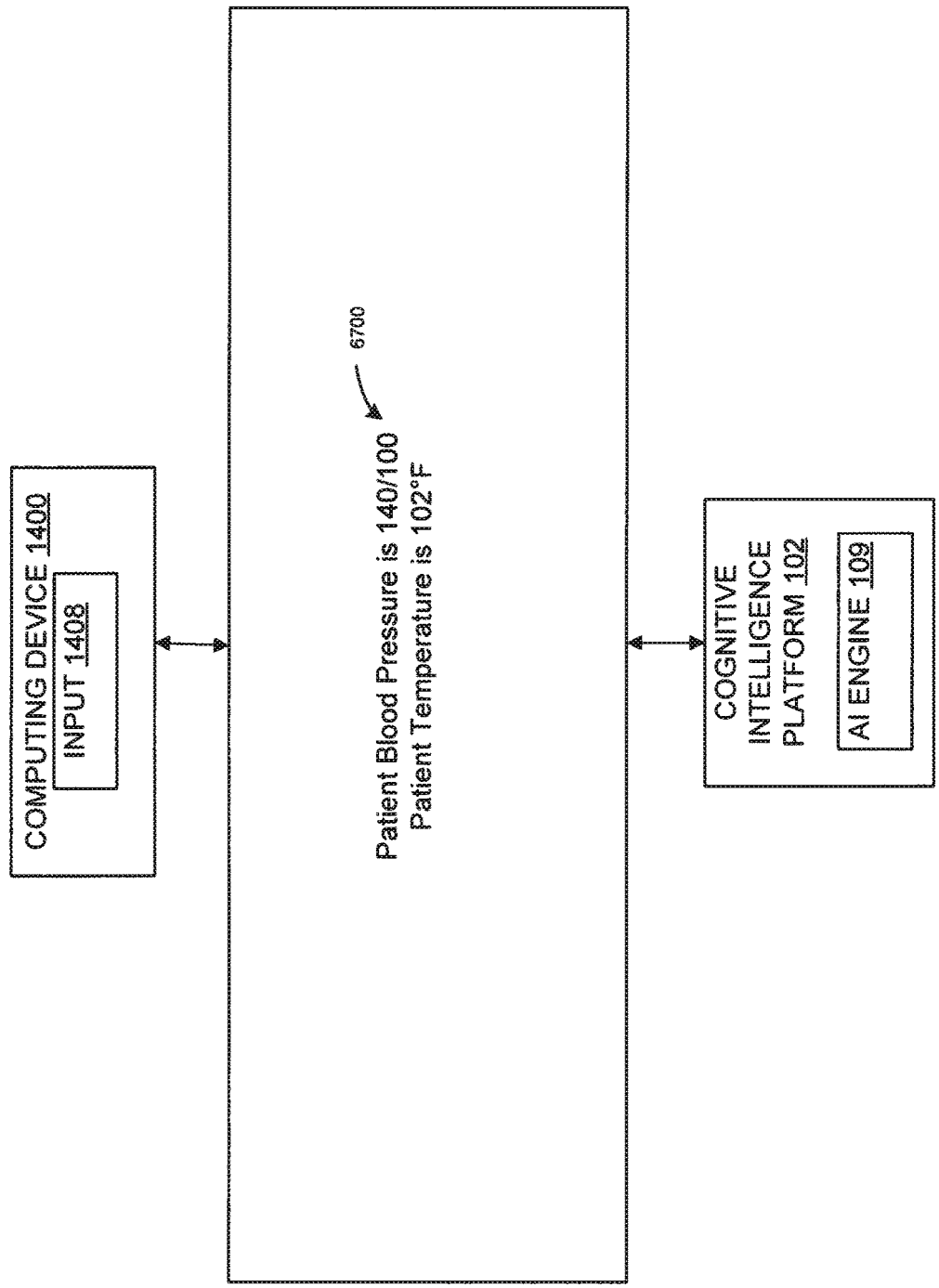
FIG. 68 shows patient notes being sent from an input of a computing device to a cognitive intelligence platform as an example of a step of the method of FIG. 63.

In some embodiments, the method 6300 further includes transmitting the patient notes to cause a data structure pertaining to the patient to be updated at the cognitive intelligence platform (block 6310). The data structure may include a patient graph for the condition of the patient. In some embodiments, the cognitive intelligence platform is the cognitive intelligence platform 102 of FIG. 1. FIG. 68 shows patient notes 6700 received by the input 1408 being transmitted by the computing device 1400 to the cognitive intelligence platform 102. In some embodiments, a tangible, non-transitory computer-readable medium stores instructions that, when executed, cause a processing device, such as the processor 1402 shown in FIG. 14 to execute the step of block 6310.

Figure 69:
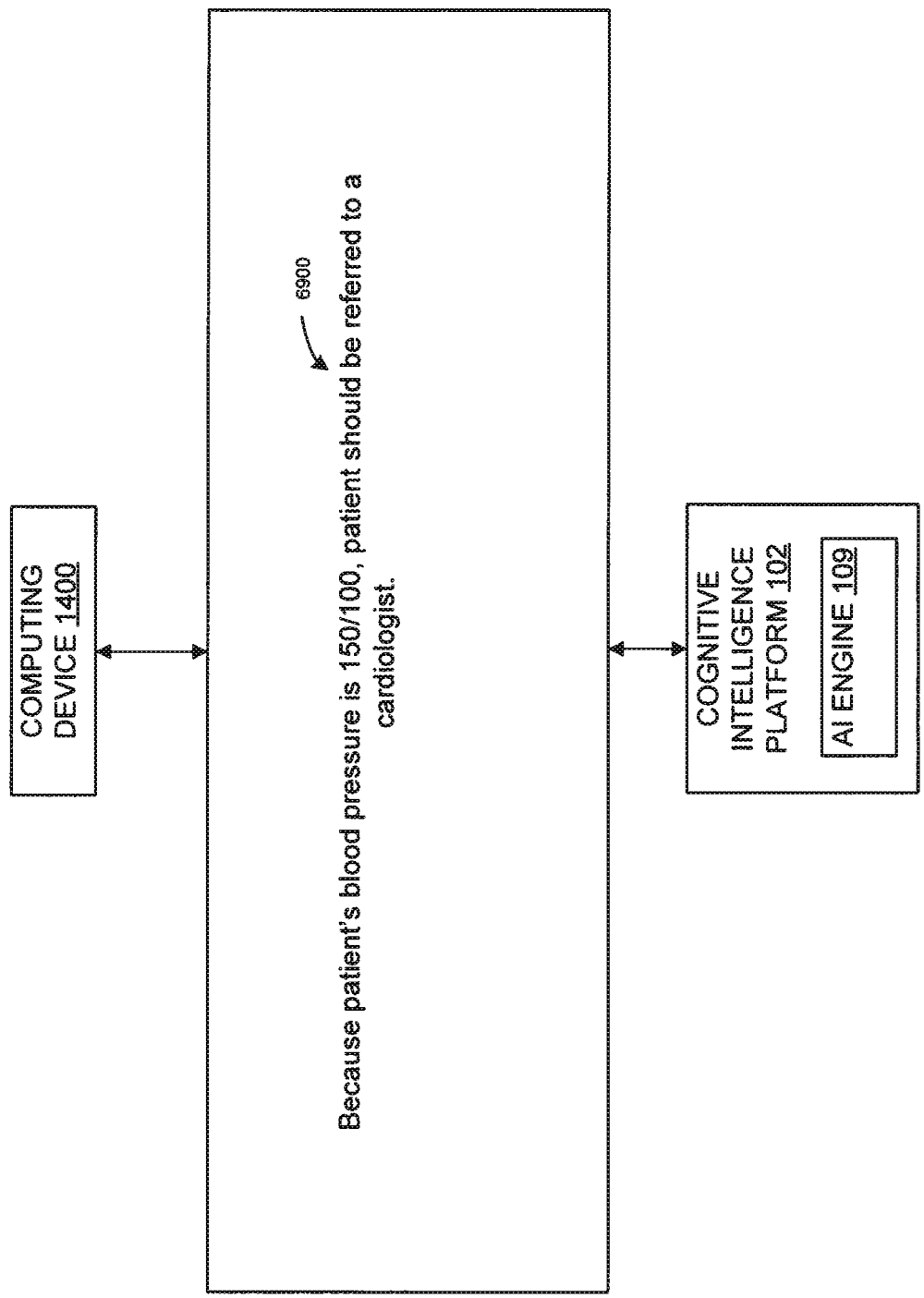
FIG. 69 shows a quality alert recommending that a medical personnel refer a patient to a cardiologist as an example of a step of the method of FIG. 63.

In some embodiments, the method 6300 further includes receiving a quality alert based on information about the patient, wherein the quality alert is based on an evidence-based guideline for the condition (block 6312). The evidence-based guideline may refer to a best practice for treating the condition based on clinical trials and/or information generated and/or approved by a certified professional. For example, the quality alert may indicate to prescribe a certain medication for a certain diagnosed condition of a patient. In some embodiments, the evidence-based guidelines are the evidence-based guidelines 212 of FIG. 2. In some embodiments, the quality alert includes a recommendation for the medical personnel to refer the patient to another medical personnel. In some embodiments, the quality alert may come from a cognitive intelligence platform, such as the cognitive intelligence platform 102 of FIG. 1. FIG. 69 shows a quality alert 6900 recommending that the medical personnel refer the patient to a cardiologist. In some embodiments, a tangible, non-transitory computer-readable medium stores instructions that, when executed, cause a processing device, such as the processor 1402 shown in FIG. 14 to execute the step of block 6312.

Figure 70:
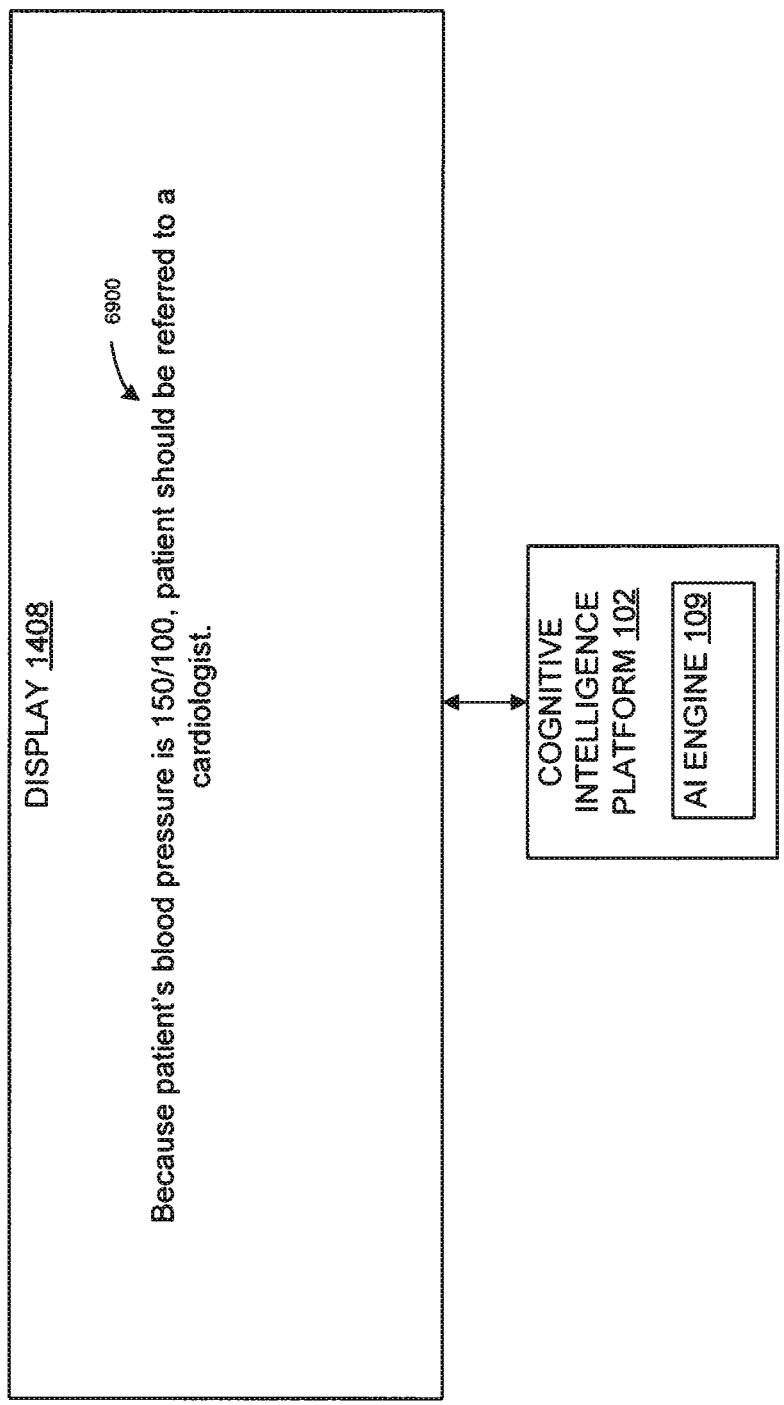
FIG. 70 shows a quality alert presented on a display of a computing device as an example of a step of the method of FIG. 63.

In some embodiments, the method 6300 further includes presenting the quality alert on the clinic viewer (block 6314). FIG. 70 shows the quality alert 6900 received from the cognitive intelligence platform 102 being presented on the display 1408 of the computing device 1400. In some embodiments, a tangible, non-transitory computer-readable medium stores instructions that, when executed, cause a processing device, such as the processor 1402 shown in FIG. 14 to execute the step of block 6314.

Figure 71:
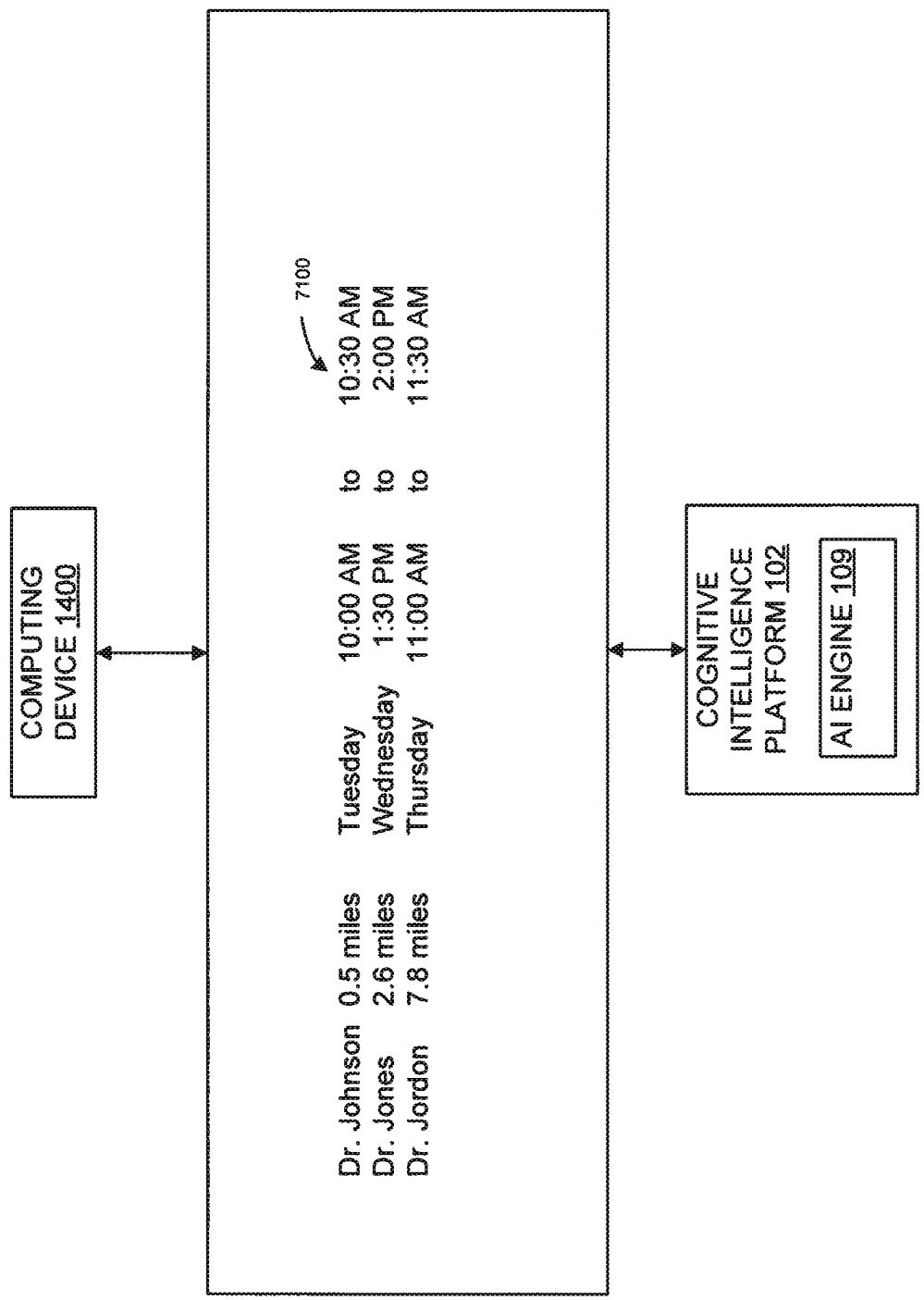
FIG. 71 shows a computing device receiving a selection to refer a patient to other medical personnel as an example of a step of the method of FIG. 63.

In some embodiments where the quality alert includes a recommendation for the medical personnel to refer the patient to another medical personnel, the method 6300 further includes receiving a selection to refer the patient to the other medical personnel (block 6316). FIG. 71 shows the computing device 1400 receiving a selection 7100 from the cognitive intelligence platform 102 to refer a patient to the other medical personnel. In the depicted example, the computing device 1400 may be operated by the medical personnel. In some embodiments, a tangible, non-transitory computer-readable medium stores instructions that, when executed, cause a processing device, such as the processor 1402 shown in FIG. 14 to execute the step of block 6316.

In some embodiments where the quality alert includes a recommendation for the medical personnel to refer the patient to another medical personnel, the method 6300 further includes transmitting a medical record of the patient to a system of the other medical personnel (block 6318). In some embodiments, the medical record is sent by a network interface, such as the network interface 1411 as shown in FIG. 14, of a computing device implementing the cognitive intelligence platform 102 and the medical record is received by a network interface in a system of the other medical personnel. In some embodiments, a tangible, non-transitory computer-readable medium stores instructions that, when executed, cause a processing device, such as the processor 1402 shown in FIG. 14 to execute the step of block 6318.

In some embodiments where the quality alert includes a recommendation for the medical personnel to refer the patient to another medical personnel, the method 6300 further includes electronically scheduling a second appointment with the other medical personnel for the patient (block 6320). In some embodiments, the process of electronically scheduling a second appointment with the other medical personnel occurs through the network interface 1411 as shown in FIG. 14. In some embodiments, a tangible, non-transitory computer-readable medium stores instructions that, when executed, cause a processing device, such as the processor 1402 shown in FIG. 14 to execute the step of block 6320.

Figure 72:
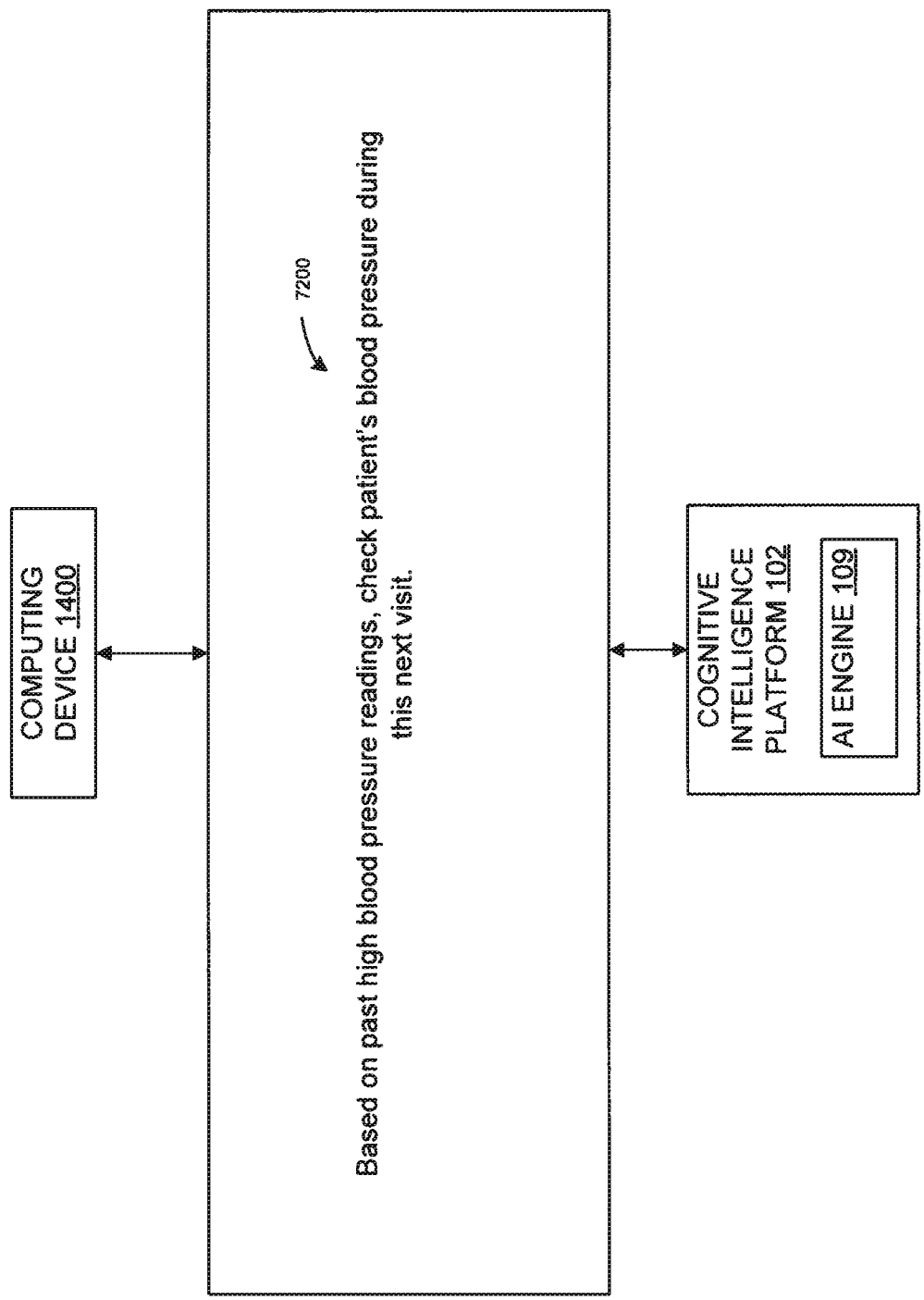
FIG. 72 shows a computing device receiving a note including an action instruction from an AI engine as an example of a step of the method of FIG. 63.

In some embodiments, the method 6300 further includes receiving a note pertaining to the patient (block 6322). The note includes an action instruction for the medical personnel to follow when providing a service to the patient, and the action instruction is generated by the artificial intelligence engine, such as the AI engine 109 of FIG. 1, based on information about the patient. FIG. 72 shows the computing device 1400 receiving a note 7200 including an action instruction from the cognitive intelligence platform 102. The note includes an action instruction stating "Based on past high blood pressure readings, check patient's blood pressure during the next visit". In some embodiments, a tangible, non-transitory computer-readable medium stores instructions that, when executed, cause a processing device, such as the processor 1402 shown in FIG. 14 to execute the step of block 6322.

Figure 73:
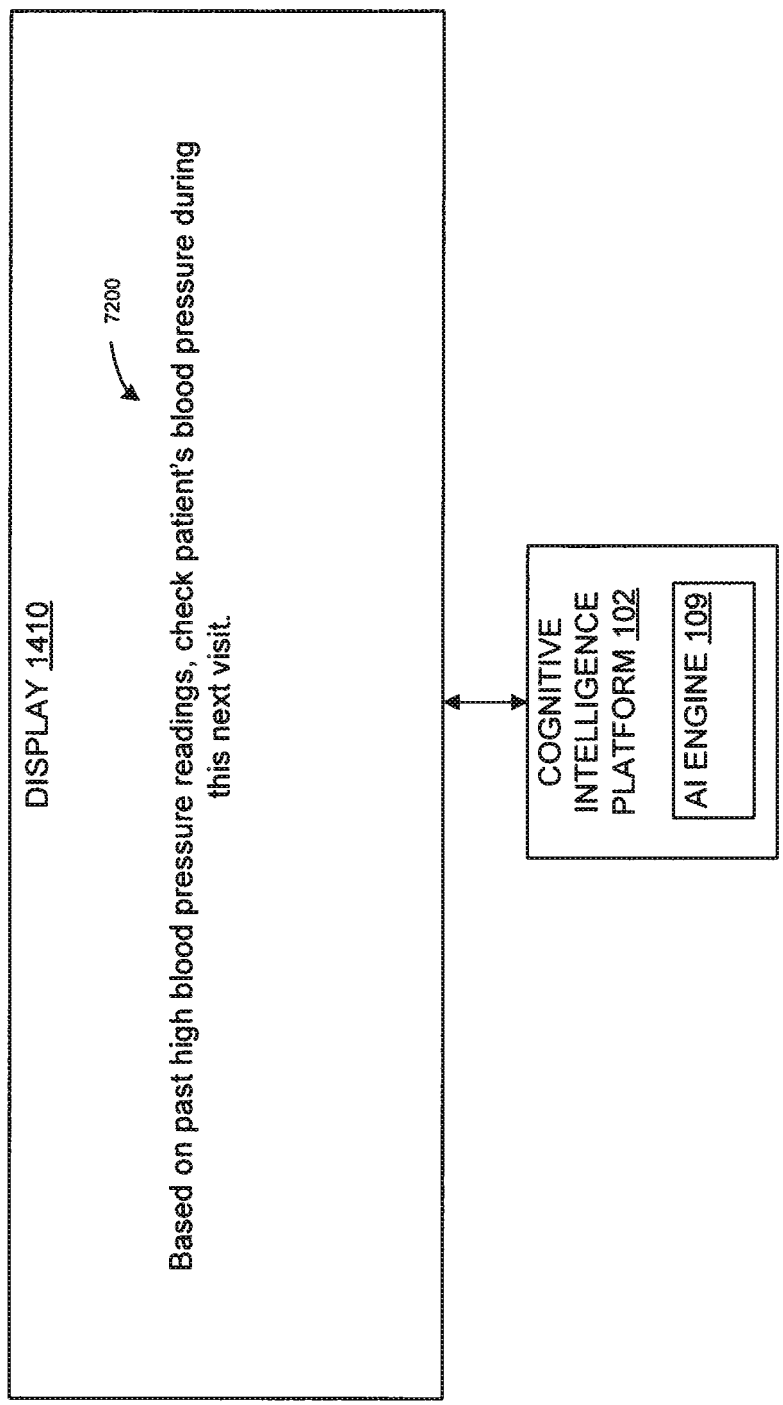
FIG. 73 shows a note being presented on a display as an example of a step of the method of FIG. 63.

In some embodiments, the method 6300 further includes presenting the note on the clinic viewer (block 6324). FIG. 73 shows the note 7200 received from the cognitive intelligence platform 102 being presented on the display 1410. In some embodiments, a tangible, non-transitory computer-readable medium stores instructions that, when executed, cause a processing device, such as the processor 1402 shown in FIG. 14 to execute the step of block 6324.

Figure 74:
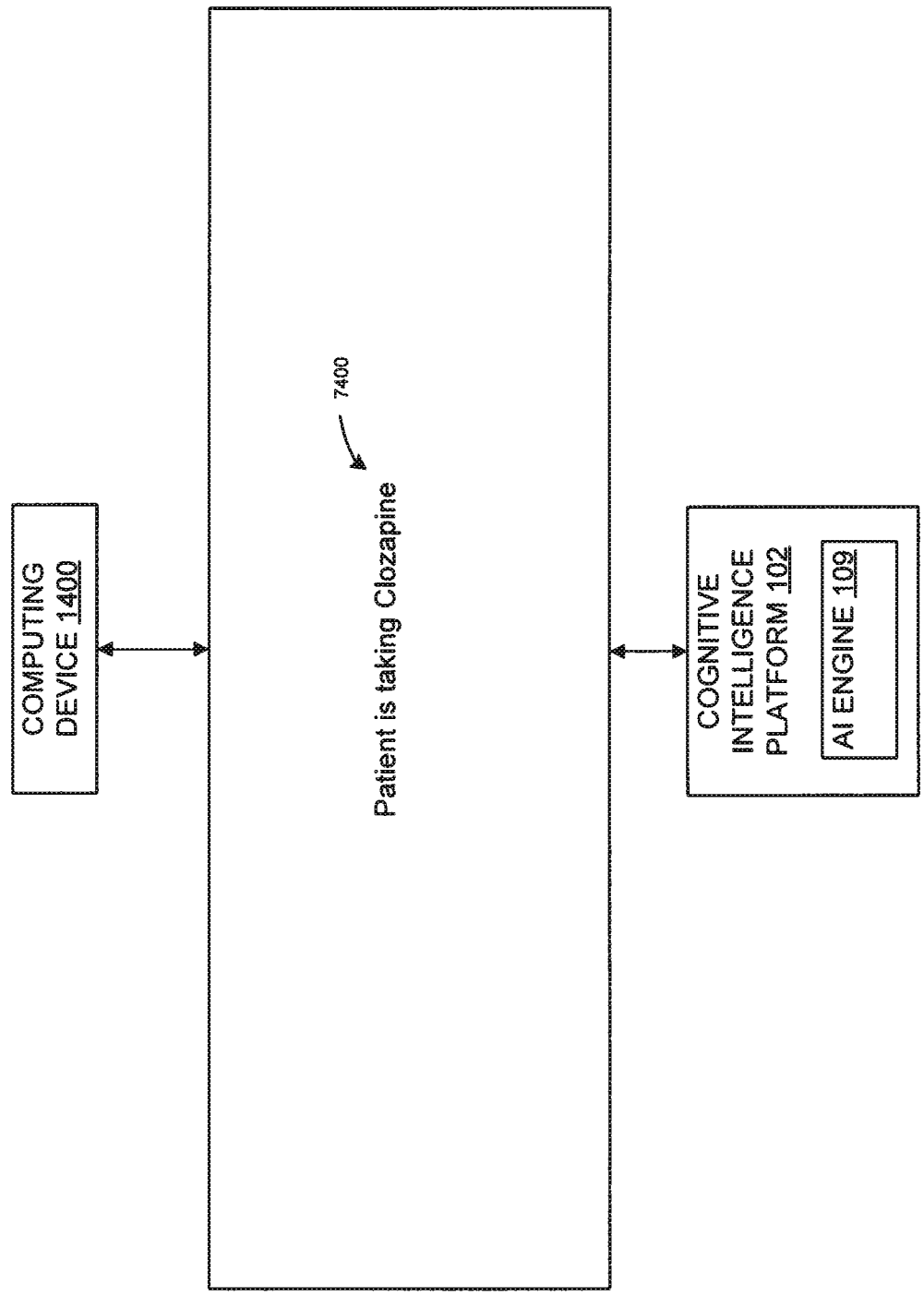
FIG. 74 shows a computing device receiving information including a medication a patient is taking as an example of a step of the method of FIG. 63.

In some embodiments, the method 6300 further includes receiving information including a medication the patient is taking (block 6326). FIG. 74 shows the computing device 1400 receiving information 7400 including a medication the patient is taking. For example, the information 7400 specifies "Patient is taking Clozapine". The medication may be obtained from a patient graph of a condition of the patient that is stored in the knowledge cloud 106. In some embodiments, a tangible, non-transitory computer-readable medium stores instructions that, when executed, cause a processing device, such as the processor 1402 shown in FIG. 14 to execute the step of block 6326.

Figure 75:
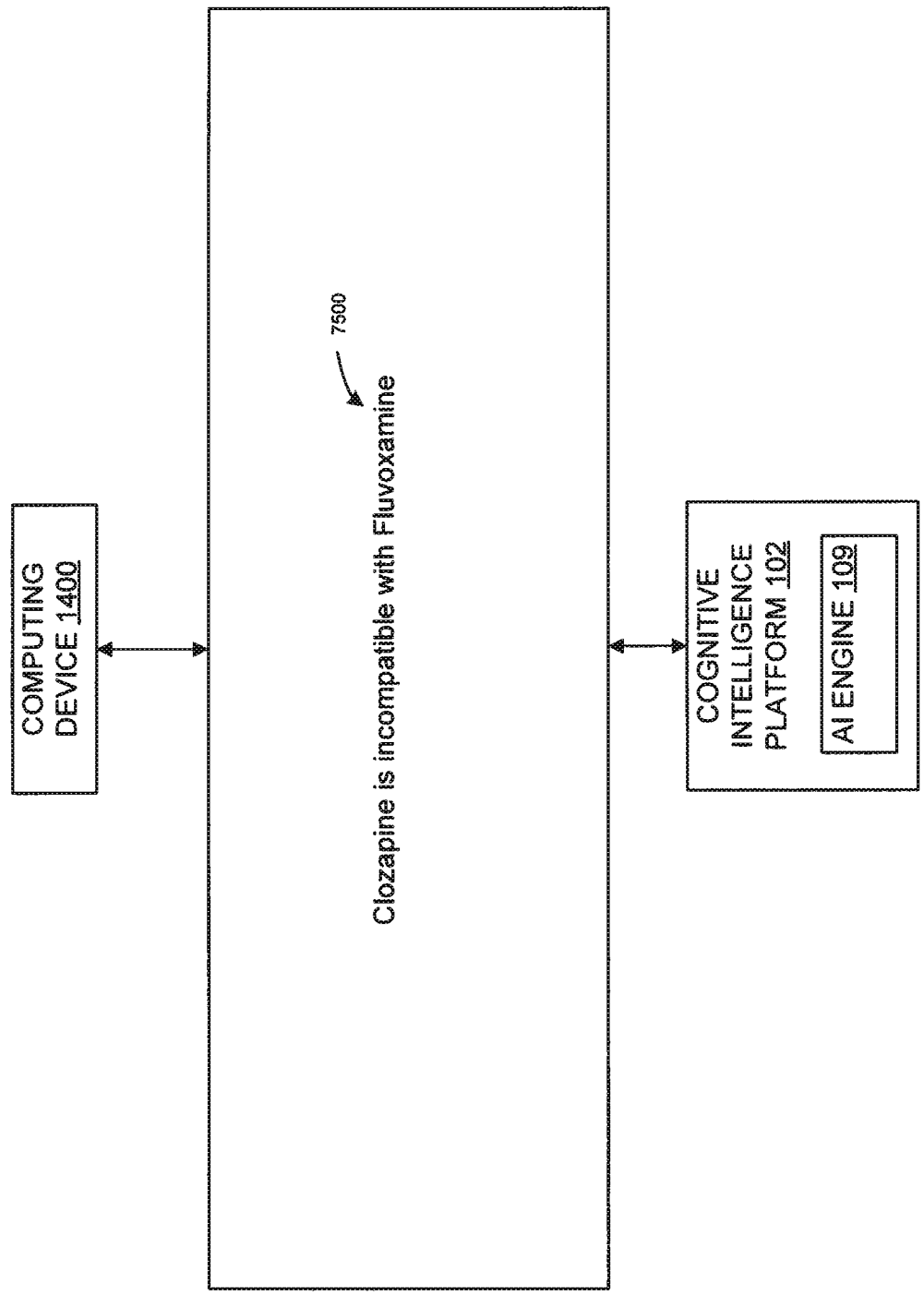
FIG. 75 shows a computing device receiving a notification that a medication is incompatible with a second medication from an AI engine as an example of a step of the method of FIG. 63.

In some embodiments, the method 6300 further includes receiving a notification that the medication is incompatible with a second medication for the condition, wherein the notification is generated by the artificial intelligence engine, such as the AI engine 109 of FIG. 1, based on a knowledge graph, such as the knowledge graph 500 shown in FIG. 5, pertaining to the condition (block 6328). FIG. 75 shows the computing device 1400 receiving a notification 7500 that the medication (e.g., Clozapine) is incompatible with a second medication (e.g., Fluvoxamine) from the cognitive intelligence platform 102. In some embodiments, a tangible, non-transitory computer-readable medium stores instructions that, when executed, cause a processing device, such as the processor 1402 shown in FIG. 14 to execute the step of block 6328.

Figure 76:
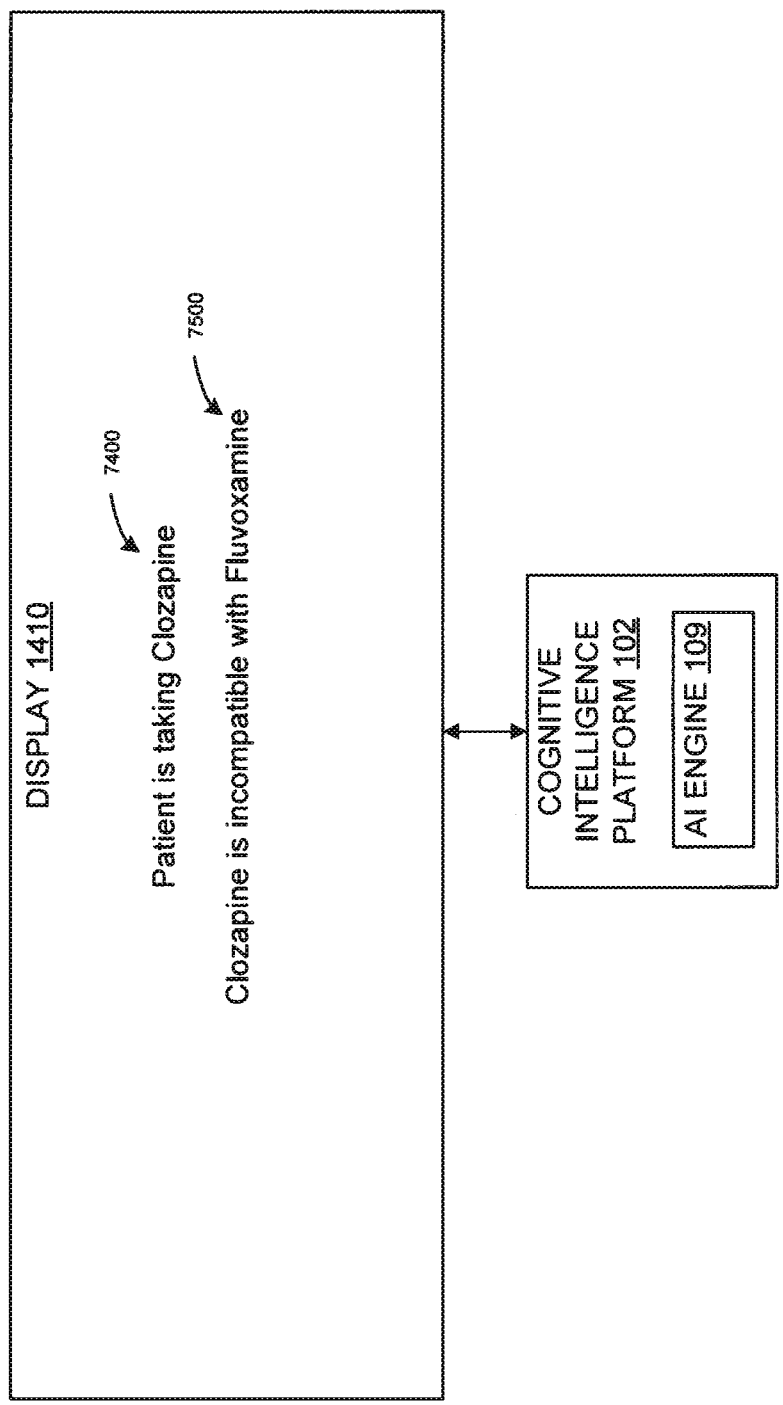
FIG. 76 shows information including a medication the patient is taking and a notification that a medication is incompatible with a second medication being presented on a display as an example of a step of the method of FIG. 63.

In some embodiments, the method 6300 further includes presenting the information and the notification on the clinic viewer (block 6330). FIG. 76 shows information 7400 including the medication the patient is taking and the notification 7500 that the medication is incompatible with a second medication being presented on the display 1410. The information 7400 and the notification 7500 may be received from the cognitive intelligence platform 102. In some embodiments, a tangible, non-transitory computer-readable medium stores instructions that, when executed, cause a processing device, such as the processor 1402 shown in FIG. 14 to execute the step of block 6330.

Figure 77:
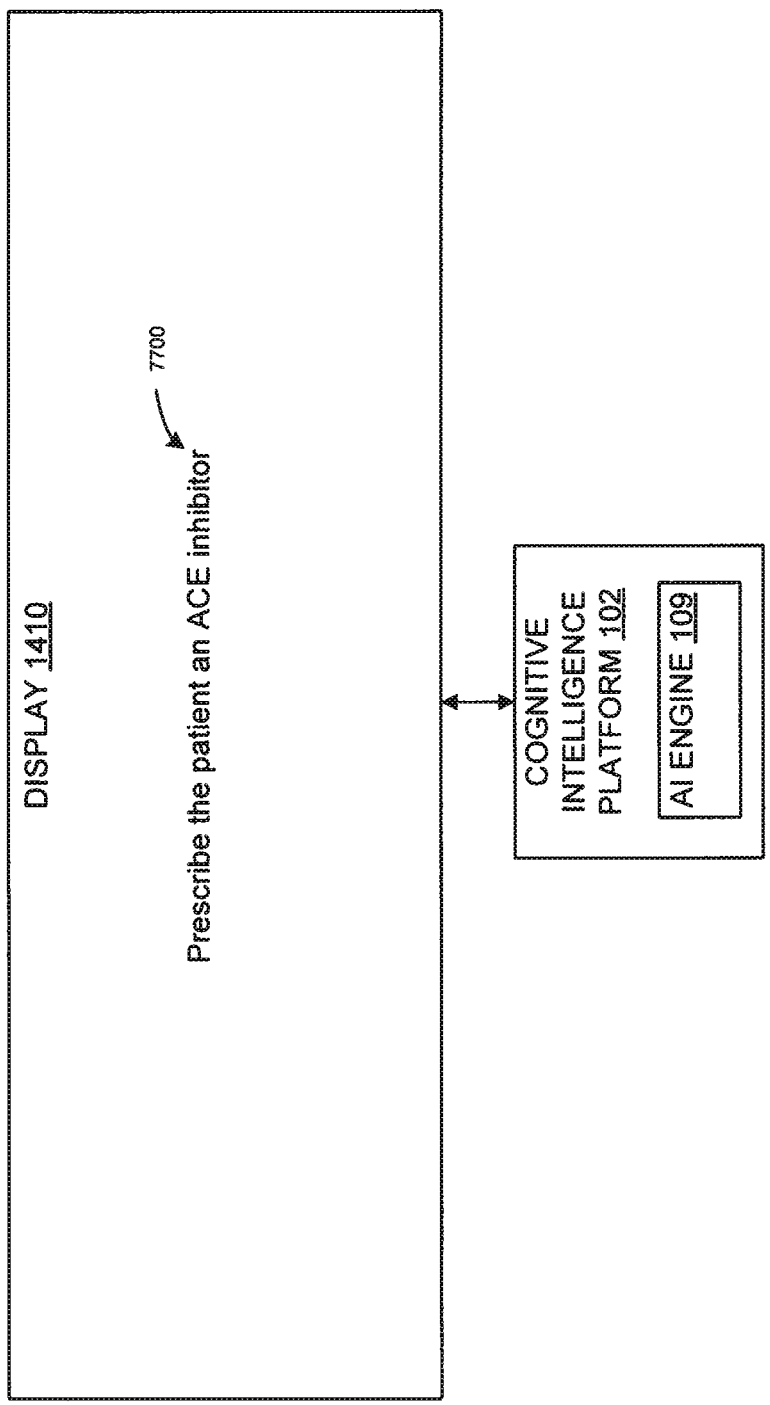
FIG. 77 shows a computing device receiving and presenting on a display an action instruction from an AI engine as an example of a step of the method of FIG. 63.

In some embodiments, the care plan includes an action instruction for the medical personnel to perform when providing a service to treat the reason, the condition, or both. An action instruction is generated based on the reason, the condition, or both by the artificial intelligence engine. The artificial intelligence engine may be the AI engine 109 of FIG. 1. The knowledge cloud 106 of FIG. 1 and/or the cognitive agent 110 may be used to generate the care plan. In some embodiments, the method 6300 further includes presenting the action instruction on the clinic viewer (block 6332). FIG. 77 shows the computing device 1410 receiving and presenting on the display 1410 an action instruction 7700 from the cognitive intelligence platform 102, for medical personnel to perform when providing a service to treat the reason, the condition, or both. In some embodiments, a tangible, non-transitory computer-readable medium stores instructions that, when executed, cause a processing device, such as the processor 1402 shown in FIG. 14 to execute the step of block 6332.

Figure 78:
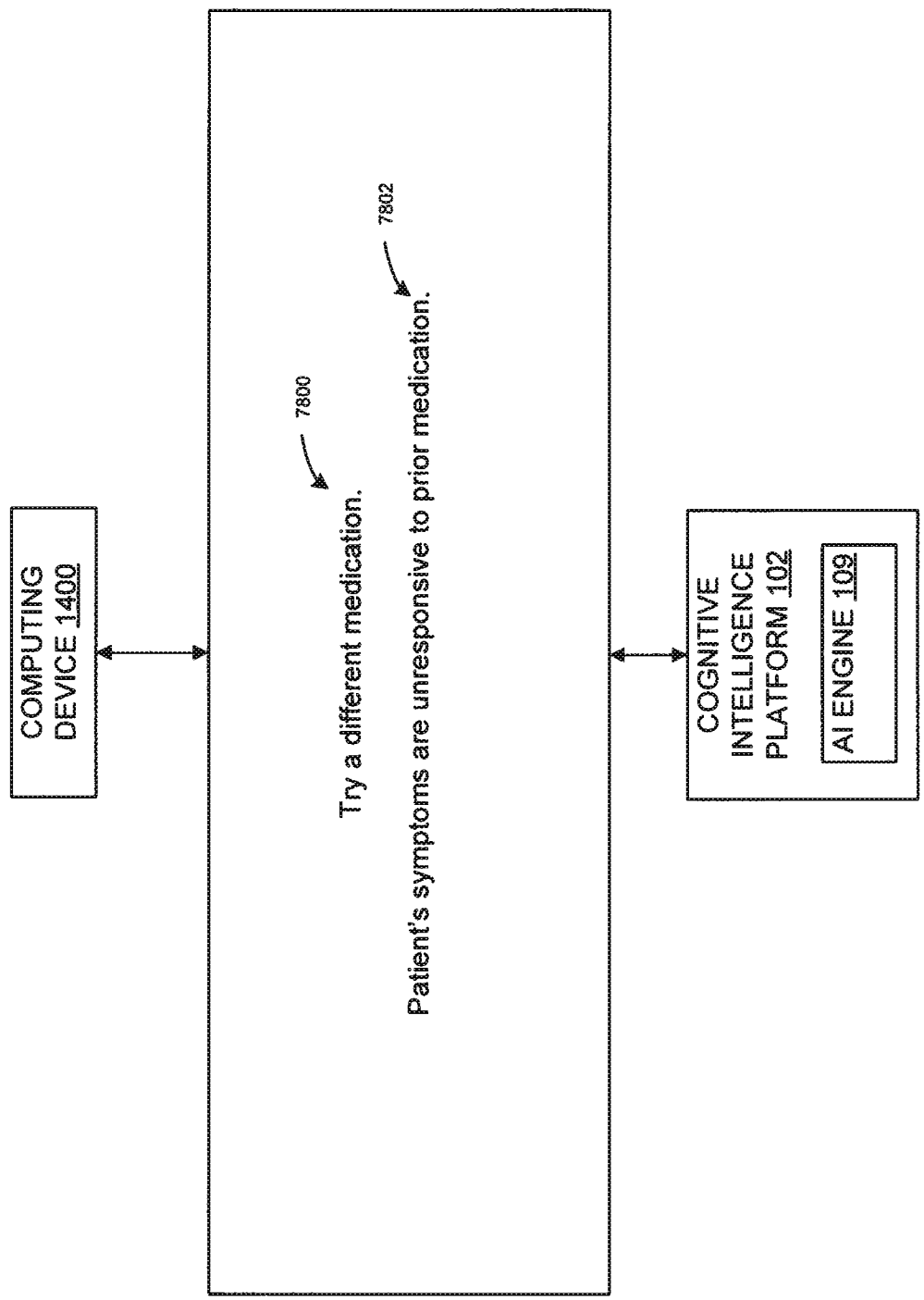
FIG. 78 shows a computing device receiving a quality of care recommendation and an evidence trail explaining why the quality of care recommendation was provided as an example of a step of the method of FIG. 63.

In some embodiments, the method 6300 further includes receiving a quality of care recommendation based on the reason, the condition, or both, and an evidence trail of reasoning for why the quality of care recommendation was provided (block 6334). FIG. 78 shows the computing device 1400 receiving, from the cognitive intelligence platform 102, a quality of care recommendation 7800 that the medical personnel should "try a different medication" and an evidence trail 7802 explaining why the quality of care recommendation 7802 was provided (in this case, that the "patient's symptoms are unresponsive to prior medication"). In some embodiments, a tangible, non-transitory computer-readable medium stores instructions that, when executed, cause a processing device, such as the processor 1402 shown in FIG. 14, to execute the step of block 6334.

Figure 79:
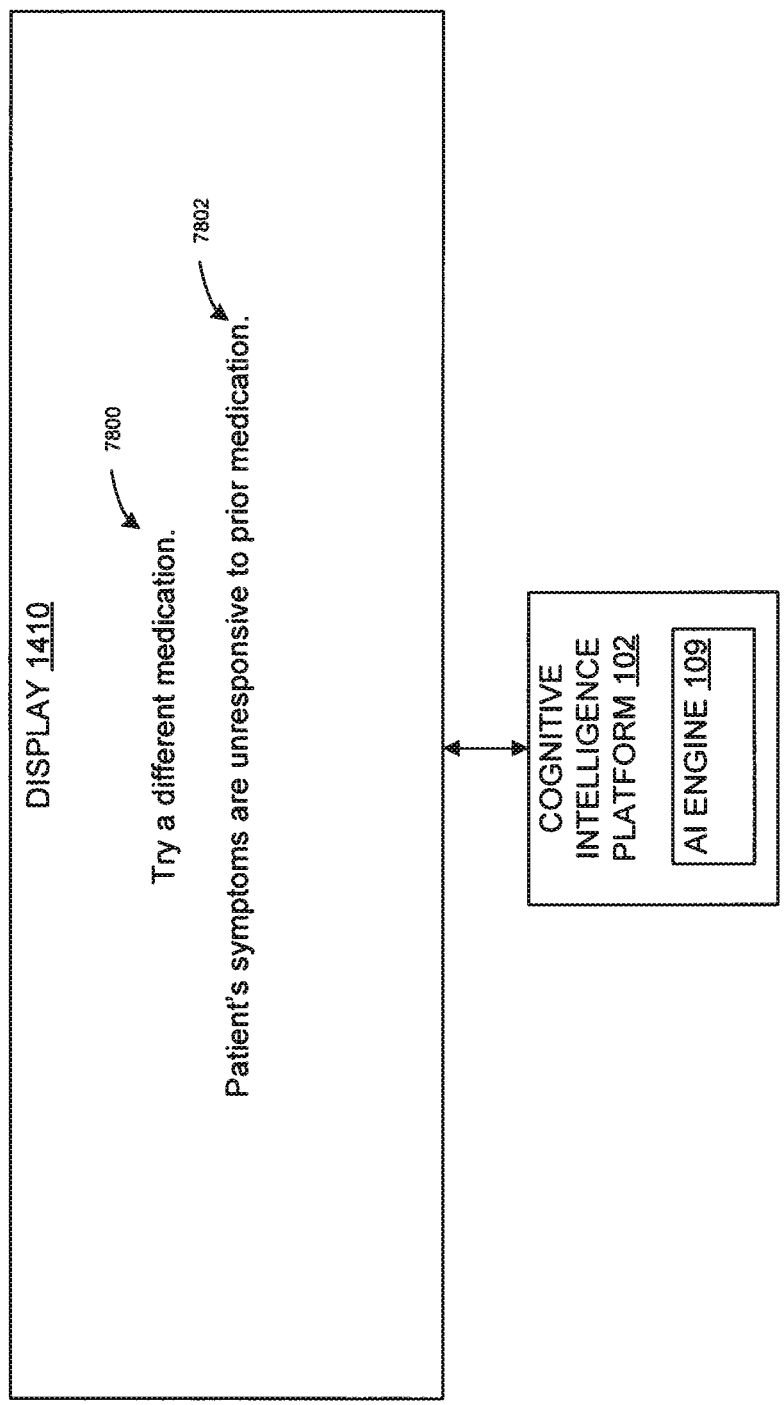
FIG. 79 shows a display presenting the quality of care recommendation and a evidence trail explaining why the quality of care recommendation was provided as an example of a step of the method of FIG. 63.

In some embodiments, the method 6300 further includes presenting the quality of care recommendation and the evidence trail (block 6336). FIG. 79 shows the display 1410 presenting the quality of care recommendation 7800 and the evidence trail 7802 explaining why the quality of care recommendation 7800 was provided. The quality of care recommendation 7800 and the evidence trail 7802 may be received from the cognitive intelligence platform 102. In some embodiments, a tangible, non-transitory computer-readable medium stores instructions that, when executed, cause a processing device, such as the processor 1402 shown in FIG. 14, to execute the step of block 6336.

Figure 80:
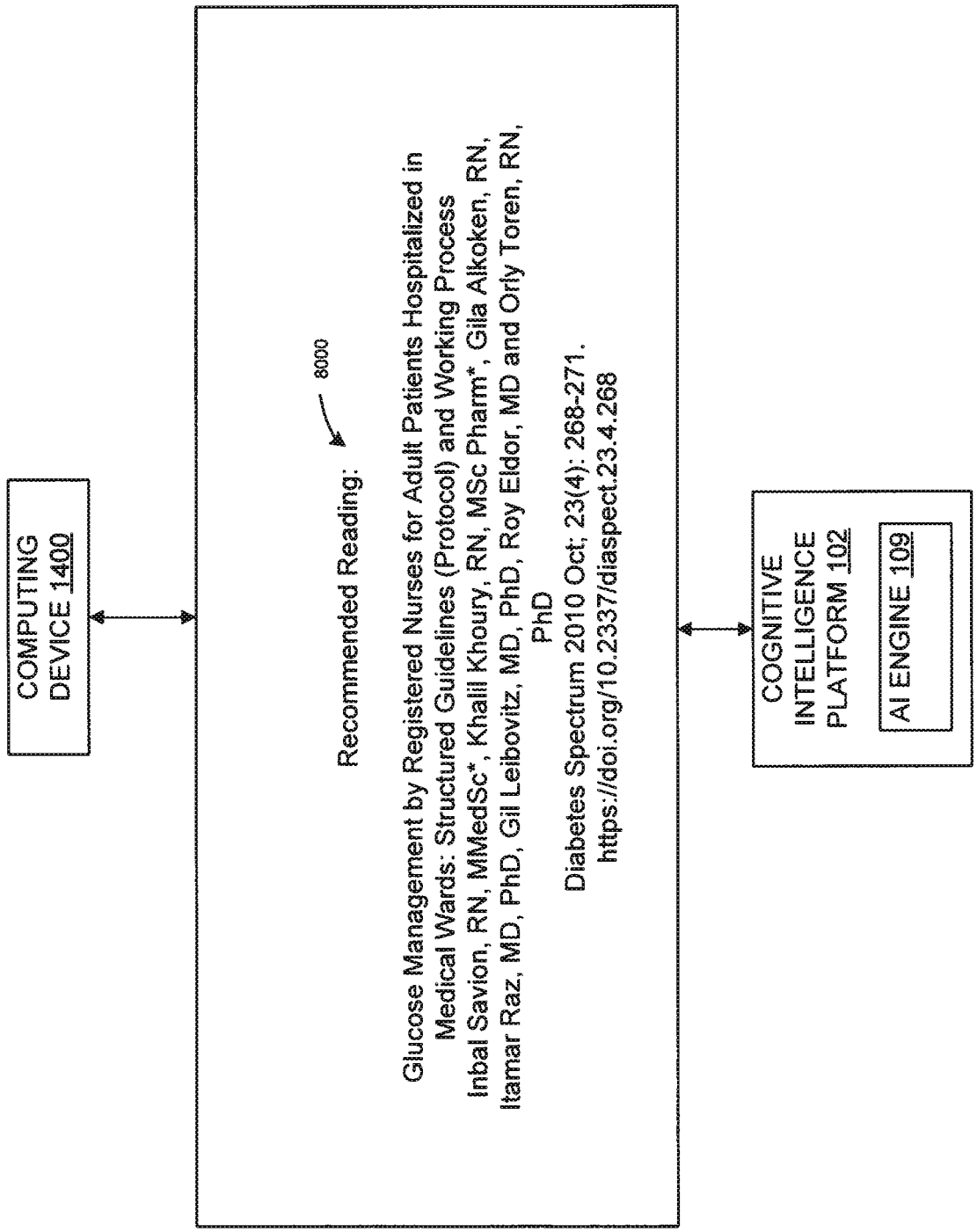
FIG. 80 shows a computing device receiving recommended curated content pertaining to a condition of a patient as an example of a step of the method of FIG. 63.

In some embodiments, the method 6300 further includes receiving recommended curated content pertaining to the condition of the patient (block 6338). FIG. 80 shows the computing device 1400 receiving, from the cognitive intelligence platform 102, recommended curated content 8000 pertaining to the condition of the patient. The recommended curated content may be identified in a knowledge graph for the condition and may be selected by the AI engine 109. In some embodiments, a tangible, non-transitory computer-readable medium stores instructions that, when executed, cause a processing device, such as the processor 1402 shown in FIG. 14 to execute the step of block 6338.

In some embodiments, the method 6300 further includes presenting the recommended curated content in the clinic viewer (block 6340). FIG. 81 shows the display 1410 presenting recommended curated content 8000 pertaining to the condition of the patient that may be received from the cognitive intelligence platform 102. As depicted, the recommended curated content 8000 was written by and/or reviewed by medical personnel having verified credentials (e.g., Inbal Savion, RN, MMedSc*, Khalil Khoury, RN, MSc Pharm*, Gila Alkoken, RN, Itamar Raz, MD, PhD, Gil Leibovitz, MD, PhD, Roy Eldor, MD and Orly Toren, RN, PhD). In some embodiments, a tangible, non-transitory computer-readable medium stores instructions that, when executed, cause a processing device, such as the processor 1402 shown in FIG. 14 to execute the step of block 6340.

In some embodiments, the method 6300 is implemented on a system. The system includes a memory device, such as the storage device 1440 of FIG. 14, containing stored instructions. The system also includes a processing device, such as the processor 1402 of FIG. 14, communicatively coupled to the memory device, as shown in FIG. 14 between the storage device 1440 and the processor 1402, wherein the processing device executes the stored instructions to perform a combination of the steps (blocks 1602-1640) of the method 6300.

Figure 82:
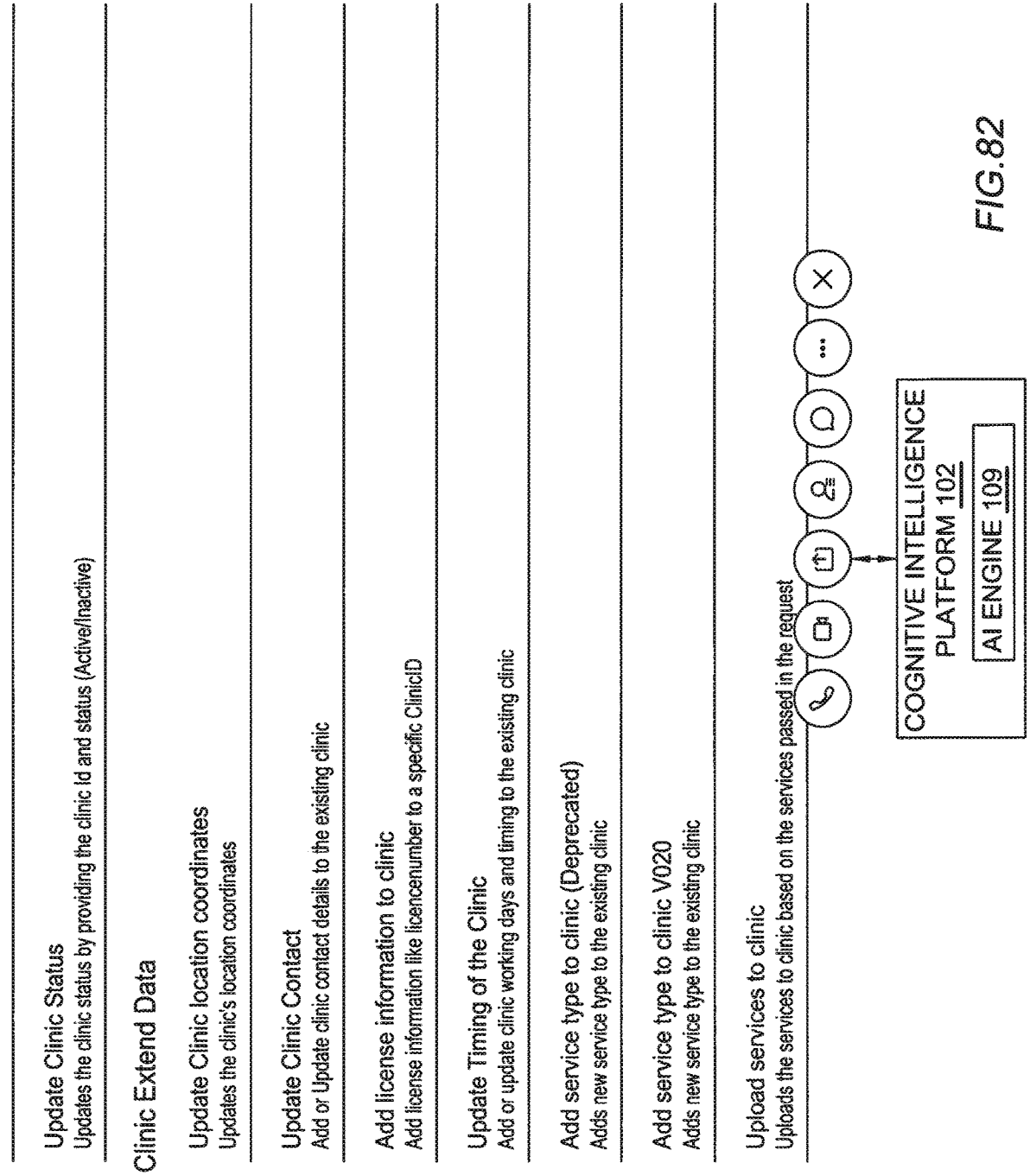
FIG. 82 shows an example user interface of a clinic viewer in which a clinic user can update information about a clinic.
Figure 83:
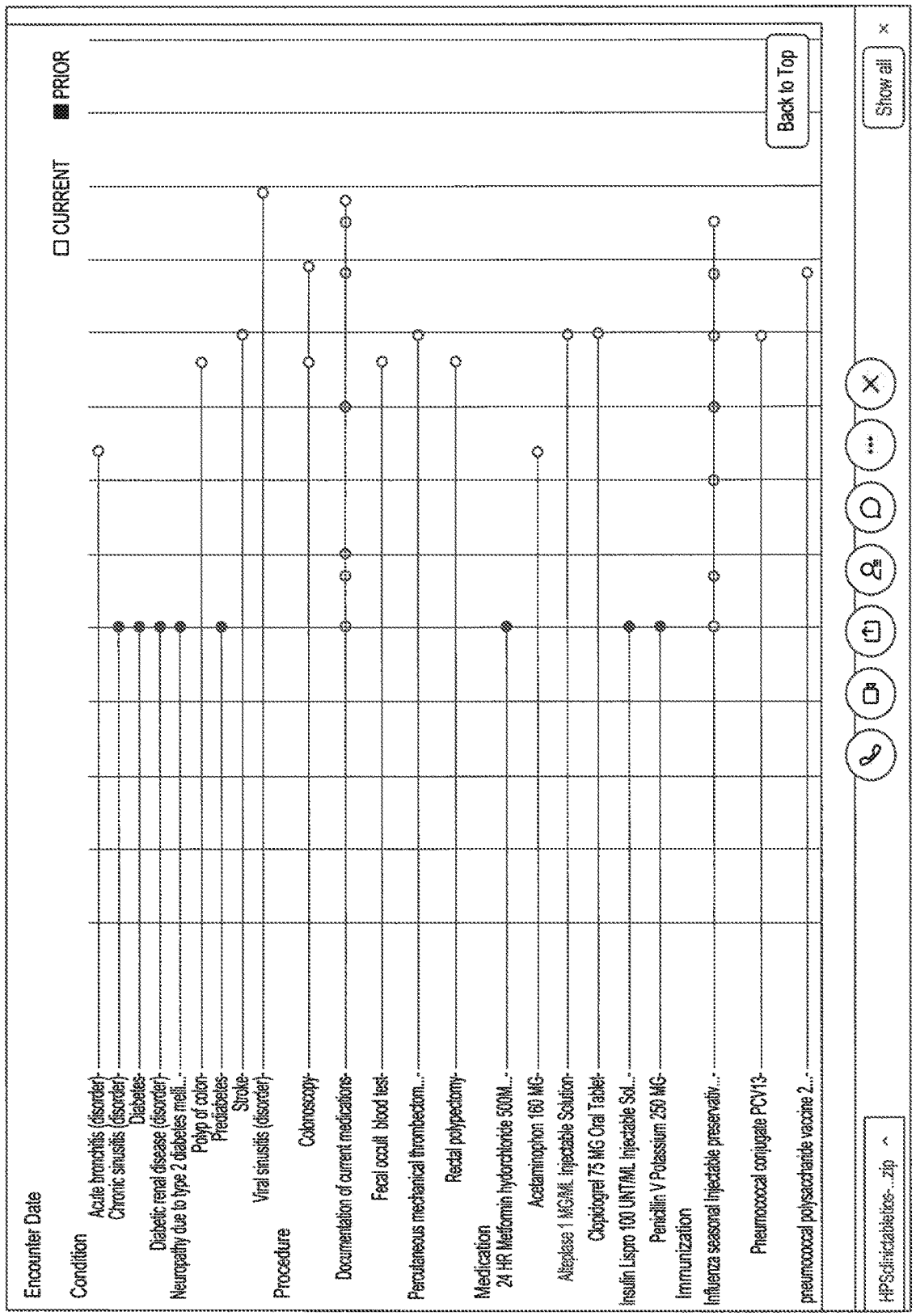
FIG. 83 shows an example user interface of the clinic viewer in which a clinic user can track information about patient conditions, procedures, medications, and immunizations.
Figure 84:
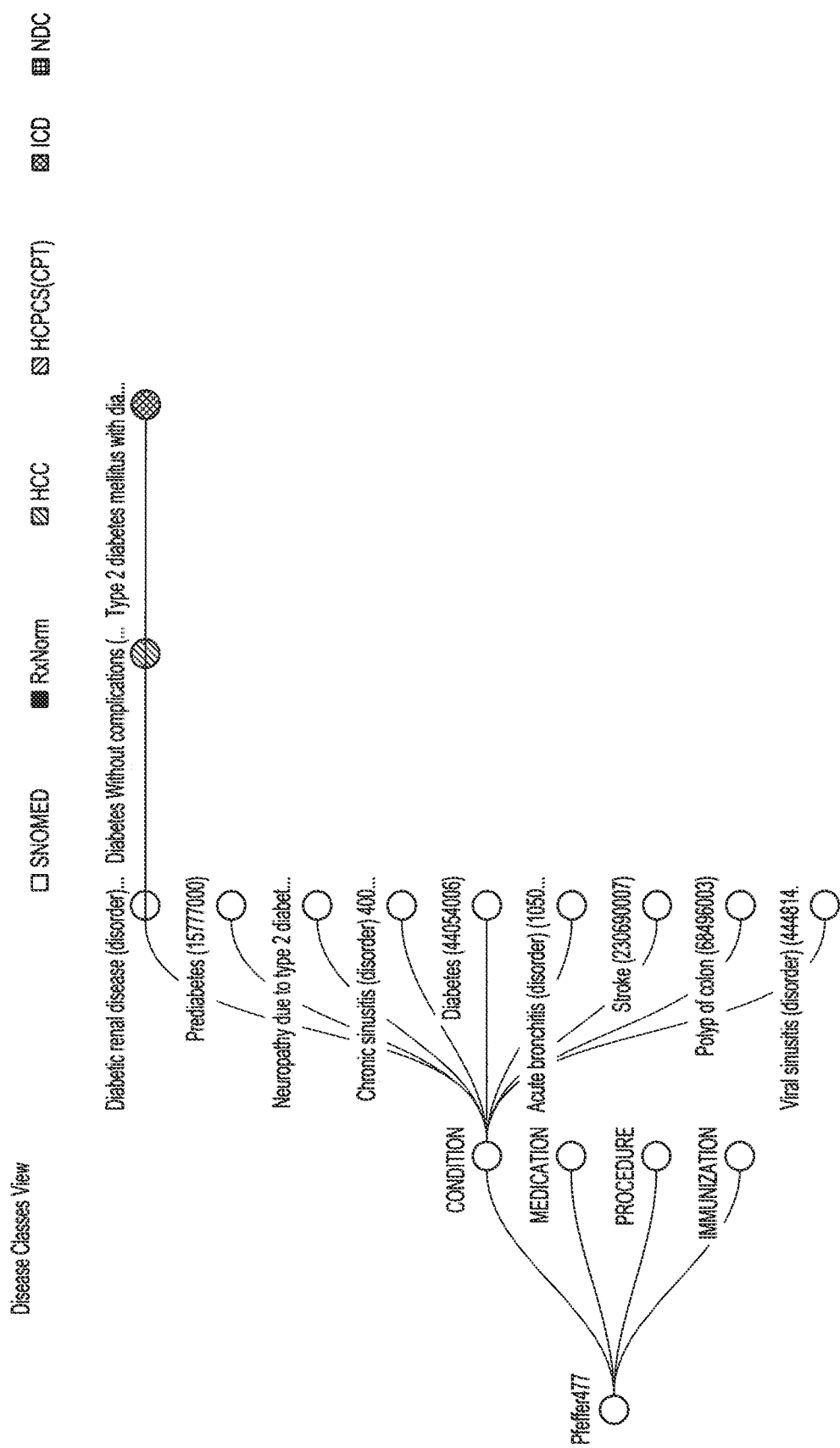
FIG. 84 shows an example user interface of the clinic viewer in which a knowledge graph is displayed to the clinic user.

FIGS. 82-84 show example user interfaces for the clinic viewer to be presented on the display 1410. The clinic viewer may be generated by the cognitive intelligence platform 102 using the AI engine 109, the cognitive agent 110, and/or the knowledge cloud 106.

FIG. 82 shows an example user interface of the clinic viewer in which a clinic user can update information about the clinic. For example, various options are presented such as "Update Clinic Status", "Update clinic location coordinates", "Update Clinic Contact", "Add license information to clinic", "Update Timing of the Clinic", "Add service type to clinic (Deprecated)", "Add service type to clinic V020", and "Upload services to clinic".

FIG. 83 shows an example user interface of the clinic viewer in which the clinic user can track information about patient conditions, procedures, medications, and immunizations. The user interface may include current and prior information about a patient. The information displayed in the user interface for the patient may be obtained from the patient graph(s) associated with the medical conditions of the patient.

FIG. 84 shows an example user interface of the clinic viewer in which a knowledge graph, such as the knowledge graph 500 of FIG. 5, is displayed to the clinic user. The knowledge graph presented depicts an example of drilling-down into a "Diabetic renal disease (disorder)". In some embodiments, the user may further drill-down to receive additional information about Type 2 diabetes mellitus. For example, population information about people having the condition may be presented such that a holistic clinical view is provided by the cognitive intelligence platform. Such a clinical view may enable statistical tracking, compliance tracking with care plans, results of care plans, risk management for populations, and the like.

Figure 85:
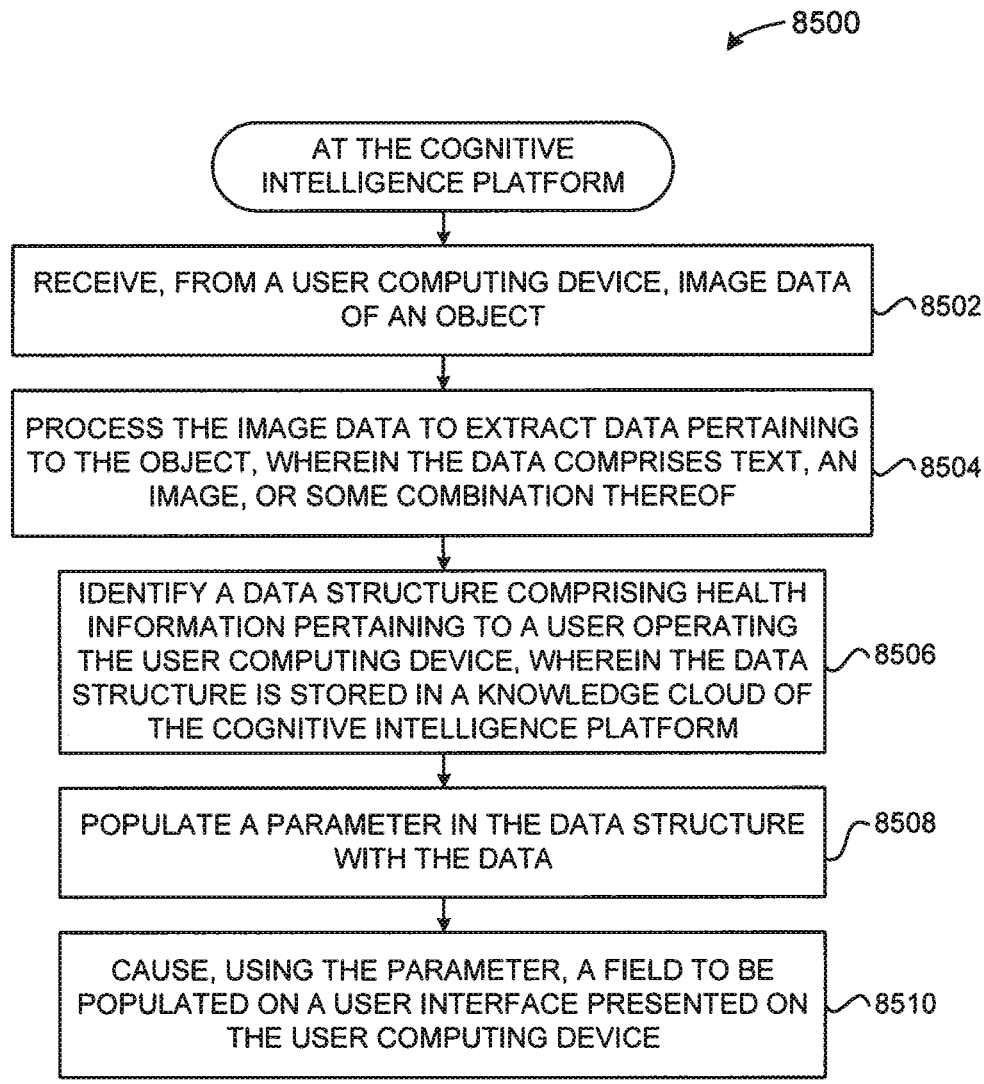
FIG. 85 shows a flowchart for a method for image and information extraction to make decisions using curated medical knowledge.

FIG. 85 shows a method 8500 for image and information extraction to make decisions using curated medical knowledge, in accordance with various embodiments described herein. Method 8500 may be implemented on a cognitive intelligence platform. For example, in an embodiment, cognitive intelligence platform 102 of FIG. 1 may implement method 8500. The method 8500 may include operations that are performed by different components of cognitive intelligence platform 102, such as by cognitive agent 110, knowledge cloud 106, and/or critical thinking engine 108 shown in FIG. 1.

As shown in FIG. 85, at a block 8502, method 8500 begins with receiving, from a user computing device, image data of an object. For example, with continued reference to FIG. 1, image data of an object may be transmitted to cognitive intelligence platform 102 from user device 104 via network 120. In an embodiment, the object may comprise an insurance card and the image data may comprise an image of the insurance card. To help further illustrate, with reference to FIG. 40A, cognitive intelligence platform 102 may receive image 4000 of insurance card 4002. For example, image 4000 may be captured by a camera of user device 104. Alternatively, or in addition to, image 4000 may be a file that is emailed to an email account of a user and accessed by the user of user device 104. In some embodiments, the image 4000 may be obtained via a scanner scanning the insurance card. In an embodiment, prior to receiving the image data, cognitive intelligence platform 102 may receive from user device 104 a selection to subscribe to an application programming interface hosted by cognitive intelligence platform 102, where the application programming interface implements the operations performed by cognitive intelligence platform 102.

As further shown in FIG. 85, at a block 8504, method 8500 continues with processing the image data to extract data pertaining to the object, where the data comprises text, an image, or some combination thereof. For example, continuing with the example discussed above with reference to FIG. 40A, cognitive intelligence platform 102 may process image 4000 of insurance card 4002 to extract insurance plan information pertaining to an insurance plan indicated on insurance card 4002. For example, as depicted in earlier FIG. 40D, cognitive intelligence platform 102 may extract the following insurance plan information by processing image 4022 of an insurance card: the insurance provider ("HMSA"), the insurance subscriber's name ("KIMO M ALOHA"), the subscriber ID ("LLA000012334456""), the insurance plan number ("80840"), Rx banking identification number (BIN) ("004336"), Rx processor control number (PCN) ("MEDDADV"), Rx group number (GRP) ("RX3982"), and Rx ID ("A000012334456").

As another example, with reference to FIG. 40C, cognitive intelligence platform 102 may extract driver's license information by processing image 4012 of a driver's license, such as: a driver's first name ("Regina b") and last name ("ranoa"), a gender of the driver ("Female"), date of birth of the driver ("06/21/1961"), address of the driver ("655 12 S 224, Oakland CA 94607"), date the driver's license was issued ("09/30/2011"), expiration date of the driver's license ("10/31/2016"), and ID number associated with the driver's license ("B82364178"). In addition, an image 4014 of the driver's face extracted from image 4012 may be used as a picture for a user profile generated by cognitive intelligence platform 102. Other additional information that may be extracted from the driver's license may include physical characteristics of the driver, such as eye color, hair color, height, weight, etc.

In embodiments, the processing of the image data may be performed by at least one technique selected from a group of techniques such as optical character recognition, facial recognition, natural language processing, machine learning, and computer vision. For example, cognitive intelligence platform 102 may perform imaging extraction techniques (such as optical character recognition) and/or use a machine learning model trained to identify and extract data from image data. In an embodiment, cognitive intelligence platform 102 may use critical thinking engine 108 which employs artificial intelligence techniques related to natural language processing. For example, cognitive intelligence platform 102 may use optical character recognition (OCR) algorithms to electronically convert an image of printed text into machine-encoded text. In some embodiments, pattern recognition and/or computer vision may be used to extract information from image data. Computer vision can involve image understanding by processing symbolic information from image data using models constructed with the aid of geometry, physics, statistics, and/or learning theory. Pattern recognition may refer to electronic discovery of regularities in data through the use of computer algorithms and with the use of these regularities to take actions, such as classifying the data into different categories and/or determining what the symbols represent in the image (e.g., words, sentences, names, numbers, identifiers, etc.).

Further, natural language understanding (NLU) may be performed on image data received by cognitive intelligence platform 102. For example, NLU techniques may process unstructured data using text analytics to extract entities, relationships, keywords, semantic roles, and so forth.

In FIG. 85, at a block 8506, method 8500 proceeds to identifying a data structure comprising health information pertaining to a user operating the user computing device, where the data structure is stored in a knowledge cloud of the cognitive intelligence platform. For example, with continued reference to FIG. 1, cognitive intelligence platform 102 may identify a data structure including health information pertaining to a user operating user device 104. The data structure may be stored in knowledge cloud 106. As previously described, cognitive intelligence platform 102 may maintain different data structures pertaining to different medical conditions of a user. For example, in an embodiment, the data structures can be represented by patient graphs including elements (or vertices) that are linked (by edges) based on relationships between the elements. These elements may represent content consumed by, actions performed by, and/or interactions performed by the user related to the health of the user. In another embodiment, the data structure may be an array comprising a collection of elements of health information pertaining to the user. More specifically, cognitive agent 110 of cognitive intelligence platform 102 may access knowledge cloud 106 to obtain one or more elements of the data structure. For example, cognitive agent 110 may search knowledge cloud 106 for a data structure that includes elements matching the data extracted at block 8504 that particularly identifies the user (e.g., the user's name, driver's license number, social security number, etc.,).

As further shown in FIG. 85, at a block 8508, method 8500 performs the step of populating a parameter in the data structure with the data. For example, after identifying the data structure comprising health information pertaining to the user, cognitive agent 110 of cognitive intelligence platform 102 may populate a parameter in the data structure with all of or a portion of the data extracted at block 8504. In an embodiment, cognitive agent 110 may identify a parameter in the data structure that is no longer valid and update the parameter in the data structure stored in knowledge cloud 106 with extracted data corresponding to the parameter. For example, cognitive agent 110 may determine that the user's last name extracted from a driver's license does not match the last name indicated in the data structure and may update the last name parameter in the data structure with the last name data extracted from the driver's license. As another example, in a situation in which a user has changed insurance plans, cognitive agent 110 may determine that an insurance plan number or a name of an insurance provider indicated in the extracted data does not match an insurance plan number or a name of an insurance provider indicated in the data structure. Cognitive agent 110 may then update any parameters in the data structure needing to be updated to account for the user changing insurance plans. Still yet, in an embodiment, cognitive agent 110 may determine when searching the data structure that the data structure does not include a parameter associated with a portion of the extracted data. In response to this determination, cognitive agent 110 may add a parameter to the data structure by inserting the portion of the extracted data to the data structure stored in knowledge cloud 106.

In FIG. 85, method 8500, at a block 8510, further causes, using the parameter, a field to be populated on a user interface presented on the user computing device. For example, with continued reference to FIG. 1, cognitive agent 110 may send, via network 120, a message including a communication intended for the user of computing device 104. The message may be related to the populated parameter and an indication of the message may be displayed to the user via a user interface displayed on user device 104. In one particular example, with reference to FIG. 40D, cognitive agent 110 may cause insurance plan information extracted from an insurance card to be displayed to a user, in accordance with various embodiments herein. As depicted in FIG. 40D, user interface 4020 displays information extracted from image 4022 of the insurance card. As shown in FIG. 40D, user interface 4020 displays various columns titled: "Accuracy", "Name", "Type", and "Value". In this particular example, the Accuracy column refers to whether the information extracted is accurate. The user may review the extracted data displayed in user interface 4022 for accuracy and change the field from a "Y" to "N" if any of the information is inaccurate. User interface 4022 may even enable the user to update any inaccurate information displayed. In another example, an action instruction—instructing the user to update an insurance plan—may be provided to user device 104 for display on a user interface based on extracted data indicating that an insurance plan has lapsed.

To help explore the step described at block 8510 of method 8500 in further detail, FIGS. 86 and 87 will now be described. FIGS. 86 and 87 display examples of a mobile user interface that enables a user to interact with cognitive intelligence platform 102. As shown in FIG. 86, a mobile device 8600 displays a mobile user interface 8602 that includes fields 8606 and 8608 displayed below a section 8604 titled "Reminders." As described in the previous example, a user may receive an action instruction alerting a user to update his or her insurance plan based on the extracted data indicating that the user's insurance policy has expired. As shown in FIG. 86, in an embodiment, a reminder indicating to the user to "Renew, change, or update health plan" may be displayed in field 8606. Moreover, field 8606 may include a clickable link or button that directs the user of mobile device 8600 to fields the user may use to enter in any information related to changes in a health insurance plan. Alternatively, or in addition to, a clicking of a link or a button of field 8606 may prompt a user to capture an image of a newly received insurance card using a camera of mobile device 8600.

In an embodiment, with continued reference to FIG. 1, artificial intelligence engine 109 of cognitive intelligence platform 102, may determine an action instruction for a user of user device 104 based on data extracted at block 8504 of method 8500. As previously described, artificial intelligence engine 109 may use one or more machine learning models to predict health related information pertaining to a user. The one or more machine learning models may be created by a training process involving providing a machine learning algorithm with training data (e.g., a patient's historical health related information) to learn from. For example, a training engine may implement a machine learning algorithm to generate the one or more machine learning models. When the machine learning algorithm is implemented, it may find patterns in a patient's historical health information and output a model that captures these patterns to enable mapping of extracted data to previously known patterns in health information pertaining to other people. These one or more models may be generated using any suitable techniques, including supervised machine learning model generation algorithms (such as supervised vector machines (SVM), linear regression, logistic regression, naïve Bayes, linear discriminant analysis, decision trees, k-nearest neighbor algorithm, neural networks, recurrent neural network, etc).

Further, artificial intelligence engine 109 may apply the extracted data to the one or more machine learning models and determine an action instruction for the user. For example, artificial intelligence engine 109 may determine, based on a birthdate extracted from a driver's license indicating that a user is over the age of 60 and historical health data that the user is diabetic identified in a patient graph of the user for diabetes, an action instruction alerting the user to schedule a screening for blood pressure and cholesterol. As shown in FIG. 86, in this particular example, action instructions are displayed to the user as a reminder to schedule a screening for blood pressure and cholesterol in fields 8606 and 8608 of user interface 8602. Alternatively, or in addition to, the action instruction may include a video informing the user that diabetics in his or her age group are prone to hypertension and high cholesterol and instructing the user to schedule a blood pressure and cholesterol screening. Additionally, in formulating an action instruction, artificial intelligence engine 109 may compare any extracted data to ontological data of a medical condition diagnosed for the user stored in a data structure (e.g., knowledge graph) in knowledge cloud 106 and to health information pertaining to the user stored in the data structure (e.g., patient graph) stored in knowledge cloud 106. In formulating an action instruction, artificial intelligence engine 109 may also compare any ontological data of a medical condition diagnosed for the user stored in a data structure in knowledge cloud 106 and to health information pertaining to the user stored in the data structure in knowledge cloud 106.

Still yet, in an embodiment, cognitive agent 110 may determine whether any parameter is missing respective data in the data structure including the health information pertaining to the user and in response to determining that a parameter in the data structure is missing respective data, may cause a notification to be presented to the user on user interface. For example, cognitive agent 110 may determine when searching knowledge cloud 106 that the data structure does not include a parameter associated with a portion of the extracted data. In response to this determination, with reference to FIG. 87, cognitive agent 110 may cause a notification to be displayed on user interface 8602 that prompts a user to fill in data respective to the parameter. For instance, as shown in FIG. 87, a notification 8702 prompting the user to provide the name of his or her primary care physician is displayed on user interface 8602. Cognitive agent 110 may then add data provided by the user to the data structure by inserting the data provided by the user to the data structure stored in knowledge cloud 106.

Figure 88:
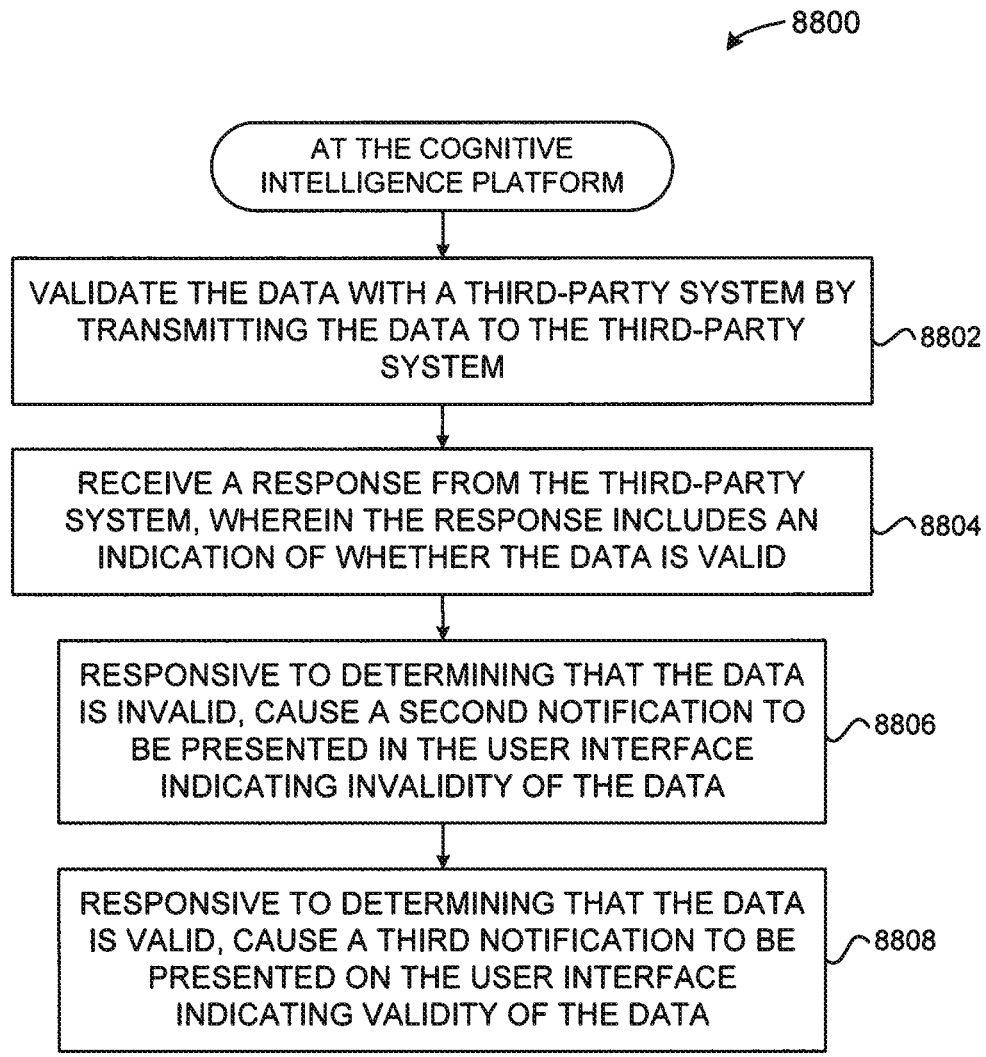
FIG. 88 shows a flowchart for a method for validating data extracted from image data of an object with a third-party system.

FIG. 88 shows a method 8800 for validating data extracted from image data of an object with a third-party system, in accordance with various embodiments described herein. Method 8800 may be implemented on a cognitive intelligence platform. For example, in an embodiment, cognitive intelligence platform 102 of FIG. 1 may implement method 8800. The method 8800 may include operations that are performed by different components of cognitive intelligence platform 102, such as by cognitive agent 110, knowledge cloud 106, and/or critical thinking engine 108 shown in FIG. 1.

As shown in FIG. 88, at a block 8802, method 8800 begins with validating the data with a third-party system by transmitting the data to the third-party system. For example, with continued reference to FIG. 1, cognitive intelligence platform 102 may validate data with a third-party system by transmitting the data to the third-party system via network 120. For example, as described in the corresponding detailed description of block 8504 of FIG. 85, the data may be data extracted by processing image data of an object. In a particular embodiment, the object may be a health insurance card that includes health insurance information pertaining to an insurance plan of a user, the data extracted may be the health insurance information, and the third-party system may be operated by an insurance provider. Continuing with this embodiment, cognitive intelligence platform 102 may perform one or more function calls to an application programming interface of a system associated with the insurance provider to validate data (such as status of the insurance policy, an insurance policy number, a deductible amount, a co-pay, and the like). In another embodiment, the object may be a driver's license issued by a state organization, the extracted data may comprise driver's license information, and the third-party system may be operated by a state organization.

Next, as shown in FIG. 88, at block 8804, method 8800 continues with receiving a response from the third-party system, wherein the response includes an indication of whether the data is valid. For example, with continued reference to FIG. 1, cognitive intelligence platform 102 may receive a response that indicates whether the data is valid from service provider 112 via network 120. To help further illustrate, service provider 112 may compare the data received from cognitive intelligence platform 102 to data accessible to service provider 112 that is associated with the user. Service provider 112 may respond as to whether the data received from cognitive intelligence platform 102 matches the data accessible to service provider 112.

At block 8806 of FIG. 88, method 8800 continues with, responsive to determining that the data is invalid, causing a second notification to be presented in the user interface indicating invalidity of the data. For example, with continued reference to FIG. 1, cognitive intelligence platform 102 may determine from the response from service provider 112 that the data is invalid and in response to this determination, provide a notification indicating that the data is invalid to user device 104 via network 120. To help further illustrate, with continued reference to FIG. 1 and with reference to FIG. 89 another example embodiment of mobile user interface 8602 of FIG. 86, a notification 8902 may be displayed in user interface 8602. In the particular situation in which extracted data pertaining to an insurance policy number does not match the insurance policy number accessible to service provider 112, notification 8902 may notify the user that "The information entered does not match available records. Please re-enter your information." As also shown in FIG. 89, notification 8902 may include a field for a user to re-enter his or her insurance policy number.

At block 8808 of FIG. 88, method 8800 continues with, responsive to determining that the data is valid, causing a third notification to be presented on the user interface indicating validity of the data. For example, with continued reference to FIG. 1, cognitive intelligence platform 102 may determine from the response from service provider 112 that the data is valid and in response to this determination, provide a notification indicating that the data is valid to user device 104 via network 120. To help further illustrate, referring to FIG. 90, a notification 9002 may be displayed in user interface 8602. Continuing with the example described above at block 8806, notification 9002 may indicate that the user has successfully entered in an insurance policy number that matches available records.

Further, in one embodiment, cognitive intelligence platform 102 may also receive a response from service provider 112 that includes a payment amount of a service based on health insurance information of an insurance plan. In response, cognitive intelligence platform 102 may transmit a request to another third-party system operated by a care provider. The request may inquire about another payment amount of the service without using the health insurance information of the insurance plan. Cognitive intelligence platform 102 may receive a response from the other third-party system including the other payment amount and cause the payment amounts to be presented in the user interface of user device 104. For example, cognitive intelligence platform 102 may retrieve the insurance plan information for the user of the user device 104. Cognitive intelligence platform 102 may further determine the amounts of a deductible and/or co-pay for the insurance plan and determine an expected payment that the user will be expected to pay for a service based on the deductible and/or co-pay.

Cognitive agent 110 may perform one or more function calls to an application programming interface of a system associated with the insurance provider (e.g., service provider 112 in FIG. 1) to determine what the user is expected to pay, an amount the insurance provider may cover, a deductible amount, a co-pay, and the like. For example, cognitive agent 110 may determine that a user has $3,000 remaining to meet an insurance policy deductible. Cognitive agent 110 may then contact a care provider (e.g., facility 114 of FIG. 1) inquiring about the costs for a service provided that costs $1,000. After receiving a response about the costs for the service from the care provider, cognitive agent 110 may provide a notification to user interface 8602 indicating the costs of the service (i.e., $1,000) and a new amount needed to meet the deductible of the insurance plan (i.e., $2,000 ($3,000–$1,000)).

Figure 91:
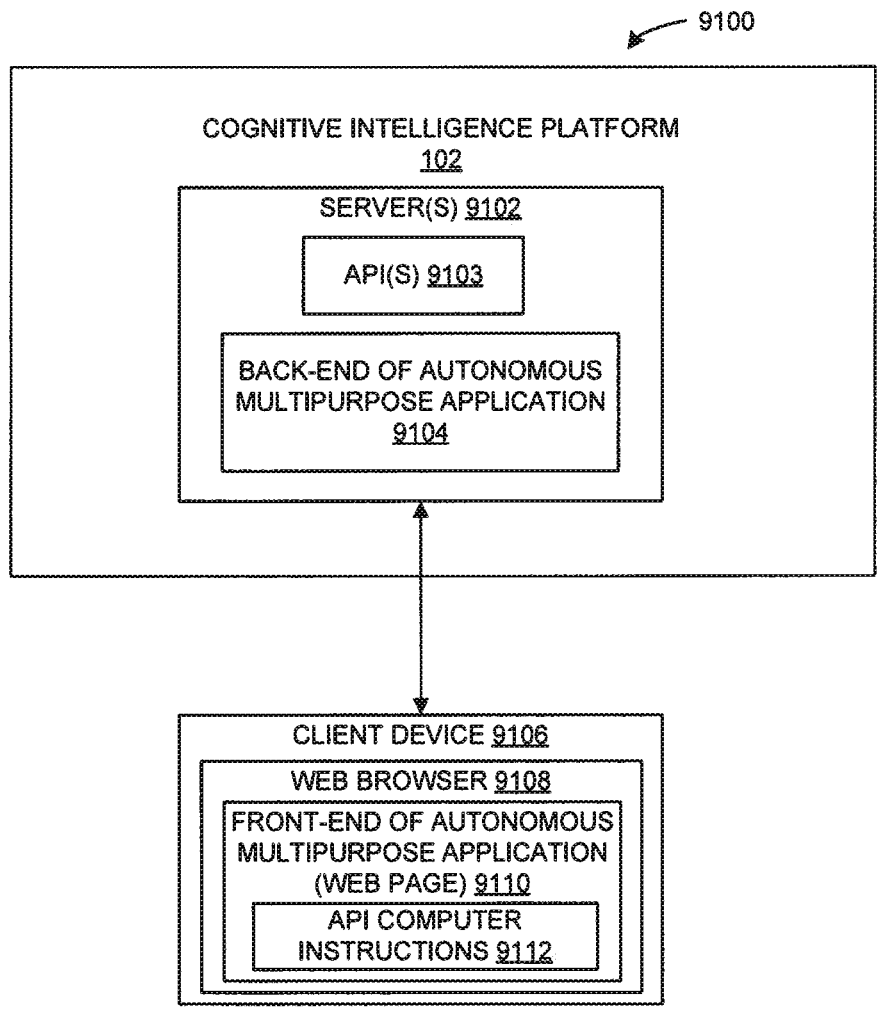
FIG. 91 is a block diagram of an example system that enables creating an autonomous multipurpose application using a platform of application programming interfaces (APIs).

FIG. 91 is a block diagram of an example system 9100 that enables creating an autonomous multipurpose application using a platform of application programming interfaces (APIs) 9103. As shown in FIG. 91, system 9100 includes server(s) 9102 and a client device 9106. As further shown in FIG. 91, one or more servers 9102 includes a back-end component of an autonomous multipurpose application 9104 and client device 9106 includes a front-end component of the autonomous multipurpose application 9110. The servers 9102 may be included in any component in the cognitive intelligence platform 102. The client device 9106 may be the user device 104 or any suitable computing device that a user uses to configure and create the autonomous multipurpose application 9104 using the platform of APIs 9103.

Back-end component of the autonomous multipurpose application 9104 (referred to as "application back-end component" hereinafter) and front-end component of the autonomous multipurpose application 9110 (referred to as "application front-end component" hereinafter) are example components of a cloud application hosted in a cloud services network. In an embodiment, with reference to cognitive intelligence platform 102 shown in FIG. 1, application back-end component 9104 is an example embodiment of cognitive agent 110 of FIG. 1 and application front-end component 9110, which is a client-facing component of cognitive intelligence platform 102, is provided to client device 9106 by application back-end component 9104. For example, as depicted in FIG. 91, application front-end component 9110 may be represented as a web page displayed in web browser 9108. In other embodiments, application front-end component 9110 may also be an Internet-enabled application executing on client device 9106. Still other implementations of application front-end component 9110 are possible.

Server(s) 9102 may include one or more server devices and/or other computing devices. Client device 9106 may be any type of stationary or mobile computing device, including a mobile computer or mobile computing device (e.g., a smart phone, a laptop computer, a notebook computer, a tablet computer such as an Apple iPad™, a netbook, etc.), a wearable computing device (e.g., a smart watch, a head-mounted device including smart glasses such as Google® Glass™, etc.), or a stationary computing device such as a desktop computer or PC (personal computer). One or more components of the cognitive intelligence platform 102 and client device 9106 may be communicatively connected via one or more networks (not pictured in FIG. 91). These one or more networks may include, for example, a local area network (LAN), a wide area network (WAN), a personal area network (PAN), and/or a combination of communication networks, such as the Internet.

Application back-end component 9104 is configured to publish one or more APIs 9103. As described previously, the one or more APIs 9103 may use artificial intelligence to perform analytics based on a knowledge graph pertaining to ontological data of a medical condition. Application back-end component 9104 is also configured to implement computer instructions 9112 of one or more APIs 9103 in application front-end component 9110 and provide front-end component application 9110 (including computer instructions 9112 of the one or more APIs 9103) to client device 9106. In embodiments, the one or more APIs 9103 may be categorized into different sets of APIs 9103. For example, the one or more APIs 9103 may be categorized based on providing similar or related functionalities. Each API in a set of APIs 9103 may run a unique process and manage its own database. Moreover, each API in a set of APIs may be configured to generate alerts, log data, support user interfaces (UIs), handle user identification or authentication, and perform various other tasks. In an embodiment, application back-end component 9104 may implement one or more APIs from different sets of APIs 9103 in application front-end component 9110. Alternatively, or in addition to, application back-end component 9104 may implement entire sets of APIs 9103 in application front-end component 9110.

Web browser 9108 executing on client device 9106 may enable interactions between a user of client device 9106 and cognitive intelligence platform 102. For example, web browser 9108 may interpret a message (e.g., via HTTP messages) received from application back-end component 9104 and display contents of the message on a window of web browser 9108 for the user of client device 9106. For example, application back-end component 9104 may cause computer instructions 9112 of the one or more APIs to be injected into application front-end component 9110 by including computer instructions 9112 in a message to web browser 9108. To help further illustrate, in an embodiment, application back-end component 9104 may append computer instructions 9112 of the one or more APIs (e.g., JavaScript) to the web page (e.g., by including computer instructions 9112 in an HTML file representing the web page) and provide it to web browser 9108 via a message. After the message is received and interpreted by web browser 9108, the web page of application front-end component 9110 containing computer instructions 9112 of the one or more APIs is displayed and computer instructions 9112 are executed in web browser 9108.

The embodiments described herein enable a user to customize his or her cognitive intelligence platform 102 user experience. For instance, a user may select or subscribe to only APIs providing functionality or capabilities that are relevant to the needs of a user, rather than downloading an entire suite of APIs provided by cognitive intelligence platform 102. This also allows users to save money as users are able to obtain different features provided by cognitive intelligence platform 102 "a la carte".

Figure 92:
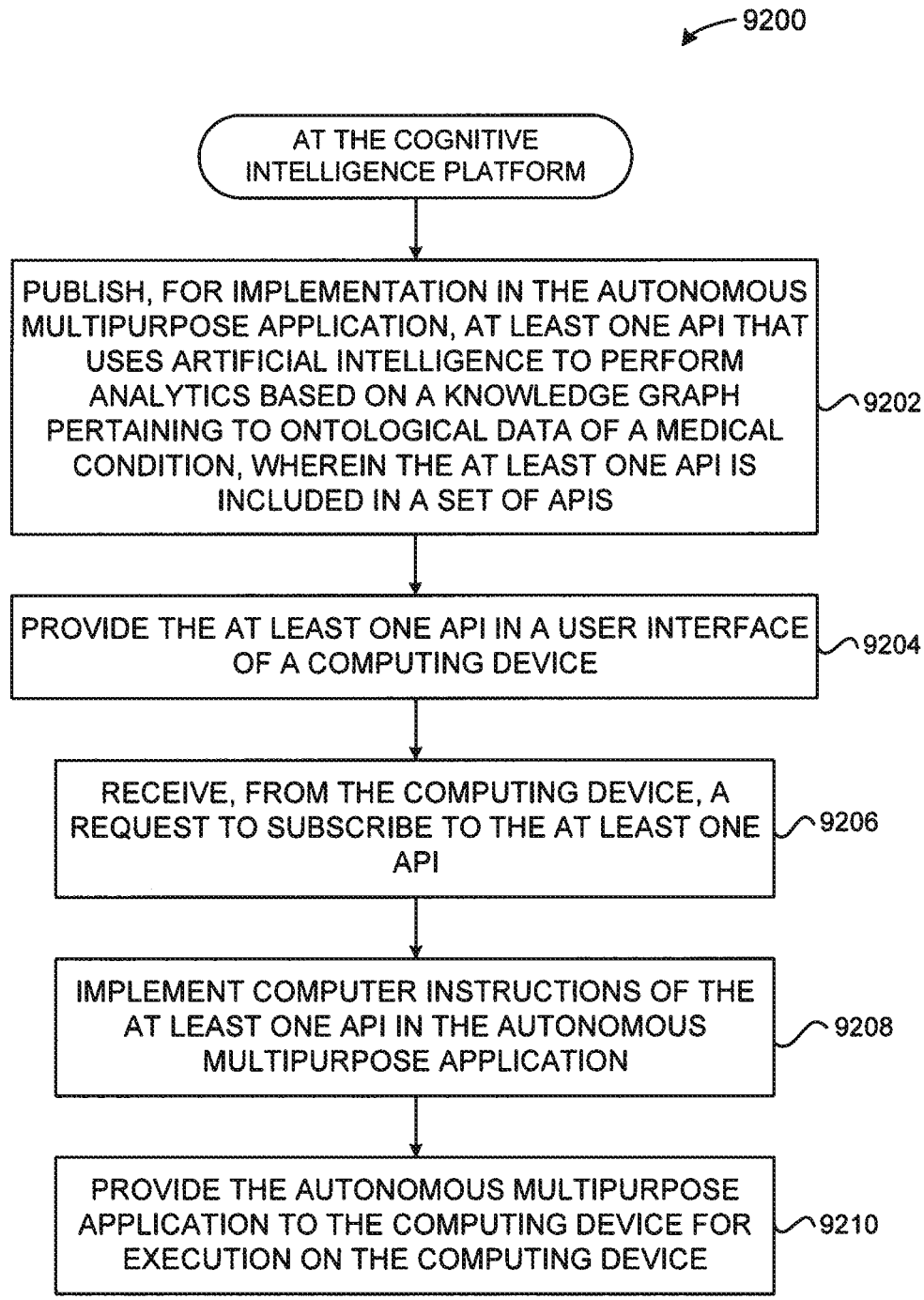
FIG. 92 is a flowchart of a method for creating an autonomous multipurpose application using a platform of application programming interfaces.

To help further illustrate the foregoing, FIG. 92 will be described. FIG. 92 is a flowchart of a method 9200 for creating an autonomous multipurpose application using a platform of application programming interfaces (APIs). As shown in FIG. 9200, the method of flowchart 9200 begins at step 902. At step 902, at least one API is published for implementation in the autonomous multipurpose application. For example, with reference to FIG. 91, application back-end component 9104 may create and expose one or more APIs 9103 that use artificial intelligence to perform analytics based on a knowledge graph (e.g., knowledge graph 500 of FIG. 5) pertaining to ontological data of a medical condition. The use of artificial intelligence by APIs to perform analytics based on a knowledge graph pertaining to ontological data of a medical condition is discussed in greater detail in hereinbefore.

Application back-end component 9104 may further categorize the one or more APIs 9103. For example, application back-end component 9104 may group the one or more APIs 9103 into the following categories. One example category may be a clinical interoperability category including an electronic medical record and clinical systems API, a physical therapy systems API, a patient identity management API, or some combination thereof. This category of APIs enable a user to maintain and access their medical records in a centralized location.

Another example category includes a value based care analytics category including a risk stratification API, a quality of care API, a healthcare utilization API, a population health API, a P360 degrees API or some combination thereof. This category of APIs may enable a user to evaluate risks associated with or quality of care he or she is receiving and compare their health or the level of care they are receiving with a population of people.

Still yet another example category includes a geo sensing services category comprising a geo coder API and a geo location API or some combination thereof. These APIs may enable the artificial intelligence engine 109 to determine a location of a patient and use that location when suggesting appointments for physicians near that location, for example.

Another category may include an operational analytics category including a wait time API, an imaging API, a quick reference codes and recognition API, or some combination thereof. This groups of APIs may allow a user to receive wait time notifications or updates for appointments, upload images of objects, and lookup health care related codes.

Another category includes an applications category including: a clinics API, a provider API, a patient API, a schedules API, a consents API, an acknowledgements API, a symptomology API, a health history API, a medicines and supplements API, an allergies API, an unified login API, or some combination thereof. This category of APIs may enable a user to track his or her personal health related information, such as medicines prescribed, appointments, and general health history. Further, the clinics API may enable a medical personnel such as a medical doctor and/or administer to view the health records of patients, care plans (generated by the artificial intelligence engine 109) for the patients, view action instructions (e.g., medication alerts, quality alerts, patient safety alerts, etc.) pertaining the care plans as described herein, and the like.

Another example category includes a financial and billing category including a checkout API, a billing API, a payment API, an eligibility API, a claim submission API, or some combination thereof. Another example category may include a configuration APIs category comprising a clinics configuration API, a providers configuration API, an appointments API, a lookups API, or some combination thereof, allowing a user to personalize and configure different APIs. Lastly, another category may be an education category comprising a search API, a lookups content API, or some combination thereof. This category may allow users to look-up and research health related information, such as curated medical content that is approved by medical personnel having certifications and/or licenses. In an embodiment, this platform of APIs represents an interoperability layer of a cognitive intelligence platform in healthcare.

Figure 93:
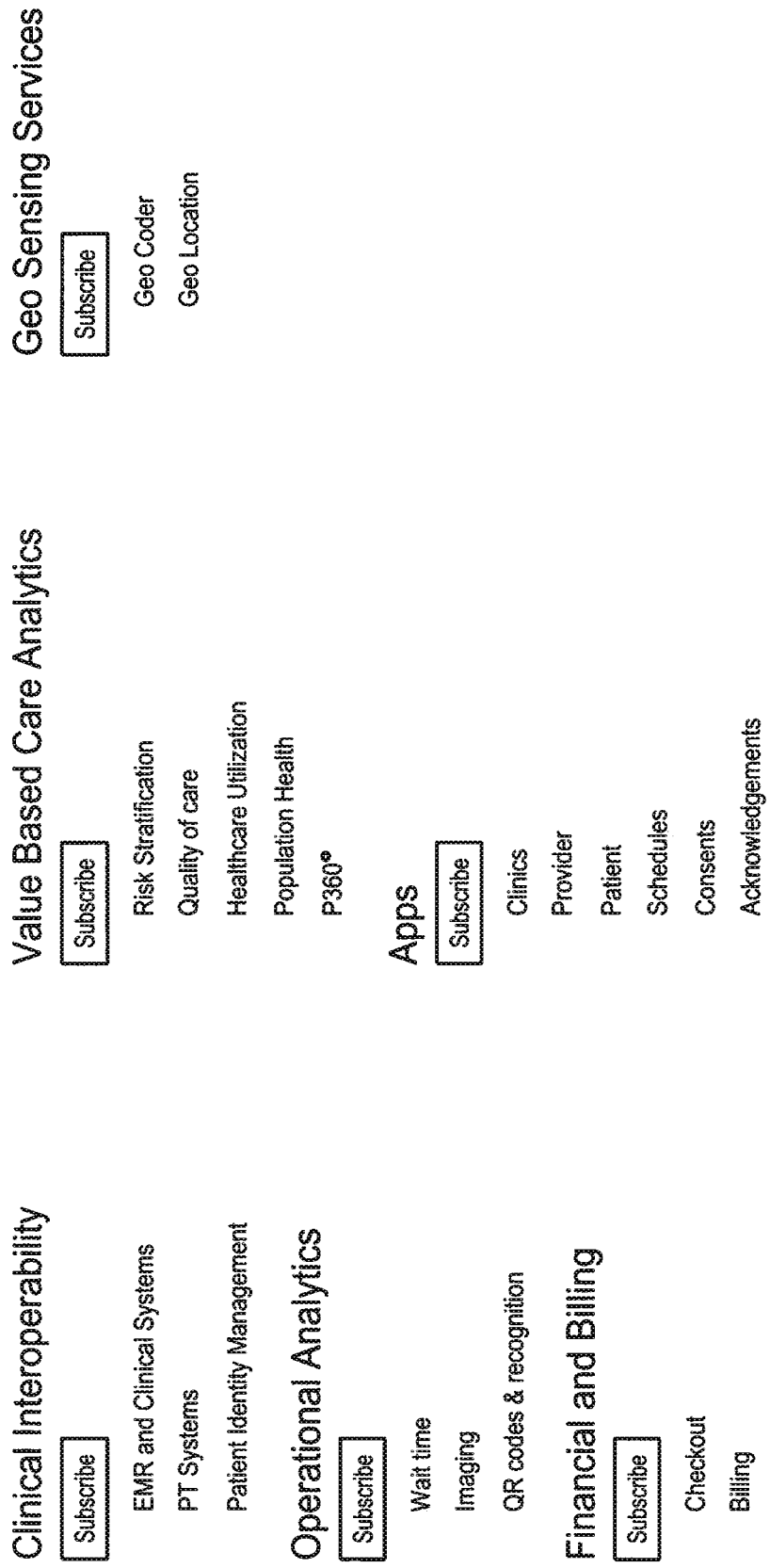
FIG. 93 provides an example user interface displaying various options to subscribe to sets of APIs.
Figure 94:
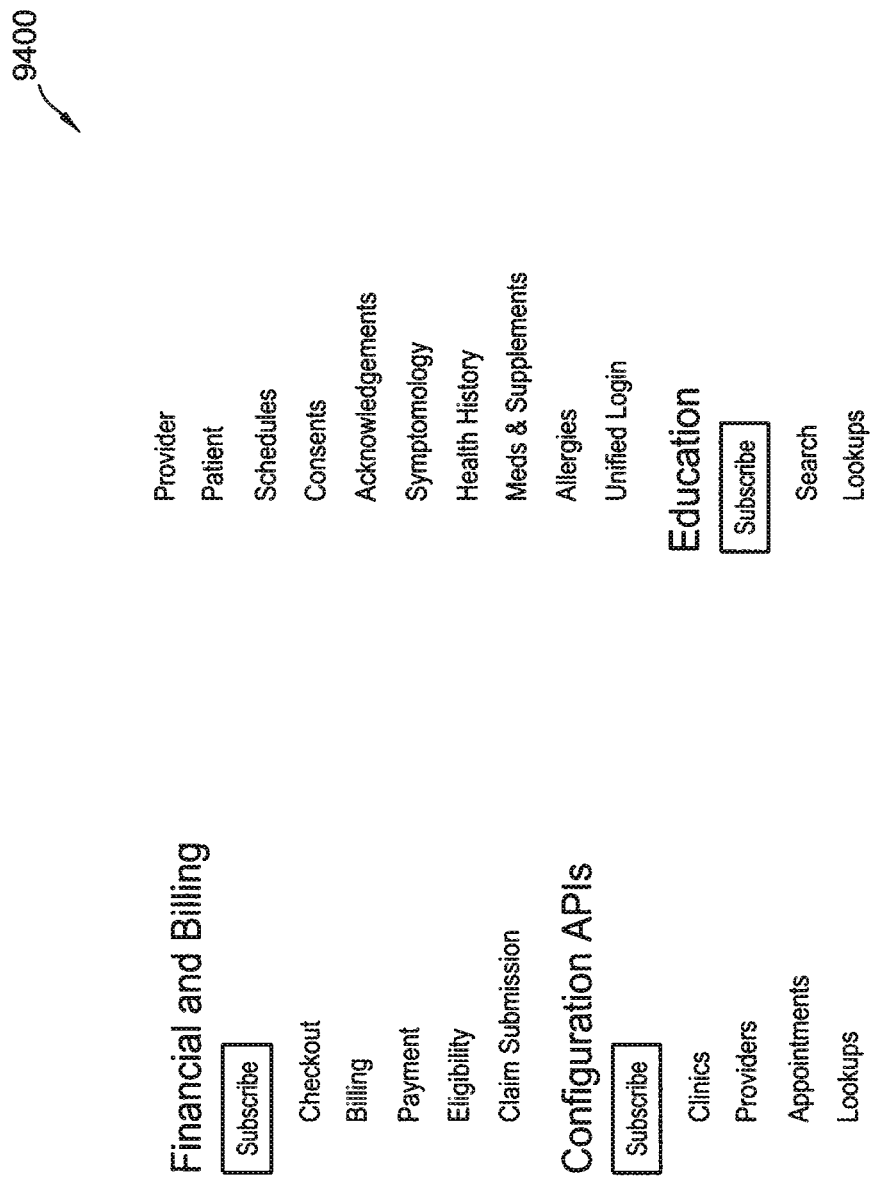
FIG. 94 provides another example user interface displaying various options to subscribe to sets of APIs.

As further shown in FIG. 92, at step 9204, method 9200 continues with providing the at least one API in a user interface of a computing device. For example, with continued reference to FIG. 91, application back-end component 9104 may provide at least one option to subscribe to an API or a set of APIs to client device 9106 to display in a user interface (e.g., web browser 9108). As shown in FIG. 93 and FIG. 94, providing an example user interface displaying various options to subscribe to sets of APIs, user interface 9300 and user interface 9400 displays sets of available APIs that are arranged into the following categories of: a clinical interoperability category, a value based care category, a geo sensing services category, an operational analytics category, a financial and billing category, an applications category, a configuration APIs category, a education category. As further shown in FIG. 92, at step 9204, method 9200 continues with receiving, from the computing device, a request to subscribe to the at least one API. For example, with continued reference to FIGS. 91, 93, and 94, application back-end component 9104 may receive, from client device 9106, a request to subscribe to at least one API. A user of client device 9106 may provide an interest in subscribing to an API by merely clicking on an API displayed in user interface 9300 and this preference may be provided to application back-end component 9104 in a message.

As further shown in FIG. 92, at step 9208, method 9200 continues with implementing computer instructions of the at least one API in the autonomous multipurpose application. For example, application back-end component 9104 may cause computer instructions 9112 of the one or more APIs to be injected into application front-end component 9110 by including computer instructions 9112 in a message to web browser 9108. To help further illustrate, in an embodiment, application back-end component 9104 may append computer instructions 9112 of the one or more APIs to the web page (e.g., by including computer instructions 9112 in an HTML file representing the web page) and provide it to web browser 9108 via a message.

Lastly, as further show in FIG. 92, method 9200 culminates with step 9210 of providing the autonomous multipurpose application to the computing device for execution on the computing device. For example, application back-end component 9104 may provide a message to client device 9106 including code for application back-end component 9104 and computer instructions 9112 of the one or more APIs for rendering in web browser 9108.

In embodiments, application back-end component 9104 may provide an option in a user interface (e.g., user interface 9300 and/or user interface 9400) to select which programming language to use for implementing the computer instructions and after receiving a selection to convert the computer instructions from a first programming language in a set of programming languages to a second programming language in the set of programming languages, application back-end component 9104 may convert the computer instructions implementing the API from the first programming language to the second programming language. The set of programming languages may include any suitable programming language. For example, the user may select to convert the computer instructions implementing an API from C # to Java.

The various aspects, embodiments, implementations or features of the described embodiments can be used separately or in any combination. Various aspects of the described embodiments can be implemented by software, hardware or a combination of hardware and software. The described embodiments can also be embodied as computer readable code on a computer readable medium. The computer readable medium is any data storage device that can store data which can thereafter be read by a computer system. Examples of the computer readable medium include read-only memory, random-access memory, CD-ROMs, DVDs, magnetic tape, hard disk drives, solid-state drives, and optical data storage devices. The computer readable medium can also be distributed over network-coupled computer systems so that the computer readable code is stored and executed in a distributed fashion.

Consistent with the above disclosure, the examples of systems and method enumerated in the following clauses are specifically contemplated and are intended as a non-limiting set of examples.

Clause 1. A cognitive intelligence platform, comprising:
a first system configured to execute a knowledge cloud, the first system comprising:
a first processor; and
a first memory coupled to the first processor, the first memory storing instructions that cause the knowledge cloud to:
receive inputs from medical facilities; and
receive inputs from service providers;
a second system configured to implement a critical thinking engine, the critical thinking engine communicably coupled to the knowledge cloud, the second system comprising:
a second processor; and
a second memory coupled to the second processor, the second memory storing instructions that cause the critical thinking engine to receive inputs from the knowledge cloud; and
a third system configured to implement a cognitive agent, the cognitive agent communicably coupled to the critical thinking engine and the knowledge cloud, the third system comprising:
a third processor; and
a third memory coupled to the third processor, the third memory storing instructions that cause the cognitive agent to:
receive an originating question from a user related to a subject matter;
execute, using the critical thinking engine, a first round of analysis to generate an answer; and
provide the answer to the user including a recommendation associated with the subject matter.

Clause 2. The cognitive intelligence platform of any preceding clause, wherein the second memory stores instructions that further cause the critical thinking engine to:
receive a first information;
receive a second information that contradicts the first information; and
process the first information and second information.

Clause 3. The cognitive intelligence platform of any preceding clause, wherein the second memory stores instructions that further cause the critical thinking engine to:
parse the originating question;
retrieve data from the knowledge cloud; and
perform a causal analysis of the data in view of the originating question, wherein the causal analysis, in part, informs the answer.

Clause 4. The cognitive intelligence platform of any preceding clause, wherein the second memory stores instructions that further cause the critical thinking engine to:
receive the originating question from the cognitive agent;
assess a first chain of logic associated with the originating question;
assess a second chain of logic associated with the originating question; and
provide the answer to the cognitive agent, wherein the answer is associated with the first chain of logic.

Clause 5. The cognitive intelligence platform of any preceding clause, wherein the third memory stores instructions that further cause the cognitive agent to communicate a logical argument that leads to a conclusion, wherein the conclusion, in part, informs the recommendation associated with the subject matter.

Clause 6. The cognitive intelligence platform of any preceding clause, wherein the third memory stores instructions that further cause the cognitive agent to:
render for display, to the user, a chain of logic that leads to the conclusion;
receive, from the user, an adjustment to the chain of logic; and
affect change in the critical thinking engine.

Clause 7. The cognitive intelligence platform of any preceding clause, wherein the third memory stores instructions that further cause the cognitive agent to:
render for display a micro survey;
receive data associated with the micro survey, wherein the data, in part, informs the recommendation associated with the subject matter.

Clause 8. The cognitive intelligence platform of any preceding clause, wherein when the cognitive agent provides the answer to the user, the third memory causes the cognitive agent to integrate data from at least three selected from the group consisting of: a micro survey, a physician's office, common sense knowledge, domain knowledge, an evidence-based medicine guideline, a clinical ontology, and curated medical advice.

Clause 9. A system comprising:
a knowledge cloud;
a critical thinking engine, the critical thinking engine communicably coupled to the knowledge cloud; and
a cognitive agent, the cognitive agent communicably coupled to the critical thinking engine and the knowledge cloud, wherein the cognitive agent is configured to interact with a user using natural language.

Clause 10. The system of any preceding clause, wherein the cognitive agent interacts with the user using at least one selected from the group consisting of: touch-based input, audio input, and typed input.

Clause 11. The system of claim any preceding clause, wherein the critical thinking engine is configured to:
  receive a first information;
  receive a second information that contradicts the first information; and
  process the first information and the second information.

Clause 12. The system of any preceding clause, wherein the cognitive agent is configured to:
  receive an originating question from the user related to a subject matter;
  execute, using the critical thinking engine, a logical reasoning to generate an answer; and
  provide the answer to the user including a recommendation associated with the subject matter.

Clause 13. The system of any preceding clause, wherein the critical thinking engine is configured to:
  parse the originating question;
  retrieve data from the knowledge cloud; and
  perform a causal analysis of the data in view of the originating question, wherein the causal analysis, in part informs the answer.

Clause 14. The system of any preceding clause, wherein the critical thinking engine is configured to:
  receive the originating question from the cognitive agent;
  assess a first chain of logic associated with the originating question;
  assess a second chain of logic associated with the originating question; and
  provide the answer to the cognitive agent, wherein the answer is associated with the first chain of logic.

Clause 15. The system of any preceding clause, wherein the cognitive agent is further configured to render for display a chain of logic that leads to a conclusion, wherein the conclusion, in part, informs the answer.

Clause 16. A computer readable media storing instructions that are executable by a processor to cause a computer to execute operations comprising:
  executing a cognitive intelligence platform that further comprises:
  a knowledge cloud;
  a critical thinking engine communicably coupled to the knowledge cloud; and
  a cognitive agent communicably coupled to the critical thinking engine and the knowledge cloud, wherein the cognitive agent is configured to:
    receive an originating question from a user related to a subject matter;
    execute, using the critical thinking engine, a logical reasoning to generate an answer; and
    provide the answer to the user including a recommendation associated with the subject matter.

Clause 17. The computer-readable media of any preceding clause, wherein the cognitive agent executing within the cognitive intelligence platform is further configured to:
  render for display a micro survey;
  receive data associated with the micro survey, wherein the data, in part, informs the recommendation associated with the subject matter.

Clause 18. The computer-readable media of any preceding clause, wherein the critical thinking engine executing within the cognitive intelligence platform is further configured to:
  receive the originating question from the cognitive agent;
  assess a first chain of logic associated with the originating question to create a first answer;
  assess a second chain of logic associated with the originating question to create a second answer, wherein the first answer contradicts the second answer; and
  provide the first answer to the cognitive agent, wherein the first answer is the answer provided to the user.

Clause 19. The computer-readable media of any preceding clause, wherein the cognitive agent executing within the cognitive intelligence platform is further configured to render for display the first chain of logic to the user.

Clause 20. The computer-readable media of any preceding clause, wherein the cognitive agent executing within the cognitive intelligence platform is further configured to integrate data from at least three selected from the group consisting of: a micro survey, a physician's office, common sense knowledge, domain knowledge, an evidence-based medicine guideline, a clinical ontology, and curated medical advice.

Clause 21. A computer-implemented method for answering a user-generated natural language medical information query based on a diagnostic conversational template, the method comprising:
  receiving a user-generated natural language medical information query at an artificial intelligence-based diagnostic conversation agent from a user interface on a mobile device;
  responsive to content of the user-generated natural language medical information query, selecting a diagnostic fact variable set relevant to generating a medical advice query answer for the user-generated natural language medical information query by classifying the user-generated natural language medical information query into one of a set of domain-directed medical query classifications associated with respective diagnostic fact variable sets;
  compiling user-specific medical fact variable values for one or more respective medical fact variables of the diagnostic fact variable set, wherein the compiling user-specific medical fact variable values for one or more respective medical fact variables of the diagnostic fact variable set further comprises:
    extracting a first set of user-specific medical fact variable values from a local user medical information profile associated with the user-generated natural language medical information query, and
    requesting a second set of user-specific medical fact variable values through natural-language questions sent to the user interface on the mobile device; and
  responsive to the user-specific medical fact variable values, generating a medical advice query answer in response to the user-generated natural language medical information query.

Clause 22. The computer-implemented method for answering a user-generated natural language medical information query based on a diagnostic conversational template of any preceding clause, wherein the compiling user-specific medical fact variable values for one or more respective medical fact variables of the diagnostic fact variable set further comprises:
  extracting a third set of user-specific medical fact variable values comprising lab result values from the local user medical information profile associated with the user-generated natural language medical information query.

Clause 23. The computer-implemented method for answering a user-generated natural language medical information query based on a diagnostic conversational template of any preceding clause, wherein the compiling user-specific medical fact variable values for one or more respective medical fact variables of the diagnostic fact variable set further comprises:

extracting a fourth set of user-specific medical fact variable values from a remote medical data service profile associated with the local user medical information profile.

Clause 24. The computer-implemented method for answering a user-generated natural language medical information query based on a diagnostic conversational template of any preceding clause, wherein the compiling user-specific medical fact variable values for one or more respective medical fact variables of the diagnostic fact variable set further comprises:

extracting a fifth set of user-specific medical fact variable values derived from demographic characterizations provided by a remote data service analysis of the local user medical information profile.

Clause 25. The computer-implemented method for answering a user-generated natural language medical information query based on a diagnostic conversational template of any preceding clause, wherein the generating the medical advice query answer in response to the user-generated natural language medical information query further comprises providing, in addition to text responsive to a medical question presented in the user-generated natural language medical information query, a treatment action-item recommendation responsive to user-specific medical fact variable values and non-responsive to the medical question presented in the user-generated natural language medical information query.

Clause 26. The computer-implemented method for answering a user-generated natural language medical information query based on a diagnostic conversational template of any preceding clause, wherein the generating the medical advice query answer in response to the user-generated natural language medical information query further comprises providing, in addition to text responsive to a medical question presented in the user-generated natural language medical information query, a medical education media resource responsive to the user-specific medical fact variable values and non-responsive to the medical question presented in the user-generated natural language medical information query.

Clause 27. The computer-implemented method for answering a user-generated natural language medical information query based on a diagnostic conversational template of any preceding clause, wherein selecting a diagnostic fact variable set relevant to generating a medical advice query answer for the user-generated natural language medical information query by classifying the user-generated natural language medical information query into one of a set of domain-directed medical query classifications associated with respective diagnostic fact variable set further comprises classifying the user-generated natural language medical information query into one of a set of domain-directed medical query classifications based on relevance to the local user medical information profile associated with the user-generated natural language medical information query.

Clause 28. A computer program product in a computer-readable medium for answering a user-generated natural language query, the computer program product in a computer-readable medium comprising program instructions which, when executed, cause a processor of a computer to perform:

receiving a user-generated natural language query at an artificial intelligence-based conversation agent from a user interface;

responsive to content of the user-generated natural language query, selecting a fact variable set relevant to generating a query answer for the user-generated natural language query by classifying the user-generated natural language query into one of a set of domain-directed query classifications associated with respective fact variable sets;

compiling user-specific fact variable values for one or more respective fact variables of the fact variable set; and responsive to the fact variable values, generating the query answer in response to the user-generated natural language query.

Clause 29. The computer program product in a computer-readable medium for answering a user-generated natural language query of any preceding clause, wherein the program instructions which, when executed, cause the processor of the computer to perform compiling user-specific fact variable values for one or more respective fact variables of the fact variable set further comprise program instructions which, when executed, cause the computer program product to perform:

extracting a first set of user-specific fact variable values from a local user profile associated with the user-generated natural language query; and requesting a second set of user-specific fact variable values through a conversational template comprising natural-language questions sent to the user interface on a mobile device.

Clause 30. The computer program product in a computer-readable medium for answering a user-generated natural language query of any preceding clause, wherein the program instructions which, when executed, cause the processor of the computer to perform compiling user-specific fact variable values for one or more respective fact variables of the fact variable set further comprise program instructions which, when executed, cause the computer program product to perform:

extracting a third set of user-specific fact variable values from a remote data service profile associated with the local user profile.

Clause 31. The computer program product in a computer-readable medium for answering a user-generated natural language query of any preceding clause, wherein the program instructions which, when executed, cause the processor of the computer to perform compiling user-specific fact variable values for one or more respective fact variables of the fact variable set further comprise program instructions which, when executed, cause the computer program product to perform:

extracting a fourth set of user-specific fact variable values derived from demographic characterizations provided by a remote data service analysis of the local user profile.

Clause 32. The computer program product in a computer-readable medium for answering a user-generated natural language query of any preceding clause, wherein program instructions which, when executed, cause the processor of the computer to perform the generating the query answer in response to the user-generated natural language query further comprise program instructions which, when executed, cause the processor of the computer to perform providing, in addition to text responsive to a question presented in the user-generated natural language query, an action-item recommendation responsive to the fact variable values and non-responsive to the question presented in the user-generated natural language query.

Clause 33. The computer program product in a computer-readable medium for answering a user-generated natural language query of any preceding clause, wherein the program instructions which, when executed, cause the processor of the computer to perform generating the query answer in response to the user-generated natural language query further comprise program instructions which, when executed, cause the processor of the computer to perform providing, in addition to text responsive to a question presented in the user-generated natural language query, an education media resource responsive to the fact variable values and non-responsive to the question presented in the user-generated natural language query.

Clause 34. The computer program product in a computer-readable medium for answering a user-generated natural language query of any preceding clause, wherein the program instructions which, when executed, cause the processor of the computer to perform selecting a fact variable set relevant to generating a query answer for the user-generated natural language query by classifying the user-generated natural language query into one of a set of domain-directed query classifications associated with respective fact variable sets further comprise program instructions which, when executed, cause the processor of the computer to perform classifying the user-generated natural language query into one of a set of domain-directed query classifications based on relevance to a local user profile associated with the user-generated natural language query.

Clause 35. A cognitive intelligence platform for answering a user-generated natural language query, the cognitive intelligence platform comprising:
  a cognitive agent configured for receiving a user-generated natural language query at an artificial intelligence-based conversation agent from a user interface;
  a critical thinking engine configured for, responsive to content of the user-generated natural language query, selecting a fact variable set relevant to generating a query answer for the user-generated natural language query by classifying the user-generated natural language query into one of a set of domain-directed query classifications associated with respective fact variable sets; and
  a knowledge cloud compiling user-specific fact variable values for one or more respective fact variables of the fact variable set; and
  wherein, responsive to the fact variable values, the cognitive agent is further configured for generating the query answer in response to the user-generated natural language query.

Clause 36. The cognitive intelligence platform of any preceding clause, wherein the knowledge cloud is further configured for:
  extracting a first set of user-specific fact variable values from a local user profile associated with the user-generated natural language query; and
  requesting a second set of user-specific fact variable values through a conversational template comprising natural-language questions sent to the user interface on a mobile device.

Clause 37. The cognitive intelligence platform of any preceding clause, wherein the knowledge cloud is further configured for:
  extracting a third set of user-specific fact variable values from a remote data service profile associated with the local user profile.

Clause 38. The cognitive intelligence platform of any preceding clause, wherein the knowledge cloud is further configured for:
  extracting a fourth set of user-specific fact variable values derived from demographic characterizations provided by a remote data service analysis of the local user profile.

Clause 39. The cognitive intelligence platform of any preceding clause, wherein cognitive agent is further configured for providing, in addition to text responsive to a question presented in the user-generated natural language query, an action-item recommendation responsive to the fact variable values and non-responsive to the question presented in the user-generated natural language query.

Clause 40. The cognitive intelligence platform of any preceding clause, wherein the critical thinking engine is further configured for providing, in addition to text responsive to a question presented in the user-generated natural language query, an education media resource responsive to the fact variable values and non-responsive to the question presented in the user-generated natural language query.

Clause 41. A computer-implemented method for answering a user-generated natural language query, the method comprising:
  receiving a user-generated natural language query at an artificial intelligence-based conversation agent from a user interface;
  responsive to content of the user-generated natural language query, selecting a fact variable set relevant to generating a query answer for the user-generated natural language query by classifying the user-generated natural language query into one of a set of domain-directed query classifications associated with respective fact variable sets;
  compiling user-specific fact variable values for one or more respective fact variables of the fact variable set; and
  responsive to the fact variable values, generating the query answer in response to the user-generated natural language query.

Clause 42. The method of any preceding clause, wherein the compiling user-specific fact variable values for one or more respective fact variables of the fact variable set further comprises:
  extracting a first set of user-specific fact variable values from a local user profile associated with the user-generated natural language query; and
  requesting a second set of user-specific fact variable values through a conversational template comprising natural-language questions sent to the user interface on a mobile device.

Clause 43. The method of any preceding clause, wherein the compiling user-specific fact variable values for one or more respective fact variables of the fact variable set further comprises:
  extracting a third set of user-specific fact variable values from a remote data service profile associated with the local user profile.

Clause 44. The method of any preceding clause, wherein the compiling user-specific fact variable values for one or more respective fact variables of the fact variable set further comprises:

extracting a fourth set of user-specific fact variable values derived from demographic characterizations provided by a remote data service analysis of the local user profile.

Clause 45. The method of any preceding clause, wherein the generating the query answer in response to the user-generated natural language query further comprises providing, in addition to text responsive to a question presented in the user-generated natural language query, an action-item recommendation responsive to the fact variable values and non-responsive to the question presented in the user-generated natural language query.

Clause 46. The method of any preceding clause, wherein the generating the query answer in response to the user-generated natural language query further comprises providing, in addition to text responsive to a question presented in the user-generated natural language query, an education media resource responsive to the fact variable values and non-responsive to the question presented in the user-generated natural language query.

Clause 47. The method of any preceding clause, wherein selecting a fact variable set relevant to generating a query answer for the user-generated natural language query by classifying the user-generated natural language query into one of a set of domain-directed query classifications associated with respective fact variable sets further comprises classifying the user-generated natural language query into one of a set of domain-directed query classifications based on relevance to a local user profile associated with the user-generated natural language query.

Clause 48. A computer-implemented method for answering natural language medical information questions posed by a user of a medical conversational interface of a cognitive artificial intelligence system, the method comprising:
receiving from a medical conversational user interface a user-generated natural language medical information query at an artificial intelligence-based medical conversation cognitive agent;
extracting from the user-generated natural language medical information query a medical question from a user of the medical conversational user interface;
compiling a medical conversation language sample, wherein the medical conversation language sample comprises items of health-information-related-text derived from a health-related conversation between the artificial intelligence-based medical conversation cognitive agent and the user;
extracting from the medical conversation language sample internal medical concepts and medical data entities present within the medical conversation language sample, wherein the internal medical concepts comprise descriptions of medical attributes of the medical data entities;
inferring a therapeutic intent of the user from the internal medical concepts and the medical data entities;
generating a therapeutic paradigm logical framework for interpreting of the medical question, wherein
the therapeutic paradigm logical framework comprises a catalog of medical logical progression paths from the medical question to respective therapeutic answers,
each of the medical logical progression paths comprises one or more medical logical linkages from the medical question to a therapeutic path-specific answer, and
the medical logical linkages comprise the internal medical concepts and external therapeutic paradigm concepts derived from a store of medical subject matter ontology data;
selecting a likely medical information path from among the medical logical progression paths to a likely path-dependent medical information answer based upon the therapeutic intent of the user; and
answering the medical question by following the likely medical information path to the likely path-dependent medical information answer.

Clause 49. The computer-implemented method for answering natural language medical information questions posed by a user of a medical conversational interface of a cognitive artificial intelligence system of any of any of the preceding clauses, further comprising relating medical inference groups of the internal medical concepts.

Clause 50. The computer-implemented method for answering natural language medical information questions posed by a user of a medical conversational interface of a cognitive artificial intelligence system of any of any of the preceding clauses, wherein the relating medical inference groups of the internal medical concepts further comprises relating groups of the internal medical concepts based at least in part on shared medical data entities for which each internal medical concept of a medical inference group of internal medical concepts describes a respective medical data attribute.

Clause 51. The computer-implemented method for answering natural language medical information questions posed by a user of a medical conversational interface of a cognitive artificial intelligence system of any of the preceding clauses, wherein selecting a likely medical information path from among the medical logical progression paths to a likely path-dependent medical information answer based upon the intent further comprises selecting a likely medical information path from among the medical logical progression paths to a likely path-dependent medical information answer based in part upon the therapeutic intent of the user and in part upon sufficiency of medical diagnostic data to complete the medical logical linkages.

Clause 52. The computer-implemented method for answering natural language medical information questions posed by a user of a medical conversational interface of a cognitive artificial intelligence system of any of the preceding clauses, wherein selecting a likely medical information path from among the medical logical progression paths to a likely path-dependent medical information answer based upon the intent further comprises selecting a likely medical information path from among the medical logical progression paths to a likely path-dependent medical information answer after requesting additional medical diagnostic data from the user.

Clause 53. The computer-implemented method for answering natural language medical information questions posed by a user of a medical conversational interface of a cognitive artificial intelligence system of any of the preceding clauses, wherein selecting a likely medical information path from among the medical logical progression paths to a likely path-dependent medical information answer based upon the intent further comprises selecting a likely medical information path from among the medical logical progression paths to a likely path-dependent medical information answer based in part upon treatment sub-intents comprising tactical constituents related to the therapeutic intent of the user by the store of medical subject matter ontology data.

Clause 54. The computer-implemented method for answering natural language medical information questions posed by a user of a medical conversational interface of a cognitive artificial intelligence system of any of the preceding clauses, wherein selecting a likely medical information path from among the medical logical progression paths to a likely path-dependent medical information answer based upon the intent further comprises selecting a likely medical information path from among the medical logical progression paths to a likely path-dependent medical information answer based in part upon the therapeutic intent of the user and in part upon sufficiency of medical diagnostic data to complete the medical logical linkages, wherein the medical diagnostic data to complete the medical logical linkages includes user-specific medical diagnostic data.

Clause 55. A cognitive intelligence platform for answering natural language questions posed by a user of a conversational interface of an artificial intelligence system, the cognitive intelligence platform comprising:
- a cognitive agent configured for receiving from a user interface a user-generated natural language query, wherein the cognitive agent is an artificial intelligence-based conversation agent;
- a knowledge cloud containing a store of subject matter ontology data;
- a critical thinking engine configured for:
  - extracting from the user-generated natural language query a question from a user of the user interface,
  - compiling a language sample, wherein the language sample comprises items of text derived from a conversation between the artificial intelligence-based conversation agent and the user,
  - extracting from the language sample internal concepts and entities present within the language sample, wherein the internal concepts comprise descriptions of attributes of the entities,
  - inferring an intent of the user from the internal concepts and the entities,
  - generating a logical framework for interpreting of the question, wherein
    - the logical framework comprises a catalog of paths from the question to respective answers,
    - each of the paths comprises one or more linkages from the question to a path-specific answer, and the linkages comprise the internal concepts and external concepts derived from the store of subject matter ontology data,
  - selecting a likely path from among the paths to a likely path-dependent answer based upon the intent, and
  - answering the question by following the likely path to the likely path-dependent answer.

Clause 56. The cognitive intelligence platform for answering natural language questions posed by a user of a conversational interface of an artificial intelligence system of any of the preceding clauses, wherein the critical thinking engine is further configured for relating groups of the internal concepts.

Clause 57. The cognitive intelligence platform for answering natural language questions posed by a user of a conversational interface of an artificial intelligence system of any of the preceding clauses, wherein the critical thinking engine is further configured for relating groups of the internal concepts by relating groups of the internal concepts based at least in part on shared entities for which each internal concept of a group of internal concepts describes a respective attribute.

Clause 58. The cognitive intelligence platform for answering natural language questions posed by a user of a conversational interface of an artificial intelligence system of any of the preceding clauses, wherein the critical thinking engine is further configured for selecting a likely path from among the paths to a likely path-dependent answer based upon the intent further comprises selecting a likely path from among the paths to a likely path-dependent answer based in part upon the intent and in part upon sufficiency of data to complete the linkages.

Clause 59. The cognitive intelligence platform for answering natural language questions posed by a user of a conversational interface of an artificial intelligence system of any of the preceding clauses, wherein the critical thinking engine is further configured for selecting a likely path from among the paths to a likely path-dependent answer based upon the intent further comprises selecting a likely path from among the paths to a likely path-dependent answer after requesting additional data from the user.

Clause 60. The cognitive intelligence platform for answering natural language questions posed by a user of a conversational interface of an artificial intelligence system of 8, wherein the critical thinking engine is further configured for selecting a likely path from among the paths to a likely path-dependent answer based upon the intent further comprises selecting a likely path from among the paths to a likely path-dependent answer based in part upon sub-intents comprising tactical constituents related to the intent by the store of subject matter ontology data.

Clause 61. The cognitive intelligence platform for answering natural language questions posed by a user of a conversational interface of an artificial intelligence system of any of the preceding clauses, wherein the critical thinking engine is further configured for selecting a likely path from among the paths to a likely path-dependent answer based upon the intent further comprises selecting a likely path from among the paths to a likely path-dependent answer based in part upon the intent and in part upon sufficiency of data to complete the linkages, wherein the data to complete the linkages includes user-specific data.

Clause 62. A computer program product in a computer-readable medium for answering natural language questions posed by a user of a conversational interface of an artificial intelligence system, the computer program product in a computer-readable medium comprising instructions, which, when executed, cause a processor of a computer to perform:
- receiving from a user interface a user-generated natural language query at an artificial intelligence-based conversation agent;
- extracting from the user-generated natural language query a question from a user of the user interface;
- compiling a language sample, wherein the language sample comprises items of text derived from a conversation between the artificial intelligence-based conversation agent and the user;
- extracting from the language sample internal concepts and entities present within the language sample, wherein the internal concepts comprise descriptions of attributes of the entities;
- inferring an intent of the user from the internal concepts and the entities;
- generating a logical framework for interpreting of the question, wherein
  - the logical framework comprises a catalog of paths from the question to respective answers,
  - each of the paths comprises one or more linkages from the question to a path-specific answer, and the linkages comprise the internal concepts and external concepts derived from a store of subject matter ontology data;
selecting a likely path from among the paths to a likely path-dependent answer based upon the intent; and
answering the question by following the likely path to the likely path-dependent answer.

Clause 63. The computer program product in a computer-readable medium for answering natural language questions posed by a user of a conversational interface of an artificial intelligence system of any of the preceding clauses, further comprising instructions, which, when executed, cause the processor of the computer to perform relating groups of the internal concepts.

Clause 64. The computer program product in a computer-readable medium for answering natural language questions posed by a user of a conversational interface of an artificial intelligence system of any of the preceding clauses, wherein the instructions, which, when executed, cause the processor of the computer to perform relating groups of the internal concepts further comprise instructions, which, when executed, cause the processor of the computer to perform relating groups of the internal concepts based at least in part on shared entities for which each internal concept of a group of internal concepts describes a respective attribute.

Clause 65. The computer program product in a computer-readable medium for answering natural language questions posed by a user of a conversational interface of an artificial intelligence system of any of the preceding clauses, wherein the instructions, which, when executed, cause the processor of the computer to perform selecting a likely path from among the paths to a likely path-dependent answer based upon the intent further comprise instructions, which, when executed, cause the processor of the computer to perform selecting a likely path from among the paths to a likely path-dependent answer based in part upon the intent and in part upon sufficiency of data to complete the linkages.

Clause 66. The computer program product in a computer-readable medium for answering natural language questions posed by a user of a conversational interface of an artificial intelligence system of any of the preceding clauses, wherein instructions, which, when executed, cause the processor of the computer to perform selecting a likely path from among the paths to a likely path-dependent answer based upon the intent further comprise instructions, which, when executed, cause the processor of the computer to perform selecting a likely path from among the paths to a likely path-dependent answer after requesting additional data from the user.

Clause 67. The computer program product in a computer-readable medium for answering natural language questions posed by a user of a conversational interface of an artificial intelligence system of any of the preceding clauses, wherein the instructions, which, when executed, cause the processor of the computer to perform selecting a likely path from among the paths to a likely path-dependent answer based upon the intent further comprise instructions, which, when executed, cause the processor of the computer to perform selecting a likely path from among the paths to a likely path-dependent answer based in part upon sub-intents comprising tactical constituents related to the intent by the store of subject matter ontology data.

Clause 68. A method for answering natural language questions posed by a user of a conversational interface of an artificial intelligence system, the method comprising:
receiving from a user interface a user-generated natural language query at an artificial intelligence-based conversation agent;
extracting from the user-generated natural language query a question from a user of the user interface;
compiling a language sample, wherein the language sample comprises items of text derived from a conversation between the artificial intelligence-based conversation agent and the user;
extracting from the language sample internal concepts and entities present within the language sample, wherein the internal concepts comprise descriptions of attributes of the entities;
inferring an intent of the user from the internal concepts and the entities;
generating a logical framework for interpreting of the question, wherein
the logical framework comprises a catalog of paths from the question to respective answers,
each of the paths comprises one or more linkages from the question to a path-specific answer, and
the linkages comprise the internal concepts and external concepts derived from a store of subject matter ontology data;
selecting a likely path from among the paths to a likely path-dependent answer based upon the intent; and
answering the question by following the likely path to the likely path-dependent answer.

Clause 69. The method for answering natural language questions posed by a user of a conversational interface of an artificial intelligence system of any of the preceding clauses, further comprising relating groups of the internal concepts.

Clause 70. The method for answering natural language questions posed by a user of a conversational interface of an artificial intelligence system of any of the preceding clauses, wherein the relating groups of the internal concepts further comprises relating groups of the internal concepts based at least in part on shared entities for which each internal concept of a group of internal concepts describes a respective attribute.

Clause 71. The method for answering natural language questions posed by a user of a conversational interface of an artificial intelligence system of any of the preceding clauses, wherein selecting a likely path from among the paths to a likely path-dependent answer based upon the intent further comprises selecting a likely path from among the paths to a likely path-dependent answer based in part upon the intent and in part upon sufficiency of data to complete the linkages.

Clause 72. The method for answering natural language questions posed by a user of a conversational interface of an artificial intelligence system of any of the preceding clauses, wherein selecting a likely path from among the paths to a likely path-dependent answer based upon the intent further comprises selecting a likely path from among the paths to a likely path-dependent answer after requesting additional data from the user.

Clause 73. The method for answering natural language questions posed by a user of a conversational interface of an artificial intelligence system of any of the preceding clauses, wherein selecting a likely path from among the paths to a likely path-dependent answer based upon the intent further comprises selecting a likely path from among the paths to a likely path-dependent answer based in part upon sub-intents comprising tactical constituents related to the intent by the store of subject matter ontology data.

Clause 74. The method for answering natural language questions posed by a user of a conversational interface of an artificial intelligence system of any of the preceding clauses, wherein selecting a likely path from among the paths to a likely path-dependent answer based upon the intent further comprises selecting a likely path from among the paths to a likely path-dependent answer based in part upon the intent and in part upon sufficiency of data to complete the linkages, wherein the data to complete the linkages includes user-specific data.

Clause 75. A computer-implemented method for providing therapeutic medical action recommendations in response to a medical information natural language conversation stream, the computer-implemented method comprising:
  receiving segments of a medical information natural language conversation stream at an artificial intelligence-based health information conversation agent from a medical information conversation user interface;
  responsive to medical information content of a user medical information profile associated with the medical information natural language conversation stream, defining a desired clinical management outcome objective relevant to health management criteria and related health management data attributes of the user medical information profile;
  identifying a set of potential therapeutic interventions correlated to advancement of the clinical management outcome objective;
  selecting from among the set of potential therapeutic interventions correlated to advancement of the clinical management outcome objective a medical intervention likely to advance the clinical management outcome objective;
  presenting in the medical information natural language conversation stream a therapeutic advice conversation stream segment designed to stimulate execution of the medical intervention likely to advance the clinical management outcome objective; and
  presenting to the user in the medical information natural language conversation stream a therapeutic advice conversation stream segment explaining a correlation between the medical intervention likely to advance the clinical management outcome objective and achievement of the clinical management outcome objective.

Clause 76. The computer-implemented method for providing therapeutic medical action recommendations in response to a medical information natural language conversation stream of any preceding clause, wherein the selecting from among the set of potential therapeutic interventions correlated to advancement of the clinical management outcome objective a medical intervention likely to advance the clinical management outcome objective further comprises:
  selecting from among the set of potential therapeutic interventions correlated to advancement of the clinical management outcome objective the medical intervention likely to advance the clinical management outcome objective based on a set of factors comprising likelihood of patient compliance with the a recommendation for the a medical intervention likely to advance the clinical management outcome objective and a statistical likelihood that the action will materially advance the clinical management outcome objective.

Clause 77. The computer-implemented method for providing therapeutic medical action recommendations in response to a medical information natural language conversation stream any preceding clause, wherein the presenting to the user in the medical information natural language conversation stream a therapeutic advice conversation stream segment designed to stimulate execution of the action likely to advance the clinical management outcome objective further comprises presenting to the user in the medical information natural language conversation stream a therapeutic advice conversation stream segment explaining a cost-benefit analysis comparing likely results of performance of the action likely to advance the clinical management outcome objective and likely results of non-performance of the action likely to advance the clinical management outcome objective.

Clause 78. The computer-implemented method for providing therapeutic medical action recommendations in response to a medical information natural language conversation stream of any preceding clause, wherein the selecting from among the set of potential therapeutic interventions correlated to advancement of the clinical management outcome objective a medical intervention likely to advance the clinical management outcome objective further comprises:
  selecting from among the set of potential therapeutic interventions correlated to advancement of the clinical management outcome objective the medical intervention likely to advance the clinical management outcome objective based on a set of factors comprising likelihood total expected cost expectation associated with the recommendation for the a medical intervention likely to advance the clinical management outcome objective.

Clause 79. The computer-implemented method for providing therapeutic medical action recommendations in response to a medical information natural language conversation stream of any preceding clause, wherein the presenting to the user in the medical information natural language conversation stream a therapeutic advice conversation stream segment designed to stimulate execution of the action likely to advance the clinical management outcome objective further comprises presenting to the user in the medical information natural language conversation stream a conversation stream reinforcing the recommendation after expiration of a delay period.

Clause 80. The computer-implemented method for providing therapeutic medical action recommendations in response to a medical information natural language conversation stream of any preceding clause, wherein the presenting to the user in the medical information natural language conversation stream a therapeutic advice conversation stream segment designed to stimulate execution of the action likely to advance the clinical management outcome objective further comprises presenting to the user in the medical information natural language conversation stream a therapeutic advice conversation stream segment explaining reasons for selection of the clinical management outcome objective.

Clause 81. The computer-implemented method for providing therapeutic medical action recommendations in response to a medical information natural language conversation stream of any preceding clause, wherein the presenting to the user in the medical information natural language conversation stream a therapeutic advice conversation stream segment designed to stimulate execution of the action likely to advance the clinical management outcome objective further comprises notifying third party service providers of the clinical management outcome objective and the recommendation.

Clause 82. A computer program product in a non-transitory computer-readable medium for providing therapeutic medical action recommendations in response to a medical information natural language conversation stream, the computer program product in a non-transitory computer-readable medium comprising instructions which, when executed cause a processor of a computer to perform:

receiving segments of a medical information natural language conversation stream at an artificial intelligence-based health information conversation agent from a medical information conversation user interface;

responsive to medical information content of a user medical information profile associated with the medical information natural language conversation stream, defining a clinical management outcome objective relevant to health management criteria and related health management data attributes of the profile;

selecting a medical intervention likely to advance the clinical management outcome objective; and presenting to the user in the medical information natural language conversation stream a therapeutic advice conversation stream segment designed to stimulate execution of the action likely to advance the clinical management outcome objective.

83. The computer program product in a non-transitory computer-readable medium of any preceding clause, wherein the instructions which, when executed cause the processor of the computer to perform selecting a medical intervention likely to advance the clinical management outcome objective further comprise instructions which, when executed cause the processor of the computer to perform:

identifying a set of potential therapeutic interventions correlated to advancement of the clinical management outcome objective; and selecting the action likely to advance the user outcome objective based on a set of factors comprising likelihood of performance of the action likely to advance the user outcome objective and likelihood that the action will materially advance the user outcome objective.

Clause 84. The computer program product in a non-transitory computer-readable medium of any preceding clause, wherein the instructions which, when executed cause the processor of the computer to perform presenting to the user in the medical information natural language conversation stream a therapeutic advice conversation stream segment designed to stimulate execution of the action likely to advance the clinical management outcome objective further comprise instructions which, when executed cause the processor of the computer to perform presenting to the user in the medical information natural language conversation stream a therapeutic advice conversation stream segment explaining a correlation between the action likely to advance the clinical management outcome objective and achievement of the clinical management outcome objective.

Clause 85. The computer program product in a non-transitory computer-readable medium of any preceding clause, wherein the instructions which, when executed cause the processor of the computer to perform presenting to the user in the medical information natural language conversation stream a therapeutic advice conversation stream segment designed to stimulate execution of the action likely to advance the clinical management outcome objective further comprise instructions which, when executed cause the processor of the computer to perform presenting to the user in the medical information natural language conversation stream a therapeutic advice conversation stream segment explaining a plan of subsequent actions likely to advance the clinical management outcome objective.

Clause 86. The computer program product in a non-transitory computer-readable medium of any preceding clause, wherein the instructions which, when executed cause the processor of the computer to perform presenting to the user in the medical information natural language conversation stream a therapeutic advice conversation stream segment designed to stimulate execution of the action likely to advance the clinical management outcome objective further comprise instructions which, when executed cause the processor of the computer to perform presenting to the user in the medical information natural language conversation stream a conversation stream reinforcing the recommendation after expiration of a delay period.

Clause 87. The computer program product in a non-transitory computer-readable medium of any preceding clause, wherein the instructions which, when executed cause the processor of the computer to perform presenting to the user in the medical information natural language conversation stream a therapeutic advice conversation stream segment designed to stimulate execution of the action likely to advance the clinical management outcome objective further comprise instructions which, when executed cause the processor of the computer to perform presenting to the user in the medical information natural language conversation stream a therapeutic advice conversation stream segment explaining reasons for selection of the clinical management outcome objective.

Clause 88. The computer program product in a non-transitory computer-readable medium of any preceding clause, wherein the instructions which, when executed cause the processor of the computer to perform presenting to the user in the medical information natural language conversation stream a therapeutic advice conversation stream segment designed to stimulate execution of the action likely to advance the clinical management outcome objective further comprise instructions which, when executed cause the processor of the computer to perform notifying third party service providers of the clinical management outcome objective and the recommendation.

Clause 89. A system for providing therapeutic medical action recommendations in response to a medical information natural language conversation stream, the system comprising:

a knowledge cloud configured for receiving segments of a medical information natural language conversation stream at an artificial intelligence-based health information from a medical information conversation user interface of a cognitive agent;

a critical thinking engine configured for:
responsive to medical information content of a user medical information profile associated with the medical information natural language conversation stream in the knowledge cloud, defining a clinical management outcome objective relevant to health management criteria and related health management data attributes of the profile, and selecting a medical intervention likely to advance the clinical management outcome objective; and the cognitive agent, wherein the cognitive agent is configure for presenting to the user in the medical information natural language conversation stream a therapeutic advice conversation stream segment designed to stimulate execution of the action likely to advance the clinical management outcome objective.

Clause 90. The system of any preceding clause, wherein the selecting a medical intervention likely to advance the clinical management outcome objective further comprises:

identifying a set of potential therapeutic interventions correlated to advancement of the clinical management outcome objective; and selecting the action likely to advance the user outcome objective based on a set of factors comprising likelihood of performance of the action likely to advance the user outcome objective and likelihood that the action will materially advance the user outcome objective.

Clause 91. The system of claim any preceding clause, wherein the presenting to the user in the medical information natural language conversation stream a therapeutic advice conversation stream segment designed to stimulate execution of the action likely to advance the clinical management outcome objective further comprises presenting to the user in the medical information natural language conversation stream a therapeutic advice conversation stream segment explaining a correlation between the action likely to advance the clinical management outcome objective and achievement of the clinical management outcome objective.

Clause 92. The system of any preceding clause, wherein the presenting to the user in the medical information natural language conversation stream a therapeutic advice conversation stream segment designed to stimulate execution of the action likely to advance the clinical management outcome objective further comprises presenting to the user in the medical information natural language conversation stream a therapeutic advice conversation stream segment explaining a plan of subsequent actions likely to advance the clinical management outcome objective.

Clause 93. The system of any preceding clause, wherein the presenting to the user in the medical information natural language conversation stream a therapeutic advice conversation stream segment designed to stimulate execution of the action likely to advance the clinical management outcome objective further comprises presenting to the user in the medical information natural language conversation stream a conversation stream reinforcing the recommendation after expiration of a delay period.

Clause 94. The system of any preceding clause, wherein the presenting to the user in the medical information natural language conversation stream a conversation stream segment designed to stimulate execution of the action likely to advance the clinical management outcome objective further comprises presenting to the user in the medical information natural language conversation stream a conversation stream segment explaining reasons for selection of the clinical management outcome objective.

Clause 95. A computer-implemented method for providing action recommendations in response to a user-generated natural language conversation stream, the method comprising:
receiving segments of a user-generated natural language conversation stream at an artificial intelligence-based conversation agent from a user interface;
responsive to content of a user profile associated with the user-generated natural language conversation stream, defining a user action outcome objective relevant to attributes of the profile;
selecting an action likely to advance the user action outcome objective; and
presenting to the user in the user-generated natural language conversation stream a conversation stream segment designed to motivate performance of the action likely to advance the user action outcome objective.

Clause 96. The method of any preceding clause, wherein the selecting an action likely to advance the user action outcome objective further comprises:
identifying a set of actions correlated to advancement of the user action outcome objective; and
selecting the action likely to advance the user outcome objective based on a set of factors comprising likelihood of performance of the action likely to advance the user outcome objective and likelihood that the action will materially advance the user outcome objective.

Clause 97. The method of any preceding clause, wherein the presenting to the user in the user-generated natural language conversation stream a conversation stream segment designed to motivate performance of the action likely to advance the user action outcome objective further comprises presenting to the user in the user-generated natural language conversation stream a conversation stream segment explaining a correlation between the action likely to advance the user action outcome objective and achievement of the user action outcome objective.

Clause 98. The method of any preceding clause, wherein the presenting to the user in the user-generated natural language conversation stream a conversation stream segment designed to motivate performance of the action likely to advance the user action outcome objective further comprises presenting to the user in the user-generated natural language conversation stream a conversation stream segment explaining a plan of subsequent actions likely to advance the user action outcome objective.

Clause 99. The method of any preceding clause, wherein the presenting to the user in the user-generated natural language conversation stream a conversation stream segment designed to motivate performance of the action likely to advance the user action outcome objective further comprises presenting to the user in the user-generated natural language conversation stream a conversation stream reinforcing the recommendation after expiration of a delay period.

Clause 100. The method of any preceding clause, wherein the presenting to the user in the user-generated natural language conversation stream a conversation stream segment designed to motivate performance of the action likely to advance the user action outcome objective further comprises presenting to the user in the user-generated natural language conversation stream a conversation stream segment explaining reasons for selection of the user action outcome objective.

Clause 101. The method of any preceding clause, wherein the presenting to the user in the user-generated natural language conversation stream a conversation stream segment designed to motivate performance of the action likely to advance the user action outcome objective further comprises notifying third party service providers of the user action outcome objective and the recommendation.

Clause 102. A method comprising:
receiving, at an artificial intelligence engine, a corpus of data for a patient, wherein the corpus of data includes a plurality of strings of characters;
identifying, in the plurality of strings of characters, indicia comprising a phrase, a predicate, a keyword, a subject, an object, a cardinal, a number, a concept, or some combination thereof;
comparing the indicia to a knowledge graph representing known health related information to generate a possible health related information pertaining to the patient;
identifying, using a logical structure, a structural similarity of the possible health related information and a known predicate in the logical structure; and
generating, by the artificial intelligence engine, cognified data based on the structural similarity.

Clause 103. The method of any preceding clause, further comprising generating the knowledge graph using the known health related information, wherein the knowledge graph represents knowledge of a disease and the knowledge graph comprises a plurality of concepts pertaining to the disease obtained from the known health related information, and the knowledge graph comprises relationships between the plurality of concepts.

Clause 104. The method of any preceding clause, wherein the cognified data comprises a health related summary of the possible health related information.

Clause 105. The method of any preceding clause, wherein generating, by the artificial intelligence engine, the cognified data further comprises:
  generating at least one new string of characters representing a statement pertaining to the possible health related information; and
  including the at least one new string of characters in the health related summary of the possible health related information.

Clause 106. The method of any preceding clause, wherein the statement describes an effect that results from the possible health related information.

Clause 107. The method of any preceding clause, further comprising codifying evidence based health related guidelines pertaining to a disease to generate the logical structure.

Clause 108. The method of any preceding clause, further comprising:
  identifying at least one piece of information missing in the corpus of data for the patient using the cognified data, wherein the at least one piece of information pertains to a treatment gap, a risk gap, a quality of care gap, or some combination thereof; and
  causing a notification to be presented on a computing device of a healthcare personnel, wherein the notification instructs entry of the at least one piece of information.

Clause 109. The method of any preceding clause, wherein using the logical structure to identify the structural similarity of the indicia and the known predicate in the logical structure further comprises identifying, based on the structural similarity of the indicia and the known predicate in the logical structure, a treatment pattern, a referral pattern, a quality of care pattern, a risk adjustment pattern, or some combination thereof in the corpus of data.

Clause 110. The method of any preceding clause, further comprising:
  receiving feedback pertaining to whether the cognified data is accurate; and
  updating the artificial intelligence engine based on the feedback.

Clause 111. The method of any preceding clause, a tangible, non-transitory computer-readable medium storing instructions that, when executed, cause a processing device to execute an artificial intelligence engine to:
  receive a corpus of data for a patient, wherein the corpus of data includes a plurality of strings of characters;
  identify, in the plurality of strings of characters, indicia comprising a phrase, a predicate, a keyword, a cardinal, a number, a concept, or some combination thereof;
  compare the indicia to a knowledge graph representing known health related information to generate a possible health related information pertaining to the patient;
  identify, using a logical structure, a structural similarity of the indicia and a known predicate in the logical structure; and
  generate cognified data based on the similarity and the possible health related information.

Clause 112. The computer-readable medium of any preceding clause, wherein the artificial intelligence engine is further to generate the knowledge graph using the known health related information, wherein the knowledge graph represents knowledge of a disease and the knowledge graph comprises a plurality of concepts pertaining to the disease obtained from the known health related information, and the knowledge graph comprises relationships between the plurality of concepts.

Clause 113. The computer-readable medium of any preceding clause, wherein the cognified data comprises a health related summary of the possible health related information.

Clause 114. The computer-readable medium of any preceding clause, wherein generating, based on the pattern, the cognified data further comprises:
  generating at least one new string of characters representing a statement pertaining to the possible health related information; and
  including the at least one new string of characters in the health related summary of the possible health related information.

Clause 115. The computer-readable medium of any preceding clause, wherein the statement describes an effect that results from the possible health related information Clause 116. The computer-readable medium of any preceding clause, wherein the artificial intelligence engine is further to codify evidence based health related guidelines pertaining to a disease to generate the logical structure.

Clause 117. The computer-readable medium of any preceding clause, wherein the artificial intelligence engine is further to:
  identify at least one piece of information missing in the corpus of data for the patient using the cognified data, wherein the at least one piece of information pertains to a treatment gap, a risk gap, a quality of care gap, or some combination thereof; and
  cause a notification to be presented on a computing device of a healthcare personnel, wherein the notification instructs entry of the at least one piece of information.

Clause 118. The computer-readable medium of any preceding clause, wherein using the logical structure to identify the structural similarity of the indicia and the known predicate in the logical structure further comprises identifying, based on the structural similarity of the indicia and the known predicate in the logical structure, a treatment pattern, a referral pattern, a quality of care pattern, a risk adjustment pattern, or some combination thereof in the corpus of data.

Clause 119. The computer-readable medium of any preceding clause, wherein the artificial intelligence engine is further to:
  receive feedback pertaining to whether the cognified data is accurate; and
  update the artificial intelligence engine based on the feedback.

Clause 120. a system, comprising:
a memory device storing instructions; and
a processing device operatively coupled to the memory device, wherein the processing device executes the instructions to:
receive, at an artificial intelligence engine, a corpus of data for a patient, wherein the corpus of data includes a plurality of strings of characters;
identify, in the plurality of strings of characters, indicia comprising a phrase, a predicate, a keyword, a cardinal, a number, a concept, or some combination thereof;
compare the indicia to a knowledge graph representing known health related information to generate a possible health related information pertaining to the patient;
identify, using a logical structure, a structural similarity of the indicia and a known predicate in the logical structure; and generate, by the artificial intelligence engine, cognified data based on the similarity and the possible health related information.

Clause 121. The system of any preceding claim, wherein the processing device is further to:
- receive feedback pertaining to whether the cognified data is accurate; and
- update the artificial intelligence engine based on the feedback.

Clause 122. A method for controlling distribution of a plurality of information pertaining to a medical condition, the method comprising:
- receiving, at a server, an electronic medical record comprising notes pertaining to a patient;
- processing the notes to obtain indicia comprising a word, a cardinal, a phrase, a sentence, a predicate, or some combination thereof;
- identifying a possible medical condition of the patient by identifying a similarity between the indicia and a knowledge graph representing knowledge pertaining to the possible medical condition, wherein the knowledge graph comprises a plurality of nodes representing the plurality of information pertaining to the possible medical condition; and
- providing, at a first time, first information of the plurality of information to a computing device of the patient for presentation on the computing device, the first information being associated with a root node of the plurality of nodes.

Clause 123. The method of any preceding claim, further comprising providing, at a second time, second information of the plurality of information to the computing device of the patient for presentation on the computing device, the second information being associated with a second node of the plurality of nodes, and the second time being after the first time.

Clause 124. The method of any preceding claim, wherein the second information pertains to how the possible medical condition affects people, signs and symptoms of the possible medical condition, a way to treat the possible medical condition, a progression of the possible medical condition, or some combination thereof.

Clause 125. The method of any preceding claim, wherein the second time is selected based on when the second information is relevant to a stage of the possible medical condition.

Clause 126. The method of any preceding claim, further comprising providing, at a third time, third information of the plurality of information to the computing device of the patient for presentation on the computing device, the third information being associated with a third node of the plurality of nodes, and the third time being after the second time.

Clause 127. The method of any preceding claim, wherein identifying the possible medical condition by identifying the similarity between the indicia and the knowledge graph further comprises using an artificial intelligence engine that is trained using feedback from medical personnel, wherein the feedback pertains to whether output regarding possible medical conditions from the artificial intelligence engine is accurate for input comprising notes of patients.

Clause 128. The method of any preceding claim, wherein the first information pertains to a name of the possible medical condition, a definition of the possible medical condition, or some combination thereof.

Clause 129. The method of any preceding claim, wherein identifying the possible medical condition by identifying the similarity between the indicia and the knowledge graph further comprises using a cognified data structure generated from the notes of the patient, wherein the cognified data structure includes a conclusion based on a logical structure representing codified evidence based guidelines pertaining to the possible medical condition.

Clause 130. The method of any preceding claim, wherein processing the patient notes to obtain the indicia further comprises inputting the notes into an artificial intelligence engine trained to identify the indicia in text based on commonly used indicia pertaining to the possible medical condition.

Clause 131. The method of any preceding claim, further comprising:
- identifying a second possible medical condition of the patient by identifying a second similarity between the indicia and a second knowledge graph representing second knowledge pertaining to the second possible medical condition, wherein the second knowledge graph comprises a second plurality of nodes representing a second plurality of information pertaining to the second possible medical condition; and
- providing, at the first time, second information of the second plurality of information to the computing device of the patient for presentation on the computing device, the second information being associated with a second root node of the second plurality of nodes.

Clause 132. A tangible, non-transitory computer-readable medium storing instructions that, when executed, cause a processing device to:
- receive an electronic medical record comprising notes pertaining to a patient;
- process the notes to obtain indicia comprising a word, a cardinal, a phrase, a sentence, a predicate, or some combination thereof;
- identify a possible medical condition of the patient by identifying a similarity between the indicia and a knowledge graph representing knowledge pertaining to the possible medical condition, wherein the knowledge graph comprises a plurality of nodes representing the plurality of information pertaining to the possible medical condition; and
- provide, at a first time, first information of the plurality of information to a computing device of the patient for presentation on the computing device, the first information being associated with a root node of the plurality of nodes.

Clause 133. The computer-readable medium of any preceding clause, wherein the processing device is further to provide, at a second time, second information of the plurality of information to the computing device of the patient for presentation on the computing device, the second information being associated with a second node of the plurality of nodes, and the second time being after the first time.

Clause 134. The computer-readable medium of any preceding clause, wherein the second information pertains to how the possible medical condition affects people, signs and symptoms of the possible medical condition, a way to treat the possible medical condition, a progression of the possible medical condition, or some combination thereof.

Clause 135. The computer-readable medium of any preceding clause, wherein the second time is selected based on when the second information is relevant to a stage of the possible medical condition.

Clause 136. The computer-readable medium of any preceding clause, further comprising providing, at a third time, third information of the plurality of information to the computing device of the patient for presentation on the computing device, the third information being associated with a third node of the plurality of nodes, and the third time being after the second time.

Clause 137. The computer-readable medium of any preceding clause, wherein detecting the possible medical condition by identifying the similarity between the indicia and the knowledge graph further comprises using an artificial intelligence engine that is trained using feedback from medical personnel, wherein the feedback pertains to whether output regarding possible medical conditions from the artificial intelligence engine is accurate.

Clause 138. The computer-readable medium of any preceding clause, wherein the first information pertains to a name of the possible medical condition, a definition of the possible medical condition, or some combination thereof.

Clause 139. The computer-readable medium of any preceding clause, wherein detecting the possible medical condition by identifying the similarity between the indicia and the knowledge graph further comprises using a cognified data structure generated from the notes of the patient, wherein the cognified data structure includes a conclusion about the predicate that is identified in a logic structure representing codified evidence based guidelines pertaining to the possible medical condition.

Clause 140. The computer-readable medium of any preceding clause, wherein processing the patient notes to obtain the indicia further comprises inputting the notes into an artificial intelligence engine trained to identify the indicia in text based on commonly used indicia pertaining to the possible medical condition.

Clause 141. a system, comprising:
a memory device storing instructions;
a processing device communicatively coupled to the memory device, the processing device executes the instructions to:
  receive, at a server, an electronic medical record comprising notes pertaining to a patient;
  process the notes to obtain indicia comprising a word, a cardinal, a phrase, a sentence, a predicate, or some combination thereof;
  identify a possible medical condition of the patient by identifying a similarity between the indicia and a knowledge graph representing knowledge pertaining to the possible medical condition, wherein the knowledge graph comprises a plurality of nodes representing the plurality of information pertaining to the possible medical condition; and
  provide, at a first time, first information of the plurality of information to a computing device of the patient for presentation on the computing device, the first information being associated with a root node of the plurality of nodes.

Clause 142. A method for diagnosing a medical condition through cognification of unstructured data, the method comprising:
receiving, at a server, an electronic medical record comprising notes pertaining to a patient;
generating cognified data using the notes, wherein the cognified data comprises a health summary of the medical condition;
generating, based on the cognified data, a diagnosis of the medical condition of the patient, wherein the diagnosis at least identifies a type of the medical condition; and
providing the diagnosis to a computing device for presentation on the computing device.

Clause 143. The method of any preceding clause, further comprising identifying, in the notes, indicia comprising a phrase, a predicate, a keyword, a cardinal, a number, a concept, or some combination thereof;

Clause 144. The method of any preceding clause, wherein generating the cognified data further comprises detecting the medical condition by identifying a similarity between the indicia and a knowledge graph.

Clause 145. The method of any preceding clause, further comprising using an artificial intelligence engine that is trained using feedback from medical personnel, wherein the feedback pertains to whether output regarding diagnoses from the artificial intelligence engine are accurate for input comprising notes of patients.

Clause 146. The method of any preceding clause, wherein the cognified data includes a conclusion that is identified based on a logic structure representing codified evidence based guidelines pertaining to the medical condition.

Clause 147. The method of any preceding clause, further comprising processing the notes to obtain indicia by inputting the notes into an artificial intelligence engine trained to identify the indicia in text based on commonly used indicia pertaining to the medical condition.

Clause 148. The method of any preceding clause, wherein generating the diagnosis further comprises:
determining a stage of the medical condition based on the cognified data; and
including the stage of the medical condition in the diagnosis.

Clause 149. The method of any preceding clause, further comprising:
determining a severity of the medical condition based on the stage and the type of the medical condition;
in response to the severity satisfying a threshold condition, providing a recommendation to seek immediate medical attention to a computing device of the patient.

Clause 150. A tangible, non-transitory computer-readable medium storing instructions that, when executed, cause a processing device to:
receive, at a server, an electronic medical record comprising notes pertaining to a patient;
generate cognified data using the notes, wherein the cognified data comprises a health summary of the medical condition;
generate, based on the cognified data, a diagnosis of the medical condition of the patient, wherein the diagnosis at least identifies a type of the medical condition; and
provide the diagnosis to a computing device for presentation on the computing device.

Clause 151. The computer-readable medium of any preceding clause, wherein the processing device is further to identify, in the notes, indicia comprising a phrase, a predicate, a keyword, a cardinal, a number, a concept, or some combination thereof;

Clause 152. The computer-readable medium of any preceding clause, wherein generating the cognified data further comprises detecting the medical condition by identifying a similarity between the indicia and a knowledge graph.

Clause 153. The computer-readable medium of any preceding clause, wherein the processing device is further to use an artificial intelligence engine that is trained using feedback from medical personnel, wherein the feedback pertains to whether output regarding diagnoses from the artificial intelligence engine are accurate for input comprising notes of patients.

Clause 154. The computer-readable medium of any preceding clause, wherein the cognified data includes a conclusion about a predicate in the notes that is identified in a logic structure representing codified evidence based guidelines pertaining to the medical condition.

Clause 155. The computer-readable medium of any preceding clause, wherein the processing device is further to process the patient notes to obtain indicia by inputting the notes into an artificial intelligence engine trained to identify the indicia in text based on commonly used indicia pertaining to the medical condition.

Clause 156. The computer-readable medium of any preceding clause, wherein generating the diagnosis further comprises:
  determining a stage of the medical condition based on the cognified data; and
  including the stage of the medical condition in the diagnosis.

Clause 157. The computer-readable medium of any preceding clause, wherein the processing device is further to:
  determine a severity of the medical condition based on the stage and the type of the medical condition;
  in response to the severity satisfying a threshold condition, provide a recommendation to seek immediate medical attention to a computing device of the patient.

Clause 158. A system, comprising:
  a memory device storing instructions; and
  a processing device communicatively coupled to the memory device, the processing device executes the instructions to:
    receive, at a server, an electronic medical record comprising notes pertaining to a patient;
    generate cognified data using the notes, wherein the cognified data comprises a health summary of the medical condition;
    generate, based on the cognified data, a diagnosis of the medical condition of the patient, wherein the diagnosis at least identifies a type of the medical condition; and
    provide the diagnosis to a computing device for presentation on the computing device.

Clause 159. The system of any preceding clause, wherein the processing device is further to identify, in the notes, indicia comprising a phrase, a predicate, a keyword, a cardinal, a number, a concept, or some combination thereof;

Clause 160. The system of any preceding clause, wherein generating the cognified data further comprises detecting the medical condition by identifying a similarity between the indicia and a knowledge graph.

Clause 161. The system of any preceding clause, wherein the processing device is further to use an artificial intelligence engine that is trained using feedback from medical personnel, wherein the feedback pertains to whether output regarding diagnoses from the artificial intelligence engine are accurate for input comprising notes of patients.

Clause 162. A method for a processing device executing an autonomous multipurpose application, comprising:
  obtaining a plurality of schedules for people having a specialty;
  determining whether a user has elected to enable electronic scheduling; and
  responsive to determining the user has elected to enable electronic scheduling:
    determining which person of the plurality of people has an available appointment based on the plurality of schedules;
    transmitting a request to book the available appointment for the person to provide a service to the user;
    receiving a response indicating the available appointment is booked as a booked appointment between the person and the user; and
    providing a notification pertaining to the booked appointment.

Clause 163. The method of any preceding clause, further comprising:
  obtaining an image of an insurance card of the user;
  processing the image to extract information pertaining to an insurance plan of the user;
  determining, based on the insurance plan, an expected payment that the user will pay for the service in view of a deductible specified in the insurance plan.

Clause 164. The method of any preceding clause, further comprising:
  determining, without considering the insurance plan, a self-pay cost the user is expected to pay for the service;
  selecting to pay using the insurance plan of the user when the expected payment is less than the self-pay cost; and
  selecting to pay without using the insurance plan of the user when the self-pay cost is less than the expected payment.

Clause 165. The method of any preceding clause, wherein determining which person of the plurality of people has the available appointment is further based on the available appointment having a future date and time that is closest to a current date and time the request was received.

Clause 166. The method of any preceding clause, further comprising:
  determining an expected payment that the user will pay for the service in view of a deductible specified in an insurance plan of the user;
  determining, without considering the insurance plan, a self-pay cost the user is expected to pay for the treatment without using the insurance plan;
  causing the expected payment, the co-pay cost, or some combination thereof to be presented on a computing device of the user, a computing device of an administrator, a computing device of the person, or some combination thereof.

Clause 167. The method of any preceding clause, wherein the processing device executing the autonomous multipurpose application obtains the plurality of schedules for the plurality of people having the specialty from at least an electronic medical record system.

Clause 168. The method of any preceding clause, wherein the obtaining the plurality of schedules for the plurality of people having the specialty further comprises obtaining the plurality of schedules for the plurality of people within a geographic radius of a location of the user.

Clause 169. The method of any preceding clause, further comprising:
  providing the notification pertaining to the booked appointment to a computing device of the user, a computing device of an administrator, a computing device of the person, or some combination thereof.

Clause 170 The method of any preceding clause, further comprising:
  receiving a selection of the specialty from a plurality of specialties comprising at least two of a dentist, a medical doctor, an optometrist, a behavioral psychologist, a chiropractor, and a physician assistant.

Clause 171. The method of any preceding clause, further comprising:
  determining, using a machine learning model, an estimated wait time based on an average amount of time it takes people having the specialty to perform the service for users; and
  providing the estimated wait time to the computing device of the user for presentation on a user interface of the computing device of the user.

Clause 172. The method of any preceding clause, further comprising:
  responsive to determining the user has not elected to enable electronic scheduling:
  determining which person of the plurality of people has an available appointment based on the plurality of schedules; and
  providing a notification pertaining to the person having the available appointment to a computing device of the user, wherein the notification comprises a recommended date and time for the available appointment.

Clause 173. The method of any preceding clause, further comprising:
  determining which documents the user has to complete for the booked appointment;
  determining whether the user has completed the documents;
  responsive to determining the user has completed the documents, providing one or more references pertaining to a condition associated with the service; and
  responsive to determining the user has not completed the documents:
  electronically filling in fields with any information the user has already provided for the documents; and
  causing the documents with the electronically filled in fields to be presented on a computing device of the user for further completion.

Clause 174. The method of any preceding clause, further comprising:
  providing, to a computing device of the user, curated content tailored to a condition associated with the service the person is going to provide to the user during the booked appointment.

Clause 175. The method of any preceding clause, further comprising:
  responsive to determining the user has not elected to enable electronic scheduling:
  determining which people of the plurality of people have available appointments based on the plurality of schedules; and
  recommending the available appointments to a computing device of the user, wherein at least two of the people associated with the available appointments provide the service at different locations.

Clause 176. A tangible, non-transitory computer-readable medium storing instructions that, when executed, cause a processing device to execute an autonomous multipurpose application to:
  receive an appointment request for a person to provide a service to a user;
  determine an expected payment that the user will pay for the service in view of a deductible specified in an insurance plan associated with the user;
  determine, without considering the insurance plan, a self-pay cost the user is expected to pay for the service; and
  cause the expected payment, the self-pay cost, or some combination thereof to be presented on a computing device of the user, a computing device of an administrator, a computing device of the person, or some combination thereof.

Clause 177. The computer-readable medium of any preceding clause, wherein the processing device is further to receive a selection to schedule the appointment based on the co-pay cost or the self-pay cost.

Clause 178. The computer-readable medium of any preceding clause, wherein the user is a dependent of a primary holder of the insurance plan.

Clause 179. The computer-readable medium of any preceding clause, wherein the processing device is further to:
  obtain a schedule for the person;
  determine whether the user has elected to enable electronic scheduling; and
  responsive to determining the user has elected to enable electronic scheduling:
  determine an available appointment based on the schedule;
  transmit a request to book the available appointment for the person to provide the service to the user;
  receive a response indicating the available appointment is booked as a booked appointment between the person and the user; and
  provide a notification pertaining to the booked appointment.

Clause 180. The computer-readable medium of any preceding clause, wherein the processing device is further to:
  check-in a user for the appointment;
  determine, using a machine learning model, an estimated wait time based on an average amount of time it takes people to perform the service for users; and
  provide the estimated wait time to the computing device of the user for presentation on a user interface of the computing device of the user.

Clause 181. A system, comprising:
  a memory storing instructions that implement an autonomous multipurpose application; and
  a processing device communicatively coupled to the memory, the processing device capable of executing the autonomous multipurpose application to:
  check-in a user for a scheduled appointment with a person having a specialty to perform a service;
  determine, using a machine learning model, an estimated wait time based on an average amount of time it takes people having the specialty to perform the service for users; and
  provide the estimated wait time to a computing device of the user for presentation on a user interface of the computing device of the user.

Clause 182. The system of any preceding clause, wherein the processing device is further to:
  determine which documents the user is required to complete for the scheduled appointment;
  determine whether the user has completed the documents;
  responsive to determining the user has completed the documents, provide curated content pertaining to a condition associated with the service; and
  responsive to determining the user has not completed the documents:
  electronically fill fields with any information the user has already provided for the documents; and
  cause the documents with the electronically filled in fields to be presented on a computing device of the user for further completion of fields missing information.

Clause 183. The system of any preceding clause, wherein the processing device is further to provide curated content tailored for the user based on the service, the specialty, a condition pertaining to the service, other conditions associated with the user, or some combination thereof.

Clause 184. The system of any preceding clause, wherein the processing device is further to maintain documents for the user and a dependent of the user and provide the documents to any requesting client device, wherein the documents comprise medical history, consent forms, medical records, or some combination thereof, and the requesting client device comprises an electronic medical record system.

Clause 185. The system of any preceding clause, wherein, prior to the scheduled appointment being scheduled, the processing device is further to:
   obtain a schedule for the person;
   determine whether the user has elected to enable electronic scheduling; and
   responsive to determining the user has elected to enable electronic scheduling:
      determine an available appointment based on the schedule;
      transmit a request to schedule the available appointment for the person to provide the service to the user;
      receive a response indicating the available appointment is booked as the scheduled appointment between the person and the user; and
      provide a notification pertaining to the scheduled appointment.

Clause 186. The system of any preceding clause, wherein, prior to the scheduled appointment being scheduled, the processing device is further to:
   receive an appointment request for the person to provide a service to the user;
   determine an expected payment that the user will pay for the service in view of a deductible specified in an insurance plan associated with the user;
   determine, without considering insurance plan, a self-pay cost the user is expected to pay for the service;
   causing the expected payment, the self-pay pocket cost, or some combination thereof to be presented on a computing device of the user, a computing device of an administrator, a computing device of the person, or some combination thereof.

Clause 187. A method, comprising:
maintaining a set of check-in documents for a user;
receiving, from a computing device, a plurality of requests to check-in the user for a plurality of scheduled appointments where a plurality of people each having a different respective specialty of a plurality of specialties are to provide a different respective service to the user;
determining respective subsets of the set of check-in documents that are required to be complete for each of the different respective specialty of each of the plurality of people; and
transmitting each of the respective subsets of the set of check-in documents to a plurality of computing devices each associated with each of the different respective specialty, wherein the respective subsets are cryptographically signed.

Clause 188. The method of any preceding clause, further comprising, for each of the plurality of scheduled appointments, determining whether check-in requirements are satisfied, wherein the check-in requirements are satisfied when required information in each of the respective subsets of the set of check-in documents has already been provided.

Clause 189. The method of any preceding clause, further comprising:
   responsive to determining the check-in requirements for one of the plurality of scheduled appointments is not satisfied because one of the respective subsets of the set of check-in documents is lacking a portion of the required information, cause the computing device to present a notification that the portion of the required information is lacking;
   receiving the portion of the required information;
   updating the one of the respective subsets of the set of check-in documents with the portion of the required information; and
   checking-in the user for the one of the plurality of scheduled appointments.

Clause 190. The method of any preceding clause, further comprising:
   responsive to determining the check-in requirements for one of the plurality of scheduled appointments is satisfied, checking-in the user for the one of the scheduled appointments.

Clause 191. The method of any preceding clause, further comprising:
   updating the set of check-in documents based on input from the user, input from the plurality of people, output from a machine learning model trained to determine when certain information needs to be updated, information obtained from a third-party source, or some combination thereof.

Clause 192. The method of any preceding clause, wherein the plurality of specialties comprises a medical doctor, a dentist, an optometrist, a physician's assistant, a chiropractor, an orthodontist, a behavioral specialist, a therapist, a masseuse, a physical therapist, or some combination thereof.

Clause 193. The method of any preceding clause, wherein the plurality of requests are received over a period of time and each of the plurality of scheduled appointments are scheduled at different dates, times, or both.

Clause 194. The method of any preceding clause, further comprising:
   checking-in the user for one of the plurality of scheduled appointments with a person having a specialty to provide a service to the user;
   determining, using a machine learning model, an estimated wait time based on an average amount of time it takes people having the specialty to perform the service for users; and
   providing the estimated wait time to a computing device of the user for presentation on a user interface of the computing device of the user.

Clause 195. The method of any preceding clause, further comprising, prior to scheduling one of the plurality of scheduled appointments:
   obtaining a schedule for a person having the different respective specialty associated with the one of the plurality of scheduled appointments;
   determining whether the user has elected to enable electronic scheduling; and
   responsive to determining the user has elected to enable electronic scheduling:
      determining an available appointment based on the schedule;
      transmitting a request to book the one of the plurality of scheduled appointments for the person to provide the different respective service to the user;
      receiving a response indicating the one of the plurality of scheduled appointments is booked as a booked appointment between the person and the user; and providing a notification pertaining to the booked appointment.

Clause 196. The method of any preceding clause, further comprising, prior to scheduling one of the plurality of scheduled appointments:
receiving an appointment request for a person to provide a service to the user;
determine an expected payment that the user will pay for the service in view of a deductible specified in an insurance plan associated with the user;
determining, without considering the insurance plan, a self-pay cost the user is expected to pay for the service; and
causing the expected payment, the self-pay cost, or some combination thereof to be presented on a computing device of the user, a computing device of an administrator, a computing device of the person, or some combination thereof.

Clause 197. A method for operating a clinic viewer on a computing device of a medical personnel, the method comprising:
receiving a reason that a patient scheduled an appointment with the medical personnel;
receiving a condition diagnosed for the patient and a care plan generated for the condition, wherein the care plan is generated by an artificial intelligence engine of a cognitive intelligence platform; and
presenting, on the clinic viewer, the care plan and a watch-list comprising the reason, the condition, or some combination thereof.

Clause 198. The method of any preceding clause, further comprising:
receiving patient notes entered by the medical personnel, wherein the patient notes pertain to a symptom of the patient, a vital sign of the patient, a characteristic of the patient, a diagnosis for the patient, or some combination thereof; and
transmitting the patient notes to cause a data structure pertaining to the patient to be updated at the cognitive intelligence platform.

Clause 199. The method of any preceding clause, further comprising:
receiving a quality alert based on information about the patient, wherein the quality alert is based on an evidence-based guideline for the condition; and
presenting the quality alert on the clinic viewer.

Clause 200. The method of any preceding clause, wherein the quality alert comprises a recommendation for the medical personnel to refer the patient to another medical personnel, and the method further comprises:
receiving a selection to refer the patient to the another medical personnel;
transmitting a medical record of the patient to a system of the another medical personnel; and
electronically scheduling a second appointment with the another medical personnel for the patient.

Clause 201. The method of any preceding clause, further comprising:
receiving a note pertaining to the patient, wherein the note comprises an action instruction for the medical personnel to follow when providing a service to the patient, and the action instruction is generated by the artificial intelligence engine based on information about the patient; and
presenting the note on the clinic viewer.

Clause 202. The method any preceding clause, wherein the care plan is generated based on a knowledge graph pertaining to the condition and information pertaining to the patient, and the information comprises any action the patient has performed pertaining to the condition.

Clause 203. The method any preceding clause, further comprising:
receiving information comprising a medication the patient is taking;
receiving a notification that the medication is incompatible with a second medication for the condition, wherein the notification is generated by the artificial intelligence engine based on a knowledge graph pertaining to the condition; and
presenting the information and the notification on the clinic viewer.

Clause 204. The method any preceding clause, wherein the care plan comprises an action instruction for the medical personnel to perform when providing a service to treat the reason, the condition, or both, and the action instruction is generated based on the reason, the condition, or both by the artificial intelligence engine, and the method further comprises:
presenting the action instruction on the clinic viewer.

Clause 205. The method any preceding clause, further comprising:
receiving a quality of care recommendation based on the reason, the condition, or both, and an evidence trail of reasoning for why the quality of care recommendation was provided; and
presenting the quality of care recommendation and the evidence trail.

Clause 206. The method any preceding clause, further comprising:
receiving recommended curated content pertaining to the condition of the patient; and
presenting the recommended curated content in the clinic viewer.

Clause 207. A tangible, non-transitory computer-readable medium storing instructions that, when executed, cause a processing device to execute a clinic viewer to:
receive a reason that a patient scheduled an appointment with a medical personnel;
receive a condition diagnosed for the patient and a care plan generated for the condition, wherein the care plan is generated by an artificial intelligence engine of a cognitive intelligence platform; and
present, on a computing device comprising the processing device, the care plan and a watch-list comprising the reason, the condition, or some combination thereof.

Clause 208. The computer-readable medium any preceding clause, wherein the processing device is further to:
receive patient notes entered by the medical personnel, wherein the patient notes pertain to a symptom of the patient, a vital sign of the patient, a characteristic of the patient, a diagnosis for the patient, or some combination thereof; and
transmit the patient notes to cause a data structure pertaining to the patient to be updated at the cognitive intelligence platform.

Clause 209. The computer-readable medium any preceding clause, wherein the processing device is further to:
receive a quality alert based on information about the patient, wherein the quality alert is based on an evidence-based guideline for the condition; and
present the quality alert on the clinic viewer.

Clause 210. The computer-readable medium any preceding clause, wherein the quality alert comprises a recommendation for the medical personnel to refer the patient to another medical personnel, and the processing device is further to:
　　receive a selection to refer the patient to the another medical personnel;
　　transmit a medical record of the patient to a system of the another medical personnel; and
　　electronically schedule a second appointment with the another medical personnel for the patient.

Clause 211. The computer-readable medium any preceding clause, wherein the processing device is further to:
　　receive a note pertaining to the patient, wherein the note comprises an action instruction for the medical personnel to follow when providing a service to the patient, and the action instruction is generated by the artificial intelligence engine based on information about the patient; and
　　present the note on the clinic viewer.

Clause 212. The computer-readable medium any preceding clause, wherein the care plan is generated based on a knowledge graph pertaining to the condition and information pertaining to the patient, and the information comprises any action the patient has performed pertaining to the condition.

Clause 213. The computer-readable medium any preceding clause, wherein the processing device is further to:
　　receive information comprising a medication the patient is taking;
　　receive a notification that the medication is incompatible with a second medication for the condition, wherein the notification is generated by the artificial intelligence engine based on a knowledge graph pertaining to the condition; and
　　present the information and the notification on the clinic viewer.

Clause 214. The computer-readable medium any preceding clause, wherein the care plan comprises an action instruction for the medical personnel to perform when providing a service to treat the reason, the condition, or both, and the action instruction is generated based on the reason, the condition, or both by the artificial intelligence engine, and the processing device is further to:
　　present the action instruction the clinic viewer.

Clause 215. The computer-readable medium any preceding clause, wherein the processing device is further to:
　　receive a quality of care recommendation based on the reason, the condition, or both, and an evidence trail of reasoning for why the quality of care recommendation was provided; and
　　present the quality of care recommendation and the evidence trail.

Clause 216. A system for operating a clinic viewer, comprising:
　　a memory device containing stored instructions;
　　a processing device communicatively coupled to the memory device, wherein the processing device executes the stored instructions to:
　　receive a reason that a patient scheduled an appointment with a medical personnel;
　　receive a condition diagnosed for the patient and a care plan generated for the condition, wherein the care plan is generated by an artificial intelligence engine of a cognitive intelligence platform; and
　　present, on the clinic viewer, the care plan and a watch-list comprising the reason, the condition, or some combination thereof.

Clause 217. A method comprising operations performed by a cognitive intelligence platform, the operations comprising:
　　receiving, from a user computing device, image data of an object;
　　processing the image data to extract data pertaining to the object, wherein the data comprises text, an image, or some combination thereof;
　　identifying a data structure comprising health information pertaining to a user operating the user computing device, wherein the data structure is stored in a knowledge cloud of the cognitive intelligence platform;
　　populating a parameter in the data structure with the data; and
　　causing, using the parameter, a field to be populated on a user interface presented on the user computing device.

Clause 218. The method any preceding clause, further comprising:
　　determining, via an artificial intelligence engine of the cognitive intelligence platform, an action instruction for the user based on the data, wherein the action instruction is presented on the user computing device.

Clause 219. The method any preceding clause, further comprising:
　　determining, via an artificial intelligence engine of the cognitive intelligence platform, an action instruction for the user based on the data, wherein the action instruction is presented on the user computing device.

Clause 220. The method any preceding clause, further comprising:
　　determining, via an artificial intelligence engine of the cognitive intelligence platform, an action instruction for the user based on the data, wherein the action instruction is presented on the user computing device.

Clause 221. The method any preceding clause, wherein the object comprises a health insurance card and the data comprises insurance plan information, and the action instruction specifies updating an insurance plan based on an expiration date in the insurance plan information.

Clause 222. The method any preceding clause, further comprising comparing the data to a data structure comprising ontological data of a medical condition diagnosed for the user and the data structure comprising health information pertaining to the user, wherein the action instruction comprises a recommended action for the user operating the user computing device to perform pertaining to the medical condition.

Clause 223. The method any preceding clause, further comprising:
　　determining whether any parameter in the data structure comprising the health information pertaining to the user is missing respective data; and
　　responsive to determining that at least one parameter is missing the respective data, causing a notification to be presented on the user interface.

Clause 224. The method any preceding clause, further comprising:
　　validating the data with a third-party system by transmitting the data to the third-party system;
　　receiving a response from the third-party system, wherein the response includes an indication of whether the data is valid;
　　responsive to determining that the data is invalid, causing a second notification to be presented in the user interface indicating invalidity of the data; and responsive to determining that the data is valid, causing a third notification to be presented on the user interface indicating validity of the data.

Clause 225. The method any preceding clause, wherein the object is a health insurance card that includes health insurance information pertaining to an insurance plan of a user, the data comprises the health insurance information, and the third-party system is operated by an insurance provider.

Clause 226. The method any preceding clause, wherein the response includes a first payment amount of a service based on the health insurance information of the insurance plan, and the method further comprises:
- transmitting a request to another third-party system operated by a care provider, wherein the request inquires about a second payment amount of the service without using the health insurance information of the insurance plan;
- receiving another response from the another third-party system, wherein the another response comprises the second payment amount; and
- causing the first payment amount and the second payment amount to be presented in the user interface of the user computing device.

Clause 227. The method any preceding clause, wherein the object is a driver license issued by a state organization, the data comprises driver license information, and the third-party system is operated by the state organization.

Clause 228. The method any preceding clause, further comprising:
- prior to receiving the image data, receiving a selection to subscribe to an API hosted by the cognitive intelligence platform, wherein the API implements the operations.

Clause 229. The method any preceding clause, wherein the processing the image data to extract the data further comprises using at least one technique selected from a group of techniques comprising optical character recognition, facial recognition, natural language processing, machine learning, and computer vision.

Clause 330. The method any preceding clause, further comprising storing the image as a profile picture for the user operating the user computing device.

Clause 331. A tangible, non-transitory computer-readable medium storing instructions that, when executed, cause a processing device to:
- receive, from a user computing device, image data of an object;
- process the image data to extract data pertaining to the object, wherein the data comprises text, an image, or some combination thereof;
- identify a data structure comprising health information pertaining to a user operating the user computing device, wherein the data structure is stored in a knowledge cloud of the cognitive intelligence platform;
- populate a parameter in the data structure with the data; and
- cause, using the parameter, a field to be populated on a user interface presented on the user computing device.

Clause 332. The computer-readable medium any preceding clause, wherein the processing device is further to:
- determine, via an artificial intelligence engine of the cognitive intelligence platform, an action instruction for the user based on the data, wherein the action instruction is presented on the user computing device.

Clause 333. The computer-readable medium any preceding clause, wherein the object comprises a health insurance card and the data comprises insurance plan information, and the action instruction specifies updating an insurance plan based on an expiration date in the insurance plan information.

Clause 334. The computer-readable medium any preceding clause, wherein the processing device is further to compare the data to a data structure comprising ontological data of a medical condition diagnosed for the user and the data structure comprising health information pertaining to the user, wherein the action instruction comprises a recommended action for the user operating the user computing device to perform pertaining to the medical condition.

Clause 335. The computer-readable medium any preceding clause, wherein the processing device is further to:
- determine whether any parameter in the data structure comprising the health information pertaining to the user is missing respective data; and
- responsive to determining that at least one parameter is missing the respective data, cause a notification to be presented on the user interface.

Clause 336. The computer-readable medium any preceding clause, wherein the processing device is further to:
- validate the data with a third-party system by transmitting the data to the third-party system;
- receive a response from the third-party system, wherein the response includes an indication of whether the data is valid;
- responsive to determining that the data is invalid, cause a second notification to be presented in the user interface indicating invalidity of the data; and
- responsive to determining that the data is valid, cause a third notification to be presented on the user interface indicating validity of the data.

Clause 337. The computer-readable medium any preceding clause, wherein the object is a health insurance card that includes health insurance information pertaining to an insurance plan of a user, the data comprises the health insurance information, and the third-party system is operated by an insurance provider.

Clause 338. A system comprising:
- a memory device storing instructions;
- a processing device communicatively coupled to the memory device, the
- processing device executes the instructions to:
- receive, from a user computing device, image data of an object;
- process the image data to extract data pertaining to the object, wherein the data
- comprises text, an image, or some combination thereof;
- identify a data structure comprising health information pertaining to a user
- operating the user computing device, wherein the data structure is stored in a knowledge
- cloud of the cognitive intelligence platform;
- populate a parameter in the data structure with the data; and
- cause, using the parameter, a field to be populated on a user interface presented
- on the user computing device.

Clause 339. The system any preceding clause, wherein the processing device is further to:
- validate the data with a third-party system by transmitting the data to the third-party system, wherein the object is a health insurance card that includes health insurance information pertaining to an insurance plan of a user, the data comprises the health insurance information, and the third-party system is operated by an insurance provider;

receive a response from the third-party system, wherein the response includes a first payment amount of a service based on the health insurance information of the insurance plan;

transmit a request to another third-party system operated by a care provider, wherein the request inquires about a second payment amount of the service without using the health insurance information of the insurance plan;

receive another response from the another third-party system, wherein the another response comprises the second payment amount; and cause the first payment amount and the second payment amount to be presented in the user interface of the user computing device.

Clause 340. A method for creating an autonomous multipurpose application using a platform of application programming interfaces (APIs), the method comprising:

publishing, for implementation in the autonomous multipurpose application, at least one API that uses artificial intelligence to perform analytics based on a knowledge graph pertaining to ontological data of a medical condition, wherein the at least one API is included in a set of APIs;

providing the at least one API in a user interface of a computing device;

receiving, from the computing device, a request to subscribe to the at least one API;

implementing computer instructions of the at least one API in the autonomous multipurpose application; and providing the autonomous multipurpose application to the computing device for execution on the computing device.

Clause 341. The method of any preceding clause, further comprising:

publishing the set of APIs; and providing the set of APIs in the user interface of the computing device, wherein the set of available APIs are arranged in categories of a clinical interoperability category, a value based care category, a geo sensing services category, an operational analytics category, a financial and billing category, an applications category, a configuration APIs category, a education category, or some combination thereof.

Clause 342. The method any preceding clause, wherein:

the clinical interoperability category comprises an electronic medical record and clinical systems API, a physical therapy systems API, a patient identity management API, or some combination thereof, the value based care analytics category comprises a risk stratification API, a quality of care API, a healthcare utilization API, a population health API, a P360 degrees API, or some combination thereof, the geo sensing services category comprises a geo coder API, a geo location API, or some combination thereof, the operational analytics category comprises a wait time API, an imaging API, a quick reference codes and recognition API, or some combination thereof, the applications category comprises a clinics API, a provider API, a patient API, a schedules API, a consents API, an acknowledgements API, a symptomology API, a health history API, a medicines and supplements API, an allergies API, an unified login API, or some combination thereof, the financial and billing category comprises a checkout API, a billing API, a payment API, an eligibility API, a claim submission API, or some combination thereof, the configuration APIs category comprises a clinics configuration API, a providers configuration API, an appointments API, a lookups API, or some combination thereof, and the education category comprises a search API, a lookups content API, or some combination thereof.

Clause 342. The method any preceding clause, further comprising:

providing an option to subscribe to the at least one API in the user interface of the computing device;

responsive to receiving a request to subscribe to the API, implementing the computer instructions of the API in the autonomous multipurpose application.

Clause 343. The method any preceding clause, wherein providing the autonomous multipurpose application further comprises deploying the autonomous multipurpose application as a website accessible by a web browser executing on the computing device, transmitting the autonomous multipurpose application for installation on the computing device, or both.

Clause 344 The method any preceding clause, further comprising:

providing an option in the user interface to select which programming language to use for implementing the computer instructions;

receiving a selection to convert the computer instructions from a first programming language in a set of programming languages to a second programming language in the set of programming languages; and converting the computer instructions implementing the API from the first programming language to the second programming language.

Clause 345. The method any preceding clause, wherein the platform of APIs represents an interoperability layer of a cognitive intelligence platform in healthcare.

Clause 346. A tangible, non-transitory computer-readable medium storing instructions for creating an autonomous multipurpose application using a platform of application programming interfaces (APIs), wherein execution of the instructions by a processing device causes the processing device to:

publish, for implementation in the autonomous multipurpose application, at least one API that uses artificial intelligence to perform analytics based on a knowledge graph pertaining to ontological data of a medical condition, wherein the at least one API is included in a set of APIs;

provide the at least one API in a user interface of a computing device;

receive, from the computing device, a request to subscribe to the at least one API;

implement computer instructions of the at least one API in the autonomous multipurpose application; and provide the autonomous multipurpose application to the computing device for execution on the computing device.

Clause 347. The computer-readable medium any preceding clause, wherein the processing device is further to:

publish the set of APIs; and provide the set of APIs in the user interface of the computing device, wherein the set of available APIs are arranged in categories of a clinical interoperability category, a value based care category, a geo sensing services category, an operational analytics category, a financial and billing category, an applications category, a configuration APIs category, a education category, or some combination thereof.

Clause 348. The computer-readable medium any preceding clause, wherein:
the clinical interoperability category comprises an electronic medical record and clinical systems API, a physical therapy systems API, a patient identity management API, or some combination thereof,
the value based care analytics category comprises a risk stratification API, a quality of care API, a healthcare utilization API, a population health API, a P360 degrees API, or some combination thereof,
the geo sensing services category comprises a geo coder API, a geo location API, or some combination thereof,
the operational analytics category comprises a wait time API, an imaging API, a quick reference codes and recognition API, or some combination thereof,
the applications category comprises a clinics API, a provider API, a patient API, a schedules API, a consents API, an acknowledgements API, a symptomology API, a health history API, a medicines and supplements API, an allergies API, an unified login API, or some combination thereof,
the financial and billing category comprises a checkout API, a billing API, a payment API, an eligibility API, a claim submission API, or some combination thereof,
the configuration APIs category comprises a clinics configuration API, a providers configuration API, an appointments API, a lookups API, or some combination thereof, and
the education category comprises a search API, a lookups content API, or some combination thereof.

Clause 349. The computer-readable medium any preceding clause, wherein the processing device is further to:
provide an option to subscribe to the at least one API in the user interface of the computing device;
responsive to receiving a request to subscribe to the API, implement the computer instructions of the API in the autonomous multipurpose application.

Clause 350. The computer-readable medium any preceding clause, wherein providing the autonomous multipurpose application further comprises deploying the autonomous multipurpose application as a website accessible by a web browser executing on the computing device, transmitting the autonomous multipurpose application for installation on the computing device, or both.

Clause 351. The computer-readable medium any preceding clause, wherein the processing device is further to:
provide an option in the user interface to select which programming language to use for implementing the computer instructions;
receive a selection to convert the computer instructions from a first programming language in a set of programming languages to a second programming language in the set of programming languages; and
convert the computer instructions implementing the API from the first programming language to the second programming language.

Clause 352. A method for creating an autonomous multipurpose application using a platform of application programming interfaces (APIs), the method comprising:
publishing, for implementation in the autonomous multipurpose application, at least one API that uses artificial intelligence to perform analytics based on a knowledge graph pertaining to ontological data of a medical condition, wherein the at least one API is included in a set of APIs;
providing the at least one API in a user interface of a computing device;
receiving, from the computing device, a request to subscribe to the at least one API;
implementing computer instructions of the at least one API in the autonomous multipurpose application; and
providing the autonomous multipurpose application to the computing device for execution on the computing device.

Clause 353. The computer-readable medium any preceding clause, wherein the platform of APIs represents an interoperability layer of a cognitive intelligence platform in healthcare.

Clause 354. A system comprising:
a memory device storing instructions for creating an autonomous multipurpose application using a platform of application programming interfaces (APIs);
a processing device communicatively coupled to the memory device, wherein the processing device executes the instructions to:
publish, for implementation in the autonomous multipurpose application, at least one API that uses artificial intelligence to perform analytics based on a knowledge graph pertaining to ontological data of a medical condition, wherein the at least one API is included in a set of APIs;
provide the at least one API in a user interface of a computing device;
receive, from the computing device, a request to subscribe to the at least one API;
implement computer instructions of the at least one API in the autonomous multipurpose application; and
provide the autonomous multipurpose application to the computing device for execution on the computing device.

Clause 355. The system any preceding clause, wherein the processing device is further to:
publish the set of APIs; and
provide the set of APIs in the user interface of the computing device, wherein the set of available APIs are arranged in categories of a clinical interoperability category, a value based care category, a geo sensing services category, an operational analytics category, a financial and billing category, an applications category, a configuration APIs category, a education category, or some combination thereof.

Clause 356. The system any preceding clause, wherein:
the clinical interoperability category comprises an electronic medical record and clinical systems API, a physical therapy systems API, a patient identity management API, or some combination thereof,
the value based care analytics category comprises a risk stratification API, a quality of care API, a healthcare utilization API, a population health API, a P360 degrees API, or some combination thereof,
the geo sensing services category comprises a geo coder API, a geo location API, or some combination thereof,
the operational analytics category comprises a wait time API, an imaging API, a quick reference codes and recognition API, or some combination thereof,
the applications category comprises a clinics API, a provider API, a patient API, a schedules API, a consents API, an acknowledgements API, a symptomology API, a health history API, a medicines and supplements API, an allergies API, an unified login API, or some combination thereof,
the financial and billing category comprises a checkout API, a billing API, a payment API, an eligibility API, a claim submission API, or some combination thereof, the configuration APIs category comprises a clinics configuration API, a providers configuration API, an appointments API, a lookups API, or some combination thereof, and the education category comprises a search API, a lookups content API, or some combination thereof.

Clause 357. The system any preceding clause, wherein the processing device is further to:

provide an option to subscribe to the at least one API in the user interface of the computing device;

responsive to receiving a request to subscribe to the API, implement the computer instructions of the API in the autonomous multipurpose application.

Clause 358. The system any preceding clause, wherein providing the autonomous multipurpose application further comprises deploying the autonomous multipurpose application as a website accessible by a web browser executing on the computing device, transmitting the autonomous multipurpose application for installation on the computing device, or both Clause 359. The system any preceding clause, wherein the processing device is further to:

provide an option in the user interface to select which programming language to use for implementing the computer instructions;

receive a selection to convert the computer instructions from a first programming language in a set of programming languages to a second programming language in the set of programming languages; and convert the computer instructions implementing the API from the first programming language to the second programming language.

The foregoing description, for purposes of explanation, used specific nomenclature to provide a thorough understanding of the described embodiments. However, it should be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method for creating an autonomous multipurpose application using a platform of application programming interfaces (APIs), the method comprising:

publishing, for implementation in the autonomous multipurpose application, at least one API that uses artificial intelligence to perform analytics based on a knowledge graph pertaining to ontological data of a medical condition, wherein the at least one API is included in a set of APIs;

providing the at least one API in a user interface of a computing device;

receiving, from the computing device, a request to subscribe to the at least one API;

responsive to receiving the request to subscribe to the at least one API, implementing computer instructions of the at least one API in the autonomous multipurpose application; and providing the autonomous multipurpose application to the computing device for execution on the computing device.

2. The method of claim 1, further comprising:

publishing the set of APIs; and providing the set of APIs in the user interface of the computing device, wherein the set of available APIs are arranged in categories of a clinical interoperability category, a value based care category, a geo sensing services category, an operational analytics category, a financial and billing category, an applications category, a configuration APIs category, an education category, or some combination thereof.

3. The method of claim 2, wherein:

the clinical interoperability category comprises an electronic medical record and clinical systems API, a physical therapy systems API, a patient identity management API, or some combination thereof, the value based care analytics category comprises a risk stratification API, a quality of care API, a healthcare utilization API, a population health API, or some combination thereof, the geo sensing services category comprises a geo coder API, a geo location API, or some combination thereof, the operational analytics category comprises a wait time API, an imaging API, a quick reference codes and recognition API, or some combination thereof, the applications category comprises a clinics API, a provider API, a patient API, a schedules API, a consents API, an acknowledgements API, a symptomology API, a health history API, a medicines and supplements API, an allergies API, an unified login API, or some combination thereof, the financial and billing category comprises a checkout API, a billing API, a payment API, an eligibility API, a claim submission API, or some combination thereof, the configuration APIs category comprises a clinics configuration API, a providers configuration API, an appointments API, a lookups API, or some combination thereof, and the education category comprises a search API, a lookups content API, or some combination thereof.

4. The method of claim 1, further comprising:

providing an option to subscribe to the at least one API in the user interface of the computing device;

responsive to receiving a request to subscribe to the API, implementing the computer instructions of the API in the autonomous multipurpose application.

5. The method of claim 1, wherein providing the autonomous multipurpose application further comprises deploying the autonomous multipurpose application as a website accessible by a web browser executing on the computing device, transmitting the autonomous multipurpose application for installation on the computing device, or both.

6. The method of claim 1, further comprising:

providing an option in the user interface to select which programming language to use for implementing the computer instructions;

receiving a selection to convert the computer instructions from a first programming language in a set of programming languages to a second programming language in the set of programming languages; and converting the computer instructions implementing the API from the first programming language to the second programming language.

7. The method of claim 1, wherein the platform of APIs represents an interoperability layer of a cognitive intelligence platform in healthcare.

8. A tangible, non-transitory computer-readable medium storing instructions for creating an autonomous multipurpose application using a platform of application programming interfaces (APIs), wherein execution of the instructions by a processing device causes the processing device to:
publish, for implementation in the autonomous multipurpose application, at least one API that uses artificial intelligence to perform analytics based on a knowledge graph pertaining to ontological data of a medical condition, wherein the at least one API is included in a set of APIs;
provide the at least one API in a user interface of a computing device;
receive, from the computing device, a request to subscribe to the at least one API;
responsive to receiving the request to subscribe to the at least one API, implement computer instructions of the at least one API in the autonomous multipurpose application; and
provide the autonomous multipurpose application to the computing device for execution on the computing device.

9. The computer-readable medium of claim 8, wherein the processing device is further to:
publish the set of APIs; and
provide the set of APIs in the user interface of the computing device, wherein the set of available APIs are arranged in categories of a clinical interoperability category, a value based care category, a geo sensing services category, an operational analytics category, a financial and billing category, an applications category, a configuration APIs category, an education category, or some combination thereof.

10. The computer-readable medium of claim 9, wherein:
the clinical interoperability category comprises an electronic medical record and clinical systems API, a physical therapy systems API, a patient identity management API, or some combination thereof,
the value based care analytics category comprises a risk stratification API, a quality of care API, a healthcare utilization API, a population health API, or some combination thereof,
the geo sensing services category comprises a geo coder API, a geo location API, or some combination thereof,
the operational analytics category comprises a wait time API, an imaging API, a quick reference codes and recognition API, or some combination thereof,
the applications category comprises a clinics API, a provider API, a patient API, a schedules API, a consents API, an acknowledgements API, a symptomology API, a health history API, a medicines and supplements API, an allergies API, an unified login API, or some combination thereof,
the financial and billing category comprises a checkout API, a billing API, a payment API, an eligibility API, a claim submission API, or some combination thereof,
the configuration APIs category comprises a clinics configuration API, a providers configuration API, an appointments API, a lookups API, or some combination thereof, and
the education category comprises a search API, a lookups content API, or some combination thereof.

11. The computer-readable medium of claim 8, wherein the processing device is further to:
provide an option to subscribe to the at least one API in the user interface of the computing device;
responsive to receiving a request to subscribe to the API, implement the computer instructions of the API in the autonomous multipurpose application.

12. The computer-readable medium of claim 8, wherein providing the autonomous multipurpose application further comprises deploying the autonomous multipurpose application as a website accessible by a web browser executing on the computing device, transmitting the autonomous multipurpose application for installation on the computing device, or both.

13. The computer-readable medium of claim 8, wherein the processing device is further to:
provide an option in the user interface to select which programming language to use for implementing the computer instructions;
receive a selection to convert the computer instructions from a first programming language in a set of programming languages to a second programming language in the set of programming languages; and
convert the computer instructions implementing the API from the first programming language to the second programming language.

14. The computer-readable medium of claim 8, wherein the platform of APIs represents an interoperability layer of a cognitive intelligence platform in healthcare.

15. A system comprising:
a memory device storing instructions for creating an autonomous multipurpose application using a platform of application programming interfaces (APIs);
a processing device communicatively coupled to the memory device, wherein the processing device executes the instructions to:
publish, for implementation in the autonomous multipurpose application, at least one API that uses artificial intelligence to perform analytics based on a knowledge graph pertaining to ontological data of a medical condition, wherein the at least one API is included in a set of APIs;
provide the at least one API in a user interface of a computing device;
receive, from the computing device, a request to subscribe to the at least one API;
responsive to receiving the request to subscribe to the at least one API, implement computer instructions of the at least one API in the autonomous multipurpose application; and
provide the autonomous multipurpose application to the computing device for execution on the computing device.

16. The system of claim 15, wherein the processing device is further to:
publish the set of APIs; and
provide the set of APIs in the user interface of the computing device, wherein the set of available APIs are arranged in categories of a clinical interoperability category, a value based care category, a geo sensing services category, an operational analytics category, a financial and billing category, an applications category, a configuration APIs category, an education category, or some combination thereof.

17. The system of claim 16, wherein:
the clinical interoperability category comprises an electronic medical record and clinical systems API, a physical therapy systems API, a patient identity management API, or some combination thereof,
the value based care analytics category comprises a risk stratification API, a quality of care API, a healthcare utilization API, a population health API, or some combination thereof,
the geo sensing services category comprises a geo coder API, a geo location API, or some combination thereof,
the operational analytics category comprises a wait time API, an imaging API, a quick reference codes and recognition API, or some combination thereof,
the applications category comprises a clinics API, a provider API, a patient API, a schedules API, a consents API, an acknowledgements API, a symptomology API, a health history API, a medicines and supplements API, an allergies API, an unified login API, or some combination thereof,
the financial and billing category comprises a checkout API, a billing API, a payment API, an eligibility API, a claim submission API, or some combination thereof,
the configuration APIs category comprises a clinics configuration API, a providers configuration API, an appointments API, a lookups API, or some combination thereof, and
the education category comprises a search API, a lookups content API, or some combination thereof.

18. The system of claim 15, wherein the processing device is further to:
provide an option to subscribe to the at least one API in the user interface of the computing device;
responsive to receiving a request to subscribe to the API, implement the computer instructions of the API in the autonomous multipurpose application.

19. The system of claim 15, wherein providing the autonomous multipurpose application further comprises deploying the autonomous multipurpose application as a website accessible by a web browser executing on the computing device, transmitting the autonomous multipurpose application for installation on the computing device, or both.

20. The system of claim 15, wherein the processing device is further to:
provide an option in the user interface to select which programming language to use for implementing the computer instructions;
receive a selection to convert the computer instructions from a first programming language in a set of programming languages to a second programming language in the set of programming languages; and
convert the computer instructions implementing the API from the first programming language to the second programming language.

* * * * *